United States Patent [19]

Peterson

[11] 4,099,014
[45] Jul. 4, 1978

[54] 3,7-INTER-M-PHENYLENE-4,5,6-TRINOR-12,13(E)-DIDEHYDRO-13,14-DEHYDRO-PGD$_1$ COMPOUNDS

[75] Inventor: David C. Peterson, Portage, Mich.

[73] Assignee: The Upjohn Company, Kalamazoo, Mich.

[21] Appl. No.: 809,248

[22] Filed: Jun. 23, 1977

Related U.S. Application Data

[62] Division of Ser. No. 614,244, Sep. 17, 1975.

[51] Int. Cl.$^2$ .................... C07C 69/76; C07C 177/00
[52] U.S. Cl. ................................. 560/53; 260/520 C; 260/520 R
[58] Field of Search .................... 260/520R, 520 C; 560/53

[56] References Cited

U.S. PATENT DOCUMENTS 4,066,836  1/1978  Morton, Jr. .......................... 560/53

OTHER PUBLICATIONS

Derwent Abstract 06868R DT 1937 921-Q, 21-01-70.
Derwent Abstract 06869R DT 1937 921-Q, 21-01-70.
Derwent Abstract 24680Y/14 NL 7610-184, 21-03-77.

*Primary Examiner*—Paul J. Killos
*Attorney, Agent, or Firm*—Robert A. Armitage

[57] ABSTRACT

Prostaglandin analogs with the following cyclopentane ring structure:

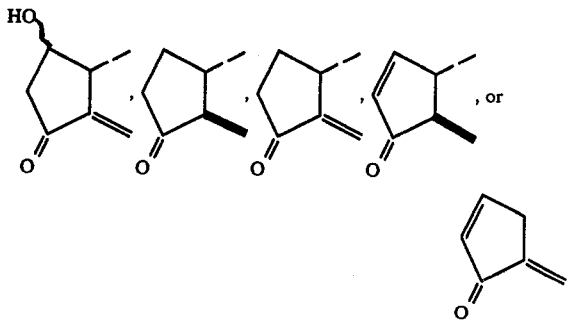

are disclosed along with intermediates useful in their preparation and processes for their preparation. These analogs are useful for some of the same pharmacological purposes as the prostaglandins, particularly and especially as blood platelet aggregation inhibitors.

25 Claims, No Drawings

3,7-INTER-M-PHENYLENE-4,5,6-TRINOR-12,13(E)-DIDEHYDRO-13,14-DEHYDRO-PGD₁ COMPOUNDS

This is a division of application Ser. No. 614,244 filed Sept. 17, 1975.

BACKGROUND OF THE INVENTION

This invention provides novel compositions of matter. This invention further provides novel processes for producing these compositions of matter. This invention further provides novel chemical intermediates useful in the above processes.

Particularly this invention provides novel analogs of some of the known prostaglandins which differ from corresponding known prostaglandins in that they contain a modified cyclopentane ring structure which exhibits oxo substitution at the C-11 position, in contrast, for example, to $PGF_\alpha$, $PGF_\beta$, or PGE compounds which are substituted at C-11 with an hydroxyl.

The known prostaglandins include the PGE compounds, e.g. prostaglandin $E_1$ ($PGE_1$), prostaglandin $E_2$ ($PHE_2$), prostaglandin $E_3$ ($PGE_3$), and dihydroprostaglandin $E_1$ (dihydro-$PGE_1$).

The known prostaglandins include $PGF_\alpha$ compounds, e.g. prostaglandin $F_{1\alpha}$($PGF_{1\alpha}$), prostaglandin $F_{2\alpha}$($PGF_{2\alpha}$), prostaglandin $F_{3\alpha}$ ($PGF_{3\alpha}$), and dihydroprostaglandin $F_{1\alpha}$ (dihydro-$PGF_{1\alpha}$).

The known prostaglandins include $PGF_\beta$ compounds, e.g. prostaglandin $F_{1\beta}$($PGF_{1\beta}$), prostaglandin $F_{2\beta}$ ($PGF_{2\beta}$), prostaglandin $F_{3\beta}$ ($PGF_{3\beta}$), and dihydroprostaglandin $F_{1\beta}$ (dihydro-$PGF_{1\beta}$).

The known prostaglandins include PGA compounds, e.g. prostaglandin $A_1$ ($PGA_1$), prostaglandin $A_2$ ($PGA_2$), prostaglandin $A_3$ ($PGA_3$), and dihydroprostaglandin $A_1$ (dihydro-$PFA_1$).

The known prostaglandins include PGB compounds, e.g. prostaglandin $B_1$ ($PGB_1$), prostaglandin $B_2$ ($PGB_2$), prostaglandin $B_3$ ($PGB_3$), and dihydroprostaglandin $B_1$ (dihydro-$PGB_1$).

Each of the above mentioned known prostaglandins (PG's) is a derivative of prostanoic acid which has the following structure and carbon atom numbering

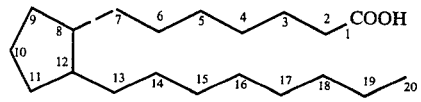

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

$PGE_1$ has the following structure:

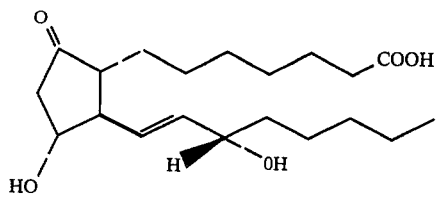

$PGE_2$ has the following structure:

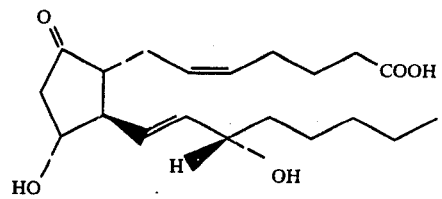

$PGE_3$ has the following structure:

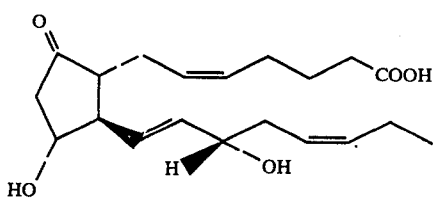

Dihydro-$PGE_1$ has the following structure:

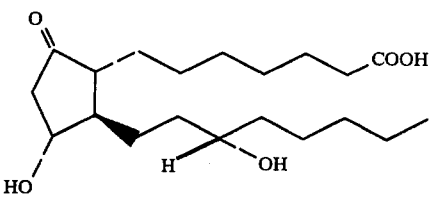

$PGF_{1\alpha}$ has the following structure:

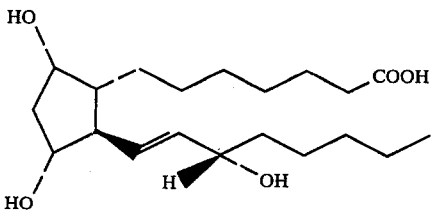

$PGF_{2\alpha}$ has the following structure:

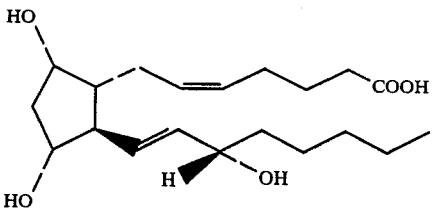

$PGF_{3\alpha}$ has the following structure:

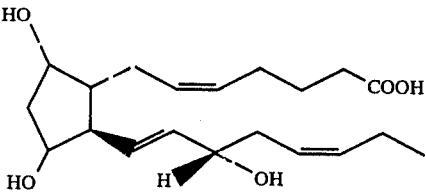

Dihydro-$PGF_{1\alpha}$ has the following structure:

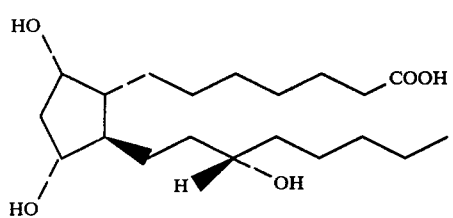

PGF$_{1\beta}$ has the following structure:

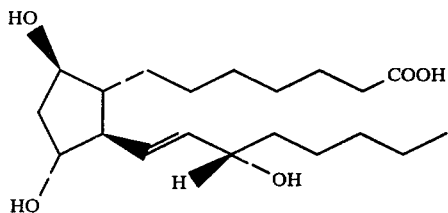

PGF$_{2\beta}$ has the following structure:

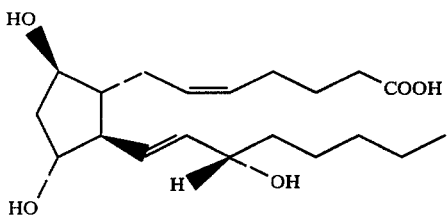

PGF$_{3\beta}$ has the following structure:

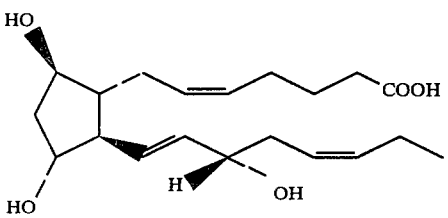

Dihydro-PGF$_{1\beta}$ has the following structure:

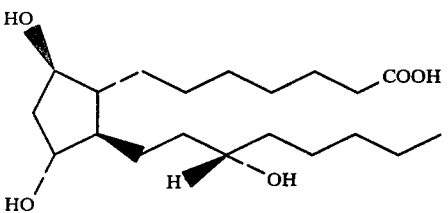

PGA$_1$ has the following structure:

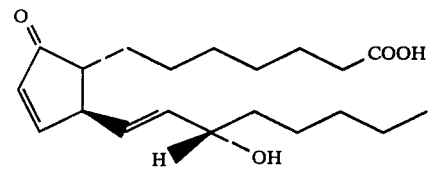

PGA$_2$ has the following structure:

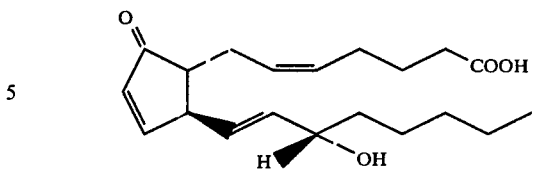

PGA$_3$ has the following structure:

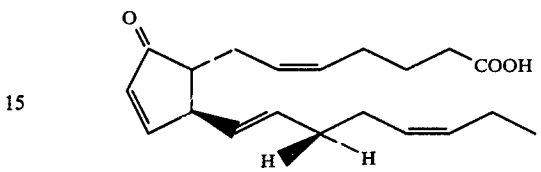

Dihydro-PGA$_1$ has the following structure:

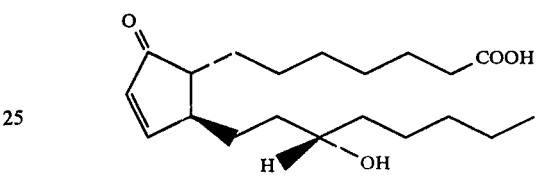

PGB$_1$ has the following structure:

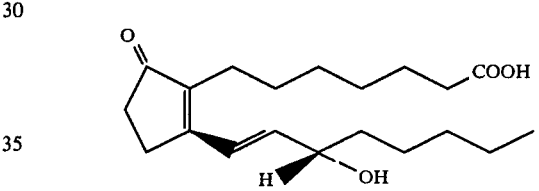

PGB$_2$ has the following structure:

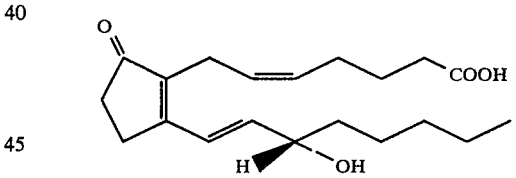

PGB$_3$ has the following structure:

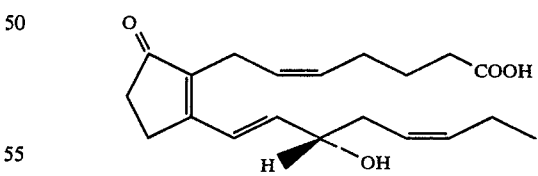

Dihydro-PGB$_1$ has the following structure:

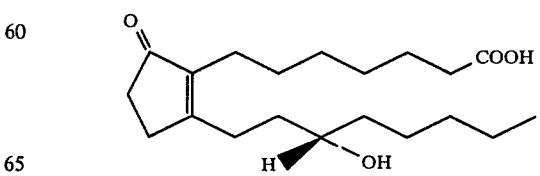

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (~) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-9, C-11, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin.

For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins is intended, the word "racemic" or "dl" will precede the prostaglandin name.

The term "prostaglandin-type" (PG-type) compound, as used herein, refers to any cyclopentane derivative herein which is useful for at least one of the same pharmacological purposes as the prostaglandins, as indicated herein.

The term prostaglandin-type intermediate, as used herein, refers to any cyclopentane derivative useful in preparing a prostaglandin-type compound.

The formulas, as drawn herein, which depict a prostaglandin-type compound or an intermediate useful in preparing a prostaglandin-type compound, each represent the particular stereoisomer of the prostaglandin-type compound which is of the same relative stereochemical configuration as a corresponding prostaglandin obtained from mammalian tissues, or the particular stereoisomer of the intermediate which is useful in preparing the above stereoisomer of the prostaglandin-type compounds.

The term "prostaglandin analog", as used herein, represents that stereoisomer of a prostaglandin-type compound which is of the same relative stereochemical configuration as a corresponding prostaglandin obtained from mammalian tissues, a mixture comprising that stereoisomer and the enantiomer thereof, or the enantiomer thereof. In particular, where a formula is used to depict a prostaglandin-type compound herein, the term prostaglandin analog refers to the compound of that formula, a mixture comprising that compound and the enantiomer thereof, or the enantiomer of the compound of that formula.

The various PG's named above, their esters, acylates and pharmacologically acceptable salts, are extremely potent in causing various biological responses. For that reason, these compounds are useful for pharmacologic purposes. See, for example, Bergstrom et al., Pharmacol. Rev. 20, 1 (1968) and references cited therein.

For the PGE compounds these biological responses include:

(a) stimulating smooth muscle (as shown by tests, for example, on guinea pig ileum, rabbit duodenum, or gerbil colon);

(b) affecting lipolytic activity (as shown by antagonism of epinephrine induced release of glycerol from isolated rat fat pads);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);

(g) affecting the reproductive organs of mammals as labor inducers, abortifacients, cervical dilators, regulators of the estrus, and regulators of the menstrual cycle; and (h) accelerating growth of epidermal cells and keratin in animals.

For the $PGF_\alpha$ compound these biological responses include:

(a) stimulating smooth muscle (as shown by tests on guinea pig ileum, rabbit duodenum, or gerbil colon);

(b) inhibiting gastric secretion and reducing undesirable gastrointestinal effects from systemic administration of prostaglandin synthetase inhibitors;

(c) decongesting nasal passages;

(d) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotonin, thrombin, and collagen); and (e) affecting the reproductive organs of mammals as labor inducers, abortifacients, cervical dilators, regulators of the estrus, and regulators of the menstrual cycle.

For the $PGF_\beta$ compounds these biological response include:

(a) stimulating smooth muscle (as shown by tests on guinea pig ileum, rabbit duodenum, or gerbil colon);

(b) inhibiting gastric secretion and reducing undesirable gastrointestinal effects from systematic administration of prostaglandin synthetase inhibitors;

(c) controlling spasm and facilitating breathing in asthmatic conditions;

(d) decongesting nasal passages;

(e) decreasing blood platelet adhesion (as shown by platelet to glass adhesiveness) and inhibiting blood platelet aggregation and thrombis formation induced by various physical stimuli (e.g., arterial injury) or chemical stimuli (e.g., ADP, ATP, serotinin, thrombin, and collager); and (f) affecting the reproductive organs of mammals as labor inducers, abortifacients, cervical dilators, regulators of the estrus, and regulators of the menstrual cycle.

For the PGA compounds these biological responses include:

(a) stimulating smooth muscle (as shown by tests on guinea pig ileum, rabbit duodenum, or gerbil colon);

(b) inhibiting gastric secretion and reducing undesirable gastrointestinal effects from systematic administration of prostaglandin synthetase inhibitors;

(d) controlling spasm and facilitating breathing in asthmatic conditions;

(d) decongesting nasal passages; and (e) increasing kidney blood flow.

For the PGB compounds these biological responses include:

(a) stimulating smooth muscle (as shown by tests on guinea pig ileum, rabbit duodenum, or gerbil colon); and (b) accelerating growth of epidermal cells and keratin in animals.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact does depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-epoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex, and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors or mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergecny situations; by inhalation in the form of aerosols or solutions for nebulizers; or by insufflation in the form of powder. Doses in the range of about 0.01 to 5 mg. per kg. of body weight are used 1 to 4 times a day, the exact doses depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose, in a dose range of about 10 $\mu$g. to about 10 mg. per ml. of a pharmacologically suitable liquid vehicle or as an aerosol spray, both for topical application.

The prostaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance of hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact does depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g. cats, dogs, rabbits, monkeys, and rats, for these purposes in order to develop new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses of just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 pg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg. ml of the prostaglandin pound.

Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prenisolone, methylprednisolone, and fluprednisolone, each of those being used in the combination at the usual concentration suitable for its use alone.

Certain prostaglandin-type compounds, structurally related to those of the present invention, are known in the prior art. See for example Belgian Pat. No. 767,704Q (Derwent Framdoc CP1 76109U-B) which discloses 9-deoxy-PGD-type compounds. See also U.S. Pat. No. 3,878,239, issued Apr. 15, 1975, which discloses certain PGD analogs substituted at C-15 or C-16 by methyl. For a disclosure of $PGD_1$ or $PGD_2$ see Nugteren, et al., Rec. Trav. Chim. Pays-Bas, 85, 104 (1966), Granstrom, et all, J. Biol. Chem. 243, 4104 (1968), C. Sih. et al., Biochem. 11, 227 (1972), J. Org. Chem., 38, 215 (1973, and Nishizawa, et al., PROSTAGLANDINS 9, 109 (1975). Finally see the following references to 9-deoxy-PGF-type compounds: Derwent Farmdoc CF1 Nos. 76438S-B; 21002T-B; 39100U-B; 21092T-B; 16843U-B; 139292U-B; and 49992T-B.

SUMMARY OF THE INVENTION

This invention provides novel prostaglandin analogs, esters of these analogs, and pharmacologically acceptable salts of these analogs.

This invention further provides lower alkanoates of these analogs.

This invention further provides novel processes for preparing these analogs.

This invention further provides novel chemical intermediates useful in the preparation of these analogs.

In particular this specification discloses, but does not claim as part of the present invention:

a prostaglandin analog of the formula

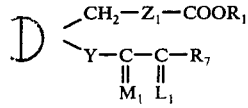

wherein D is

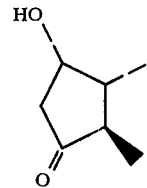

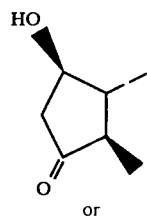

or

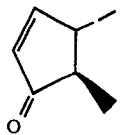

wherein Y is cis—CH=CH—, trans-CH=CH—, or —CH₂CH₂—; wherein Z₁ is
(1) cis-CH=CH—CH₂—(CH₂)_g—CF₂—,
(2) cis-CH=CH—CH₂—(CH₂)_g—CH₂—,
(3) cis-CH₂—CH=CH—(CH₂)_g—CH₂—,
(4) —(CH₂)₃—(CH₂)_g CF₂—,
(5) —(CH₂)₃—(CH₂)_g—CH₂—,
(6) —CH₂—O—CH₂—(CH₂)_g—(CH₂—,
(7) —(CH₂)₃—O—(CH₂)_g—,
(8) —(CH₂)₃—O—(CH₂)_g—,

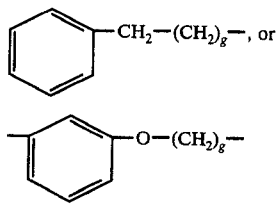

wherein g is 1, 2, or 3;
wherein M₁ is

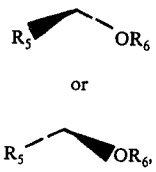

wherein R₅ and R₆ are hydrogen or methyl, with the proviso that one of R₅ and R₆ is methyl only when the other is hydrogen;
wherein L₁ is

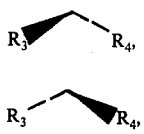

or a mixture of

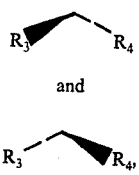

wherein R₃ and R₄ are hydrogen, methyl, or fluoro, being the same or different, with the proviso that one of R₃ and R₄ is hydrogen or fluoro only when the other is hydrogen or fluoro;
wherein R₇ is
(1) —(CH₂)_m—CH₃,

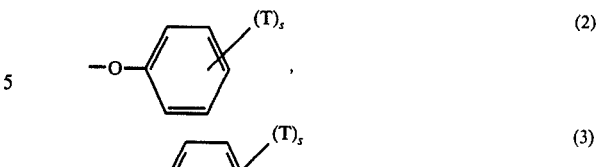

(4) cis—CH=CH—CH₂—CH₃,
wherein m is one to 5, inclusive, T is chloro, floro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that R₇ is

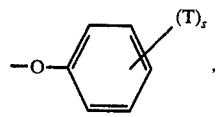

wherein T and s are as defined above, only when R₃ and R₄ are hydrogen or methyl, being the same or different;
wherein R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted wth one, two, or three chloro or alkyl of one to 3 carbon atoms, inclusive, or a pharmacologically acceptable cation; with the further proviso that
(1) D is

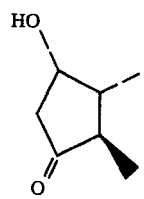

Z₁ is cis-CH=CH—(CH₂)₃— or —(CH₂)₅—, R₇ is —(CH₂)₃—CH₃, Y is trans-CH=CH— and one or both of R₃ and R₅ is or are methyl only when R₄ is fluoro or R₆ is methyl;
(2) D is

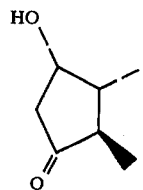

Z₁ is cis-CH=CH—(CH₂)₃— or —(CH₂)₅—, R₇ is —(CH₂)₃—CH₃, Y is trans-CH=CH—, R₃, R₄, and R₅ are hydrogen, only when R₆ is methyl;
(3) D is

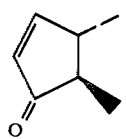

only when Y is cis- or trans-CH=CH—; and
(4) D is

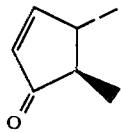

$Z_1$ is cis-CH=CH—$CH_2$—$(CH_2)_g$—$CH_2$—, Y is trans-CH=CH—, $R_5$ and $R_6$ are hydrogen, and $R_7$ is —$(CH_2)_m$—$CH_3$, wherein g and m are as defined above, only when at least one of $R_3$ and $R_4$ is methyl or fluoro;

Further this specification discloses, and expressly claims as part of the present invention:

(a) a prostaglandin analog of the formula

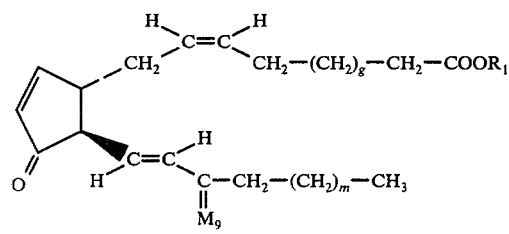

wherein $M_9$ is

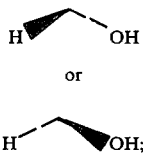

wherein g is one to 3, inclusive; wherein m is one to 5, inclusive; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or a pharmacologically acceptable cation; or (b) a prostaglandin analog of the formula

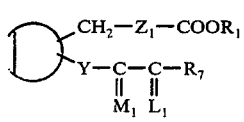

wherein D is

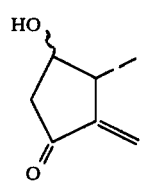

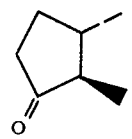

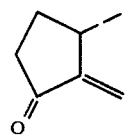

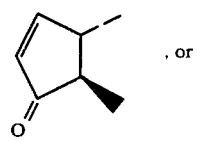, or

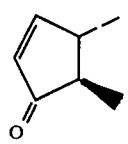;

wherein Y is cis-CH=CH—, trans-CH=CH—, —$CH_2CH_2$—, or =CH—$CH_2$, with the proviso that Y is =CH—$CH_2$— when and only when D is

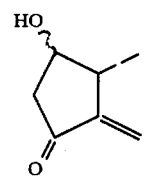,

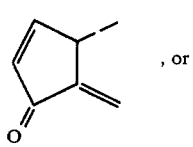, or

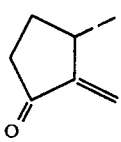;

wherein $Z_1$ is
(1) cis-CH=CH—$CH_2$—$(CH_2)_g$—$CF_2$—,
(2) cis-CH=CH—$CH_2$—$(CH_2)_g$—$CH_2$—,
(3) cis-$CH_2$—CH=CH—$(CH_2)_g$—$CH_2$—,
(4) —$(CH_2)_3$—$(CH_2)_g$—$CF_2$—,
(5) —$(CH_2)_3$—$(CH_2)_g$—$CH_2$—,
(6) —$CH_2$—O—$CH_2$—$(CH_2)_g$—$CH_2$—,
(7) —$(CH_2)_2$—O—$(CH_2)_g$—$CH_2$—,
(8) —$(CH_2)_3$O—$(CH_2)_g$—,

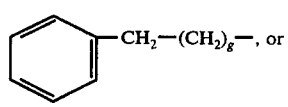, or (9)

-continued

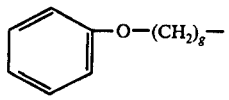

wherein g is 1, 2, or 3;
wherein $M_1$ is

or

wherein $R_5$ and $R_6$ are hydrogen or methyl, with the proviso that one of $R_5$ and $R_6$ is methyl only when the other is hydrogen;
wherein $L_1$ is

or a mixture of

and

wherein $R_3$ and $R_4$ are hydrogen, methyl, or fluoro, being the same or different, with the proviso that one of $R_3$ and $R_4$ is hydrogen or fluoro when the other is hydrogen or fluoro;
wherein $R_7$ is
(1) $-(CH_2)_m-CH_3$,

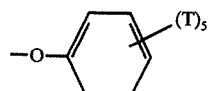 (2)

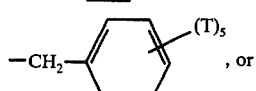, or (4) cis-$CH=CH-CH_2-CH_3$,
wherein m is 1 to 5, inclusive, T is chloro, fluoro, trifluoromethyl, alkyl of 1 to 3 carbon atoms, inclusive, or alkoxy of 1 to 3 carbon atoms, inclusive, and s is 0, 1, 2, or 3, the various T's being the same or different, with the proviso that not more than two T's are other than alkyl, with the further proviso that $R_7$ is

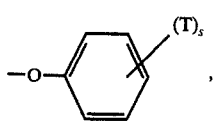

wherein T and s are as defined above, only when $R_3$ and $R_4$ are hydrogen or methyl, being the same or different;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro or alkyl of 1 to 3 carbon atoms, inclusive, or a pharmacologically acceptable cation; with the further provisos that
(1) D is

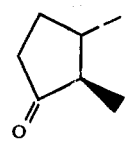

Y is $-CH_2CH_2-$, $R_3$, $R_4$, and $R_6$ are hydrogen or methyl being the same or different, $R_7$ is $-(CH_2)_m-CH_3$, wherein m is as defined above and $Z_1$ is $-(CH_2)_3$ only when $R_5$ is methyl; and
(2) D is

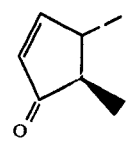

only when Y is $-CH_2CH_2-$.
Finally this specification discloses but does not claim as part of the present invention:
a prostanglandin analog of the formula

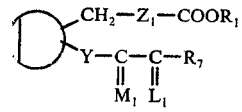

wherein D is

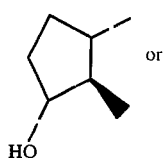 or

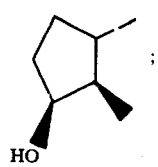;

wherein Y is cis-$CH=CH-$, trans-$CH=CH-$, or $-CH_2CH_2-$;
wherein $M_1$ is

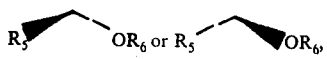

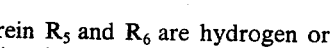

wherein $R_5$ and $R_6$ are hydrogen or methyl, with the proviso that one of $R_5$ and $R_6$ is methyl only when the other is hydrogen;
wherein $L_1$ is

or a mixture of

and

wherein $R_3$ and $R_4$ are hydrogen, methyl, or fluoro, being the same or different, with the proviso that one of $R_3$ and $R_4$ is hydrogen or fluoro only when the other is hydrogen or fluoro;

wherein $R_7$ is (1) $-(CH_2)_m-CH_3$,

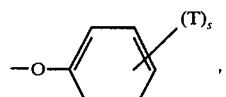   (2)

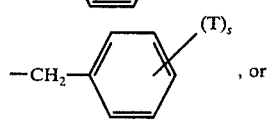, or   (3)

(4) cis-$CH=CH-CH_2-CH_3$, wherein $m$ is 1 to 5, inclusive, T is chloro, fluoro, trifluoromethyl, alkyl of 1 to 3 carbon atoms, inclusive, or alkoxy of 1 to 3 carbon atoms, inclusive, and $s$ is 0, 1, 2, or 3, the various T's being the same or different, with the proviso that not more than two T's are other than alkyl, with the further proviso that $R_7$ is

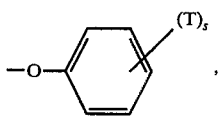

wherein T and $s$ are as defined above; only when $R_3$ and $R_4$ are hydrogen or methyl, being the same or different;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation;

wherein $Z_1$ is (1) cis-$CH=CH-CH_2(CH_2)_g-CF_2-$,
(2) cis-$CH=CH-CH_2-(CH_2)_g-CH_2-$,
(3) cis-$CH_2-CH=CH-(CH_2)_g-CH_2-$,
(4) $-(CH_2)_3-(CH_2)_g-CF_2-$,
(5) $-(CH_2)_3-(CH_2)_g-CH_2-$,
(6) $-CH_2-O-CH_2-(CH_2)_g-CH_2-$,
(7) $-(CH_2)_2-O-(CH_2)_g-CH_2-$,
(8) $-(CH_2)_3-O-(CH_2)_g-$,

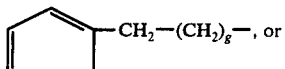   (9)

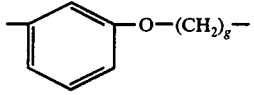   (10)

wherein $g$ is 1, 2, or 3; with the further provisos that:
(1) $Z_1$ is $-(CH_2)_5$, Y is $-CH_2CH_2-$, $M_1$ is

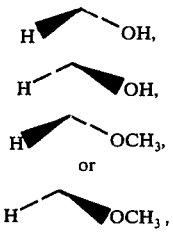

$R_7$ is $-(CH_2)_m-CH_3$, wherein $m$ is as defined above, only when at least one of $R_3$ and $R_4$ is fluoro;

(2) $Z_1$ is $-(CH_2)_3-(CH_2)_g-CH_2-$, Y is trans-$CH=CH-$, $M_1$ is

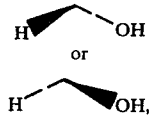

and $R_7$ is $-(CH_2)_m-CH_3$, wherein $g$ and $m$ are as defined above, only when at least one of $R_3$ and $R_4$ is fluoro;

(3) $Z_1$ is cis-$CH=CH-CH_2-(CH_2)_g-CH_2-$, Y is trans-$CH=CH-$, $M_1$ is

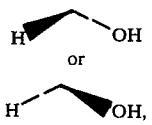

$R_7$ is $-(CH_2)_m-CH_3$, wherein $g$ and $m$ are as defined above, only when at least one of $R_3$ and $R_4$ is fluoro; and (4) D is

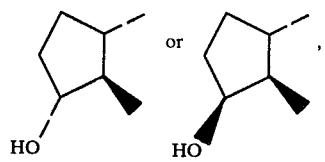

$Z_1$ is $-(CH_2)_3-(CH_2)_g-CH_2$, Y is trans-$CH=CH-$, $R_3$ and $R_4$ are both hydrogen, and $R_7$ is $-(CH_2)_m-CH_3$, wherein $g$ and $m$ are as defined above, only when $R_6$ is methyl.

Within the scope of the novel prostaglandin analogs described in this specification there are represented above (a) PGD-type compounds when D is (b) 9β-PGD-type compounds when D is

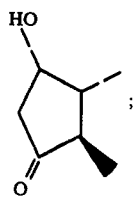

(c) 12,13(E)-didehydro-13,14-dihydro-PGD-type compounds when D is

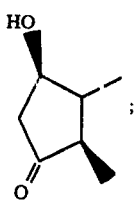

(d) 12,13-(E)-didehydro-13,14-dihydro-9β-PGD-type compounds when D is

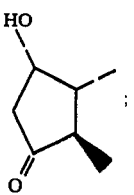

(e) 9-deoxy-PGD-type compounds when D is

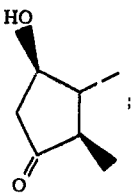

(f) 9-deoxy-PGF-type compounds when D is

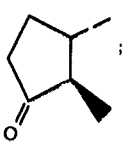

(g) 12,13(E)-didehydro-13,14-dihydro-9-deoxy-PGD-type compounds when D is

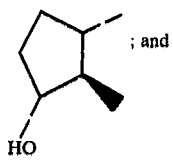

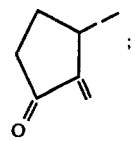

(h) 9-deoxy-9,10-didehydro-PGD-type compounds when D is

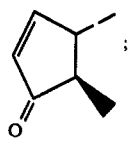

and (i) 9-deoxy-9,10-didehydro-12,13-(E)-didehydro-13,14-dihydro-PGD-type compounds when D is

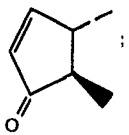

(j) 9-deoxy-11β-PGF-type compounds when D is

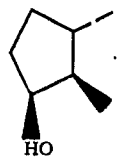

Those prostaglandin analogs herein wherein $Z_1$ is cis-CH=CH—CH$_2$—(CH$_2$)$_g$—CH$_2$— or cis CH=CH—CH$_2$—(CH$_2$)$_g$—CF$_2$— are named as "PG$_2$" compounds. The latter compounds are further characterized as "2,2-difluoro" PG-type compounds. When g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —(CH$_2$)$_3$—(CH$_2$)$_g$—CH$_2$— or —(CH$_2$)$_3$—(CH$_2$)$_g$—CF$_2$, wherein g is as defined above, the compounds so described are "PG$_1$" compounds. When g is 2 or 3, the "2a-homo" and "2a,2b-dihomo" compounds are described as is discussed in the preceding paragraph.

When $Z_1$ is —CH$_2$—O—CH$_2$—(CH$_2$)$_g$—CH$_2$— the compounds so described are named as "5-oxa-PG$_1$" compounds. When g is 2 or 3, the compounds so described are "2a-homo" or "2a,2b-dihomo" compounds, respectively, as discussed above.

When $Z_1$ is —(CH$_2$)$_2$—O—(CH$_2$)$_g$—CH$_2$—, wherein g is as defined above, the compounds so described are named as "4-oxa-PG$_1$" compounds. When g is 2 or 3, the compounds so described are additionally characterized as "2a-homo" or "2a,2b-dihomo" compounds, respectively, as is discussed above.

When $Z_1$ is —(CH$_2$)$_3$—O—(CH$_2$)$_g$—, wherein g is as defined above, the compounds so described are named as "3-oxa-PG$_1$" compounds. When g is 2 or 3, the compounds so described are further characterized as "2a-homo" or "2a,2b-dihomo" compounds, respectively, as is discussed above.

When $Z_1$ is cis-CH$_2$-CH=CH—(CH$_2$)$_g$—CH$_2$—, wherein g is as defined above, the compounds so described are named "cis-4,5-didehydro-PG$_1$" compounds. When g is 2 or 3, the compounds so described are further characterized as "2a-homo" or "2a,2b-dihomo" compounds, respectively, as discussed above.

For the novel compounds of this invention wherein $Z_1$ is

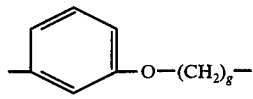

or

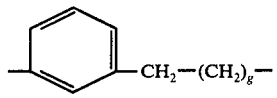

there are described, respectively, 3-oxa-3,7-inter-m-phenylene-4,5,6-trinor or 3,7-inter-m-phenylene-4,5,6-trinor-PG-type compounds, when g is 1. When g is 2 or 3, the above compounds are additionally described as "2a-homo" or "2a,2b-dihomo" PG-type compounds, respectively.

The novel prostaglandin analogs of this invention which contain a cis-CH=CH— moiety at the C-13 to C-14 position, are accordingly, referred to as "cis-13" compounds.

When the —CH$_2$CH$_2$— moiety is present at C-13 to C-14, the compounds so described are "13,14-dihydro" compounds.

Further when the C-13 to C-14 moiety (Y) is =CHCH$_2$ the compounds so described are named according to the cyclopentane ring structure, as discussed above. Accordingly, "12,13-didehydro-13,14-dihydro" compounds are described. As depicted herein, the formulas which represent 12,13-didehydro-13,14-dihydro compounds represent the E geometric isomers, using the E and Z nomenclature of describing the possible geometric isomers of a ring carbon atom and doubly bonded to a carbon atom not of the ring. Accordingly, these compounds are additionally characterized as "12,13-(E)-didehydro-13,14-dihydro" PG analogs. See Blackwood, J. E. et al., J. of Chem. Doc. 8, 30 (1968).

When R$_7$ is —(CH$_2$)$_m$—CH$_3$, wherein m is as defined above, the compounds so described are named as "19,20-dinor", "20-nor", "20-methyl", or "20-ethyl" compounds when m is 1, 2, 4, or 5, respectively.

When R$_7$ is

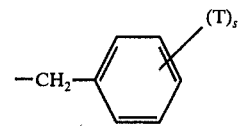

wherein T and s are as defined above, the compounds so described are named as "17-phenyl-18,19,20-trinor" compounds, when s is 0. When s is 1, 2, or 3, the corresponding compounds are named as "17-(substituted phenyl)-18,19,20-trinor" compounds.

When R$_7$ is

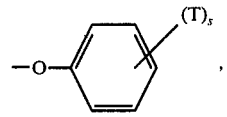

wherein T and s are as defined above, and neither R$_3$ nor R$_4$ is methyl, the compounds so described are named as "16-phenoxy-17,18,19,20-tetranor" compounds, when s is 0. When s is 1, 2, or 3, the corresponding compounds are named as "16-(substituted phenoxy)-17,18,19,20-tetranor" compounds. When one and only one of R$_3$ and R$_4$ is methyl or both R$_3$ and R$_4$ are methyl, then the corresponding compounds wherein R$_7$ is as defined in this paragraph are named as "16-phenoxy or 16-(substituted phenoxy)-18,19,20-trinor" compounds or "16-methyl-16-phenoxy or 16-(substituted phenoxy)-18,19,20-trinor" compounds, respectively.

When R$_7$ is cis-CH=CH—CH$_2$—CH$_3$, the compounds so described are "PG$_3$" or "cis-17,18-didehydro" compounds depending on whether $Z_1$ is cis-CH=CH—(CH$_2$)$_g$—C(R$_2$)$_2$, wherein R$_2$ is hydrogen or fluoro, or another moiety, respectively.

When at least one of R$_3$ and R$_4$ is not hydrogen then (except for the 16-phenoxy compounds discussed above) there are described the "16-methyl" (one and only one of R$_3$ and R$_4$ is methyl), "16,16-dimethyl" (R$_3$ and R$_4$ are both methyl), "16-fluoro" (one and only one of R$_3$ and R$_4$ is fluoro), "16,16-difluoro" (R$_3$ and R$_4$ are both fluoro) compounds. For those compounds wherein R$_3$ and R$_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When R$_5$ is methyl, the compounds so described are named as "15-methyl" compounds. When R$_6$ is methyl, the compounds so described are named as "15-methyl ether" compounds.

Some formulas of 13-cis-cyclopentane derivatives described hereinafter contain a moiety of the formula:

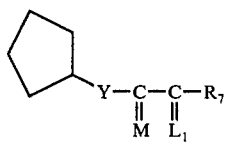

wherein the cyclopentane ring is variously substituted, wherein M is variously defined according to the subscripts provided herein; wherein L$_1$ and R$_7$ is as defined above; and wherein Y is cis-CH=CH—. Optionally the above formula is depicted with one or both of L$_1$ and M above the carbon atom to which it is attached, e.g., as follows:

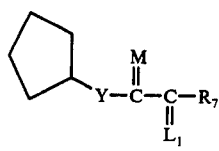

When the above representation is employed, it is hereby defined to indicate the following convention with respect to the representation of the cis-13 double bond:

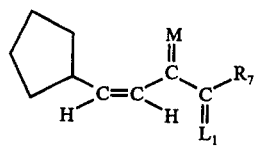

Further in employing this convention when M is, for example,

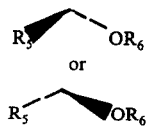

then the corresponding representations:

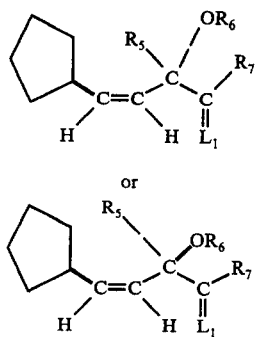

are intended, respectively. Accordingly all the formulas herein which represent 13-cis cyclopentane derivatives are depicted by the same convention as that for the cis-13-PGE₁ when drawn as follows:

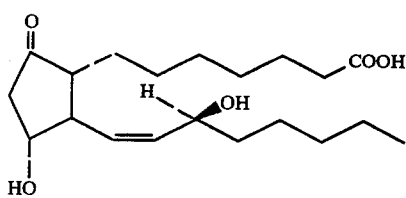

Thus, by this convention the (15S)-hydroxy of cis-13-PGE₁ is in the beta configuration.

cis-13-PG-type compounds as drawn herein which have an hydroxy or methoxy at C-15 in the alpha configuration are of the opposite relative stereochemical configuration at C-15 as that of cis-13-PGE₁, and are therefore named as "15-epi" compounds. When the beta hydroxy or methoxy configuration is present, no special designation of this stereochemistry is provided.

Accordingly, 15-epi-16,16-difluoro-cis-13-PGD₂ is depicted herein as follows:

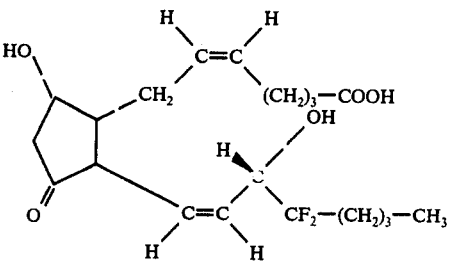

Alternate representations of cis-13-PGE₁ affect the depiction of C-15 as an alpha or beta hydroxy. Thus, by a representation contrary to the instant convention, cis-13-PGE₁ appears as follows:

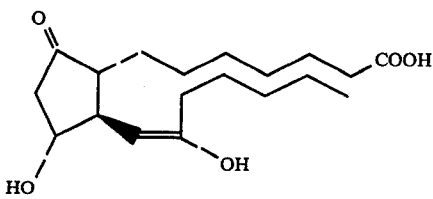

Accordingly, care must be taken to consistently draw the formulas of cis-13-PG-type compounds herein such that the C-15 carbon atom is properly represented, i.e., all cis-13-15-epi-PG's are 15α-OH.

13,14-trans or saturated cyclopentane derivatives which contain the moiety

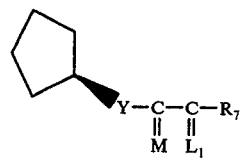

wherein the cyclopentane ring is variously substituted, wherein M is variously defined according to the subscripts provided herein; wherein $L_1$ and $R_7$ are as defined above; and wherein Y is trans-CH=CH— or —CH₂CH₂—. When this representation is employed, it is hereby defined to indicate the following convention with respect to the representation of the C-13 to C-14 moiety:

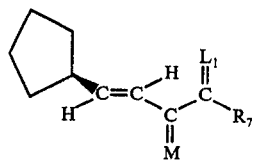

or

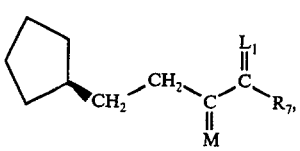

respectively. Likewise in employing this convention when M is, for example

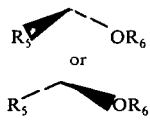

then the corresponding representation for the trans-13:

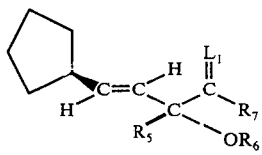

or

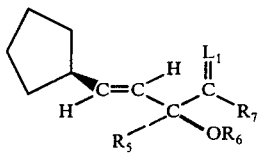

and the 13,14-saturated:

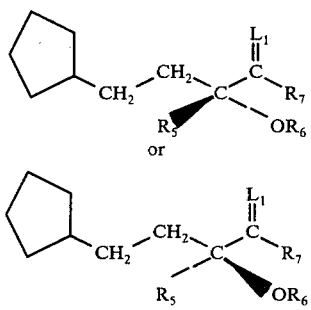

are intended, respectively. Accordingly all the formulas herein which represent trans-13 or 13,14-saturated cyclopentane derivatives are depicted by the same convention as that for $PGE_1$ when drawn as above, i.e.,

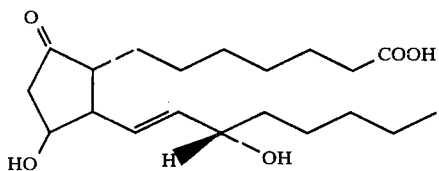

Finally the 12,13(E)-didehydro-13,14-dihydro-PG-type compounds as drawn herein follow the same convention as described above for the depiction of 13,14-saturated cyclopentane derivatives.

Thus, for all trans-13 or 13,14-dihydro-PG-type compounds, as drawn herein the 15α-hydroxy configuration corresponds to the relative C-15 stereochemical configuration of $PGE_1$ as obtained from mammalian tissues. No special designation of the C-15 stereochemistry is provided in naming these compounds. For compounds of the opposite stereochemical configuration at C-15 (i.e., 15β-hydroxy), the description "15-epi" will be employed.

Examples of alkyl of one to 12 carbon atoms, inclusive, are methyl, ethyl, propyl, butyl, pentyl, hexyl, heptyl, octyl, nonyl, decyl, undecyl, and isomeric forms.

Examples of cycloalkyl of 3 to 10 carbon atoms, inclusive, are cyclopropyl and 2-methylcyclopropyl.

Examples of aralkyl of 7 to 12 carbon atoms, inclusive, are benzyl, 2-phenylethyl and 1-phenylethyl.

Examples of phenyl substituted by one to 3 chloro or alkyl of one to 4 carbon atoms, inclusive, are p-chlorophenyl and m-chlorophenyl, Examples of

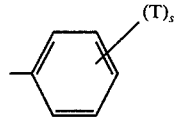

wherein T is alkyl of 1 to 3 carbon atoms, inclusive, fluoro, chloro, trifluoromethyl, or alkoxy of 1 to 3 carbon atoms, inclusive; and s is 0, 1, 2, or 3, with the proviso that not more than two T's are other than alkyl, are phenyl, (o-, m-, or p-)tolyl, (o-, m-, or p-)-ethylphenyl, 2-ethyl-p-tolyl, 4-ethyl-o-tolyl, 5-ethyl-m-tolyl, (o-, m-, or p-(propylphenyl, 2-propyl-(o-, m-, or p-)tolyl, 4-isopropyl-2,6-xylyl, 3-propyl-4-ethylphenyl., (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)methyl-2-fluorophenyl, o-, m-, or p-trifluoromethylphenyl, (o-, m-, or p-)methoxyphenyl, (o-, m-, or p-)ethoxyphenyl, and (4- or 5-)chloro-2-methoxyphenyl.

The novel prostaglandin analogs of this invention correspond to each of the prostaglandins described above, in that the novel prostaglandin analogs exhibit prostaglandin-like activity.

Specifically the novel prostaglandin analogs of this invention correspond to the prostaglandins, in that each of these novel analogs is useful for each of the abovedescribed purposes, for which any corresponding prostaglandin is used, and are used in the same manner as the corresponding prostaglandin as discussed above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, short, or smaller doses, and make possible self-administration by the patient.

Accordingly, the novel prostaglandin analogs of this invention are administered in various ways for various purposes: e.g., intraveneously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as shown in the art are used. For tissue implants, a sterile tablet or silicone rubber capsule or other object containing or impregnated with the substance is used.

The novel PG analogs of this invention are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl, and particularly methyl, are especially preferred for optimum absorption of the compound by the body or experimental animal system; and straight-chain octyl, nonyl, decyl, undecyl and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g. lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentrylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof. e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mon-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel PG analogs of this invention used for the purposes described above in free hydroxy form or also in the form wherein the hydroxy moieties are transformed to lower alkanoate moieties are acetoxy, propionyloxy, butryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

It is preferred that in the carboxy-terminated side g is one or 3; it is especially preferred that g be one, i.e., the chain is of the natural chain length of the prostalgandins. Further when $R_7$ is $-(CH_2)_m-CH_3$, it is preferred that m be 3. For those compounds wherein $R_7$ is

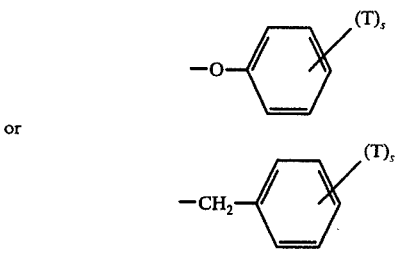

or it is preferred that s be zero or one and T be chloro, fluoro, or trifluoromethyl.

For those compounds wherein at least one of $R_3$ and $R_4$ is methyl or fluoro, it is preferred that $R_5$ and $R_6$ both be hydrogen. For those compounds wherein at least one of $R_5$ and $R_6$ is methyl, it is preferred that $R_3$ and $R_4$ both be hydrogen. For those compounds wherein $R_7$ is

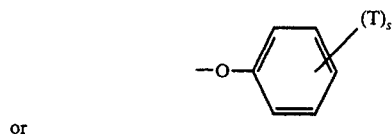

or

-continued

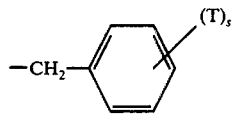

it is preferred that $R_3$, $R_4$, $R_5$, and $R_6$ all be hydrogen.

For those compounds wherein an oxa is substituted for a methylene (i.e., —O— for —CH$_2$—), it is preferred that such substitution occur at C-5, over C-4 and C-3.

It is further preferred that the 15-hydroxy or 15-methoxy be of the alpha configuration, i.e., that the hydroxy be in the 15-epi configuration for the novel cis-13-PG analogs as drawn herein and not be in the 15-epi configuration when non-cis-13-PG analogs are considered.

The Charts herein describe methods whereby the novel prostaglandin analogs disclosed herein are prepared.

With respect to the charts below:

T and s are as defined above, $R_1$ is as defined above, but for the various transformations herein $R_1$ is not a pharmacologically acceptable cation, but rather hydrogen or an ester.

$R_2$ is hydrogen or fluoro. $R_{53}$ is hydrogen or methyl. $R_3$, $R_4$, $R_5$, $R_6$, and $R_7$ are as defined above.

$R_9$ is an acyl protecting group.

$R_{10}$ is a blocking group.

$R_{22}$ and $R_{26}$ are hydrocarbyl, e.g. alkyl, cycloalkyl, aralkyl, and the like. Preferably $R_{22}$ and $R_{26}$ are alkyl, being most preferably lower alkyl (e.g., methyl or ethyl).

$R_{51}$ is $R_{30}$-SO$_2$, wherein $R_{30}$ is alkyl, cycloalkyl, aralkyl, phenyl, or phenyl substituted with alkyl or halogen. Preferably $R_{30}$ is methyl or p-tolyl.

$R_{55}$ and $R_{56}$ are alkyl of one to 4 carbon atoms, inclusive, being the same or different, or when taken together represent a group of the formula

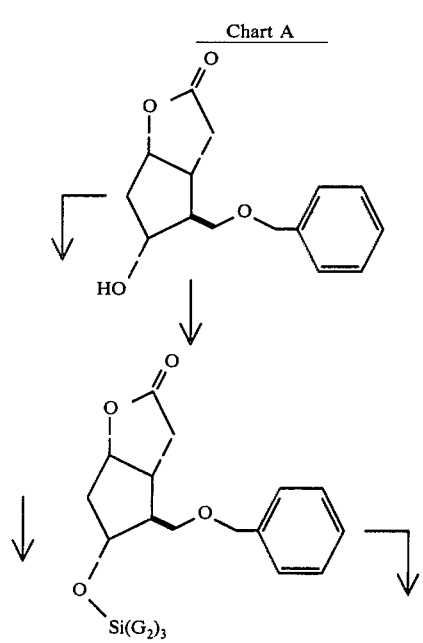

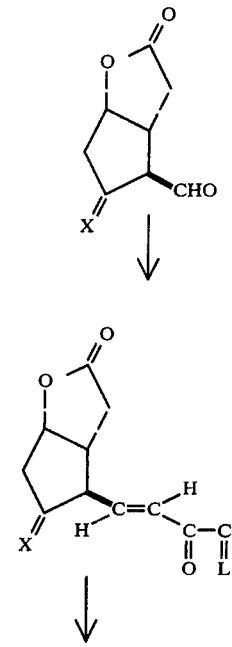

XVIII 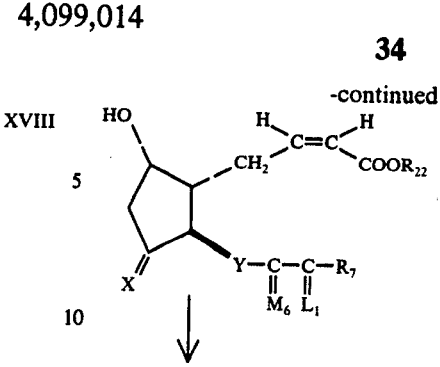 XXVII
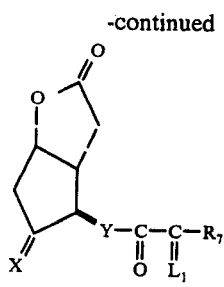
XIX 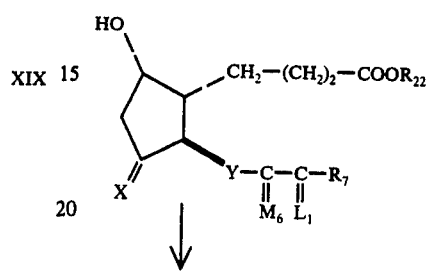 XXVIII
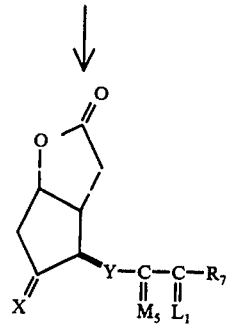
XX 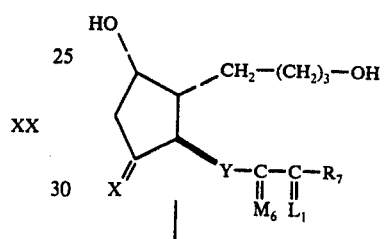 XXIX
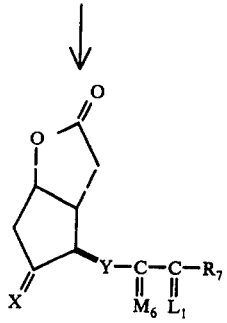
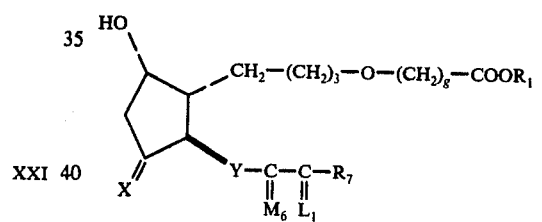 XXX
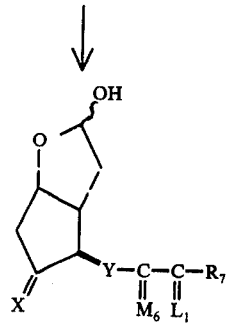
XXI
Chart C
XXXI 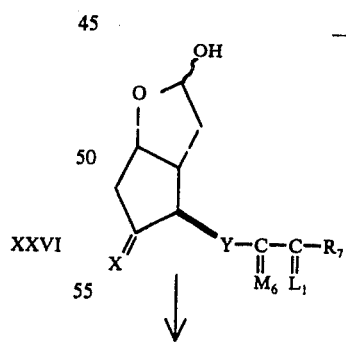
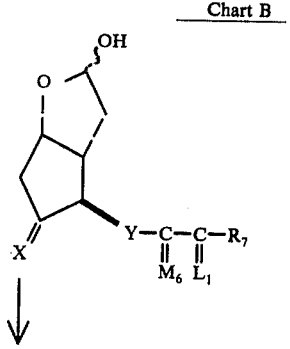
Chart B
XXVI
XXXII 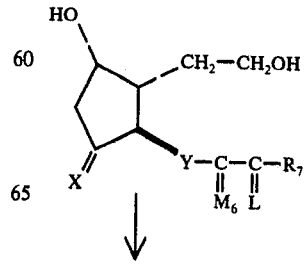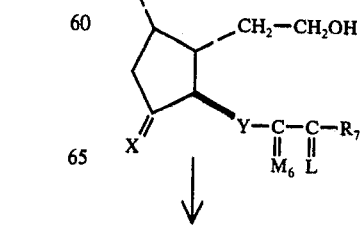

-continued
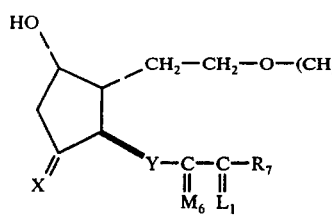
XXXIII
Chart D
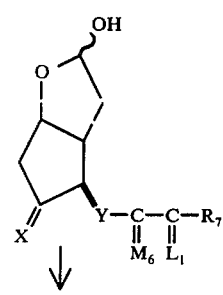
XXXVI
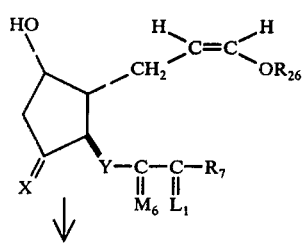
XXXVII
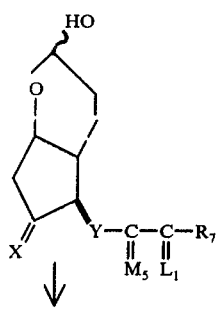
XXXVIII
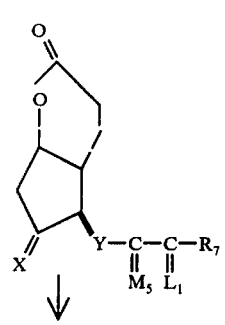
XXXIX
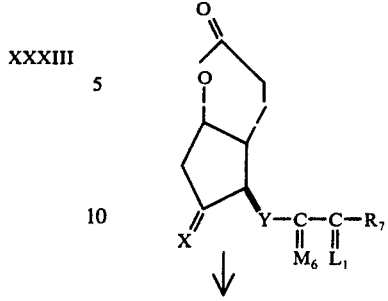
XL
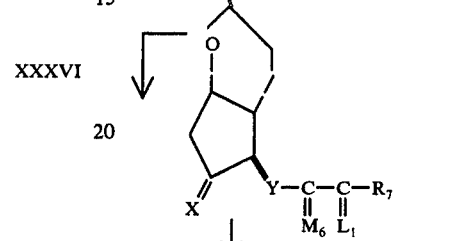
XLI
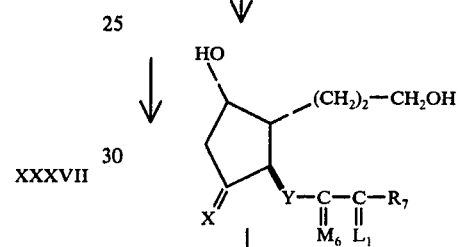
XLII
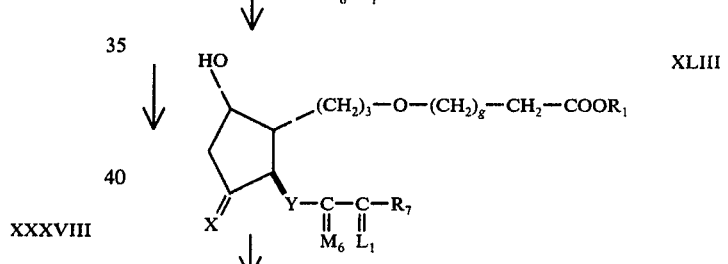
XLIII
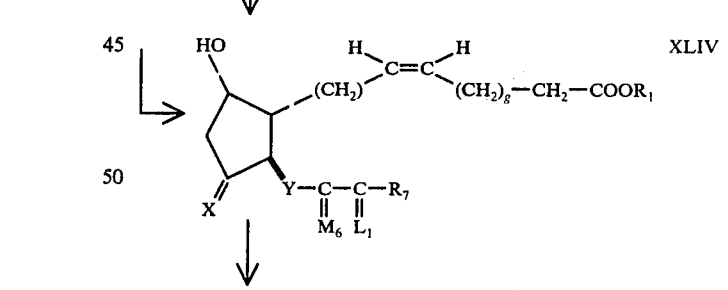
XLIV
Chart E
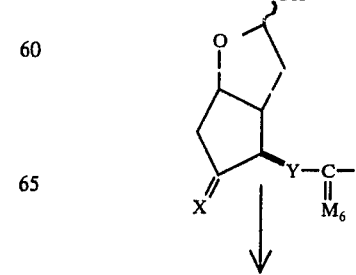
XLVI 4,099,014
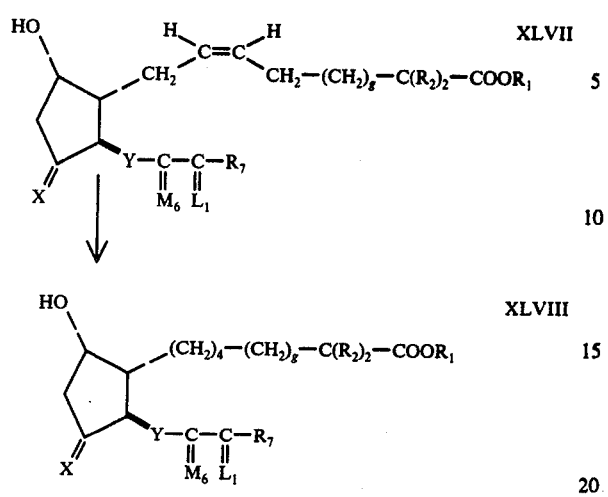
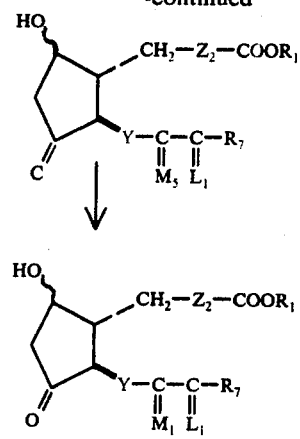
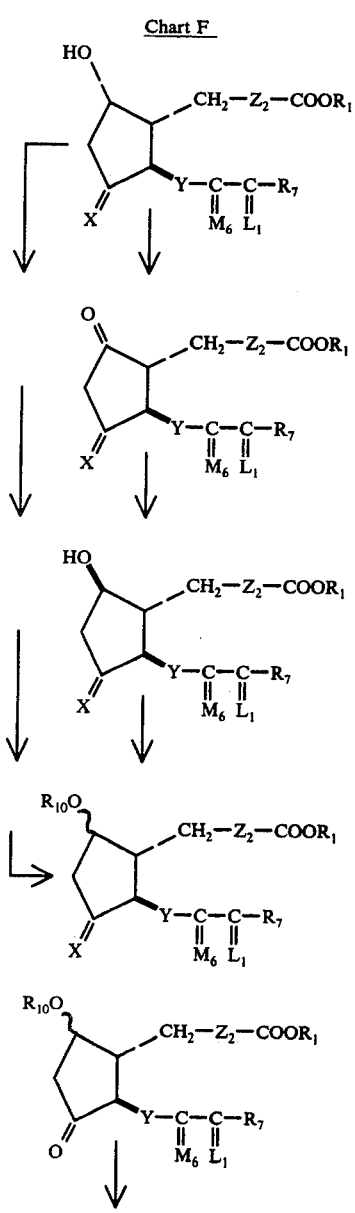
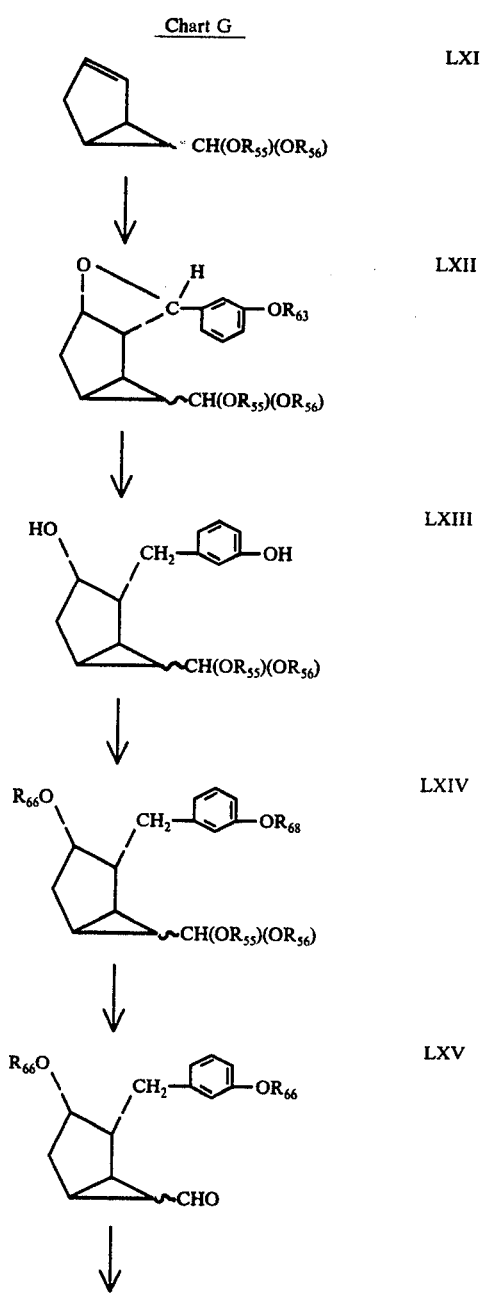

Chart G
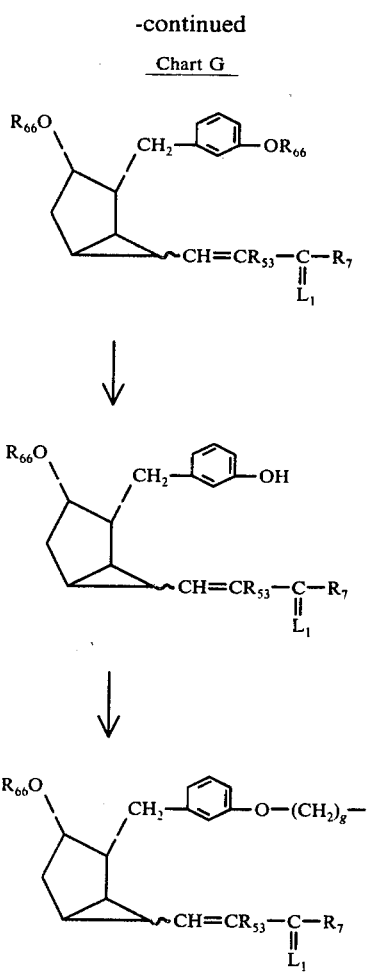
Chart G (continued)
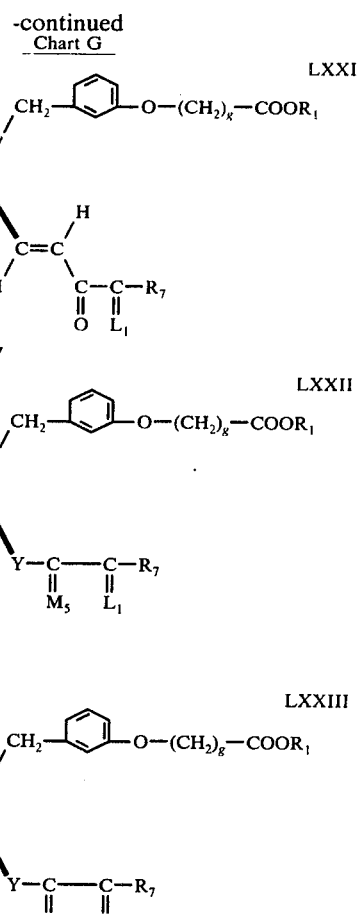
Chart H
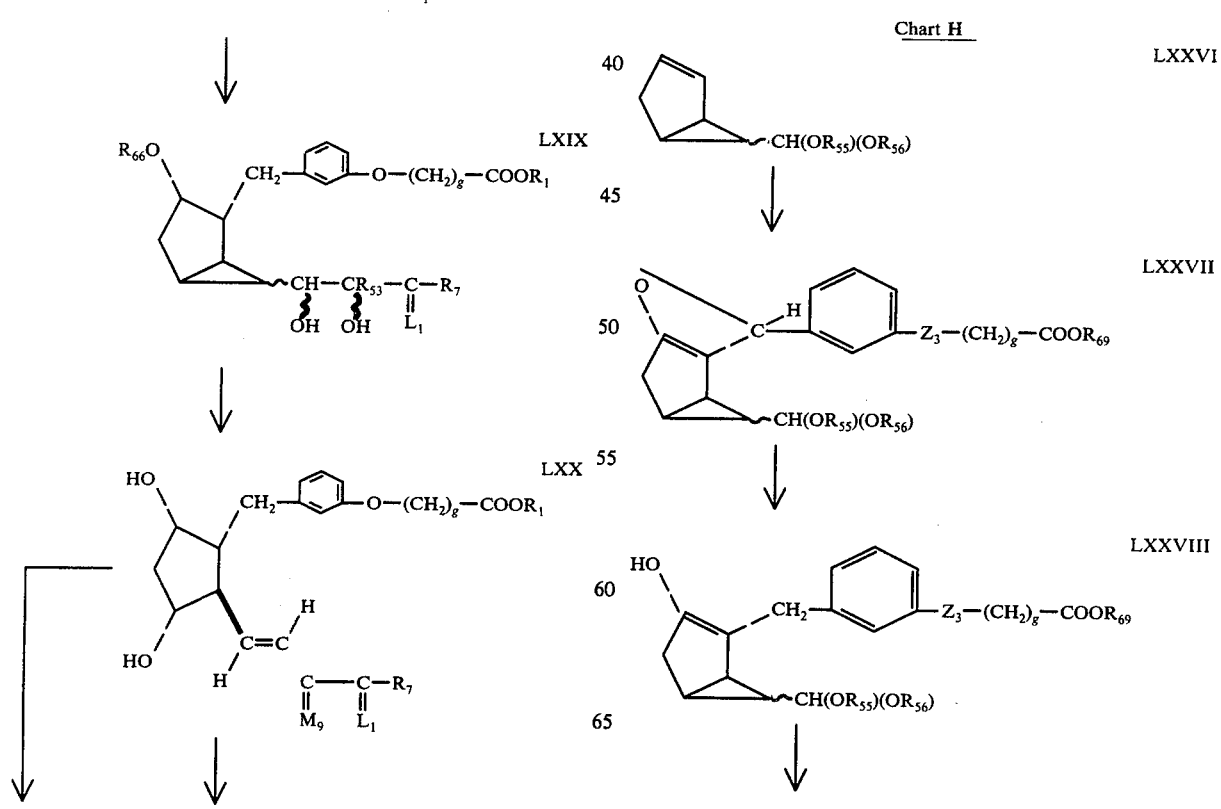

4,099,014
41
-continued
Chart H
LXXIX
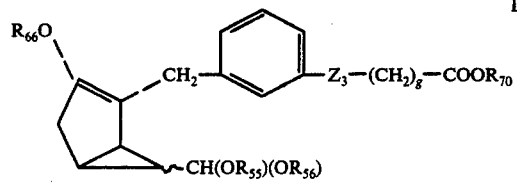
↓
LXXX
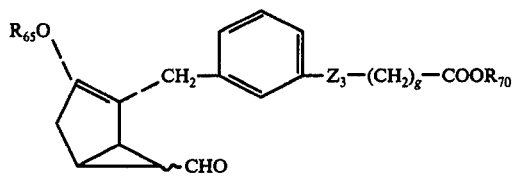
↓
LXXXI
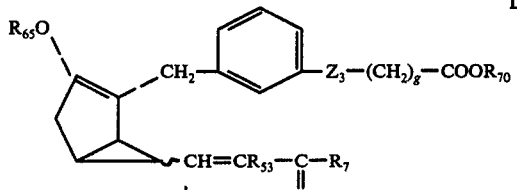
↓
LXXXII
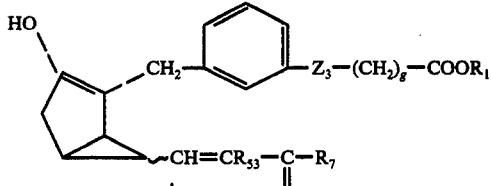
↓
LXXXIII
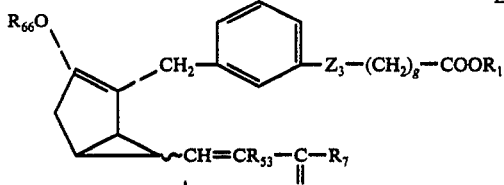
↓
LXXXIV
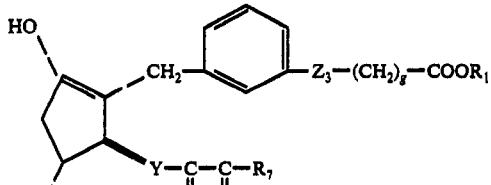
Chart I
42
-continued
LXXXVI
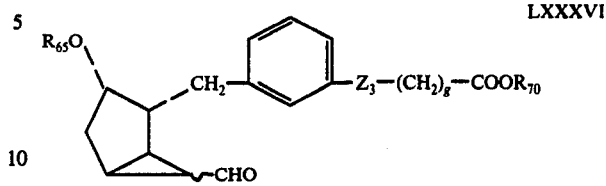
↓
LXXXVII
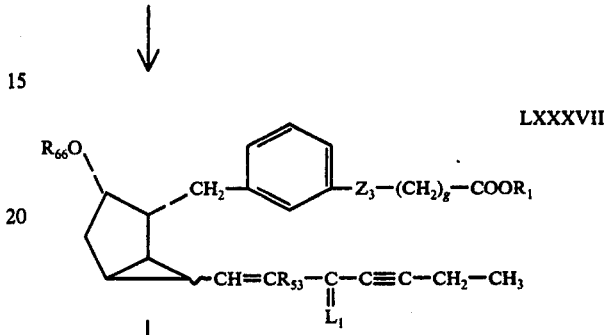
↓
LXXXVIII
↓
LXXXIX
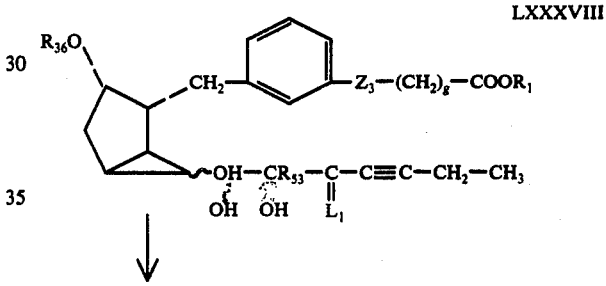
↓
XC
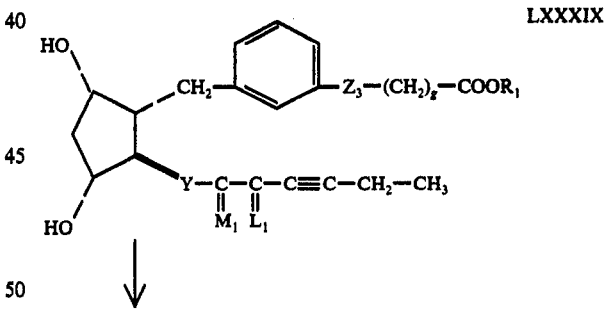
Chart J -continued
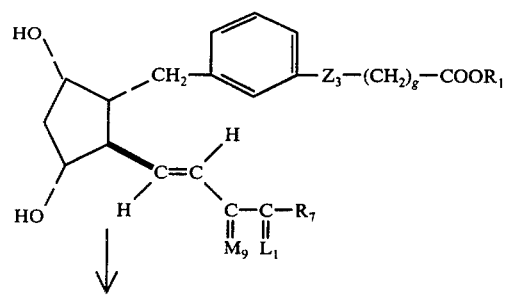
XCI
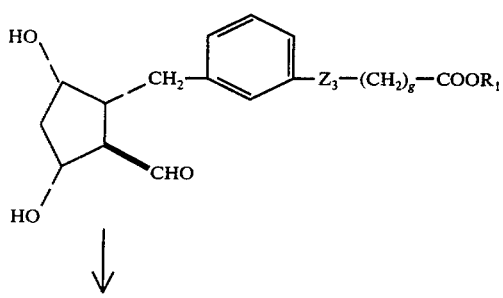
XCII
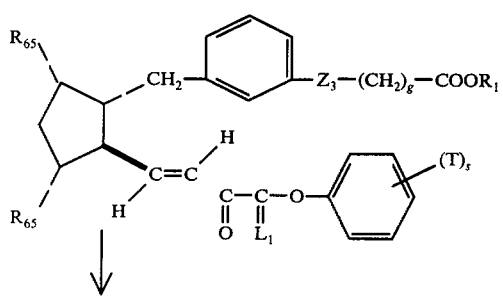
XCIII
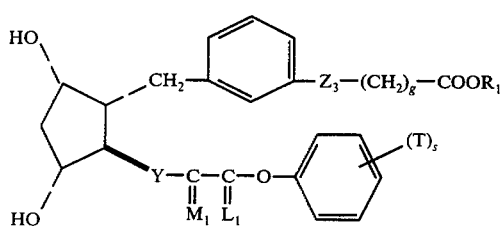
XCIV
Chart K
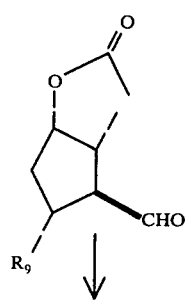
-continued
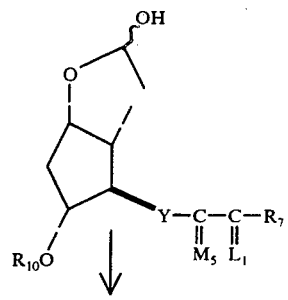
XCVI
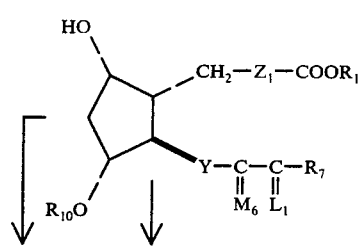
XCVII
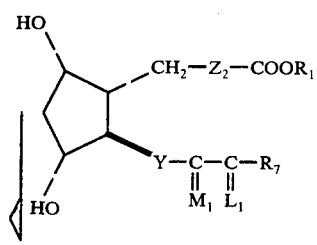
XCVIII
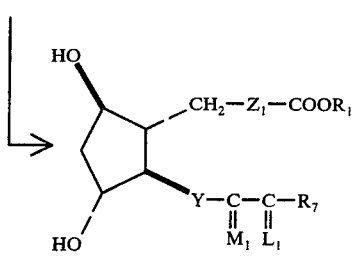
XCIX
Chart L
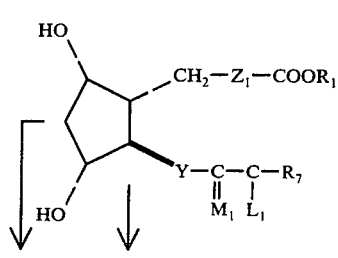
CI
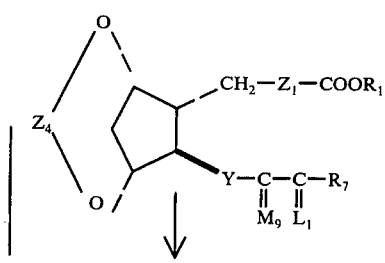
CII

4,099,014

Chart M

Chart N

Chart O

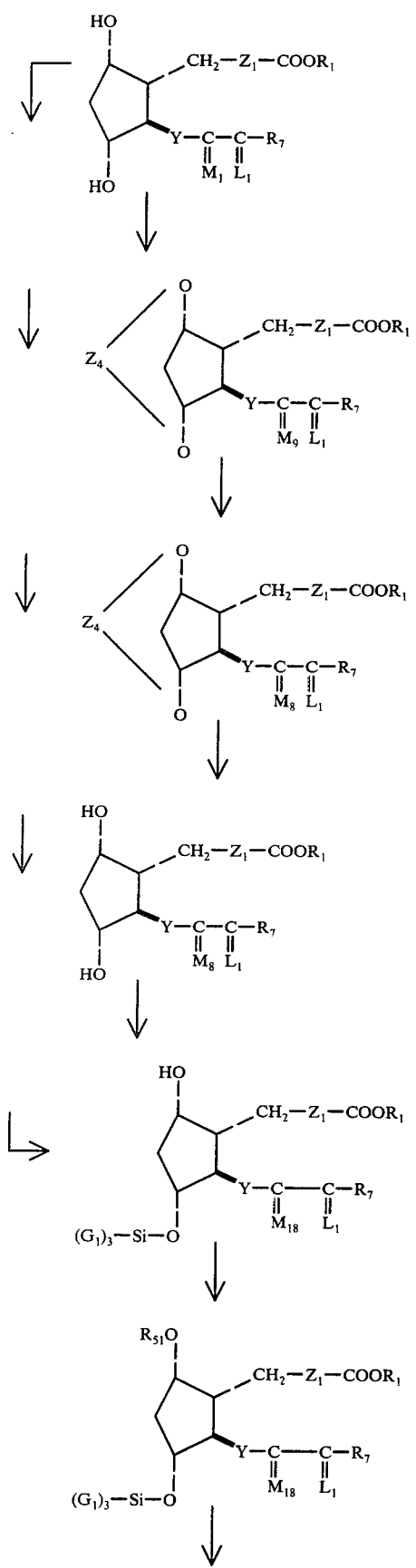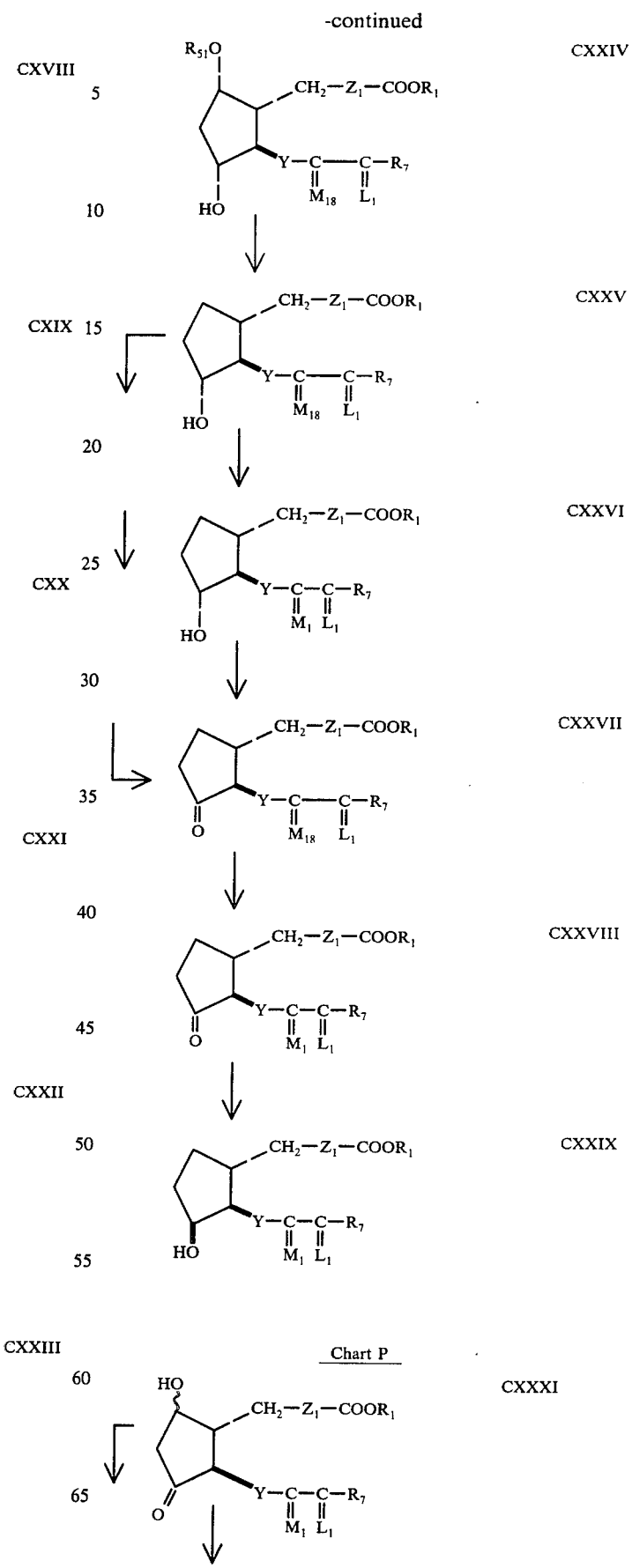

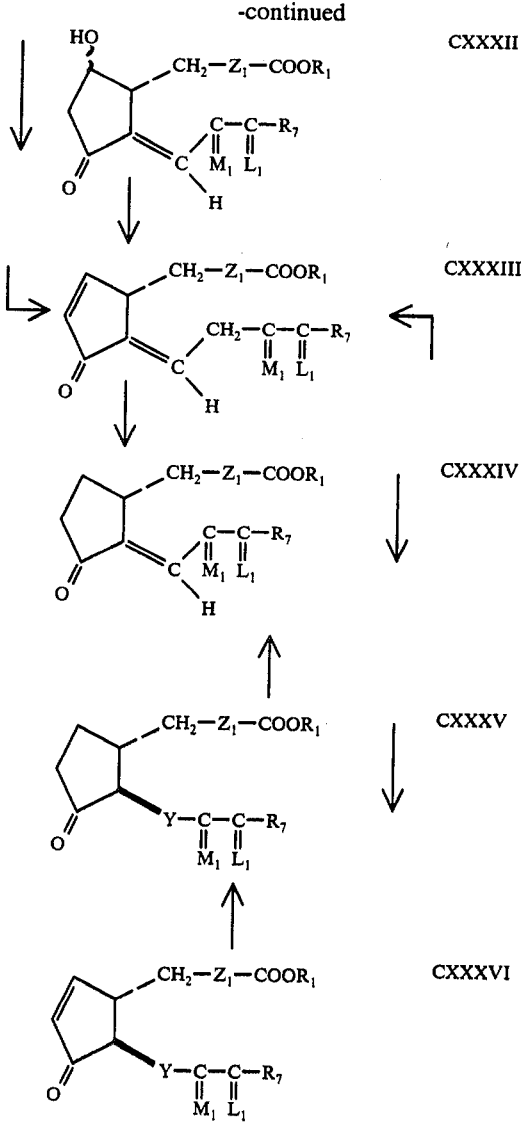
Chart Q
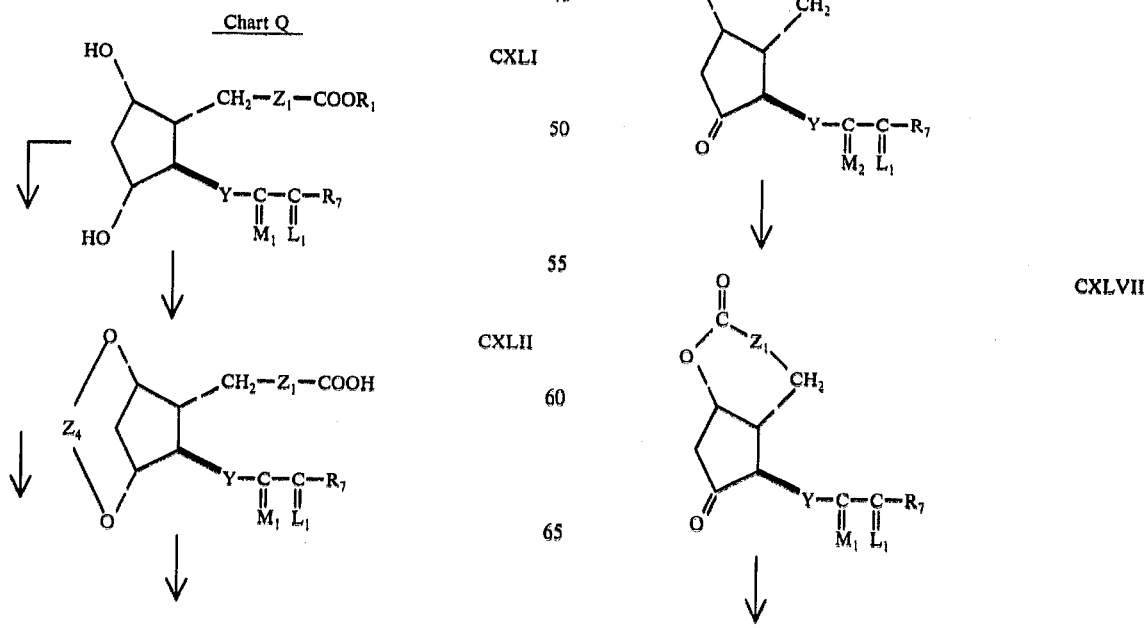

-continued
Chart Q

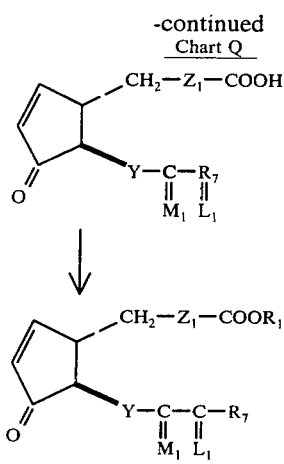

CXLVIII

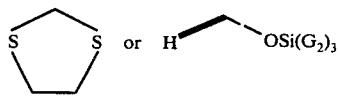 or wherein one of the $G_2$ moieties is tertiary alkyl of 4 to 6 carbon atoms, inclusive and the remaining two are straight chained alkyl of one to 3 carbon atoms, inclusive. Preferably —$Si(G_2)_3$ is t-butyldimethylsilyl.

Y and $Z_1$ are as defined above. $Z_2$ is cis—CH=CH—$CH_2$—$(CH_2)_g$—$C(R_2)_2$—, cis—$CH_2$—CH=CH—$(CH_2)_g$—$CH_2$, —$(CH_2)_3$—$(CH_2)_g$—$C(R_2)_2$—, $CH_2$—O—$CH_2$—$(CH_2)_g$—$CH_2$—, or —$(CH_2)_3$—O—$(CH_2)_g$—, wherein $R_2$ and g are as defined above. $Z_3$ is oxa or methylene, e.g., —O— or —$CH_2$—, respectively. $Z_4$ is $CH_3$—$(CH_2)_h$—B< wherein $h$ is 2 to 4, inclusive, preferably 3. $L_1$, $M_1$, and $M_9$ are as defined above. $M_2$ is

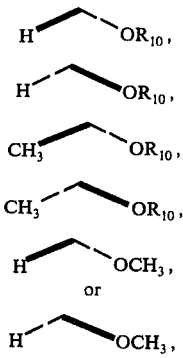

CXLIX

wherein $R_{57}$, $R_{58}$, $R_{59}$, $R_{60}$, $R_{61}$, and $R_{62}$ are hydrogen, alkyl of one to 4 carbon atoms, inclusive, or phenyl, being the same or different, with the proviso that not more than one of $R_{57}$, $R_{58}$, $R_{59}$, $R_{60}$, $R_{61}$, and $R_{62}$ is phenyl and that the total number of carbon atoms in $R_{57}$, $R_{58}$, $R_{59}$, $R_{60}$, $R_{61}$, and $R_{62}$ is from 2 to 10, inclusive, and $h$ is 0 or 1.

$R_{63}$ is carboxyacyl of the formula $$R_{64}\overset{O}{\underset{\|}{C}}-,$$

wherein $R_{64}$ is hydrogen, alkyl of one to 19 carbon atoms, inclusive, or aralkyl of 7 to 12 carbon atoms, inclusive, wherein the above alkyl or aralkyl are substituted with 0 to 3 fluoro, chloro, bromo, or iodo. $R_{66}$ is hydrogen or a blocking group, according to $R_{65}$. Blocking groups according to $R_{65}$ useful for the purposes of this invention include all blocking groups according to $R_{10}$, as enumerated herein, and additionally —$Si(G_1)_3$, wherein $G_1$ is alkyl of one to 4 carbon atoms, inclusive, cycloalkyl of 3 to 10 carbon atoms, inclusive, aralkyl of 7 to 12 carbon atoms, inclusive, phenyl, or phenyl substituted with 1 or 2 fluoro, chloro, or alkyl of one to 4 carbon atoms, inclusive. In the use of these silyl blocking groups, according to $R_{65}$, methods known in the art for the preparation of the necessary reagents and appropriate reaction conditions for replacing hydroxy hydrogens with these silyl blocking groups and subsequently hydrolyzing these silyl blocking groups, are employed. $R_{68}$ is hydrogen, carboxyacyl according to $R_{63}$, or an acyl protecting group according to $R_9$. $R_{69}$ is hydrogen or alkyl of one to 4 carbon atoms, inclusive. $R_{70}$ is hydrogen, alkyl of one to 4 carbon atoms, inclusive, or silyl of the formula -$Si(G_1)_3$, wherein $G_1$ is as defined above.

=X is thioketal of the formula wherein $R_{10}$ is as defined above.

$M_5$ is

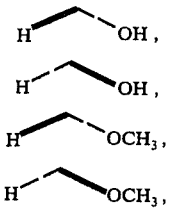

or a mixture of

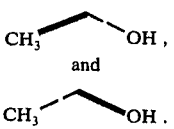

$M_6$ is

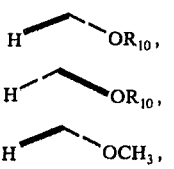

-continued

or a mixture of

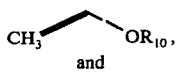
and
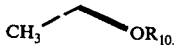

$M_7$ is

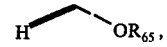

or

wherein $R_{65}$ is as defined above.
$M_8$ is

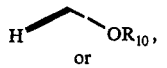
or

wherein $R_{10}$ is as defined above.
$M_{18}$ is

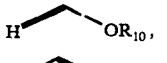

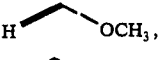

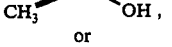

or

wherein $R_{10}$ is as defined above.

Acyl protecting groups, according to $R_9$, include:
(a) benzoyl;
(b) benzoyl substituted with 1, 2, 3, 4, or 5 alkyl of one to 4 carbon atoms, inclusive, phenyl alkyl of 7 to 10 carbon atoms, inclusive, or nitro, with the proviso that not more than 2 substituents are other than alkyl, and that the total number of carbon atoms in the substituents does not exceed 10 carbon atoms, with the further proviso that the substituents may be the same or different;
(c) benzoyl substituted with alkoxy carbonyl wherein the alkoxy carbonyl moiety is of 2 to 5 carbon atoms, inclusive;
(d) naphthoyl;
(e) naphthoyl substituted with one to 9, inclusive, alkyl of one to 4 carbon atoms, inclusive, phenyl alkyl of 7 to 10 carbon atoms, inclusive, or nitro, with the proviso that not more than 2 substituents on either of the naphthyl rings other than alkyl, and the total number of carbon atoms in the substituents does not exceed 10 carbon atoms, with the further proviso that the various substituents are the same or different; or
(f) alkanoyl of 2 to 12 carbon atoms, inclusive.

In preparing these acyl derivatives of the hydroxy-containing compounds herein methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. a tertiary amine such as pyridine, triethylamine, or the like. The reaction is carried out under a variety of conditions, using procedures generally known in the art. Generally mild conditions are employed: 20°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_2OH$), anhydrides $(R_9)_2O$, or acyl chlorides ($R_9Cl$): benzoyl; substituted benzoyl, e.g., (2-, 3-, or 4-)-methylbenzoyl, (2-, 3-, or 4-)-ethylbenzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,5-trimethylbenzoyl, pentamethylbenzoyl, alpha-phenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching site.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor is reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include:

(a) tetrahydropyranyl;
(b) tetrahydrofuranyl; and
(c) a group of the formula $$-C(OR_{11})(R_{12})-CH(R_{13})(R_{14}),$$

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with 1 to 3 alkyl of 1 to 4 carbon atoms, inclusive, wherein $R_{12}$ and $R_{13}$ are alkyl of 1 to 4 carbon atoms, inclusive, phenyl, phenyl substituted with one, 2, or 3 alkyl of 1 to 4 carbon atoms, inclusive, or when $R_{12}$ and $R_{13}$ are taken together $-(CH_2)_a-$ or $-(CH_2)_b-O-(CH_2)_c-$, wherein $a$ is 3, 4, or 5, or $b$ is 1, 2, or 3, and $c$ is 1, 2, or 3, with the proviso that $b$ plus $c$ is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula $$-C(OR_{11})(R_{12})-CH(R_{13})(R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(OR_{11})(R_{12})=C(R_{13})(R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

The charts herein describe the methods whereby the novel compounds disclosed in this specification are prepared. For the starting material of each of the Charts, as well as resultant products, such compounds are available in either enantiomerically pure form or as mixtures of enantiomers; or may be prepared as such by methods available in the art.

With respect to Chart A a method is provided whereby a bicyclic lactol intermediate useful in the preparation of the PGD-type compounds disclosed herein is prepared.

The formula XI starting material is known in the art or readily prepared by methods known in the art. See, for example, Journal of the American Chemical Society, 93, 1490 (1971).

The formula XI compound is thereafter transformed to the corresponding formula XII or formula XIV compound. The formula XII compound is prepared from the formula XI compound by oxidation, using, for example, the Collins reagent or the Jones reagent. Conventional reaction conditions, known to the art, are employed. The formula XIV compound is prepared from the formula XI compound by silylation employing methods known in the art, e.g., tert-butyldimethylsilyl chloride. See, for reference Pierce, Silylation of Organic Compounds, Pierce Chemical Co., Rockford, Ill. (1968).

The formula XII compound is then transformed to the formula XIII compound by thioketalization of the formula XII ketone. For this purpose a reagent such as 1,2-ethanedithiol is employed in the presence of a Lewis acid, such as boron trifluoride etherate. The reaction is conveniently run at room temperature, and ordinarily proceeds to completion within several hours. The formula XV primary alcohol is then prepared from either the formula XIV or formula XIII compound. Preparation proceeds by cleavage of the phenyl ether, employing methods known in the art. For example, as is known in the art, boron tribromide is conveniently employed for this purpose. The reaction advantageously proceeds in a diluent such as methylene chloride or n-pentane at temperatures at or below 0° C. In the transformation of the formula XIV to formula XV compound the method of Corey, et al., Journal of the American Chemical Society 94, 6190 (1972), is employed. The formula XV alcohol is then transformed to the corresponding formula XVI aldehyde by oxidation. For this oxidation the Collins reagent is advantageously employed, as is known in the art.

The formula XVII compound is prepared from the formula XVI compound by a Wittig alkylation. Reagents known in the art or prepared by methods known in the art are employed. The transenone lactone is obtained stereospecifically. See for reference D. H. Wadsworth, et al., Journal of Organic Chemistry 30, 680 (1965).

In the preparation of the formula XVII compound, certain phosphonates are employed in the Wittig reaction. These phosphonates are of the general formula

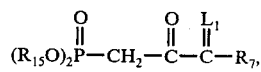

wherein L₁ and R₇ are as defined above (but not cis-CH=CH-CH₂CH₃) and R₁₅ is alkyl of 1 to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methyl phosphonate as produced using n-butyllithium. For this purpose, acids of the general formula

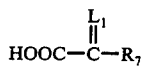

are employed in the form of their lower alkyl esters, preferably methyl or ethyl. The methyl esters for example are readily obtained by reaction of the corresponding acids with diazomethane.

For example, when R₇ is

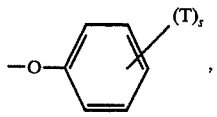

wherein T and s are as defined above, and R₃ and R₄ of the L₁ moiety are both hydrogen, the corresponding phenoxy or substituted phenoxy acetic acids are known in the art or readily available in the art. Those known in the art include those wherein the R₇ moiety is: phenoxy-, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of R₃ and R₄ of the L₁ moiety is methyl and R₇ is phenoxy or substituted phenoxy. These 2-phenoxy or 2-substituted phenoxy propionic acids include those wherein the R₇ moiety is p-fluorophenoxy- (o-, m-, or p-)chlorophenoxy-, (2,3-, 2,4-, 2,5-, 2,6-, 3,4-, or 3,5-)dichlorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted phenoxy)propionic acids, which are useful in the preparation of the above acids wherein R₃ and R₄ of the L₁ moiety are both methyl and R₇ is phenoxy or substituted phenoxy. These 2-methyl-2-phenoxy-, or (2-substituted)phenoxypropionic acids include those wherein R₇ is: phenoxy-, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the (T)ₛ-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein R₇ is benzyl or substituted benzyl.

For example, when R₃ and R₄ of the L₁ moiety are both hydrogen there are available the following phenyl or substituted phenyl propionic acids: (o-, m-, or p-)-chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of R₃ and R₄ of the L₁ moiety is methyl there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both R₃ and R₄ are methyl there are available, for example, the following 2,2-dimethyl-3-phenyl or substituted phenyl propionic acids: phenyl- and p-methylphenyl.

When one and only one of R₃ and R₄ is fluoro, there is available, for example, 2-fluoro-3-phenyl propionic acid.

Phenyl substituted acids (as above wherein R₇ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted benzyl chloride. Thus, the above acid is obtained by the following reaction:

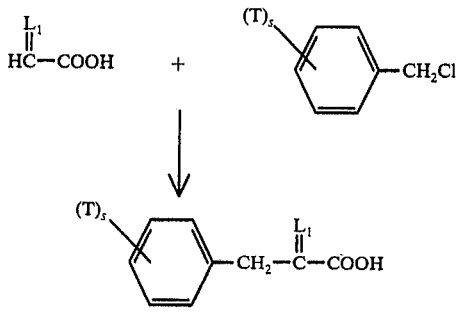

The above reaction proceeds smoothly, ordinarily at 0° C. The product acid is recovered using conventional methods.

For the acids of the above formula wherein R₇ is n-alkyl, many such acids are readily available.

For example, when R₃ and R₄ of the L₁ moiety are both hydrogen there are available butyric, pentanoic, hexanoic, heptanoic, and octanoic acids.

For example, when one and only one of R₃ and R₄ of the L₁ moiety is methyl, there are available the following 2-methyl alkanoic acids: butyric, pentanoic, hexanoic, heptanoic, and octanoic.

For example, when one of R₃ and R₄ of the L₁ moiety is fluoro there are available the following 2-fluoro alkanoic acids: butyric, pentanoic, hexanoic, heptanoic, and octanoic.

The acids of the above general formula wherein R₇ is alkyl and R₃ and R₄ of the L₁ moiety are fluoro are conveniently prepared from the corresponding 2-oxoalkanoic acids, i.e. butyric, pentanoic, hexanoic, heptanoic, and octanoic. The transformation of these 2-oxoalkanoic acids to the corresponding 2,2-difluoroalkanoic acids proceeds by methods known in the art, using known ketonic fluorinating reagents. For example, $M_0F_8 \cdot BF_3$ is advantageously employed in the fluorination.

When $R_7$ is 1-butenyl, the formula XVII compound is prepared from the formula XVI compound by transformation of the formula XVI 2$\beta$-carboxaldehyde to a corresponding 2$\beta$-(2-formyl-trans-1-ethenyl) compound followed by a Grignard reaction employing a reagent prepared from

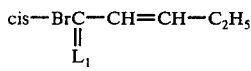

Thereupon the (3RS)-3-hydroxy compound corresponding to formula XVII is prepared, which is optionally oxidized to the formula XVII compound with the Collins reagent, as transformed to a formula XVIII compound wherein Y is trans-CH=CH- and $R_5$ and $R_6$ are hydrogen.

The formula XVIII compound wherein Y is cis-CH=CH— is prepared from the formula XXII compound by photoisomerization, followed by separating the resulting trans-cis mixture of isomers. The photoisomerization proceeds by use of a conventional photon generating source which is capable of producing photons whose wave length is between about 2800 to 4000 Angstroms. It is preferred to use a conventional photon generating source which is capable of producing photons whose wave length is about 3500 Angstroms. Irradiation continues until an equilibrium mixture of cis and trans isomers is obtained. The progress of the photoisomerization is conveniently monitored by conventional methods, e.g. silica gel thin layer chromatography (TLC). The resulting equilibrium mixture is then separated using conventional methods. For example, silica gel chromatography is advantageously employed.

The formula XVIII wherein Y is —$CH_2CH_2$— is advantageously prepared by catalytic hydrogenation using conventional metal catalysts on suitable support. However, when X is thioketal, it is necessary to employ extremely large amounts of catalyst or preferably employ $NaBH_4$ in methanol at ambient temperature.

The formula XIX compound is prepared from the formula XVIII 3-oxo bicyclic lactone by transformation of the 3-oxo-moiety to an $M_5$ moiety.

The above 3-oxo bicyclic lactone (formula XVIII) is transformed to the corresponding 3$\alpha$- or 3$\beta$-hydroxy bicyclic lactone, wherein $M_9$ is

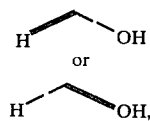

by reduction of the 3-oxo moiety, followed by separation of the 3$\alpha$- and 3$\beta$-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium(tri-tert-butoxy)aluminum hydride, metal trialkyl borohydrides, e.g. sodium trimethoxy borohydride, lithium borohydride, and the like. In those cases in which carbon-carbon double bond reduction need not be avoided, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

For the transformation of the 3-oxo bicyclic lactone to the corresponding 3-methoxy bicyclic lactone the 3-hydroxy moiety of the 3-hydroxy bicyclic lactone prepared above is alkylated, employing methods known in the art.

The alkylation described in the above paragraph proceeds, for example, by reaction of the 3-hydroxy bicyclic lactone with diazomethane, preferably in the presence of a Lewis acid (e.g., boron trifluoride etherate, aluminum chloride, or fluoboric acid). See for reference Fieser, et al., "Reagents for Organic Synthesis," John Wiley and Sons, New York, N. Y., (1967), especially page 191. The reaction is carried out by mixing a solution of the diazomethane in a suitable inert diluent, preferably diethyl ether, with the 3-hydroxy bicyclic lactone prepared above. This reaction proceeds at about 25° C.

An alternate method for the alkylation of the 3-hydroxy compound is by reaction with methanol in the presence of boron trifluoride etherate. Thus, the methanol and boron trifluoride etherate are reacted with the 3-hydroxy compound at 25° C., the reaction being monitored conveniently by thin layer chromatography (TLC).

The 3-oxo bicyclic lactone is transformed into the corresponding (3RS)-3-methyl bicyclic lactone wherein $M_5$ is a mixture of

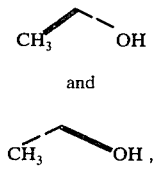

by reaction of the 3-oxo bicyclic lactone with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a (3RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters. Accordingly, the corresponding PG-type, methyl ester is subjected to silica gel chromatography or high pressure liquid chromatography (HPLC), and thereby the C-15 epimers are separated.

The formula XX compound is then prepared from the formula XIX compound by replacing any free hydroxy moieties with blocking groups according to $R_{10}$ by the procedure described above. The formula XXI compound is then prepared from the formula XX compound by reduction of the formula XX lactone to its corresponding lactol. Methods known in the art are employed. For example, diisobutylaluminum hydride is employed at −60° to −70° C.

Chart B provides a method whereby the formula XXVI lactol, prepared according to Chart A, is transformed into a corresponding formula XXX 3-oxa-PG-type intermediate.

The formula XXVII compound is obtained from the formula-XXVI lactol by the Wittig reaction, with a (carbalkoxy-methylene)triphenylphosphorane $R_{22}OO-C-CH=P(C_6H_5)_3$ wherein $R_{22}$ is as defined above. The reaction is conveniently carried out at 25° C., using methods and reactants known in the art.

The formula XXVIII compound is then obtained by reduction of the ethylenic group in the carboxyl containing side chain. For this purpose a reducing agent is used which does not reduce the Y or $R_7$, when such reduction is not desired, for example hydrogen in the presence of a catalyst such as palladium on carbon or rhodium on alumina. Mild conditions are sufficient, and mixtures of products conveniently separated by chromatography.

The formula XXIX alcohol is obtained from the formula XXVIII compound by reduction, for example, with lithium aluminum hydride or lithium trimethoxy aluminum hydride. A solvent such as diethyl ether or tetrahydrofuran is conveniently used.

The formula XXX compound is obtained by a Williamson synthesis, condensing the formula XXIX alcohol with a haloalkanoate, $Hal(CH_2)_gCOOR_1$ wherein Hal is chloro, bromo, or iodo and $R_1$ is as above defined, in the presence of a base. For the base, there is used, for example, n-butyllithium, phenyllithium, triphenylmethyllithium, sodium hydride, or potassium t-butoxide. It is preferred that only one molecular equivalent of the base be used. The alkanoate is employed in about 100% stoichiometric excess. Instead of a haloalkanoic acid ester, a salt, for example lithium chloroacetate, is useful. After the condensation, the salt is transformed to the XXX compound by methods known in the art. The condensation is conveniently run in a solvent such as dimethyl formamide, tetrahydrofuran, dimethyl sulfoxide, or hexamethylphosphoramide.

With respect to Chart C a method is provided whereby the formula XXXI lactol is transformed into the corresponding formula XXXIII 5-oxa-Pg-type intermediate. The formula XXXII alcohol is obtained by a ring opening of the lactol, to its hydroxy aldehyde form, followed by reduction of the aldehyde so obtained for example, with aqueous methanolic or ethanolic sodium borohydride to the formula XXXII primary alcohol. Alternatively and preferably, the formula XXXII compound is obtained by a one step reduction of the formula XXXI lactone, for example, with lithium aluminum hydride or diisobutyl aluminum hydride at a temperature ranging from 0° to 35° C. For preparing the formula XXXIII compound a Williamson synthesis is employed. For example, the formula XXXII compound is condensed with a haloalkanoic acid or appropriate halo ester within the scope of

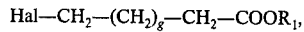

wherein Hal is chloro, bromo, or iodo and $g$ is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethylsulfoxide or, especially if an organolithium compound is employed, preferably in dimethylformamide or hexamethylphosphoramide. The reaction proceeds smoothly at −20° to 50° C., but is preferably performed at ambient temperature.

Chart D provides a method whereby the formula XXXVI compound is transformed into the corresponding formula XLIII 4-oxa-PG-type intermediate or formula XLIV cis-4,5-didehydro-PG-type intermediate.

The formula XXXVI compound undergoes condensation to form the formula XXXVII enol. For this purpose a hydrocarbyloxy-, preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below −10° C. The formula XXXVI lactol is mixed with the above reagent and the condensation proceeds smoothly within the temperature range of −30° C. to +30° C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxy-methylenetriphenylphosphorane. Various hydrocarbyloxymethylenetriphenylphosphoranes which are optionally substituted for the alkoxymethylenetriphenylphosphoranes and are accordingly useful for preparing the formula XXXVII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl-butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and phenoxymethylenetriphenylphosphorane. See for reference, Organic Reactions, Vol. 14, pg. 346–348, John Wiley and Sons, New York, New York, (1965). The formula XXXVII enol intermediates are then hydrolyzed to the formula XXXVIII lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature, for example using acetic acid-water-tetrahydrofuran at about 60° C. for several hr. is sufficient to accomplish the hydrolysis.

The formula XXXIX compound is then prepared from the formula XXXVIII compound by oxidation of the formula XXXVIII lactol to a lactone. This transformation is carried out, using for example, silver oxide as an oxidizing reagent, followed by treatment with pyridine hydrochloride.

The formula XXXIX lactone may then be converted to the formula XL ether by transformation of any free hydroxy moieties to blocking groups, according to $R_{10}$, following the procedures hereinabove described for these transformations.

Thereafter the formula XLI compound is prepared from the formula XL compound by reduction of the formula XL lactone to a lactol. For example, diisobutylaluminum hydride is employed as is described above for the reduction of lactones to lactols. The formula XLI lactol so prepared is then used alternatively for the preparation of the formula XLIII or XLIV compound.

In the preparation of the formula XLIII compound, the formula XLI lactol is first transformed into the formula XLII compound by reducing the lactol ring of the formula XLI lactol. The formula XLII compound is then transformed into the corresponding formula XLIII compound by a Williamson synthesis. Methods and corresponding reagents employed in the transformation of the formula XLI compound to the formula XLII and thereafter the transformation of the formula XLII compound to the formula XLIII compound are analogous to methods described hereinabove for the transformation of the formula XXXI compound to the formula XXXII compound and thereafter the transformation of the formula XXXII compound to the formula XXXIII compound.

Accordingly, the formula XLIII 4-oxa-PG-type intermediate is prepared.

The formula XLIV compound is prepared from the formula XLI compound by a Wittig alkylation, using the appropriate ($\omega$-carboxyalkyl)triphenylphosphonium bromide, $HOOC-CH_2-(CH_2)_g-CH_2-P(C_6H_5)_3Br$, wherein $g$ is as defined above. The reaction proceeds as is generally known in the art, by first mixing the appropriate ($\omega$-carboxyalkyl)triphenylphosphonium bromide with sodio dimethyl sulfinylcarbanide, at ambient temperature, and adding the formula XLI lactol to this mixture. Thereafter the carboxy hydrogen of the compound so formed is transformed to an $R_1$ moiety by the methods and procedures hereinbelow described. Accordingly, there is prepared the formula XLIV cis-4,5-didehydro-PG-type intermediate.

Chart E provides a method whereby the formula XLVI compound is transformed to the corresponding formula XLVII PG-type intermediate or formula XLVIII PG-type intermediate.

The formula XLVII compound is prepared from the formula XLVI compound using the appropriate ($\omega$-carboxyalkyl)triphenylphosphonium bromide, $HOOC-C(R_2)_2-(CH_2)_g-CH_2-P-(C_6H_5)_3Br$, as is described above followed by transformation of the carboxy hydrogen to an $R_1$ moiety as described below. The formula XLVIII compound is then prepared from the formula XLVII compound by catalytic hydrogenation of the cis-5,6-double bond. Hydrogenation methods known in the art are employed, but very large amounts of catalyst are required when X is thioketal. Mixtures of compounds thereby produced are conveniently separated by silica gel chromatography.

With respect to Chart F a method is provided whereby the formula LI PG-type intermediate is transformed to the corresponding novel formula LVII PGD- or 9$\beta$-PGD-type compound disclosed in the specification.

The formula LI compound is transformed to the corresponding formula LII compound by oxidation. Suitable reagents for this purpose include the Jones reagent or the Collins reagent, employed as is known to the art. Thereafter the formula LIII compound is prepared from the formula LII compound by a ring carbonyl reduction. Methods employed for ring carbonyl reduction of known prostaglandin derivatives are useful for this purpose. This reduction is followed by a chromatographic separation of the 9$\alpha$- and 9$\beta$-hydroxy epimers produced in the reduction step.

Prostaglandin cyclopentane ring carbonyl reductions are carried out using those methods known in the art for ring carbonyl reductions of known prostaglandin acid derivatives, as discussed above. See for reference Bergstrom, et al., Arkiv. Kemi 19, 563 (1963); Octa. Chem. Scand. 16, 969 (1962); and British Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium, and zinc borohydrides, the metal trialkoxy borohydrides, e.g. sodium trimethoxyborohydride. As indicated above, the above mixtures of alpha and beta hydroxy isomers at C-9 are separated into individual alpha or beta isomers by methods known in the art for separation of analogous pairs of known isomeric prostaglandin acid derivatives. See, for example Bergstrom, et al., cited in the preceding paragraph or Granstrom, et al., Journal of Biological Chemistry 240, 456 (1965) and Green, et al., Journal of Lipid Research 5, 117 (1964). Alternatively, useful separation methods are partition chromatographic procedures (both normal and reversed phase), preparative thin layer chromatography, and counter current distribution procedures.

The formula LIV compound is then prepared from the formula LIII compound or the formula LI compound by replacing the 9-hydroxy hydrogen of either the formula LIII or formula LI compound with a blocking group according to $R_{10}$. Methods employed are those described hereinabove for the replacement hydroxy hydrogens with blocking groups.

The formula LIV compound wherein X is $-Si(G_2)_3$ is transformed to the corresponding formula LV compound by selective hydrolysis of the tert-butyl-dimethylsilyl group over any blocking groups according to $R_{10}$. This selective removal of the silyl group is accomplished by methods known in the art. See for reference Corey, et al., Journal of the American Chemical Society 94, 6190 (1972). An especially useful reagent for this purpose is tetra-n-butyl-ammonium fluoride in tetrahydrofuran. Thereafter, the 11-hydroxy compounds so obtained is oxidized at a C-11 position to form a corresponding 11-oxo compound. Procedures known in the art are employed. For example, see Tetrahedron Letters, 2235 (1974). Useful reagents for this purpose include those oxidizing agents discussed herein as being useful for oxidizing hydroxy moieties attached to the cyclopentane ring of prostaglandin-type products or intermediates (e.g., the Jones reagent).

Additionally the formula LV compound is prepared from the formula LIV compound wherein X represents a thioketal moiety by dethioketalization. Any one of several dethioketalization procedures known in the art are useful in this transformation. For example, see reference cited in "Annual Reports in Organic Synthesis 1972", J. McMurry and R. B. Miller, Editors, Academic Press, New York, N. Y., 1973, pages 112–114. Accordingly, a highly useful procedure for this purpose comprises reacting the formula LIV compound with a mixture of cupric chloride and cupric oxide. The dethioketalization proceeds to completion within several hours, being conveniently monitored by thin layer chromatography, with the reaction being run, for convenience, at ambient temperatures.

The formula LVI compound is then prepared from the formula LV compound by removal of any blocking groups according to $R_{10}$. Reaction conditions and reagents discussed hereinabove for removal of blocking groups according to $R_{10}$ are herein employed.

In the preceding steps of Chart F, and in the steps of the preceding Charts it is preferred that X be silyl rather than thioketal. Further, when X is thioketal the introduction of blocking groups according to $R_{10}$ (LI or LII to LIV) is optionally omitted. Accordingly, removal of such blocking groups, i.e., LV to LVI, is likewise omitted.

The formula LVII compound is then prepared from the formula LVI compound by separation of any C-15 epimeric mixtures present in the formula LVI compound when $R_5$ is methyl. For this separation it is preferred that $R_1$ be methyl and that conventional silica gel chromatography or high pressure liquid chromatography be employed.

Charts G, H, I, and J provide methods whereby 3-oxa-3,7-inter-m-phenylene-4,5,6-trinor- or 3,7-inter-m-phenylene-4,5,6-trinor-PG-type intermediates are prepared. With respect to Charts G and H, $R_7$ is preferred to be —$(CH_2)_m$—$CH_3$, or

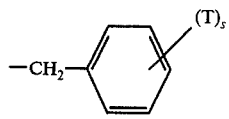

wherein m, T, and s are as defined above. In Charts I or J a method is provided for preparing those novel compounds of this specification wherein $R_7$ is preferably cis-CH CH—$CH_2$—$CH_3$, or

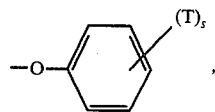

wherein T and s are as defined above respectively. Accordingly the Charts G-J provide methods whereby intermediates useful in producing all inter-m-phenylene PG-type compounds are prepared.

In Chart G both the endo and exo forms of bicyclo hexene LXI are available or are made by methods known in the art, in either their racemic or enantiomerically pure forms. See U.S. Pat. No. 3,711,515. Either the endo or exo starting material will yield the ultimate intermediates of formula LXXIII by the process of Chart G.

Oxetane LXII is obtained by reaction of the formula LXI bicyclo hexene with an aldehyde of the formula

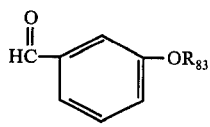

wherein $R_{63}$ is carboxyacyl of the formula

wherein $R_{64}$ is hydrogen, alkyl of one to 19 carbon atoms, inclusive, or aralkyl of 7 to 12 carbon atoms, inclusive, wherein alkyl or aralkyl are substituted with zero to 3 halo atoms.

The above benzyl aldehydes are available or readily prepared by methods known in the art. Examples of such compounds within this scope are:

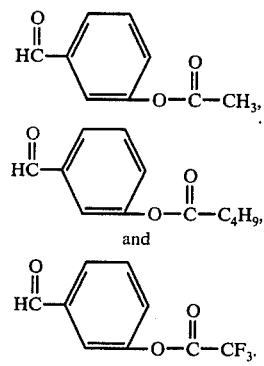

The formation of oxetane LXII is accomplished by photolysis of a mixture of the bicyclo hexene and the aldehyde in a solvent. The bicyclo hexene is preferably used in excess over the molar equivalent, for example 2 to 4 times the stoichiometric equivalent amount. The solvent is a photochemically inert organic liquid, for example liquid hydrocarbons, including benzene or hexane, 1,4-dioxane, and diethyl ether. The reaction is conveniently done at ambient conditions, for example, 25° C., but may be done over a wide range of temperature, from about −78° C. to the boiling point of the solvent. The irradiation is done with mercury vapor lamps of the low or medium pressure type, for example those peaking at 3500 Å. Such sources are available from The Southern New England Ultraviolet Co., Middletown, Conn. Alternatively, those lamps which emit a broad spectrum of wavelengths and which may be filtered to transmit only light of λ ~ 3000–3700 Å may also be used. For a review of photolysis see D. R. Arnold in "Advances in Photochemistry", Vol. 6, W. A. Noyes et al., Wiley-inter-science, New York, 1968, pp. 301–423.

The cleavage of the oxetane ring to yield the formula LXIII compound from the formula LXII compound is accomplished with an alkali metal in the presence of a primary amine or an alcohol. Preferred is lithium in ethylamine, or sodium in butyl alcohol. See L. J. Altman et al., Synthesis 129 (1974). The cleavage transformation may also be accomplished by catalytic hydrogenation over an inert metal catalyst, e.g. Pd on carbon, in ethyl acetate or ethanol.

The formula LXIV compound is prepared from the formula LXIII diol by preferably blocking the two hydroxyl groups with carboxyacyl groups according to $R_{63}$, i.e.

as defined above. For example, the diol is treated with an acid anhydride such as acetic anhydride, or with an acyl halide in a tertiary amine. Especially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{64}C(O)Cl$, $R_{64}C(O)Br$, or $R_{64}C(O)F$, and carboxy acid anhydrides, $(R_{64}C-)_2O$, wherein $R_{64}$ is as defined above. The preferred reagent is an acid anhydride. Examples of acid anhydrides useful for this purpose are acetic anhydride, propionic anhydride, butyric anhydride, pentanoic anhydride, nonanoic anhydride, trideconoic anhydride, steric anhydride, (mono, di, or tri)chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, phenoxyacetic anhydride, benzoic anhydride, (o, m, or p)-bromobenzoic anhydride, 2,4 (or 3,4)-dichlorobenzoic anhydride, o-trifluoromethylbenzoic benzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 5)-biphenylcarboxylic anhydride, 3-chloro-4-biphenylcarboxylic anhydride, 5-isopropyl-6-nitro-3-biphenylcarboxylic anhydride, and (1 or 2)-naphthoic anhydride. The choice of anhydride depends upon the identity of $R_{64}$ in the final acylated product, for example when $R_{64}$ is to be methyl, acetic anhydride is used; when $R_{64}$ is to be 2-chlorobutyl, 3-chlorovaleric anhydride is used.

When $R_{64}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, the formula LXIII diol is reacted with two equivalents of sodium hydride and then with excess ethyl formate.

In formula LXIV, $R_{68}$ may also represent a blocking group including benzoyl, substituted benzoyl, monoesterified phthaloyl and substituted or unsubstituted naphthoyl. For introducing those blocking groups, methods known in the art are used. Thus, an aromatic acid of the formula $R_{63}OH$, wherein $R_{63}$ is as defined above, for example benzoic acid, is reacted with the formula LXIII compound in the presence of a dehydrating agent, e.g. zinc chloride, or phosphoryl chloride; or an anhydride of the aromatic acid of the formula $(R_{63})_2O$, for example benzoic anhydride, is used.

Preferably, however, an acyl halide e.g. $R_{63}Cl$, for example benzoyl chloride, is reacted with the formula LXII compound in the presence of a tertiary amine such as pyridine, triethylamine, and the like. The reaction is carried out under a variety of conditions using procedures generally known in the art. Generally, mild conditions are employed, e.g. 20°-60° C., contacting the reactants in a liquid medium, e.g. excess pyridine or an inert solvent such as benzene, toluene, or chloroform. The acylating agent is used either in stoichiometric amount or in excess.

As examples of reagents providing $R_{63}$ for the purposes of this invention, see the discussion above pertaining to the use of acyl protecting groups.

the formula LXIV acetal is converted to aldehyde LXV by acid hydrolysis, known in the art, using dilute mineral acids, acetic or formic acids, and the like. Solvents such as acetone, dioxane, and tetrahydrofuran are used.

For the conversion of LXV to LXIX, it is optional whether $R_{66}$ be hydrogen or a "blocking group" as defined below. For efficient utilization of the Wittig reagent it is preferred that $R_{66}$ be a blocking group. If the formula LXIV compound is used wherein $R_{68}$ is hydrogen, the formula LXV intermediate will have hydrogen at $R_{66}$. If $R_{66}$ is to be a blocking group, that may be readily provided prior to conversion of LXV to LXVI by reaction with suitable reagents as discussed below.

The blocking group, $R_{65}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{63}$ above, i.e. acetyl, and also benzoyl, naphthoyl, and the like; (b) blocking groups according to $R_{10}$; and (c) $-Si(G_1)_3$ wherein $G_1$ is as defined above.

In replacing the hydrogen atoms of the hydroxyl groups with a carboxyacyl blocking group, methods known in the art are used. The reagents and conditions are discussed above for $R_{68}$ on the compound of formula LXIV.

When the blocking group is according to $R_{10}$ appropriate reagents and conditions are as defined above.

When the blocking group is silyl of the formula $-Si(G_1)_3$, the formula LXV compound is transformed to a silyl derivative of formula LXV by procedures known in the art. See, for example, Pierce, "Silylation of Organic Compounds," Pierce Chemical Co., Rockford, Ill. (1968). The necessary silylating agents for these transformations are known in the art or are prepared by methods known in the art. See, for example, Post "Silicones and Other Silicone Compounds," Reinhold Publishing Corp., New York, N.Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotrim-tolysilane, and tribenzylchlorosilane. Alternatively, a chlorosilane is used with a corresponding disilazane. Examples of other silylating agents suitable for forming the formula LXV intermediates include pentamethylsilylamine, pentaethylsilylamine, N-trimethylsilydiethylamine, 1,1,1-triethyl-N,N-dimethylsilylamine, N,N-diisopropyl-1,1,1-trimethylsilylamine, 1,1,1-tributyl-N,N-dimethylsilylamine N,N-dibutyl-1,1,1-trimethylsilylamine, 1-isobutyl-N,N-1,1-tetramethylsilylamine, N-benzyl-N-ethyl-1,1,1-trimethylsilylamine, N,N-1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In transforming the formula LXV compound to the formula LXVI compound the aldehyde group is transformed by the Wittig reaction to a moiety of the formula

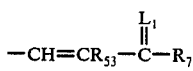

For this purpose a phosphonium salt prepared from an organic chloride or bromide of the formula

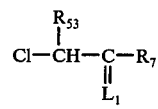

or

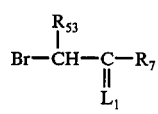

is employed, wherein $L_1$, $R_7$, and $R_{53}$ are as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and references cited therein.

The formula LXVII compound is obtained by deblocking if necessary. When $R_{66}$ is a hindered carboxyacyl, $R_{66}$ on the phenolic hydroxy is selectively replaced with hydrogen by hydrolysis with sodium or potassium hydroxide or carbonate ethanol-water. Other water-miscible solvents may be substituted, for example 1,4-dioxane, tetrahydrofuran, or 1,2-dimethoxyethane. The selective hydrolysis is preferably carried out at $-15°$ to $25°$ C. Higher temperatures may be used but with some increase in selectivity.

Total hydrolysis of $R_{66}$ blocking groups on the formula LXVI compound is accomplished, when $R_{66}$ is carboxyacyl, with an alkali alkoxide in an alcoholic solvent, preferably sodium methoxide in methanol at a temperature from 25° C. to 50° C. When $R_{66}$ is trialkylsilyl, either aqueous acid or base are used at 25° to 50° C.

Continuing with Chart G, a Williamson synthesis is employed to obtain the formula LXVIII compound. The formula LXVII phenol is condensed with a haloalkanoate within the scope of Hal—(CH$_2$)$_g$—COOR$_1$ wherein Hal is chloro, bromo, or iodo and g and $R_1$ are as defined above. Normally the reaction is done in the presence of a base such as n-butyllithium, phenyllithium, triphenylmethyllithium, sodium hydride, potassium t-butoxide, sodium hydroxide, or potassium hydroxide.

In transformation of the formula LXVIII compound to the formula LXIX is accomplished by any one of several routes known in the art. See U.S. Pat. No. 3,711,515. Thus, the alkene LXVIII is hydroxylated to glycol LXIX. For this purpose osmium tetroxide is a suitable reagent, for example in conjunction with N-methylmorpholine oxide-hydrogen peroxide complex (see Fieser et al., "Reagents for Organic Synthesis", p. 690, John Wiley and Sons, Inc., New York (1967)). Thereafter, several methods are available for obtaining the formula LXX product. In one method the glycol is converted to a bis(alkanesulfonic acid) ester and subsequently hydrolyzed to the formula LXX compound by methods known in the art (See, for example German Offenlegungsschrift No. 1,936,676, Derwent Farmdoc No. 6862R). Another method is by way of a diformate by formolysis of the glycol (see U.S. Pat. No. 3,711,515).

Still another method is by way of a cyclic ortho ester. For this purpose, glycol LXIX is reacted with an ortho ester of the formula

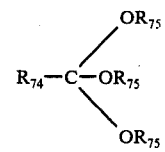

wherein $R_{74}$ is hydrogen, alkyl of one to 19 carbon atoms, inclusive, or aralkyl of 7 to 12 carbon atoms, inclusive, substituted with zero to 3 halo atoms; and $R_{75}$ is methyl or ethyl. There is then formed a cyclic orthoester of the formula

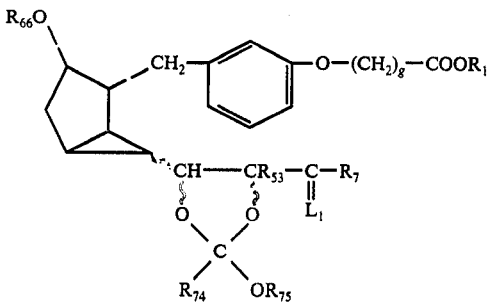

wherein g, $R_1$, $R_{53}$, $R_{66}$, $R_{74}$, $R_{75}$, $L_1$ and $R_7$ are as defined above. The reaction goes smoothly in a temperature range of $-50°$ C. to $+100°$ C., although for convenience 0° C. to $+50°$ C. is generally preferred. From 1.5 to 10 molar equivalents of the ortho ester are employed, together with an acid catalyst. The amount of the catalyst is usually a small fraction of the weight of the glycol, e.g., about 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:

trimethyl orthoformate,
triethyl orthoacetate,
triethyl orthopropionate,
trimethyl orthobutyrate,
trimethyl orthovalerate,
trimethyl orthooctanoate, trimethyl orthophenylacetate, and
trimethyl ortho (2,4-dichlorophenyl)acetate.

Preferred are those ortho esters wherein $R_{74}$ is alkyl of one to 7 carbon atoms; especially preferred are those wherein $R_{74}$ is alkyl of one to 4.

Next, the cyclic orthoester depicted above is reacted with anhydrous formic acid to yield a diol diester of the formula

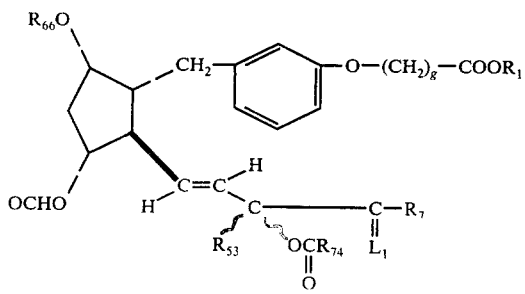

wherein $g$, $R_1$, $R_7$, $R_{53}$, $R_{66}$, and $L_1$ are as defined above.

Anhydrous formic acid refers to formic acid containing not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°–30° C. and is usually completed within about 10 minutes.

Finally, the diol diester above is converted to product LXX by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from −50° C. to 100° C. The time for completion of the reaction varies with the nature of $R_{74}$ and the base, proceeding in the case of alkali carbonates in a few minutes when $R_{74}$ is hydrogen but taking up to several hours when $R_{74}$ is ethyl, for example.

When the solvolysis proceeds too long or when conditions are too severe, an ester group ($R_1$) is often removed. They are, however, readily replaced by methods known in the art. See the discussion below.

The formula LXXI compound is prepared from the formula LXX compound by oxidation of the C-15 hydroxy to a 15-oxo. Accordingly, as is known in the art, 2,3-dichloro-5,6-dicyano-1,4-benzoquinone, activated manganese dioxide, or nickel peroxide (See Fieser, et al., "Reagents for Organic Synthesis", John Wiley and Sons, New York, N.Y., pgs. 215, 637, and 731) is advantageously employed. Thereafter, the formula LXXI compound is prepared from the 15-oxo compound by transforming the C-9 and C-11 hydroxy hydrogens to silyl derivatives. Procedures known in the art are employed. See for reference Pierce, "Silylation of Organic Compounds," Pierce Chemical Company, Rockford, Ill. (1968). In employing the silylation, sufficient silylating reagent must be used so that the reaction proceeds to completion. The necessary silylating reagents for these transformations are known in the art or are prepared by methods known in the art. See for reference, Post, "Silicones and Other Silicone Compounds," Reinhold Publishing Corp., New York, N.Y. (1949).

The formula LXXII compound is then prepared from the formula LXXI compound by first photoisomerizing the formula LXXI compound when Y is cis-CH=CH— and thereafter transforming the C-15 oxo to an $M_5$ moiety, for example by use of a Grignard reagent or trimethylaluminum (when 15-methyl intermediates are to be prepared) or reduction of a carbonyl to an alcohol when 15-hydroxy compounds are to be prepared or reduction of the carbonyl to an alcohol followed by alkylation of the hydroxy compounds so formed when a 15-methyl ether is to be prepared. Thereafter, the silyl groups are hydrolyzed, using, for example, dilute aqueous acetic acid in a water miscible solvent, such as ethanol (sufficient to yield a homogeneous reaction mixture). At 25° C, the hydrolysis is ordinarily complete in 2 to 12 hr. Further, the hydrolysis is preferably carried out in an inert atmosphere, e.g., nitrogen or argon.

The formula LXXIII compound is represented by the formula LXX compound when Y is trans-CH=CH and $M_1$ and $M_9$ are the same. Alternatively, the formula LXXIII compound is prepared from the formula LXXII compound by separation of the C-15 epimers. Such separation proceeds by methods discussed in the preceding Chart for accomplishment of this purpose (e.g., thin layer chromatography or high pressure liquid chromatography).

Referring to Chart H, there are shown process steps by which the formula LXXVI bicyclo hexene is transformed first to an oxetane (Formula LXXVII) with a fully developed side chain, e.g.,

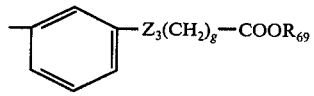

wherein $Z_3$ is oxa or methylene and ultimately to the formula LXXXIV compound. In Chart H, $R_{69}$ is hydrogen or alkyl of one to 4 carbon atoms, inclusive, and $R_{70}$ is hydrogen, alkyl of one to 4 carbon atoms, inclusive, or silyl of the formula $(G_1)_3Si$— wherein $G_1$ is as defined herein above.

In transforming LXXVI to LXXVII in Chart H, there is employed an aldehyde of the formula

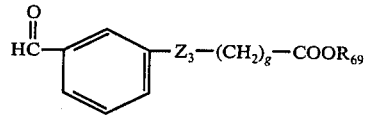

wherein $Z_3$ and $R_{69}$ are as defined above. Such aldehydes are available or are readily prepared by methods known in the art, e.g.,

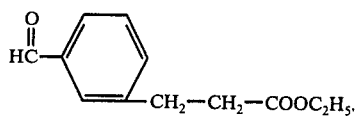

The conditions for this transformation are essentially the same as for the corresponding step of Chart G (i.e., LXI to LXII). Thereafter, the preparation of the formula LXXXI compound proceeds by methods analogous to the corresponding steps of Chart G (i.e., LXII to LXVI) with the preference that LXXVII to LXXVIII is accomplished catalytically.

The steps transforming LXXXI to LXXXIV then proceed in similar fashion, employing the same or similar reagents and conditions as the corresponding steps of Chart G discussed above.

Referring next to Chart I the process steps are shown whereby aldehyde LXXX of Chart H is transformed to a 17,18—tetradehydro-PG intermediate (formula LXXXIX) and 17,18—didehydro-PG intermediate (formula XC).

In Chart I, a Wittig reagent is employed which is prepared from a phosphonium salt of a haloalkyne of the formula

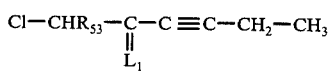

or

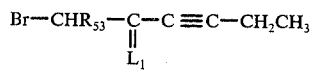

wherein $R_{53}$ and $L_1$ are as defined above, (See, for example, U. Axen et al., Chem. Comm. 1969, 303, and ibid. 1970, 602) in transforming LXXXVI to LXXXVII.

Thereafter, in subsequent transformations yielding the 17,18-tetradehydro compound LXXXIX, the reagents and conditions are similar to those employed for the corresponding reactions shown in Chart H.

Transformation of the formula LXXXIX compound to the formula XC compound is accomplished by hydrogenation of LXXXIX using a catalyst which catalyzes hydrogenation of —C≡C— only to cis-CH=CH—, as known in the art. See, for example, Fieser et al., "Reagents for Organic Syntheses", pp. 566–567, John Wiley amd Sons, Inc., New York (1967). Preferred is Lindlar catalyst in the presence of quinoline. See Axen, references cited above.

As discussed above, Chart J provides a method whereby the formula XCI PG-type intermediate, prepared according to Chart G or Chart H is transformed to the corresponding formula XCIV 16-phenoxy-PG-type intermediates.

The formula XCII compound is prepared from the formula XCI compound by cleavage of the 13,14-trans double bond, conveniently by ozonolysis. Ozonolysis proceeds by bubbling dry oxygen, containing about 3 percent ozone, through a mixture of a formula XCI compound in a suitable nonreactive diluent. For example, n-hexane is advantageously employed. The ozone may be generated using methods known in the art. See, for example, Fieser, et al., "Reagents for Organic Synthesis," John Wiley and Sons, Inc. (1967), pages 773–777. Reaction conditions are maintained until the reaction is shown to be complete, for example, by silica gel thin layer chromatography or when the reaction mixture no longer rapidly decolorizes a dilute solution of bromine in acetic acid.

The formula XCIII compound is then prepared from the formula XCII compound by blocking with an $R_{65}$ blocking group and thereafter employing a phosphonate of the formula:

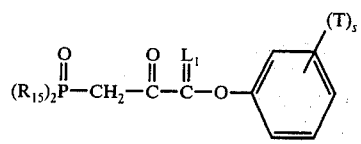

wherein $R_{15}$, $L_1$, T and s are as defined above. Phosphonates of this general formula are prepared by methods known in the art. See the text hereinabove accompanying Chart A for discussion of the preparation and the appropriate reaction conditions by which the Wittig reaction proceeds. The formula XCIV compound is prepared from the formula XCIII compound by transformation of the 15-oxo moiety to an $M_1$ moiety. Methods hereinabove, particularly those discussed in Charts G and H above, are employed.

Optionally the method of Chart J is used to introduce the various other $R_7$ moieties to the formula XCII compound using the appropriate phosphonate.

Chart K provides a method whereby the formula XCV bicyclic lactone aldehyde is transformed to the corresponding formula XCIX PGF$_{2\alpha}$-type intermediate which is useful according to the procedures of Charts L and M in preparing the novel PGD- and 9β-PGD-type compounds disclosed in this specification.

The formula XCV compound is known in the art. This compound is available in either of its two pure and enantiomeric forms or as a mixture comprising both of these enantiomers. The formula XCVI compound is prepared from the formula XCV compound using reagents and conditions analogous to the preparation of the formula XXI compound of Chart A from the formula XVI compound. Thus, methods generally known to the art are employed. The formula XCVII compound is then prepared from the formula XCVI compound using reaction conditions and reagents analogous to the preparation of the formula XXX compound from the formula XXVI compound (Chart B), the preparation of the formula XXXIII compound from the formula XXXI compound (Chart C), the preparation of the formula LXIV compound from the formula XXXVI compound (Chart D), or the preparation of the formula XLVIII compound from the formula XLVI compound (Chart E). Thereafter the formula XCVIII compound is prepared from the formula XCVII compound by first hydrolyzing any blocking groups according to $R_{10}$, (using procedures and methods hereinabove described), and second separating the C-15 epimers when $R_5$ is methyl. Methods herein described (e.g., silica gel chromatography or high pressure liquid chromatography) are employed. The formula XCIX compound is prepared from the formula XCVII compound by first oxidizing the C-9 hydroxy of the formula XCVII compound, for example, using either the Jones or Collins reagent, thereafter performing a ring carbonyl reduction on the 9-oxo PG-type intermediate so formed and separating the 9β-hydroxy epimer from the 9-epimeric mixture so produced, and finally following the procedure described above for the transformation of the formula XCVII compound to the formula XCVIII compound. The above ring carbonyl reduction and subsequent separation of the 9-epimeric mixture thereby produced is carried out by methods known in the art as hereinabove described.

Chart L provides a method whereby the formula CI PGF$_\alpha$-type intermediate is transformed to the corresponding novel formula CV PGD-type compound of this invention. The formula CI compound is prepared by methods and procedures described hereinabove.

The formula CII compound is prepared from the formula CI compound by cyclo(alkylboronization). Accordingly, the bicyclic formula CII compound is prepared by reaction of the formula CI compound with a slight stoichiometric excess of butylboronic acid. The course of the reaction is conveniently monitored by silica gel thin layer chromatography and the reaction is preferably carried forth under vigorous stirring at reflux temperatures. The preferred reaction diluent for this transformation is methylene chloride, though other suitable organic solvents are likewise employed. The formula CII compound so formed is then etherified by replacing the free hydroxy hydrogen of the $M_9$ moiety with a blocking group according to $R_{10}$. Procedures hereinabove are advantageously employed. Thereafter the formula CIV compound is prepared from the formula CIII compound by decycloboronization. For this purpose an alkaline metal hydroxide (e.g., sodium, lithium, or potassium hydroxide) is combined with the formula CIII compound in a water miscible diluent capable of yielding a homogeneous reaction mixture (e.g., methanol or ethanol), and the resulting solution thereafter treated with dilute aqueous hydrogen peroxide. The formula CV compound is then prepared either from the formula CI (when $R_5$ or $R_6$ is methyl) compound or the formula CIV (when $R_5$ and $R_6$ are hydrogen) compound by one of two methods.

By the first method the formula CI or CIV compound is selectively oxidized at the C-11 over the C-9 position using, for example, the Jones reagent. In order to achieve high selectivity, it is desirable that the reaction be carried out at between $-20°$ and $-60°$ C. Especially preferred are reaction temperatures between $-55°$ and $-30°$ C. Accordingly, upon separation of mixtures of product, pure formula CV PGD-type product is obtained.

By the second procedure the formula CV compound is prepared from the formula CI or CIV compound first selectively silylating the C-11 hydroxy of the formula CI or CIV compound over the C-9 hydroxy. Silyl groups according to the formula $—Si—(G_1)_3$ are advantageously employed. For selective monosilylation procedures see U.S. Pat. No. 3,822,303, issued July 2, 1974, German Offenlegungsschrift No. 2259195, Derwent Farmdoc CPI 36457U-B or Netherlands Patent 7214142, Derwent Farmdoc CPI 26221U-B. Thereafter the silylation compound so formed is transformed to the corresponding C-9 ether, employing blocking groups according to $R_{10}$, in place of the 9-hydroxy. Thereafter the C-11 silyl moiety is hydrolyzed by methods hereinabove described and the resulting 11-hydroxy compound oxidized by the procedure described above, yielding the corresponding 11-oxo compound. Thereafter, the formula CV compound is prepared from this 11-oxo compound by replacing any blocking groups according to $R_{10}$ with hydroxy hydrogens. Methods described hereinabove are employed.

Chart M provides a method whereby the formula CVI PGF$_\alpha$-type intermediate is transformed to the corresponding formula CX 9$\beta$-PGD-type compound. The formula CVI compound is prepared as described in the preceding Charts. Thereafter the formula CVII compound is prepared from the formula CVI compound following the procedure described in Chart L for preparing the formula CIV compound from the formula CI compound. Thereafter the formula CVIII compound is prepared from the formula CVII compound by selective silylation as discussed in the text accompanying Chart L for the second method of preparing the formula CV compound from the formula CIV compound. See references therein cited. Thereafter the formula CIX compound is prepared from the formula CVIII compound by first oxidizing the C-9 hydroxy of the formula CVIII compound to the corresponding 9-oxo compound and thereafter reducing the 9-oxo compound so formed to a mixture of 9$\alpha$ and $\beta$ hydroxy epimers. Thereafter the formula CIX compound is prepared by separating the 9$\beta$-hydroxy epimer from this epimeric mixture. Thereafter the formula CX compound is prepared by the method described in Chart F for the preparation of the formula LVII compound from the formula LIII compound wherein X is a silyloxy group, with the exception that the separation of C-15 epimeric mixtures is omitted.

Chart N provides a method whereby formula CXI PGD-type compound is transformed variously into the formula CXII 9-deoxy-9,10-didehydro-PGD-type compound, the formula CXIII 9-deoxy-PGF or 9-deoxy-11$\beta$-PGF-type compound, or the formula CXVII 9-deoxy-PGD-type compound.

The formula CXII compound is prepared from the formula CXI compound by mild acid catalyzed dehydration of the formula CXI compound. Organic acids such as acetic acid, trifluoroacetic acid, citric acid, oxalic acid, or p-toluenesulfonic acid are useful for this purpose. Diluents such as tetrahydrofuran, methanol, ethanol, or water are usefully employed. Preferably, however, a diluent is employed which will result in a homogeneous reaction mixture. The dehydration proceeds rapidly at temperatures between ambient temperature and 40° C. Alternatively, a formula CXI compound is left standing on a column of acid washed silica gel, thereby dehydrating to the formula CXII product, usually within one to 5 days. The formula CXIII compound is thereafter prepared from the CXII compound by reduction of the formula CXII compound followed by separation of the C-11 epimeric mixtures so produced. This reduction selectively reduces the endocyclic double bond and transforms the 11-oxo to an 11-hydroxy, without affecting side chain unsaturation. For this purpose, an alkali metal borohydride, e.g. sodium, potassium, or lithium borohydride is effectively employed in alcoholic solution. The reaction is carried out at about $-20°$ C. and is ordinarily complete within a few minutes. The subsequent optional separation proceeds by conventional methods, e.g. silica gel chromatography, high pressure liquid chromatography, and the like.

The formula CXII compound is optionally converted into the formula CXVII compound by selective catalytic hydrogenation of the endocyclic double bond. This transformation is selectively effective without affecting side chain unsaturation. For this purpose the 5 to 10 percent palladium or rhodium catalyst on carbon, alumina, or other suitable support is employed. The reaction is carried out in any suitable organic solvent, e.g. ethyl acetate, methanol, ethanol, or diethyl ether, at temperatures of between $-30°$ and 50° C. and pressures greater than or equal to atmospheric pressure.

Lastly the formula CXII compound is converted to the formula CXIV compound by replacing the $M_1$ moiety with an $M_7$ moiety. This replacement requires the introduction of a blocking group according to $R_{65}$, when $R_6$ of the $M_1$ moiety is hydrogen. In this transformation, methods described hereinabove are employed.

The formula CXV compound is then prepared from the formula CXIV compound by reduction as described above in the transformation of the formula CXII compound to the formula CXIII compound. Thereafter the formula CXVI compound is prepared from the formula CXV compound by a cyclopentane ring oxidation. For this purpose an oxidizing agent such as the Jones reagent (acidified chromic acid) is employed. See for reference, Journal of the Chemical Society 39 (1946). A slight stoichiometric excess beyond the amount necessary to oxidize one of the secondary hydroxy groups of the formula CXV compound is employed. Acetone is a useful diluent for this purpose. Reaction temperatures at least as low as about 0° C. are useful. Preferred reaction temperatures are in the range of $-10°$ to $-50°$ C. An especially useful reagent for this purpose is the Collins reagent (chromium trioxide in pyridine). See for reference J. C. Collins, et al., Tetrahedron Letters 3363 (1968). Dichloromethane is a suitable diluent for this purpose. Reaction temperatures below 30° C. are preferred. Reaction temperatures in the range of about $-10°$ to $+10°$ C. are especially preferred. The oxidation proceeds rapidly and is ordinarily complete within several minutes. Pure product is then isolated by conventional means, e.g. silica gel chromatography.

Examples of other oxidation agents useful for this transformation are mixtures of chromium trioxide in pyridine (Journal of the American Chemical Society 75, 422 (1953)), and tert-butyl chromate in pyridine (Biological Chemistry Journal, 84, 195 (1962)), mixtures of sulfur trioxide in pyridine and dimethyl sulfoxide (Journal of the American Chemical Society 89, 5505 (1967)), and mixtures of dicyclohexylcarbodiimide and dimethylsulfoxide (Journal of the American Chemical Society 87, 5661 (1965)).

Thereafter the formula CXVII compound is prepared from the formula CXVI compound by hydrolysis of blocking groups according to $R_{65}$, as described hereinabove.

Chart O provides a method whereby the formula CXVIII PGF$_\alpha$-type compound is transformed to the corresponding formula CXXVI 9-deoxy-PGF-type compounds, formula CXXVIII 9-deoxy-PGD-type compounds, or formula CXXIX 9-deoxy-11$\beta$-PGF-type compounds.

The transformation of the formula CXVIII compound to the corresponding formula CXIX compound and thereafter the transformation of the formula CXIX compound to the corresponding formula CXX and CXXI compounds proceeds as described in Chart L for the transformation of the formula CI compound to the formula CIV compound. Thereafter the formula CXXII compound is prepared from the formula CXXI or the formula CXVIII compound by selective monosilylation of the C-11 hydroxy over the C-9 hydroxy. Methods and reagents employed for this procedure are known in the art. See for reference U.S. Pat. No. 3,822,303, issued July 2, 1974; German Offenlegungsschrift No. 2259195, Derwent Farmdoc CPI 36457U-B; or Netherlands Pat. No. 7214142, Derwent Farmdoc CPI 26221U-B. For this purpose, for example, trimethylsilyldiethylamine is a useful reagent.

Thereafter, the formula CXXIII compound is prepared from the formula CXXII compound by transforming the formula CXXII compound into a 9-hydrocarbylsulfonyl derivative. For this purpose for example methanesulfonyl chloride or p-toluenesulfonyl chloride is condensed with the formula CXXII compound, in the presence of a base, especially a tertiary amine (e.g. triethylamine). The reaction proceeds to completion, preferably at temperatures at or below 10° C., in several minutes. A slight stoichiometric excess of the hydrocarbylsulfonyl chloride reagent is employed to assure that the reaction proceeds to completion.

Thereafter, the formula CXXIV compound is prepared from the formula CXXIII compound by hydrolysis of the 11-silyl moiety. Hydrolysis proceeds conveniently in an organic acid combined with water or water and a water-miscible organic solvent such as ethanol. For example, a two percent aqueous solution of citric acid in methanol is advantageously employed.

The preparation of the formula CXXV compound from the formula CXXIV compound then proceeds by cleavage of the 9-hydrocarbylsulfonyloxy moiety of the formula CXXIV compound, using any one of several general methods known to the art.

Thus, by one method the cleavage proceeds by use of reducing agents such as a metal borohydride (e.g., sodium borohydride or a metal cyanoborohydride (e.g. sodium cyanoborohydride) in an aprotic solvent (e.g., dimethyl sulfoxide). A second method requires a reduction with lithium aluminum hydride and, followed by a transformation of the primary alcohol so formed to the carboxy free acid, employing a hydrogen pre-reduced aqueous suspension of platinum dioxide (Adams catalyst, Fieser and Fieser, Reagents for Organic Synthesis, New York, New York, 1967, page 890).

Yet another method for this reaction requires the use of lithium bromide (to prepare a bromo derivative) followed by treatment of the resulting product with chromium (II) perchlorate in an aqueous dimethylformamide and a complexing agent (ethylenediamine).

The formula CXXVI compound is prepared from the formula CXXV compound by hydrolysis of any blocking groups. Methods hereinabove are advantageously employed.

Alternatively, the formula CXXV compound is used to prepare the formula CXXVII compound. When so used the formula CXXV compound is oxidized, using for example those oxidation agents discussed hereinabove for preparation of the formula CXVI compound from the formula CXV compound.

Thereafter the formula CXXVIII compound is prepared from the formula CXXVII compound by hydrolysis of any blocking groups. Methods discussed hereinabove are employed.

Thereafter the formula CXXIX compound is prepared from the formula CXXVIII compound by a cyclopentane ring carbonyl reduction, using methods hereinabove described (e.g., see Chart F, wherein the formula LII compound is transformed to the formula LIII compound.

Thereafter, the 11$\beta$-hydroxy epimer is separated from the resulting epimeric mixture using conventional separation techniques. For example, silica gel chromatography or high pressure liquid chromatographic separation is employed.

In preparing the formula CXXVI compound, there is used optionally, in place of the formula CXXII compound, the corresponding 11,15-bis ether compound, i.e.,

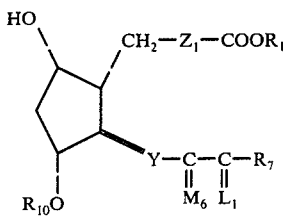

wherein $R_1$, $Z_1$, $M_6$, $L_1$, and $R_7$ are as defined above. These 11,15-bis-ethers are known in the art or conveniently prepared by the methods described in Chart K.

Chart P provides a method whereby the various novel prostaglandin analogs disclosed in this specification wherein Y is trans-CH=CH— are transformed to corresponding novel 12,13-didehydro-13,14-dihydro-PG-type compounds disclosed in this specification.

The formula CXXXI compound, prepared hereinabove, is transformed to the formula CXXXII or formula CXXXIII compound by treatment with mild base. When substantial quantities of the formula CXXXII compound are desired treatment of the formula CXXXI compound with mild bases such as triethylamine or 1,5-diazobicyclo[4.3.0]-non-5-ene (DBN) are preferably employed. When bases such as DBN Florisil, or potassium acetate in methanol are employed, a preponderence of the E-epimer is produced, while triethylamine yields substantially an EZ-epimeric mixture.

Alternatively the formula CXXXIII compound is prepared from the formula CXXXVI compound by treatment with mild base, as described above for the preparation of the formula CXXXII or formula CXXXIII compounds. Also the formula CXXXVI compound is used to prepare the formula CXXXV compound (as discussed in Chart N) which is thereafter useful in preparing the formula CXXXIV compound, employing the basic treatment described above. Alternatively the formula CXXXIV compound is prepared from the formula CXXXIII compound by the methods discussed hereinabove in Chart N.

Chart Q provides a preferred method whereby the formula CXLIX 9-deoxy-9,10-didehydro-PGD-type compounds are prepared.

With respect to Chart Q the formula CXLI $PGF_{2\alpha}$-type compound is known in the art, or prepared by methods hereinabove described. Thereafter the formula CXLII, formula CXLIII, and formula CXXXIV compounds are prepared by cyclo(alkyl boronization), optional C-15 etherification, and hydrolysis of the 9,11-n-alkyl boronate derivative. Methods employed in previous charts, for example, Chart L (particularly the transformations of the formula CI compound to the formula CII, formula CIII, and formula CIV compounds) are employed.

Thereafter, the formula CXLIV compound is transformed to the formula CXLV compound by 1,9-lactonization. For accomplishing 1,9-lactonization, the formula CXLI or formula CXLIV compound is combined with 2-pyridyldisulfide in a benzene solvent with stirring for 3–24 hr. Thereafter, additional benzene solvent is added and the reaction mixture is heated to reflux til the lactonization is shown to be complete by conventional methods (silica gel TLC). Thereafter, the formula CXLVI compound is prepared from the formula CXLV compound by oxidation of the C-11 hydroxy to an 11-oxo. For this purpose, oxidation methods and reagents described hereinabove are useful. See for example Chart L wherein the formula CIV compound is transformed to the formula CV compound.

The formula CXLVII compound is prepared from the formula CXLVI compound by subjection of the formula CXLVI compound to silica gel, or mild acid for varying periods of time. For example, the formula CXLVI compound is left standing on a column of silica gel or acid washed silica gel for 1 to 5 days, thereby preparing the formula CXLVII compound.

The formula CXLVIII compound is prepared from the formula CXLVII compound by hydrolysis of any blocking groups, using procedures hereinabove described.

Thereafter the formula CXLIX compound is prepared from the formula CXLVIII compound by transformation of the carboxy acid to an $R_1$ moiety, employing methods hereinbelow described.

In the employment of the processes above when C-15 tertiary alcohols are to be prepared ($R_5$ is methyl), the use of blocking groups at C-15 is not required. Accordingly, in the steps of the above charts the introduction and hydrolysis of blocking groups are thereby omitted by the preferred process.

Certain (3RS)-3-methyl lactones of chart A may be separated into their respective (3R) and (3S)-epimers by silica gel chromatographic separation or high pressure liquid chromatographic techniques. Where such separation is possible, this route is preferred. Accordingly, in these cases the separation is effected and $M_5$ is

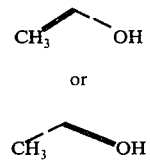

or

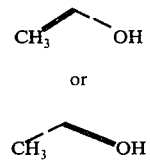

and $M_6$ is

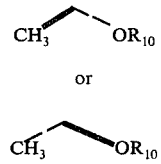

or

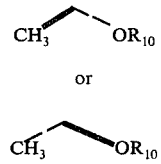

wherein $R_{10}$ is a blocking group. Accordingly, the corresponding separation procedures are omitted when the optional lactone separation is employed.

Optically active PG-type products are obtained from optically active intermediates, according to the process steps of the above charts. Likewise enantiomeric PG-type compounds are obtained from corresponding enantiomeric PG-type intermediates following the procedures in the above charts. When racemic intermediates are used in the reactions above, racemic products are obtained. These products may be used in their racemic form or they may be resolved as optically active enantiomers following procedures known in the art. For example, when a PG-type free acid is obtained, the racemic form thereof is resolved into d and l forms by reacting said free acid by known procedures with an optically active base (e.g., brucine or strychnine) thereby yielding a mixture of two diastereomers which are separable by procedures known in the art (fractional crystallization to yield the separate diastereomeric salts). The optically active acid may then be prepared from the salt by general procedures known to the art.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to acids ($R_1$ is hydrogen) or to esters.

When the alkyl ester has been obtained and an acid is desired, saponification procedures, as known in the art for PGF-type compounds are employed.

Enzymatic processes for transformation of esters to their acid forms is employed using methods known in the art when saponification procedures would cause an undesired dehydration of the prostaglandin analog. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N. Y., Vol. 8, pp. 389–394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tertbutyl iodide, cyclopropyl iodide, cyclopentyl iodide, benzyliodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a tertiary amine salt, reacted with pivaloyl halide to give the mixed acid anhydride and then reacted with the aromatic alcohol. Alternatively, instead of pivaloyl halide, an alkyl or phenylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York, (1967). The PG-type compound is contacted with one to ten molar equivalents of the aromatic alcohol in the presence of 2–10 molar equivalents of dicyclohexylcarbodiimide in pyridine as a solvent.

One preferred novel process for the preparation of these esters, however, comprises the steps:

(a) forming a mixed anhydride with the PG-type compound and isobutylchloroformate in the presence of a tertiary amine and (b) reacting the anhydride with an appropriate aromatic alcohol.

The mixed anhydride described above is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Althought the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water of addition of a water-miscible solvent of moderate polarity, for example, a lower alkanol or a lower alkanone, gives the solid inorganic salt if that form is desired.

To product an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, or hexanoic anhydride gives the corresponding carboxyacylate.

The carboxyacylation is advantageously carried out by mixing the hydroxy compound and the acid anhydride, preferably in the presence of a tertiary amine such as pyridine or triethylamine. A substantial excess of anhydride is used, preferably about 10 to about 10,000 moles of anhydride per mole of the hydroxy compound reactant. The excess anhydride serves as a reaction diluent and solvent. An inert organic diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

PREPARATION 1

Dimethyl-3,3-dimethyl-2-oxo-4-phenylbutylphosphonate,

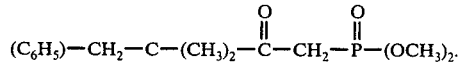

A. To a solution of 101.2 g. of diisopropylamine in 125 ml. of n-butyllithium in hexane. To the resulting solution is added dropwise with cooling 46.5 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hr. This stirred mixture is then diluted with diethyl ether and excess cold dilute hydrochloride acid. The organic layer is washed with saline and thereafter dried, concentrated, and the residue distilled under vacuum. Accordingly, there is prepared 2,2-dimethyl-3-phenylpropionic acid.

B. A mixture of 48 g. of the product of part A of this example and 82 g. of thionyl chloride are heated with stirring on a steam bath for 2 hr. The mixture is then concentrated under vacuum. Thereafter dry benzene is added and the resulting mixture is concentrated again, removing all traces of thionyl chloride. Distillation of this residue yields 48.2 g. of 2,2-dimethyl-3-phenylpropionyl chloride.

C. To a solution of 63 g. of dimethylmethylphosphonate in 600 ml. of tetrahydrofuran under nitrogen at −75° C. is added with stirring 312 ml. of 1.6 molar n-butyllithium in hexane. The addition rate is adjusted so that the reaction temperature remains below 55° C. Ten minutes after the addition is complete, 48.2 g. of the reaction product of part B of this example and 50 ml. of tetrahydrofuran are added dropwise at such a rate as to maintain the reaction temperature below −60° C. The resulting mixture is then stirred at −75° C. for 2 hr. and then ambient temperature overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute bicarbonate solution. The organic layer is then washed with brine, dried, and concentrated. The residue was crystallized from diethyl ether, yielding 54 g. of dimethyl 3,3-dimethyl-2-oxo-4-phenylbutylphosphonate (8.0 g.), the title compound. The melting point is 48°–50° C.

Following the procedure of Preparation 1, but using in place of benzyl chloride substituted benzyl chlorides of the formula

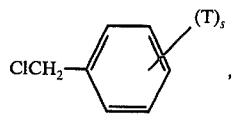

wherein T is fluoro, chloro, trifluoromethyl, alkyl of 1 to 3 carbon atoms, inclusive, and wherein s is 0, 1, 2, or 3, with the proviso that not more than two T's are other than alkyl, and with the further proviso that the various T's may be the same or different, there are prepared the corresponding dimethyl 3,3-dimethyl-2-oxo-4-(substituted phenyl)butylphosphonates. For example, there is prepared by this procedure dimethyl 3,3-dimethyl-2-oxo-4-(p-fluorophenyl)butylphosphonate.

Further, following the procedure of Preparation 1, but using in place of the isobutyric acid of Preparation 1, part A, propionic acid, there is prepared dimethyl 3-methyl-2-oxo-4-phenylbutylphosphonate. Following the procedure of Preparation 1, but using the substituted benzyl chlorides described above in place of benzyl chloride and propionic acid in place of isobutyric acid there are prepared the various dimethyl 3-methyl-2-oxo-4-(substituted phenyl)butylphosphonates wherein the phenyl substitution is as described above.

Further, following the procedure of Preparation 1, but using acetic acid in place of isobutyric acid as used in Preparation 1, part A, there is prepared dimethyl 2-oxo-4-phenylbutylphosphonate. Using acetic acid in combination with the various substituted benzyl chlorides described above according to the procedure of Preparation 1, there are prepared the various dimethyl 2-oxo-4-(substituted phenyl) butyl phosphonates, wherein the phenyl substitution is as described above.

Following the procedure of Preparation 1, but using 2,2-difluoroacetic acid in place of isobutyric acid as used in part A of Preparation 1, there is prepared dimethyl 3,3-difluoro-2-oxo-4-phenylbutylphosphonate. Further, following the procedure of Preparation 1, but using 2,2-difluoro acetic acid in combination with substituted benzyl chlorides described above, there are prepared the corresponding dimethyl 3,3-difluoro-2-oxo-4-(substituted-phenyl)butylphosphonate, wherein the phenyl substitution is as described above.

Further, following the procedure of Preparation 1, but using 2-fluoro acetic acid in place of isobutyric acid there is prepared dimethyl 3-fluoro-2-oxo-4-phenylbutylphosphonate.

Using 2-fluoro acetic acid and the various substituted benzyl chlorides described above according to the procedure of Preparation 1, there are prepared the various dimethyl 3-fluoro-2-oxo-4-(substituted phenyl)butyl phosphonates, wherein the phenyl substitution is as described above.

Following the procedure of Japanese Application Number 0018-459, 3α-t-butyldimethylsilyloxy-5α-hydroxy-2β-carboxaldehyde-1α-cyclopentaneacetic acid γ-lactone is transformed to 3α-t-butyldimethylsilyloxy-5α-hydroxy-2β-(2-formyl-trans-1-ethenyl)-1α-cyclopentane acid γ-lactone. This product is then reacted with a Grignard reagent of the formula cis-BrMgCH₂—CH=CH—CH₂CH₃, thereby preparing 3α-t-butyldimethylsilyloxy-5α-hydroxy-2β-[(3RS)-3-hydroxy-trans-1, cis-5-octadienyl]-1α-cyclopentaneacetic acid γ lactone. Finally the product of this Grignard reaction is oxidized with the Collins reagent, preparing 3α-t-butyldimethylsilyloxy-5α-hydroxy-2β-[3-oxo-trans-1, cis-5-octadienyl]-1α-cyclopentaneacetic acid γ lactone.

Further, following the procedure of the preceeding paragraph but using Grignard reagents of the formula:

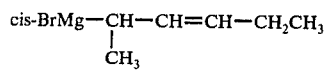

or

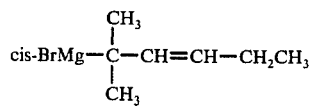

(prepared from the corresponding 1-methyl or 1,1-dimethyl 1-bromo-cis-2-(pentenes) there are prepared the corresponding γ lactones.

PREPARATION 2

Triphenylphosphonium salt of 2,2-difluoro-5-bromopentanoic acid, $Br(C_6H_5)P—(CH_2)_3—CF_2—COOH$.

A. Methyl furoate is dissolved in 180 ml. of methanol. Thereafter 1 g. of 5 percent palladium-on-charcoal is added. This mixture is then hydrogenated at 1 to 3 atmospheres. After 45 hr. 0.79 moles of hydrogen are consumed. The black mixture is then filtered through Celite using 50 ml. of methanol to wash the reaction flask and filter. Evaporation of the filtrate under reduced pressure at 40°–45° C. bath temperature yields 51 g. of a yellow oil which is thereafter distilled, collecting that fraction boiling at 32°–35° C. Thereby, methyl tetrahydrofuroate (46.7 g.) is prepared.

B. Anhydrous hydrobromic acid is bubbled through 50 ml. of acetic anhydride with cooling until a specific gravity of 1.3 is obtained. This reagent is then added to 25 g. of the reaction product of step A of this example, with exclusion of moisture while cooling and stirring. Stirring in the ice water bath is continued for 15 min.; thereafter, the mixture is allowed to stand at room temperature overnight. The reaction mixture is then poured into 600 g. of crushed ice and water with stirring and extracted with diethyl ether. The ether extract is washed with aqueous sodium hydroxide, dried over sodium sulfate, filtered, and thereafter evaporated under reduced pressure to yield 38 g. of a pale yellow oil, which is thereafter distilled under high vacuum, yielding 31.6 g. of methyl 2-acetoxy-5-bromo-pentanoate.

C. To a solution of 60 g. of the reaction product of part B of this example in 200 ml. of methanol is added 100 ml. of methanol, which is saturated with hydrobromic acid at 0° C. and 1.3 specific gravity before the addition. The reaction mixture is then allowed to stand at room temperature overnight. The solvent is thereafter evaporated under reduced pressure at 35° C. bath temperature and 400 ml. of toluene is thereafter added. The solvent is again evaporated. This residue is then dissolved in 2 l. of ethyl acetate, washed with 5 percent aqueous sodium hydroxide solution and sodium chloride solution before being dried over sodium sulfate. Filtration and evaporation of the solvent under reduced pressure at 45° C. yields 42 g. of oil which is distilled under high vacuum, yielding 28.8 g. of methyl 2-hydroxy-5-bromopentanoate.

D. To a solution of 34.4 g. of the reaction product of part C of this example and 400 ml. of acetone is added with stirring and cooling 75 ml. of Jones reagent (26.73 G. of $CrO_3$ in 23 ml. of concentrated sulfuric acid, diluted to 100 ml. with water) at such a rate that the reaction temperature is maintained between 30° and 40° C. The reaction is complete in approximately 20 min. Thereafter the reaction mixture is stirred for 1.5 hr. Thereafter 150 ml. of isopropyl alcohol are slowly added with stirring during 30 min. The reaction mixture is then diluted with 1.8 l. of water and extracted with 2.4 l. of methylene chloride. These extracts are washed with brine and dried with sodium sulfate. Filtration and evaporation of the solvent under reduced pressure yields 30.8 g. of a pale yellow oil, containing methyl 2-oxo-5-bromopentanoate. This oil is used in the following steps of this example without further purification.

E. With the exclusion of moisture under a nitrogen atmosphere 195 ml. of $M_0F_6 \cdot BF_3$ is cooled in a dry-ice acetone bath. A solution of 30.8 g. of the reaction product of step D of this example and 40 ml. of methylene chloride is added dropwise with stirring over a period of 15 min. The reaction temperature is maintained between −35° and −45° C. Stirring in the dry ice acetone bath is continued for one hr., the cooling bath thereafter is removed, and the reaction mixture thereafter diluted with 200 ml. of methylene chloride and 400 ml. of water. The organic and aqueous layers are separated, the aqueous layer being extracted with methylene chloride and the combined methylene chloride extracts washed with 250 ml. of water, 250 ml. of 5 percent aqueous potassium bicarbonate, 250 ml. of brine, and thereafter dried over sodium sulfate. Filtration and evaporation of the solvents yields 31.1 g. of a dark brown oil, which when distilled under high vacuum yields methyl 2,2-difluoro-5-bromopentanoate (14 g.).

F. The reaction product of part E of this example (28 g.) is stirred in 175 ml. of aqueous hydrobromic acid (specific gravity 1.71) for 3 hr. at room temperature. The reaction mixture is then cooled in an ice bath, and diluted with 1300 ml. of diethyl ether. The organic and aqueous layers are separated and the aqueous layer is extracted with diethyl ether. The combined ethereal extracts are washed with water and the aqueous phase backwashed with 400 ml. of diethyl ether. The combined ethereal solutions are then dried over sodium sulfate. Filtration and evaporation of the solvent yields 27.7 g. of a pale yellow oil, 2,2-difluoro-5-bromopentanoic acid, which is used in the following step of this example without further purification.

G. A mixture of 15.2 g. of the reaction product of part F of this example, 80 ml. of acetonitrile and 22 g. of triphenylphosphine are heated to reflux with stirring for 30 hr. The reaction mixture is then heated to 110° C., diluted with 160 ml. of toluene, and the mixture is allowed to cool slowly at room temperature for 12 hr. with stirring. The reaction mixture is then stored at 5° C. for 24 hr. A precipitate is collected, washed with 50 ml. of toluene, and dried under vacuum at room temperature. The title compound (20.9 g.) of this example is thereby obtained.

PREPARATION 3

(6-Carboxyhexyl)triphenylphosphonium bromide.

A mixture of 63.6 g. of 7-bromophetanoic acid, 80 g. of triphenylphosphine, and 30 ml. of acetonitrile, is refluxed for 68 hr. Thereafter 200 ml. of acetonitrile is removed by distillation. After the remaining solution is cooled to room temperature, 30 ml. of benzene is added with stirring. The mixture is then allowed to stand for 12 hr. A solid separates which is collected by filtration, yielding 134.1 g. of product, melting point 185°–187° C.

Following the procedure of Preparation 3, but using 3-bromopropionic acid, 4-bromobutanoic acid, 5-bromopentanoic acid, or 6-bromohexanoic acid, in place of 7-bromoheptanoic acid, there are prepared the corresponding (ω-carboxyalkyl)triphenylphosphonium bromides.

EXAMPLE 1

3-Oxo-5α-hydroxy-2β-benzyloxymethyl-1α-cyclopentaneacetic acid γ-lactone, 3-(ethylenethioketa) (Formula XII).

Refer to Chart A.

3α,5α-Dihydroxy-2β-benzyloxymethyl-1α-cyclopentaneacetic acid, γ-lactone (Formula XI, 12.43 g.) and 400 ml. of acetone are combined under a nitrogen atmosphere, with cooling to 0° C. To this solution is then added the Jones reagent (21.3 ml., prepared from 66.8 g. of chromium trioxide and 57.5 g. of concentrated sulfuric acid diluted to a total volume of 250 ml. with water). The resulting solution is then stirred at 0° C. for 20 min. and thereafter isopropanol (5 ml.) is added, followed by addition of solid sodium bicarbonate, adjusting the pH to 7. The reaction mixture is then filtered, concentrated, washed with brine, and extracted with ethyl acetate. The organic extracts are then washed with brine, dried over sodium sulfate, and concentrated to yield crude 3-oxa-5α-hydroxy-2β-benzyloxymethyl-1α-cyclopentaneacetic acid γ-lactone (12.74 g.) as a pale yellow oil.

The oil of the preceding paragraph (formula XII) is then dissolved in 200 ml. of carbon tetrachloride and 30 ml. of 1,2-ethanedithiol. Upon establishing an oxygen free atmosphere, boron trifluoride etherate (0.75 ml.) is then added to the reaction mixture. The resulting mixture is then stirred at 25° C. for 2 hr., and thereafter an additional portion of boron trifluoride etherate (0.25 ml.) is added. Stirring is continued for an additional hour and thereafter the reaction mixture is added to 300 ml. of a mixture of brine and 5 percent aqueous sodium hydroxide (ice-cold). The resulting aqueous phase is extracted with chloroform and combined with the organic fractions, and the combined fractions thereafter washed with a mixture of brine and 5 percent aqueous sodium hydroxide (ice-cold), brine, and dried over magnesium sulfate. The reaction mixture is then concentrated, yielding a pale yellow oil (20.81 g. ) of crude product. Purification by silica gel chromatography (using a column packed with 10 percent ethyl acetate and Skellysolve B) eluting with 10 to 60 percent ethyl acetate in Skellysolve B yields pure product (9.72 g.) as a colorless crystalline solid. Recrystallization from ethyl acetate and Skellysolve B yields a melting point of 115.3°–117.3° C. NMR absorptions are observed at 2.07–3.0, 3.27, 3.6–3.92, 4.52, 4.77–5.17, and 7.32 δ. Infrared absorptions are observed at 1765, 1580, 1495, 1165, 1090, 1040, 750, and 700 cm.$^{-1}$. The mass spectrum shows absorptions at 336, 308, 245, 202, 170, 127, 92, 91, 65, 61, and 44.

EXAMPLE 2

3α-(t-butyldimethylsilyloxy)-5α-hydroxy-2β-(3-oxo-trans-1-octenyl)-1α-cyclopentaneacetic acid γ-lactone (Formula XVII: $R_3$ and $R_4$ of the $L_1$ moiety are hydrogen, $R_7$ is n-butyl, and X is

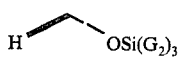

wherein —OSi($G_2$)$_3$ is t-butyldimethylsilyloxy).

Refer to Chart A.

A. 3α,5α-Dihydroxy-2β-benzyloxymethyl-1α-cyclopentaneacetic acid γ-lactone (Formula XI, 2.03 g.), 4 ml. of N,N-dimethylformamide, t-butyldimethylsilyl chloride (0.40 g.) and imidazole (1.32 g.) are combined with stirring for 10 hr. at 35° C. Thereafter, the mixture is cooled to ambient temperature, diluted with 300 ml. of brine and extracted with diethyl ether. The ethereal extracts are then washed with 1.2 N. aqueous hydrochloric acid, saturated aqueous sodium bicarbonate, brine, and dried over magnesium sulfate. Concentration under reduced pressure yields a pale tan oil (3.0 g.) which crystallizes on standing. Recrystallization from n-hexane yields 2.33 g. of pure product. Further, recrystallizations yield a melting point 43.7°–44.6° C. NMR absorptions are observed at 0.03, 0.86, 1.86–2.97, 3.35, 4.15, 4.47, 4.90, and 7.32 δ. Infrared absorptions are observed at 3060, 3040, 1755, 1600, 1585, 1500, 1355, 1255, 1180, 1175, 1125, 1110, 1095, 1030, 965, 890, 840, 780, 750, and 700 cm.$^{-1}$. The mass spectrum shows peaks at 376, 319, 181, 92, 77, 75, and 73.

B. The reaction product of part A above (1.00 g.), 30 ml. of tetrahydrofuran, and 200 ml. of 10 percent palladium-on-charcoal is hydrogenated at 16 pounds per square inch at ambient temperature for 13 hr. The resulting mixture is then filtered through Celite and concentrated under vacuum to yield a pale tan solid (0.89 g.). Recrystallization from n-hexane and ethyl acetate yields colorless plates (0.55 g.), melting point 67.2°–69.9° C. NMR absorptions are observed at 0.05, 0.87, 1.67–3.08, 3.60, 4.18, and 4.97 δ. The mass spectrum shows peaks at 286, 271, 229, 211, 194, 183, 168, 170, 137, 111, 105, 93, 91, 75, and 73.

C. Under a nitrogen atmosphere 65 ml. of tetrahydrofuran, cooled to 0° C. is combined with 0.46 g. of a 57 percent sodium hydride dispersion. To this mixture is added dropwise dimethyl (2-oxoheptyl)phosphonate (2.49 g.) in 10 ml. of tetrahydrofuran. The reaction mixture is allowed to warm to ambient temperature and left standing for about 1.5 hr. The resulting mixture is thereafter cooled to 0° C., thereby preparing the Wittig reagent.

Under a nitrogen atmosphere 82 ml. of methylene chloride is combined with 5.19 g. of pyridine. Cooling this mixture to 0° C. chromium trioxide (3.27 g.) is slowly added with stirring, allowing the resulting mixture to warm to ambient temperature. After cooling to 0° C. the formula XV alcohol (1.56 g.) in 10 ml. of methylene chloroform is added with vigorous stirring. The resulting mixture is then stirred at ambient temperature for 30 min. and thereafter combined with the Wittig reagent prepared above. After one hr. the reaction mixture is quenched by addition of 50 ml. of saturated aqueous sodium bisulfate, diluted with brine, and extracted with methylene chloride. The combined organic extracts are then washed with 1.2 N aqueous hydrochloric acid solution, saturated aqueous sodium bicarbonate, brine, and then dried over magnesium sulfate. Concentration under reduced pressure yields 3.62 g. of a dark oil. This oil is then chromatographed on silica gel (packed in 10 percent ethyl acetate in Skellysolve B), eluting with 10 to 50 percent ethyl acetate and Skellysolve B. From the 50 percent ethyl acetate in Skellysolve B elutant, there is obtained a crude yellow oil (2.2 g.) which on further chromatographic purification yields 1.78 g. of pure product. Crystallization from n-hexane yields colorless needles. Melting point is 61.3°–62.4° C. NMR absorptions are observed at 0.03, 0.86, 0.67–3.07, 4.07, 4.97, and 5.93–6.87 δ. The mass spectrum shows peaks at 324, 323, 113, 99, 75, 73, 71, 59, 43, and 41.

Following the procedure of Example 2, but using in place of dimethyl 2-oxo-heptylphosphonate, any of the various dimethyl phosphonates described hereinabove there are prepared the corresponding 3α-t-butyldimethylsilyloxy-5α-hydroxy-1α-cyclopentaneacetic acid γ lactones with a 2β-(3-oxo-trans-1-alkenyl)-substituent, optionally substituted, as follows:

4,4-difluorohexenyl; 4,4-difluoroheptenyl; 4,4-difluoroocetnyl; 4,4-difluorononenyl; 4,4-difluorodeceny; 4-fluorohexenyl; 4-fluoroheptenyl, 4-fluorooctenyl; 4-fluorononenyl; 4-fluorodecenyl; 4,4-dimethylhexenyl; 4,4-dimethylheptenyl, 4,4-dimethyloctenyl; 4,4-dimethylnonenyl; 4,4-dimethyldecenyl; 4-methylhexenyl; 4-methylheptenyl, 4-methyloctenyl, 4-methylnonenyl; 4-methyldecenyl; hexenyl; heptenyl; nonenyl; decenyl; 5-phenylpentenyl; 5-(m-trifluoromethylphenyl)-pentenyl; 5-(m-fluorophenyl)-pentenyl; 5-(m-chlorophenyl)-pentenyl; 5-(p-trifluromethylphenyl)-pentenyl; 5-(p-fluorophenyl)-pentenyl; 5-(p-chlorophenyl)-pentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pententyl; 4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-(m-chlorophenyl)pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4-fluoro-5-(m-chlorophenyl)-pentenyl; 4-fluoro-5-(p-trifluoromethylphenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenol; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)butenyl; 4-methyl-4-(p-chlorophenoxy)-butenyl; 4,4-dimethyl4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

EXAMPLE 3

3-Oxo-5α-hydroxy-2β-(3-oxo-trans-1-octenyl)-1α-cyclopentaneacetic acid γ-lactone, 3-(ethylenethioketal) (Formula XVII: $R_3$ and $R_4$ of the $L_1$ moiety are hydrogen, $R_7$ is n-butyl, and X is ethylenethioketal).

Refer to Chart A.

A. Employing boron tribromide, 3-oxo-5α-hydroxy-2β-benzyloxymethyl-1α-cyclopentaneacetic acid γ-lactone, 3-(ethylenethioketal) (Example 1, 9.75 g.) is deetherified, yielding 3-oxo-5α-hydroxy-2β-hydroxymethyl-1α-cyclopentaneacetic acid γ-lactone 3-(ethylenethioketal), 5.64 g. NMR absorptions at 1.95–3.27, 2.36, 3.33, 3.94, and 4.73–5.25 δ. Infrared absorptions are observed at 3430, 1770, 1745, 1225, 1190, 1160, and 1245. The mass spectrum shows absorptions at 246, 218, 147, 118, 61, 59, 58, 45, 41, and 27.

B. Following the procedure of Example 2, part C, the title compound is prepared (2.17 g.) as a colorless solid. Melting pont 65.4°–67.4° C. NMR absorptions are observed at 0.90, 0.9–1.9, 3.25, 4.77–5.18, and 6.05–7.10 δ. Infrared absorptions are observed at 1775, 1675, 1635, 1250, 1225, 1190, 1040, and 980 cm.$^{-1}$. Mass spectrum shows absorptions at 340, 312, 279, 241, 174, 99, 95, 71, 55, 43, 41, 29, and 27.

Following the procedure of Example 3, but using the various reagents described following Example 2, there are prepared the various 3-(ethylenethioketal) compounds corresponding to the 3-(t-butyldimethylsilyl ethers) described following Example 2.

EXAMPLE 4

3α-(t-Butyldimethylsilyloxy)-5α-hydroxy-2β-(3-oxo-cis-1-octenyl)-1α-cyclopentaneacetic acid γ-lactone (Formula XVIII: $R_3$ and $R_4$ of the $L_1$ moiety are hydrogen, $R_7$ is n-butyl, X is

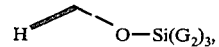

wherein -OSi $(G_2)_3$ is t-butyldimethylsilyloxy, and Y is cis-CH=CH—).

Refer to Chart A.

A solution of 16.3 g. of the reaction product of Example 2 in one l. of acetone (agitated by bubbling nitrogen through the solution) is irradiated for 3 hr. in a Raynot Photochemical Reactor (RPR-208, using 8 lamps) wherein the photo emission spectrum shows substantial intensity at a wave length at or around 3500 Angstroms. The solvent is then evaporated and the residue chromatographed on 1.5 kg. of silica gel packed in 10 percent ethyl acetate in cyclohexane. Elution, collecting 1.5 l. fractions, with 4.5 l. each of 10 percent, 15 percent, 20 percent, 25 percent, 30 percent, 35 percent, and 40 percent ethyl acetate in cyclohexane yields starting material and crude 3α-t-butyldimethylsilyloxy-5α-hydroxy-2β-(3-oxo-cis-1-octenyl)-1α-cyclopentaneacetic acid γ lactone. Further, chromatographic purification yields pure cis isomer.

Following the procedure of Example 4, but using in place of dimethyl 2-oxo-heptylphosphonate, any of the various dimethyl phosphonates described hereinabove there are prepared the corresponding 3α-t-butyldimethylsilyloxy-5α-hydroxy-1α-cyclopentaneacetic acid γ lactones with a 2β-(3 -oxo-cis-1-alkenyl)-substituent, optionally substituted. as follows:

4,4-difluorohexenyl; 4,4-difluoroheptenyl; 4,4-difluoroocetnyl; 4,4-difluorononenyl; 4,4-difluorodecenyl; 4-fluorohexenyl; 4-fluoroheptenyl, 4-fluoroocetenyl; 4-fluorononenyl; 4-fluorodecenyl; 4,4-dimethylhexenyl; 4,4-dimethylheptenyl, 4,4-dimethyloctenyl; 4,4-dimethylnonenyl; 4,4-dimethyldecenyl; 4-methylhexenyl; 4-methylheptenyl, 4-methyloctenyl; 4-methylnonenyl; 4-methyldecenyl; hexenyl; heptenyl; nonenyl; decenyl; 5-phenylpentenyl; 5-(m-trifluoromethylphenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5-(p-chlorophenyl)-pentenyl; 4-methyl-5-phenylpentenyl; 4-methyl-5-(m-trifluoromethylphenyl)-pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl; 4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-

(m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4-fluoro-5-(m-chlorophenyl)-pentenyl; 4-fluoro-5-(p-trifluoromethylphenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluormethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

Following the procedure of Example 4, but using dimethyl 2-oxo-cis-4-heptenylphosphonate in place of dimethyl 2-oxo-heptylphosphonate in Example 2 there is prepared 3α-t-butyldimethylsilyloxy-5α-hydroxy2β-(3-oxo-cis,cis-1,5-octadienyl)-1α-cyclopentaneacetic acid γ lactone. This cis,cis-1,5-octadienyl compound is separated from the mixture of cis,cis-1,5, and trans-1-cis-5-geometric isomers produced by the photoisomerization described in Example 4 by the chromatographic separation method described therein. The various other 3α-t-butyldimthylsilyloxy-5α-hydroxy-1α-cyclopentaneacetic acid γ lactones with 2β-(3-oxo-cis,cis-1,5-octadienyl)substituents are likewise prepared, e.g. 4-fluoro; 4-methyl; 4,4-dimethyl; and 4,4-difluoro.

EXAMPLE 5

3α-(t-Butyldimethylsilyloxy)-5α-hydroxy-2β-(3-oxo-octyl)-1α-cyclopentaneacetic acid γ-lactone (Formula XVIII: $R_3$ and $R_4$ of the $L_1$ moiety are hydrogen, $R_7$ is n-butyl, Y is —CH$_2$CH$_2$—, and X is

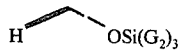

wherein —OSi(G$_2$)$_3$ is t-butyldimethylsilyloxy).

Refer to Chart A.

A mixture of the reaction product of Example 2, in methanol and sodium borohydride in water and methanol are stirred at ambient temperature under nitrogen for 20 min. Thereafter, acetic acid, water, and citric acid are successively added adjusting pH to 3. Thereafter, product is isolated and treated with Collins reagent at −20° C. for 20 min. Finally, the reaction is quenched and pure product is recovered.

Following the procedure of Example 4 or 5, but using the compound of Example 3 in place of the compound of Example 2 as starting material, there is prepared the 3-(ethylenethioketal) product corresponding to the 3-(5-butyldimethylsilyl ether) product of Example 4 or 5.

Following the procedure of Example 5, but using in place of dimethyl 2-oxo-heptylphosphonate, any of the various dimethyl phosphonates described hereinabove there are prepared the corresponding 3α-t-butyldimethylsilyloxy-5α-hydroxy-1α-cyclopentaneacetic acid γ lactones with a 2β-(3-oxo-alkyl)-substituent, optionally substituted, as follows:

4,4-difluorohexyl; 4,4-difluoroheptyl; 4,4-difluorooctyl; 4,4-difluorononyl; 4,4-difluorodecyl; 4-fluorohexyl; 4-fluoroheptyl; 4-fluorooctyl; 4-fluorononyl; 4-fluorodecyl 4,4-dimethylhexyl; 4,4-dimethylheptyl; 4,4-dimethyloctyl 4,4-dimethylnonyl; 4,4-dimethyldecyl; 4-methylhexyl; 4-methylheptyl, 4-methyloctyl, 4-methylnonyl; 4-methyldecyl; hexyl; heptyl; nonyl; decyl; 5-phenylpentyl; 5-(m-trifluoromethylphenyl)-pentyl; 5-(m-fluorophenyl)-pentyl; 5-(m-chlorophenyl)-pentyl; 5-(p-trifluoromethylphenyl)-pentyl; 5-(p-fluorophenyl)-pentyl; 5-(p-chlorophenyl)-pentyl; 4-methyl-5-phenylpentyl; 4-methyl-5-(m-trifluoromethylphenyl)-pentyl; 4-methyl-5-(m-fluorophenyl)-pentyl; 4-methyl-5-(p-trifluoromethylphenyl)-pentyl; 4-methyl-5-(p-fluorophenyl)-pentyl: 4-methyl-5-(p-chlorophenyl)-pentyl; 4,4-dimethyl-5-(m-trifluoromethylphenyl)-pentyl; 4,4-dimethyl-5-(m-fluorophenyl)-pentyl; 4,4-difluoro-5-(m-chlorophenyl)-pentyl; 4,4-dimethyl-5-(p-trifluoromethylphenyl)-pentyl; 4,4-dimethyl-5-(p-fluorophenyl)-pentyl; 4,4-dimethyl-5-(p-chlorophenyl)-pentyl; 4-fluoro-5-phenylpentyl; 4-fluoro-5-(m-trifluoromethylphenyl)-pentyl; 4-fluoro-5-(m-fluorophenyl)-pentyl; 4-fluoro-5-(m-chlorophenyl)-pentyl; 4-fluoro-5-(p-trifluoromethylphenyl)-pentyl; 4-fluoro-5-(p-fluorophenyl)-pentyl; 4-fluoro-5-(p-chlorophenyl)-pentyl; 4,4-difluoro-5-phenylpentyl; 4,4-difluoro-5-(m-trifluoromethylphenyl)-pentyl; 4,4-difluoro-5-(m-fluorophenyl)-pentyl; 4,4-difluoro-5-(m-chlorophenyl)-pentyl; 4,4-difluoro-5-(p-trifluoromethylphenyl)-pentyl; 4,4-difluoro-5-(p-fluorophenyl)-pentyl; 4,4-difluoro-5-(p-chlorophenyl)-pentyl; 4-phenoxybutyl; 4-(m-trifluoromethylphenoxy)-butyl; 4-(p-fluorophenoxy)-butyl; 4-(m-chlorophenoxy)-butyl; 4-(m-trifluoromethylphenoxy)-butyl; 4-(p-fluorophenoxy)-butyl; 4-(p-chlorophenoxy)-butyl; 4-methyl-4-phenoxy-butyl; 4-methyl-4-(m-trifluoromethylphenoxy)-butyl; 4-methyl-4-(m-fluorophenoxy)-butyl; 4-methyl-4-(m-chlorophenoxhy)-butyl; 4-methyl-4-(p-trifluoromethylphenoxy)-butyl; 4-methyl-4-(p-fluorophenoxy)-butyl; 4-methyl-4-(p-chlorophenoxy)-butyl; 4,4-dimethyl-4-phenoxybutyl; 4,4-dimethyl-4-(trifluoromethylphenoxy)-butyl; 4,4-dimethyl-4-(m-fluorophenoxy)-butyl; 4,4-dimethyl-4-(m-chlorophenoxy)-butyl; 4,4-dimethyl-4-(p-trifluoromethylphenoxy)-butyl; 4,4-dimethyl-4-(p-fluorophenoxy)-butyl; 4,4-dimethyl-4-(p-chlorophenoxy)-butyl; and the like.

Following the procedure of Example 5, but using the 2β-(3-oxo-trans-1, cis-5-octadienyl)-compounds described above, there is prepared 3α-t-butyldimethylsilyloxy-5α-hydroxy-2β-(3-oxo-cis-5-octenyl)-1α-cyclopentaneacetic acid γ lactone. This cis-5-octenyl compound is separated from the mixture of compounds produced by the reduction described in Example 5, by chromatographic separation. The various other 3α-t-butyldimethylsilyloxy-5α-hydroxy-1α-cyclopentaneacetic acid γ lactones with 2β-(3-oxo-cis-5-octenyl) substituents are likewise prepared, e.g. 4-fluoro-,4-methyl-, and 4,4-dimethyl-.

EXAMPLE 6

3α-(t-Butyldimethylsilyloxy)-5α-hydroxy-2β-[(3S)-3-hydroxy-trans-1-octenyl]-1α-cyclopentaneacetic acid γ-lactone, (Formula XIX: R₃ and R₄ of the L₁ moiety are hydrogen, R₇ is n-butyl, M₅ is

and X is

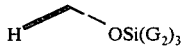

wherein —OSi(G₂)₃ is t-butyldimethylsilyloxy) or its (3R) epimer.

Refer to Chart A.

Sodium borohydride (0.23 g.) is combined with 25 ml. of absolute methanol under a nitrogen atmosphere, and to the resulting mixture cooled to −25° C. is added the title product of Example 2 (1.64 g.) in 10 ml. of methanol and 8 ml. of tetrahydrofuran. The mixture is stirred for 2.5 hr. at −25° C. and 1.3 ml. of acetic acid (−25° C.) is added. The reaction mixture is then allowed to warm to ambient temperature, concentrated under reduced pressure, and partitioned between 200 ml. of brine and 200 ml. of ethyl acetate. The organic fractions are then washed with 2M potassium bisulfate, saturated sodium bicarbonate, brine, and dried over magnesium sulfate. Concentration under reduced pressure yields a pale yellow oil (1.71 g.) which is subjected to silica gel chromatography, eluting with 35% ethyl acetate in Skellysolve B. There is obtained 1.00 g. of pure title product as a colorless oil and 0.72 g. of the (3R) epimer. The title product shows NMR absorptions at 0.03, 0.86, 0.62–3.00, 3.80–4.25, 4.97, and 5.38–5.68 δ. For the (3R)-epimer $R_f$ is 0.26 (silica gel TLC; 50 percent ethyl acetate in Skellysolve B).

Following the procedure of Example 6, but using in place of the compound of Example 2, the compound of Example 3, there is prepared the 3-(ethylenethioketal) product corresponding to the 3-(t-butyldimethylsilyl ether) of Example 6. Likewise, the corresponding (3R)-epimer is prepared. For the (3S)-epimer NMR absorptions are observed at 0.90, 0.9–1.85, 2.25–3.07, 3.27, 3.93–4.35, 4.68–5.13, and 5.63–5.80 δ. Infrared absorptions are observed at 3450, 1775, 1420, 1245, 1170, 1040, and 975 cm.⁻¹. The mass spectrum shows parent peak absorption at 414.1709. For the (3R)-epimer NMR absorptions are observed at 0.90, 0.9–1.80, 2.3–3.08, 3.27, 3.93–4.38, 4.70–5.13, and 5.72–5.80 δ. Infrared absorptions are observed at 3450, 1770, 1420, 1245, 1175, 1160, 1035, and 975 cm.⁻¹. The mass spectrum shows parent peak absorption at 414.1713 and other peaks at 399, 386, 343, 286, 199, and 173.

Following the procedure of Example 6, but using in place of the 3α-t-butyldimethylsilyloxy-5α-hydroxy-2β-(3-oxo-trans-1-octenyl)-1α-cyclopentaneacetic acid γ lactone starting material employed therein, the various 3α-t-butyldimethylsilyloxy-5α-hydroxy-2β-(3-oxo-cis- or trans-, 1-alkenyl; cis or trans-1, cis-5alkadienyl; alkyl, or substituted alkenyl; or alkadienyl; or alkyl)-1α-cyclopentaneacetic acid γ lactones there are prepared the corresponding (3R)- or (3S)-hydroxy products.

For example, there are obtained the above 3α-t-butyldimethylsilyloxy-5α-hydroxy-1α-cyclopentaneacetic acid γ lactones wherein the 2β-side chain in either the (3R) or (3S) form consists of 3-hydroxy-trans-1-hexenyl; 3-hydroxy-trans-1-heptenyl; 3-hydroxy-trans-1-nonenyl; 3-hydroxy-trans-1-decenyl; 3-hydroxy-trans-1, cis-5-octadienyl; 3-hydroxy-4-methyl-trans-1-octenyl; 3-hydroxy-4,4-dimethyl-trans-1,cis-5-octadienyl; 3-hydroxy-4,4-difluoro-trans-1,cis-5-octadienyl; 3-hydroxy-4-fluoro-trans-1-octenyl; 3-hydroxy-4,4-difluorotrans-1-octenyl; 3-hydroxy-5-phenyl-trans-1-pentenyl; 3-hydroxy-5-(p-fluorophenyl)-trans-1-pentenyl; 3-hydroxy-5-(m-chlorophenyl)-trans-1-pentenyl, 3-hydroxy-5-(m-trifluoromethylphenyl)-trans-1-pentenyl; 3-hydroxy-4,4-dimethyl-5-phenyl-trans-1-pentenyl; 3-hydroxy-4,4-dimethyl-5-(p-fluorophenyl)-trans-1-pentenyl; 3-hydroxy-4,4-dimethyl-5-(m-chlorophenyl)-trans-1-pentenyl; 3-hydroxy-4,4-dimethyl-5-(m-trifluoromethylphenyl)-trans-1-pentenyl; 3-hydroxy-4,4-difluoro-5-phenyl-trans-1-pentenyl; 3-hydroxy-4,4-difluoro-5-(p-fluorophenyl)-trans-1-pentenyl; 3-hydroxy-4,4-difluoro-5-(m-chlorophenyl)-trans-1-pentenyl; 3-hydroxy-4,4-difluoro-5-(m-trifluoromethylphenyl)-trans-1-pentenyl; 3-hydroxy-4-phenoxy-trans-1-butenyl; 3-hydroxy-4-(p-fluorophenoxy)-trans-1-butenyl; 3-hydroxy-4-(m-chlorophenoxy)-trans-1-butenyl; 3-hydroxy-4-(m-trifluoromethylphenoxy)-trans-1-butenyl; 3-hydroxy-4,4-dimethyl-4-phenoxy-trans-1-butenyl; 3-hydroxy-4,4-dimethyl-4-(p-fluorophenoxy)-trans-1-butenyl; 3-hydroxy-4,4-dimethyl-4-(m-chlorophenoxy)-trans-1-butenyl; 3-hydroxy-4,4-dimethyl-4-(n-trifluoromethylphenoxy)-trans-1-butenyl; 3-hydroxy-cis-1-hexenyl; 3-hydroxy-cis-1-heptenyl; 3-hydroxy-cis-1-octenyl; 3-hydroxy-cis-1-nonenyl; 3-hydroxy-cis-1-decenyl; 3-hydroxy-cis, cis-1,5-octadienyl; 3-hydroxy-4-methyl-cis-1-octenyl; 3-hydroxy-4,4-dimethyl-cis-1-octenyl; 3-hydroxy-4-fluoro-cis-1-octenyl; 3-hydroxy-4,4-difluoro-cis-1-octenyl; 3-hydroxy-5-phenyl-cis-1-pentenyl; 3-hydroxy-5-(p-fluorophenyl)-cis-1-pentenyl; 3-hydroxy-5-(m-chlorophenyl)-cis-1-pentenyl; 3-hydroxy-5-(m-trifluoromethylphenyl)-cis-1-pentenyl; 3-hydroxy-4,4-dimethyl-5-phenyl-cis-1-pentenyl; 3-hydroxy-4,4-dimethyl-5-(n-fluorophenyl)-cis-1-pentenyl; 3-hydroxy-4,4-dimethyl-5-(m-chlorophenyl)-cis-1-pentenyl; 3-hydroxy-4,4-dimethyl-5-(m-trifluoromethylphenyl)-cis-1-pentenyl; 3-hydroxy-4,4-difluoro-5-phenyl-cis-1-pentenyl; 3-hydroxy-4,4-difluoro-5-(p-fluorophenyl)-cis-1-pentenyl; 3-hydroxy-4,4-difluoro-5-(m-chlorophenyl)-cis-1-pentenyl; 3-hydroxy-4,4-difluoro-5-(m-trifluoromethylphenyl)-cis-1-pentenyl; 3-hydroxy-4-phenoxy-cis-1-butenyl; 3-hydroxy-4-(p-fluorophenoxy)-cis-1-butenyl; 3-hydroxy-4-(m-chlorophenoxy)-cis-1-butenyl; 3-hydroxy-4-(m-trifluoromethylphenoxy)-cis-1-butenyl; 3-hydroxy-4,4-dimethyl-4-phenoxy-cis-1-butenyl; 3-hydroxy-4,4-dimethyl-4-(p-fluorophenoxy)-cis-1-butenyl; 3-hydroxy-4,4-dimethyl-4-(m-chlorophenoxy)-cis-1-butenyl; 3-hydroxy-4,4-dimethyl-4-(m-trifluoromethylphenoxy)-cis-1-butenyl; 3-hydroxy-hexyl; 3-hydroxy-heptyl; 3-hydroxy-octyl; 3-hydroxy-nonyl; 3-hydroxy-decyl; 3-hydroxy-cis-5-octenyl; 3-hydroxy-4-methyl-octyl; 3-hydroxy-4,4-dimethyl-cis-5-octenyl; 3-hydroxy-4,4-difluoro-cis-5-octenyl; 3-hydroxy-4,4-dimethyl-octyl; 3-hydroxy-4-fluoro-octyl; 3-hydroxy-4,4-difluoro-octyl; 3-hydroxy-5-phenyl-pentyl; 3-hydroxy-5-(p-fluorophenyl)-pentyl; 3-hydroxy-5-(m-chlorophenyl)-pentyl; 3-hydroxy-5-(m-trifluoromethylphenyl)-pentyl; 3-hydroxy-4,4-dimethyl-5-phenyl-pentyl; 3-hydroxy-4,4-dimethyl-5-(p- fluorophenyl)-pentyl; 3-hydroxy-4,4-dimethyl-5-(m-chlorophenyl)-pentyl; 3-hydroxy-4,4-dimethyl-5-(m-trifluoromethylphenyl)pentyl; 3-hydroxy-4,4-difluoro-5-phenylpentyl; 3-hydroxy-4,4-difluoro-5-(p-fluorophenyl)-pentyl; 3-hydroxy-4,4-difluoro-5-(m-chlorophenyl)-pentyl; 3-hydroxy-4,4-difluoro-5-(m-trifluoromethylphenyl)-pentyl; 3-hydroxy-4-phenoxybutyl; 3-hydroxy-4-(p-fluorophenoxy)-butyl; 3-hydroxy-4-(m-chlorophenoxy)-butyl; 3-hydroxy-4-(m-trifluoromethylphenoxy)-butyl; 3-hydroxy-4,4-dimethyl-4-phenoxy-butyl; 3-hydroxy-4,4-dimethyl-4-(p-fluorophenoxy)-butyl; 3-hydroxy-4,4-dimethyl-4-(m-chlorophenoxy)-butyl; 3-hydroxy-4,4-dimethyl-4-(m-trifluoromethylphenoxy)-butyl; and the like.

EXAMPLE 7

3α-(t-Butyldimethylsilyloxy)-5α-hydroxy-2β-[(3S)-3-methoxy-trans-1-octenyl]-1α-cyclopentaneacetic acid γ-lactone (Formula XIX: R₃ and R₄ of the L₁ moiety are hydrogen, R₇ is n-butyl, M₅ is

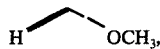

Y is trans-CH=CH—, and X is

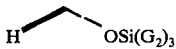

wherein —OSi(G₂)₃ is t-butyldimethylsilyloxy) or its (3R)-epimer.

Refer to Chart A.

The title compound of Example 6 (1.91 g.) silver oxide (4.08 g.), in 50 ml. of methyl iodide are stirred and heated at reflux for 68 hr. Thereafter chloroform (25 ml.) is added and the mixture is filtered. The filtrate is then concentrated to an oil which is taken up in chloroform (50 ml.) This solution is then washed with brine, dried over magnesium sulfate, and concentrated to an oil. Title product is then separated from the resulting mixture by silica gel chromatography, eluting with ethyl acetate and Skellysolve B.

The (3R)-epimeric product is likewise obtained from (3R)-epimeric starting material.

Reacting successively with NaH and CH₃I, the 3-(ethylenethioketal) starting material described following Example 6, is transformed to a 3-(ethylenethioketal) product corresponding to the 3-(t-butyldimethylsilyl ether) product of Example 7.

Following the procedure of Example 7, but using in place of the 3α-t-butyldimethylsilyloxy-5α-hydroxy-2β-[(3R)- or (3S)-hydroxy-trans-1-octenyl]-1α-cyclopentaneacetic acid γ lactone starting material employed therein, the various 3α-t-butyldimethylsilyloxy-5α-hydroxy-2β-[(3R) or (3S)-hydroxy-cis- or trans-1-alkenyl; cis- or trans-1,cis-5-alkadienyl; or alkyl; or substituted alkenyl; alkadienyl; or alkyl)]-1α-cyclopentaneacetic acid γ lactones there are prepared the corresponding (3R)- or 3(S)- methoxy products. For example, there are obtained the above 3α-t-butyldimethylsilyloxy-5α-hydroxy-1α-cyclopentaneacetic acid γ lactones wherein the 2β-side chain in either the (3R) or (3S) form consists of 3-methoxy-trans-1-hexenyl; 3-methoxy-trans-1-heptenyl; 3-methoxy-trans-1-octenyl; 3-methoxy-trans-1-nonenyl; 3-methoxy-trans-1-decenyl; 3-methoxy-trans-1, cis-5-octadienyl; 3-methoxy-4-methyl-trans-1-octenyl; 3-methoxy-4,4-dimethyl-trans-1-octenyl; 3-methoxy-4,4-dimethyl-trans-1,cis-5-octadienyl; 3-methoxy-4,4-difluoro-trans-1,cis-5-octaidenyl; 3-methoxy-4-fluoro-trans-1-octenyl; 3-methoxy-4-fluoro-trans-1-octenyl; 3-methoxy-4,4-difluoro-trans-1-octenyl; 3-methoxy-5-phenyl-trans-1-pentenyl; 3-methoxy-5-(p-fluorophenyl)-trans-1-pentenyl; 3-methoxy-5-(m-chlorophenyl)-trans-1-pentenyl; 3-methoxy-5-(m-trifluoromethylphenyl)-trans-1-pentenyl; 3-methoxy-4,4-dimethyl-5-phenyl-trans-1-pentenyl; 3-methoxy-4,4-dimethyl-5-(p-fluorophenyl)-trans-1-pentenyl; 3-methoxy-4,4-dimethyl-5-(m-chlorophenyl)-trans-1-pentenyl; 3-methoxy-4,4-dimethyl-5-(m-trifluoromethylphenyl)-trans-1-pentenyl; 3-methoxy-4,4-difluoro-5-phenyl-trans-1-pentenyl; 3-methoxy-4,4-difluoro-5-(p-fluorophenyl)-trans-1-pentenyl; 3-methoxy-4,4-difluoro-5-(m-chlorophenyl)-trans-1-pentenyl; 3-methoxy-4,4-difluoro-5-(m-trifluoromethylphenyl)-trans-1-pentenyl; 3-methoxy-4-phenoxy-trans-1-butenyl; 3-methoxy-4-(p-fluorophenoxy)-trans-1-butenyl; 3-methoxy-4-(m-chlorophenoxy)-trans-1-butenyl; 3-methoxy-4-(m-trifluoromethylphenoxy)-trans-1-butenyl; 3-methoxy-4,4-dimethyl-4-phenoxy-trans-1-butenyl; 3-methoxy-4,4-dimethyl-4-(p-fluorophenoxy)-trans-1-butenyl; 3-methoxy-4,4-dimethyl-4-(m-chlorophenoxy)-trans-1-butenyl; 3-methoxy-4,4-dimethyl-4-(m-trifluoromethylphenoxy)-trans-1-butenyl; 3-methoxy-cis-1-hexenyl; 3-methoxy-cis-1-heptenyl; 3-methoxy-cis-1-octenyl; 3-methoxy-cis-1-nonenyl; 3-methoxy-cis-1-decenyl; 3-methoxy-cis,cis-1,5-octadienyl; 3-methoxy-4-methyl-cis-1-octenyl; 3-methoxy-4,4-dimethyl-cis-1-octenyl; 3-methoxy-4,4-dimethyl-cis,cis-1,5-octadienyl; 3-methoxy-4,4-difluoro-cis,cis-1,5-octadienyl; 3-methoxy-4-fluoro-cis-1-octenyl; 3-methoxy-4,4-difluoro-cis-1-octenyl; 3-methoxy-5-phenyl-cis-1-pentenyl; 3-methoxy-5-(p-fluorophenyl)-cis-1-pentenyl; 3-methoxy-5-(m-chlorophenyl)-cis-1-pentenyl; 3-methoxy-5-(m-trifluoromethylphenyl)-cis-1-pentenyl; 3-methoxy-4,4-dimethyl-5-phenyl-cis-1-pentenyl; 3-methoxy-4,4-dimethyl-5-(p-fluorophenyl)-cis-1-pentenyl; 3-methoxy-4,4-dimethyl-5-(m-chlorophenyl)-cis-1-pentenyl; 3-methoxy-4,4-dimethyl-5-(m-trifluoromethylphenyl)-cis-1-pentenyl; 3-methoxy-4,4-difluoro-5-phenyl-cis-1-pentenyl; 3-methoxy-4,4-difluoro-5-(p-fluorophenyl)-cis-1-pentenyl; 3-methoxy-4,4-difluoro-5-(m-chlorophenyl)-cis-1-pentenyl; 3-methoxy-4,4-difluoro-5-(m-trifluoromethylphenyl)-cis-1-pentenyl; 3-methoxy-4-phenoxy-cis-1-butenyl; 3-methoxy-4-(p-fluorophenoxy)-cis-1-butenyl; 3-methoxy-4-(m-chlorophenoxy)-cis-1-butenyl; 3-methoxy-4-(m-trifluoromethylphenoxy)-cis-1-butenyl; 3-methoxy-4,4-dimethyl-4-phenoxy-cis-1-butenyl; 3-methoxy-4,4-dimethyl-4-(p-fluorophenoxy)-cis-1-butenyl; 3-methoxy-4,4-dimethyl-4-(m-chlorophenoxy)-cis-1-butenyl; 3-methoxy-4,4-dimethyl-4-(m-trifluoromethylphenoxy)-cis-1-butenyl; 3-methoxyhexyl; 3-methoxy-heptyl; 3-methoxy-octyl; 3-methoxy-nonyl; 3-methoxy-decyl; 3-methoxy-cis-5-octenyl; 3-methoxy-4-methyl-octyl; 3-methoxy-4,4-dimethyl-octyl; 3-methoxy 4,4-dimethyl-cis-5-octenyl; 3-methoxy-4,4-difluoro-cis-5-octenyl; 3-methoxy-4-fluoro-octyl; 3-methoxy-4,4-difluorooctyl; 3-methoxy-5-phenyl-pentyl; 3-methoxy-5-(p-fluorophenyl)-pentyl; 3-methoxy-5-(m-chlorophenyl)-pentyl; 3-methoxy-5-(m-trifluoromethylphenyl)-pentyl; 3-methoxy-4,4-dimethyl-5-phenyl-pentyl; 3-methoxy-4,4-dimethyl-5-(p-fluorophenyl)-pentyl; 3-methoxy-4,4-dimethyl-5-(m-chlorophenyl)-pentyl; 3-methoxy-4,4-dimethyl-5-(m-trifluoromethylphenyl)-pentyl; 3-methoxy-4,4-difluoro-5-phenyl-pentyl; 3-methoxy-4,4-difluoro-5-(p-fluorophenyl)-pentyl; 3-methoxy-4,4-difluoro-5-(m-chlorophenyl)-pentyl; 3-methoxy-4,4-difluoro-5-(m-trifluoromethylphenyl)-pentyl; 3-methoxy-4-phenoxybutyl; 3-methoxy-4-(p-fluorophenoxy)-butyl; 3-hydroxy-4-(m-chlorophenoxy)-butyl; 3-methoxy-4-(m-trifluoromethylphenoxy)-butyl; 3-methoxy-4,4-dimethyl-4-phenoxybutyl; 3-methoxy-4,4-dimethyl-4-(p-fluorophenoxy)-butyl; 3-methoxy-4,4-dimethyl-4-(m-chlorophenoxy)-butyl; 3-methoxy-4,4-dimethyl-4-(m-trifluoromethylphenoxy)-butyl; and the like.

EXAMPLE 8

3α-t-Butyldimethylsilyloxy-5α-hydroxy-2α-[(3RS)-3-hydroxy-3-methyl-trans-1-octenyl]-1α-cyclopentaneacetic acid γ-lactone (Formula XIX: $R_3$ and $R_4$ of the $L_1$ moiety are hydrogen, $R_7$ is n-butyl, $M_5$ is a mixture of

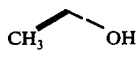

and

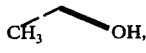

Y is trans-CH=CH—, and X is

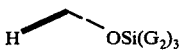

wherein —OSi($G_2$)$_3$ is t-butyldimethylsilyloxy).

Refer to Chart A.

A solution of 18 g. of 3α-t-butyldimethylsilyloxy-5α-hydroxy-2β-(3-oxo-cis-1-octenyl)-1α-cyclopentaneacetic acid γ lactone at 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hr. at 20°-25° C. then cooled to 10° C. Thereupon 370 ml. of saturated ammonium chloride is slowly added at such a rate so as to maintain the reaction mixture at ambient temperature. After 0.5 hr. the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield 20 g. of an oil, which is chromatographed on one kg. of silica gel packed in 10 percent ethyl acetate in Skellysolve B, eluting with 10 to 16 percent ethyl acetate in Skellysolve B (18 l.), thereby yielding pure 3(RS)-product.

Following the procedure of Example 7, but using in place of the 3α-t-butyldimethylsilyloxy-5α-hydroxy-2β-(3-oxo-trans-1-octenyl)-1α-cyclopentaneacetic acid γ lactone starting material employed therein, the various 3α-t-butyldimethylsilyloxy-5α-hydroxy-2β-(3-oxo-cis- or transalkenyl; cis- or trans-1,cis-5-alkadienyl; alkyl, or substituted alkenyl; alkadienyl; or alkyl)-1α-cyclopentaneacetic acid γ lactones there are prepared the corresponding 3-methyl-(3RS)-hydroxy products.

For example, there are obtained the above 3α-t-butyl-dimethylsilyloxy-5α-hydroxy-1α-cyclopentaneacetic acid γ lactones wherein the 2β-side chain in (3RS) form consists of 3-methyl-3-hydroxy-trans-1-hexenyl; 3-methyl-3-hydroxy-trans-1-heptenyl; 3-methyl-3-hydroxy-trans-1-nonenyl; 3-methyl-3-hydroxy-trans-1-decenyl; 3-methyl-3-hydroxy-trans-1,cis-5-octadienyl; 3-methyl-3-hydroxy-4-methyl-trans-1-octenyl; 3-methyl-3-hydroxy-4,4-dimethyl-trans-1-octenyl; 3-methyl-4,4-dimethyl-trans-1,cis-5-octadienyl; 3-methyl-3-hydroxy-4,4-difluoro-trans-1,cis-5-octadienyl; 3-methyl-3-hydroxy-4-fluoro-trans-1-octenyl; 3-methyl-3-hydroxy-4,4-difluoro-trans-1-octenyl; 3-methyl-3-hydroxy-5-phenyl-trans-1-pentenyl; 3-methyl-3-hydroxy-5-(p-fluorophenyl)-trans-1-pentenyl; 3-methyl-3-hydroxy-5-(m-chlorophenyl)-trans-1-pentenyl; 3-methyl-3-hydroxy-5-(m-trifluoromethylphenyl)-trans-1-pentenyl; 3-methyl-3-hydroxy-4,4-dimethyl-5-phenyl-trans-1-pentenyl; 3-methyl-3-hydroxy-4,4-dimethyl-5-(p-fluorophenyl)-trans-1-pentenyl; 3-methyl-3-hydroxy-4,4-dimethyl-5-(m-chlorophenyl)-trans-1-pentenyl; 3-methyl-3-hydroxy-4,4-dimethyl-5-(m-trifluoromethylphenyl)-trans-1-pentenyl; 3-methyl-3-hydroxy-4,4-difluoro-5-phenyl-trans-1-pentenyl; 3-methyl-3-hydroxy-4,4-difluoro-5-(p-fluorophenyl)-trans-1-pentenyl; 3-methyl-3-hydroxy-4,4-difluoro-5-(m-chlorophenyl)-trans-1-pentenyl; 3-methyl-3-hydroxy-4,4-difluoro-5-(m-trifluoromethylphenyl)-trans-1-pentenyl; 3-hydroxy-4-phenoxy-trans-1-butenyl; 3-methyl-3-hydroxy-4-(p-fluorophenoxy)-trans-1-butenyl; 3-methyl-3-hydroxy-4-(m-chlorophenoxy)-trans-1-butenyl; 3-methyl-3-hydroxy-4-(m-trifluoromethylphenoxy)-trans-1-butenyl; 3-methyl-3-hydroxy-4,4-dimethyl-4-phenoxy-trans-1-butenyl; 3-3-hydroxy-4,4-dimethyl-4-(p-fluorophenoxy)-trans-1-butenyl; 3-methyl-3-hydroxy-4,4-dimethyl-4-(m-chlorophenoxy)-trans-1-butenyl; 3-methyl-3-hydroxy-4,4-dimethyl-4-(m-trifluoromethylphenoxy)-trans-1-butenyl; 3-methyl-3-hydroxy-cis-1-hexenyl; 3-methyl-3-hydroxy-cis-1-heptenyl; 3-methyl-3-hydroxy-cis-1-octenyl; 3-methyl-3-hydroxy-cis-1-nonenyl; 3-methyl-3-hydroxy-cis-1-decenyl; 3-methyl-3-hydroxy-cis,cis-1,5-octadienyl; 3-methyl-3-hydroxy-4,4-dimethyl-cis,cis-1,5-octadienyl; 3-methyl-3-hydroxy-4,4-difluoro-cis,cis-1,5-octadienyl; 3-methyl-3-hydroxy-4-methyl-cis-1-octenyl; 3-methyl-3-hydroxy-4,4-dimethyl-cis-1-octenyl; 3-methyl-3-hydroxy-4-fluoro-cis-1-octenyl; 3-methyl-3-hydroxy-4,4-difluoro-cis-1-octenyl; 3-methyl-3-hydroxy-5-phenyl-cis-1-pentenyl; 3-methyl-3-hydroxy-5-(p-fluorophenyl)-cis-1-pentenyl; 3-methyl-3-hydroxy-5-(m-chlorophenyl)-cis-1-pentenyl; 3-methyl-3-hydroxy-5-(m-trifluoromethylphenyl)-cis-1-pentenyl; 3-methyl-3-hydroxy-4,4-dimethyl-5-phenyl-cis-1-pentenyl; 3-methyl-3-hydroxy-4,4-dimethyl-5-(p-fluorophenyl)-cis-1-pentenyl; 3-methyl-3-hydroxy-4,4-dimethyl-5-(m-chlorophenyl)-cis-1-pentenyl; 3-methyl-3-hydroxy-4,4-dimethyl-5-(m-trifluoromethylphenyl)-cis-1-pentenyl; 3-methyl-3-hydroxy-4,4-difluoro-5-phenyl-cis-1-pentenyl; 3-methyl-3-hydroxy-4,4-difluoro-5-(p-fluorophenyl)-cis-1-pentenyl; 3-methyl-3-hydroxy-4,4-difluoro-5-(m-chlorophenyl)-cis-1-pentenyl; 3-methyl-3-hydroxy-4,4-difluoro-5-(m-trifluoromethylphenyl)-cis-1-pentenyl; 3-methyl-3-hydroxy-4-phenoxy-cis-1-butenyl; 3-methyl-3-hydroxy-4-(p-fluorophenoxy)-cis-1-butenyl; 3-methyl-3-hydroxy-4-(m-chlorophenoxy)-cis-1-butenyl; 3-methyl-3-hydroxy-4-(m-trifluoromethylphenoxy)-cis-1-butenyl; 3-methyl-3-hydroxy-4,4-dimethyl-4-phenoxy-cis-1-butenyl; 3-methyl-3-hydroxy-4,4-dimethyl-4-(p-fluorophenoxy)-cis-1-butenyl; 3-methyl-3-hydroxy-4,4-dimethyl-4-(m-chlorophenoxy)-cis-1-butenyl; 3-methyl-3-hydroxy-4,4- dimethyl-4-(m-trifluoromethylphenoxy)-cis-1-butenyl; 3-methyl-3-hydroxy-hexyl; 3-methyl-3-hydroxy-heptyl; 3-methyl-3-hydroxy-octyl; 3-methyl-3-hydroxy-nonyl; 3-methyl-3-hydroxy-decyl; 3-methyl-3-hydroxy-cis-5-octenyl; 3-methyl-3-hydroxy-4,4-dimethyl-cis-5-octenyl; 3-methyl-3-hydroxy-4,4-difluoro-cis-5-octenyl; 3-methyl-3-hydroxy-4-methyl-octyl; 3-methyl-3-hydroxy-4,4-dimethyl-octyl; 3-methyl-3-hydroxy-4-fluoro-octyl; 3-methyl-3-hydroxy-4,4-difluoro-octyl; 3-methyl-3-hydroxy-5-phenyl-pentyl; 3-methyl-3-hydroxy-4-(p-fluorophenyl)-pentyl; 3-methyl-3-hydroxy-5-(m-chlorophenyl)-pentyl; 3-methyl-3-hydroxy-5-(m-trifluoromethylphenyl)-pentyl; 3-methyl-3-hydroxy-4,4-dimethyl-5-phenyl-pentyl; 3-methyl-3-hydroxy-4,4-dimethyl-5-(p-fluorophenyl)-pentyl; 3-methyl-3-hydroxy-4,4-dimethyl-5-(m-chlorophenyl)-pentyl; 3-methyl-3-hydroxy-4,4-dimethyl-5-(m-trifluoromethylphenyl)-pentyl; 3-methyl-3-hydroxy-4,4-difluoro-5-phenyl-pentyl; 3-methyl-3-hydroxy-4,4-difluoro-5-(p-fluorophenyl)-pentyl; 3-methyl-3-hydroxy-4,4-difluoro-5-(m-chlorophenyl)-pentyl; 3-methyl-3-hydroxy-4,4-difluoro-5-(m-trifluoromethylphenyl)-pentyl; 3-methyl-3-hydroxy-4-phenoxy-butyl; 3-methyl-3-hydroxy-4-(p-fluorophenoxy)-butyl; 3-methyl-3-hydroxy-4-(m-chlorophenoxy)-butyl; 3-methyl-3-hydroxy-4-(m-trifluoromethylphenoxy)-butyl; 3-methyl-3-hydroxy-4,4-dimethyl-4-phenoxy-butyl; 3-methyl-3-hydroxy-4,4-dimethyl-4-(p-fluorophenoxy)-butyl; 3-methyl-3-hydroxy-4,4-dimethyl-4-(m-chlorophenoxy)-butyl; 3-methyl-3-hydroxy-4,4-dimethyl-4-(m-trifluoromethylphenoxy)-butyl; and the like.

EXAMPLE 9

3α-(t-Butyldimethylsilyloxy)-5α-hydroxy-2β-[(3S)-31-hydroxy-trans-1-octenyl]-1α-cyclopentaneacetaldehyde γ lactol, 3-(tetrahydropyranyl ether) (Formula XXI: $R_3$ and $R_4$ of the $L_1$ moiety are both hydrogen, $M_6$ is

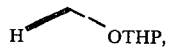

$R_7$ is n-butyl, Y is trans-CH=CH—, and Y is

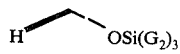

wherein —OSi($G_2$)$_3$ is t-butyldimethylsilyloxy) or its (3R) epimer.

Refer to Chart A.

A. The title product of Example 6 (1.00 g.). 20 ml. of methylene cloride, 1.5 g. of dihydropyran, and 0.15 g. of pyridine hydrochloride are combined with stirring at ambient temperature for 2 days, and thereafter partitioned between 300 ml. of ethyl acetate and 300 ml. of saturated aqueous sodium bicarbonate. The organic fraction is washed with brine, dried over sodium sulfate, and concentrated under reduced pressure to yield 1.36 g. of crude product, an oil, which is purified on 60 g. of silica gel packed in 10 percent ethyl acetate in Skellysolve B eluting with 10 to 30 percent ethyl acetate in Skellysolve B. Thereafter pure 3α-(t-butyldimethylsilyloxy)-5α-hydroxy-2β-[(3S)-3-hydroxy-trans-1-octenyl]-1α-cyclopentaneacetic γ lactone, 3-(tetrahydropyranyl ether), 1.19 g., is obtained as an oil. NMR absorptions are observed at 0.03, 0.86, 0.63–3.08, 3.17–4.33, 4.65, 4.93, and 5.28–5.68 δ.

B. The reaction product of step A above (1.19 g.) is combined with 15 ml. of toluene under a nitrogen atmosphere, with cooling to −78° C. A solution of 10 percent diisobutylaluminum hydride in toluene (7.6 ml.) is then added dropwise during 5 to 10 min. After 1.5 hr. (maintaining the reaction temperature at −78° C.) excess hydride is destroyed by cautious addition of 10 ml. of tetrahydrofuran and water (2:1). The reaction mixture is then allowed to warm to ambient temperature, with stirring, filtered through Celite, diluted with 300 ml. of ethyl acet, and washed successively with 2M aqueous potassium bisulfate, saturated aqueous sodium bicarbonate, and brine. The mixture is then dried over sodium sulfate and concentrated under reduced pressure to yield title product (1.24 g.) as a colorless oil which slowly solidified. $R_f$ values are 0.19 and 0.24 in 25% ethyl acetate in Skellysolve B and 0.54 and 0.59 in 50% ethyl acetate in Skellysolve B (silica gel TLC).

Following the procedure of Example 9, but using in place of the 3α-t-butyldimethylsilyloxy-5α-hydroxy-2β-[(3S)-3-hydroxy-trans-1-octenyl]-1α-cyclopentaneacetic acid γ lactone starting material employed therein, the various 3α-t-butyldimethylsilyloxy-5α-hydroxy-2β-[(3R)- or (3S)-3-hydroxy-cis- or trans-1-alkenyl; cis- or trans-1,cis-5-alkadienyl; alkyl; or substituted alkenyl; alkadienyl; or alkyl;]-1α-cyclopentaneacetic acid γ lactones described following Example 6, there are prepared the corresponding 3-(tetrahydropyranyl ethers) of the (3R)- or (3S)-3-hydroxy products.

For example, there are obtained the above 3α-t-butyldimethylsilyloxy-5α-hydroxy-1α-cyclopentaneacetaldehyde γ lactol 3-(tetrahydropyranyl ethers) wherein the 2β-side chain in either the (3R) or (3S) form consists of the 3-(tetrahydropyranyl ethers) of 3-hydroxy-trans-1-hexenyl; 3-hydroxy-trans-1-heptenyl; 3-trans-1-nonenyl; 3-hydroxy-trans-1-decenyl; 3-hydroxy-trans-1,cis-5-octadienyl; 3-hydroxy-4,4-dimethyl-trans-1,cis-5-octadienyl; 3-hydroxy-4,4-difluoro-trans-1-cis-5-octadienyl; 3-hydroxy-4-methyl-trans-1-octenyl; 3-hydroxy-4,4-dimethyl-trans-1-octenyl; 3-hydroxy-4-fluoro-trans-1-octenyl; 3-hydroxy-4,4-difluoro-trans-1-octenyl; 3-hydroxy-5-phenyl-trans-1-pentenyl; 3-hydroxy-5-(p-fluorophenyl)-trans-1-pentenyl; 3-hydroxy-5-(m-chlorophenyl)-trans-1-pentenyl; 3-hydroxy-5-(m-trifluoromethylphenyl)-trans-1-pentenyl; 3-hydroxy-4,4-dimethyl-5-phenyl-trans-1-pentenyl; 3-hydroxy-4,4-dimethyl-5-(p-fluorophenyl)-trans-1-pentenyl; 3-hydroxy-4,4-dimethyl-5-(m-chlorophenyl)-trans-1-pentenyl; 3-hydroxy-4,4-dimethyl-5-(m-trifluoromethylphenyl)-trans-1-pentenyl; 3-hydroxy-4,4-difluoro-5-phenyl-trans-1-pentenyl; 3-hydroxy-4,4-difluoro-5-(p-fluorophenyl)-trans-1-pentenyl; 3-hydroxy-4,4-difluoro-5-(m-chlorophenyl)-trans-1-pentenyl; 3-hydroxy-4,4-difluoro-5-(m-trifluoromethylphenyl)-trans-1-pentenyl; 3-hydroxy-4-phenoxy-trans-1-butenyl; 3-hydroxy-4-(p-fluorophenoxy)-trans-1-butenyl; 3-hydroxy-4-(m-chlorophenoxy)-trans-1-butenyl; 3-hydroxy-4-(m-trifluoromethylphenoxy)-trans-1-butenyl; 3-hydroxy-4,4-dimethyl-4-phenoxy-trans-1-butenyl; 3-hydroxy-4,4-dimethyl-4-(p-fluorophenoxy)-trans-1-butenyl; 3-hydroxy-4,4-dimethyl-4-(m-chlorophenoxy)-trans-1-butenyl; 3-hydroxy-4,4-dimethyl-4-(m-trifluoromethylphenoxy)-trans-1-butenyl; 3-hydroxy-cis-1-hexenyl; 3-hydroxy-cis-1-heptenyl; 3-hydroxy-cis-1-octenyl; 3-hydroxy-cis-1-nonenyl; 3-hydroxy-cis-1-decenyl; 3-hydroxy-cis,cis-1,5-octadienyl; 3-hydroxy-4- methyl-cis-1-octenyl; 3-hydroxy-4,4-dimethyl-cis-1-octenyl; 3-hydroxy-4-fluoro-cis-1-octenyl; 3-hydroxy-4,4-difluoro-cis-1-octenyl; 3-hydroxy-5-phenyl-cis-1-pentenyl; 3-hydroxy-5-(p-fluorophenyl)-cis-1-pentenyl; 3-hydroxy-5-(m-chlorophenyl)-cis-1-pentenyl; 3-hydroxy-5-(m-trifluoromethylphenyl)-cis-1-pentenyl; 3-hydroxy-4,4-dimethyl-5-phenyl-cis-1-pentenyl; 3-hydroxy-4,4-dimethyl-5-(p-fluorophenyl)-cis-1-pentenyl; 3-hydroxy-4,4-dimethyl-5-(m-chlorophenyl)-cis-1-pentenyl; 3-hydroxy-4,4-dimethyl-5-(m-trifluoromethylphenyl)-cis-1-pentenyl; 3-hydroxy-4,4-difluoro-5-phenyl-cis-1-pentenyl; 3-hydroxy-4,4-difluoro-5-(p-fluorophenyl)-cis-1-pentenyl; 3-hydroxy-4,4-difluoro-5-(m-chlorophenyl)-cis-1-pentenyl; 3-hydroxy-4,4-difluoro-5-(m-trifluoromethyl-phenyl)-cis-1-pentenyl; 3-hydroxy-4-phenoxy-cis-1-butenyl; 3-hydroxy-4-(p-fluorophenoxy)-cis-1-butenyl; 3-hydroxy-4-(m-chlorophenoxy)-cis-1-butenyl; 3-hydroxy-4-(m-trifluoromethylphenoxy)-cis-1-butenyl; 3-hydroxy-4,4-dimethyl-4-phenoxy-cis-1-butenyl; 3-hydroxy-4,4-dimethyl-4-(p-fluorophenoxy)-cis-1-butenyl; 3-hydroxy-4,4-dimethyl-4-(m-chlorophenoxy)-cis-1-butenyl; 3-hydroxy-4,4-dimethyl-4-(m-trifluoromethylphenoxy)-cis-1-butenyl; 3-hydroxy-hexyl; 3-hydroxy-heptyl; 3-hydroxy-octyl; 3-hydroxy-nonyl; 3-hydroxy-decyl; 3-hydroxy-cis-5-octenyl; 3-hydroxy-4,4-dimethyl-cis-5-octenyl; 3-hydroxy-4,4-difluoro-cis-5-octenyl; 3-hydroxy-4-methyl-octyl; 3-hydroxy-4,4-dimethyl-octyl; 3-hydroxy-4-fluoro-octyl; 3-hydroxy-4,4-difluoro-octyl; 3-hydroxy-5-phenyl-pentyl; 3-hydroxy-5-(p-fluorophenyl)-pentyl; 3-hydroxy-5-(m-chlorophenyl)-pentyl; 3-hydroxy-5-(m-trifluoromethylphenyl)-pentyl; 3-hydroxy-4,4-dimethyl-5-phenyl-pentyl; 3-hydroxy-4,4-dimethyl-5-(p-fluorophenyl)-pentyl; 3-hydroxy-4,4-dimethyl-5-(m-chlorophenyl)-pentyl; 3-hydroxy-4,4-dimethyl-5-(m-trifluoromethylphenyl)-pentyl; 3-hydroxy-4,4-difluoro-5-phenyl-pentyl; 3-hydroxy-4,4-difluoro-5-(p-fluorophenyl)-pentyl; 3-hydroxy-4,4-difluoro-5-(m-chlorophenyl)-pentyl; 3-hydroxy-4,4-difluoro-5-(m-trifluoromethylphenyl)-pentyl; 3-hydroxy-4-phenoxy-butyl; 3-hydroxy-4-(p-fluorophenoxy)-butyl; 3-hydroxy-4-(m-chlorophenoxy)-butyl; 3-hydroxy-4-(m-trifluoromethylphenoxy)-butyl; 3-hydroxy-4,4-dimethyl-4-phenoxy-butyl; 3-hydroxy-4,4-dimethyl-4-(p-fluorophenoxy)-butyl; 3-hydroxy-4,4-dimethyl-4-(m-chlorophenoxy)-butyl; 3-hydroxy-4,4-dimethyl-4-(m-trifluoromethylphenoxy)-butyl; and the like.

Following the procedure of Example 9, part B, but using in place of the 3α-t-butyldimethylsilyloxy-5α-hydroxy-2β-[(3R)- or (3S)-3-hydroxy-trans-1-octenyl]-1α-cyclopentaneacetic acid γ lactone starting material employed therein, the various 3α-t-butyldimethylsilyloxy-5α-hydroxy-2β-[(3R)- or (3S)-3-methoxy-cis- or trans-1-alkenyl; cis- or trans-1,cis-5-alkadienyl; alkyl; or substituted alkenyl; alkadienyl; or alkyl]-1α-cyclopentaneacetic acid γ lactones described following Example 7, there are prepared the corresponding (3R)- or (3S)-3-methoxy products.

For example, there are obtained the above 3α-t-butyl-dimethylsilyloxy-5α-hydroxy-1α-cyclopentaneacetaldehyde γ lactols wherein the 2β-side chain in either the (3R) or (3S) form consists of 3-methoxy-trans-1-hexenyl; 3-methoxy-trans-1-heptenyl; 3-methoxy-trans-1-octenyl; 3-methoxy-trans-1-nonenyl; 3-methoxy-trans-1-decenyl; 3-methoxy-trans-1,cis-5-octadienyl; 3-methoxy-4,4-dimethyl-trans-1,cis-5-octadienyl; 3-methoxy-4,4-difluoro-trans-1,cis-5-octadienyl; 3-methoxy-4-methyl-trans-1-octenyl; 3-methoxy-4,4-dimethyl-trans-1-octenyl; 3-methoxy-4-fluoro-trans-1-octenyl; 3-methoxy-4,4-difluoro-trans-1-octenyl; 3-methoxy-5-phenyl-trans-1-pentenyl; 3-methoxy-5-(p-fluorophenyl)-trans-1-pentenyl; 3-methoxy-5-(m-chlorophenyl)-trans-1-pentenyl; 3-methoxy-5-(m-trifluoromethylphenyl)-trans-1-pentenyl; 3-methoxy-4,4-dimethyl-5-phenyl-trans-1-pentenyl; 3-methoxy-4,4-dimethyl-5-(p-fluorophenyl)-trans-1-pentenyl; 3-methoxy-4,4-dimethyl-5-(m-chlorophenyl)-trans-1-pentenyl; 3-methoxy-4,4-dimethyl-5-(m-trifluoromethylphenyl)-trans-1-pentenyl; 3-methoxy-4,4-difluoro-5-phenyl-trans-1-pentenyl; 3-methoxy-4,4-difluoro-5-(p-fluorophenyl)-trans-1-pentenyl; 3-methoxy-4,4-difluoro-5-(m-chlorophenyl)-trans-1-pentenyl; 3-methoxy-4,4-difluoro-5-(m-trifluoromethylphenyl)-trans-1-pentenyl; 3-methoxy-4-phenoxy-trans-1-butenyl; 3-methoxy-4-(p-fluorophenoxy)-trans-1-butenyl; 3-methoxy-4-(m-chlorophenoxy)-trans-1-butenyl; 3-methox-4-(m-trifluoromethylphenoxy)-trans-1-butenyl; 3-methoxy-4,4-dimethyl-4-phenoxy-trans-1-butenyl; 3-methoxy-4,4-dimethyl-4-(p-fluorophenoxy)-trans-1-butenyl; 3-methoxy-4,4-dimethyl-4-(m-chlorophenoxy)-trans-1-butenyl; 3-methoxy-4,4-dimethyl-4-(m-trifluoromethylphenoxy)-trans-1-butenyl; 3-methoxy-cis-1-hexenyl; 3-methoxy-cis-1-hepten-yl; 3-methoxy-cis-1-octenyl; 3-methoxy-cis-1-nonenyl; 3-methoxy-cis-1-decenyl; 3-methoxy-cis,cis-1,5-octadienyl; 3-methoxy-4,4-dimethyl-cis,cis-1,5-octadienyl; 3-methoxy-4,4-difluoro-cis,cis-1,5-octadienyl; 3-methoxy-4-methyl-cis-1-octenyl; 3-methoxy-4,4-dimethyl-cis-1-octenyl; 3-methoxy-4-fluoro-cis-1-octenyl; 3-methoxy-4,4-difluoro-cis-1-octenyl; 3-methoxy-5-phenyl-cis-1-pentenyl; 3-methoxy-5-(p-fluorophenyl)-cis-1-pentenyl; 3-methoxy-5-(m-chlorophenyl)-cis-1-pentenyl; 3-methoxy-5-(m-trifluoromethylphenyl)-cis-1-pentenyl; 3-methoxy-4,4-dimethyl-5-phenyl-cis-1-pentenyl; 3-methoxy-4,4-dimethyl-5-(p-fluorophenyl)-cis-1-pentenyl; 3-methoxy-4,4-dimethyl-5-(m-chlorophenyl)-cis-1-pentenyl; 3-methoxy-4,4-dimethyl-5-(m-trifluoromethylphenyl)-cis-1-pentenyl; 3-methoxy-4,4-difluoro-5-phenyl-cis-1-pentenyl; 3-methoxy-4,4-difluoro-5-(p-fluorophenyl)-cis-1-pentenyl; 3-methoxy-4,4-difluoro-5-(m-chlorophenyl)-cis-1-pentenyl; 3-methoxy-4,4-difluoro-5-(m-trifluoromethylphenyl)-cis-1-pentenyl; 3-methoxy-4-phenoxy-cis-1-butenyl; 3-methoxy-4-(p-fluorophenoxy)-cis-1-butenyl; 3-methoxy-4-(m-chlorophenoxy)-cis-1-butenyl; 3-methoxy-4-(m-trifluoromethylphenoxy)-cis-1-butenyl; 3-methoxy-4,4-dimethyl-4-phenoxy-cis-1-butenyl; 3-methoxy-4,4-dimethyl-4-(p-fluorophenoxy)-cis-1-butenyl; 3-methoxy-4,4-dimethyl-4-(m-chlorophenoxy)-cis-1-butenyl; 3-methoxy-4,4-dimethyl-4-(m-trifluoromethylphenoxy)-cis-1-butenyl; 3-methoxy-hexyl; 3-methoxy-heptyl; 3-methoxy-octyl; 3-methoxy-nonyl; 3-methoxy-decyl; 3-methoxy-cis-5-octenyl; 3-methoxy-4,4-dimethyl-cis-5-octenyl; 3-methoxy-4,4-difluoro-cis-5-octenyl; 3-methoxy-4-methyl-octyl; 3-methoxy-4,4-dimethyl-octyl; 3-methoxy-4-fluoro-octyl; 3-methoxy-4,4-difluoro-octyl; 3-methoxy-5-phenyl-pentyl; 3-methoxy-5-(p-fluorophenyl)-pentyl; 3-methoxy-5-(m-chlorophenyl)-pentyl; 3-methoxy-5-(m-trifluoromethylphenyl)-pentyl; 3-methoxy-4,4-dimethyl-5-phenyl-pentyl; 3-methoxy-4,4-dimethyl-5-(p-fluorophenyl)-pentyl; 3-methoxy-4,4-dimethyl-5-(m-chlorophenyl)-pentyl; 3-methoxy-4,4-dimethyl-5-(m-trifluoromethylphenyl)-pentyl; 3-methoxy-4,4-difluoro-5-phenylpentyl; 3-methoxy-4,4-difluoro-5-(p-fluorophenyl)-pentyl; 3-methoxy-4,4-difluoro-5-(m-chlorophenyl)-pentyl; 3-methoxy-4,4-difluoro-5-(m-trifluoromethylphenyl)-pentyl; 3-methoxy-4-phenoxybutyl; 3-methoxy-4-(p-fluorophenoxy)-butyl; 3-hydroxy-4-(m-chlorophenoxy)-butyl; 3-methoxy-4-(m-trifluoromethylphenoxy)-butyl; 3-methoxy-4,4-dimethyl-4-phenoxy-butyl; 3-methoxy-4,4-dimethyl-4-(p-fluorophenoxy)-butyl; 3-methoxy-4,4-dimethyl-4-(m-chlorophenoxy)-butyl; 3-methoxy-4,4-dimethyl-4-(m-trifluoromethylphenoxy)-butyl; and the like.

Following the procedure of Example 9, part B but using in place of the 3α-t-butyldimethylsilyloxy-5α-hydroxy-2β-[(3S)-3-hydroxy-trans-1-octenyl]-1α-cyclopentaneacetic acid γ lactone starting material employed therein, the various 3α-t-butyldimethylsilyloxy-5α-hydroxy-2β-[(3RS)-3-methyl-3-hydroxy cis- or trans-1-alkenyl; cis- or trans-1,cis-5-alkadienyl; alkyl; or substituted alkenyl; alkadienyl; or alkyl]-1α-cyclopentaneacetic acid γ lactones described following Example 8, there are prepared the corresponding 3-(tetrahydropyranyl ethers) of the (3RS)-3-methyl-3-hydroxy products.

For example, there are obtained the above 3α-t-butyldimethylsilyloxy-5α-hydroxy-1α-cyclopentaneacetaldehyde γ lactols wherein the 2β-side chain in (3RS) form consists of the 3-(tetrahydropyranyl ethers) of 3-methyl-31-hydroxy-trans-1-hexenyl; 3-methyl-3-hydroxy-trans-1-heptenyl; 3-methyl-3-hydroxy-trans-1-octenyl; 3-methyl-3-hydroxy-trans-1-nonenyl; 3-methyl-3-hydroxy-trans-1-decenyl; 3-hydroxy-trans-1,cis-5-octaidenyl; 3-methyl-3-hydroxy-4,4-dimethyl-trans-1,cis-5-octadienyl; 3-methyl-3-hydroxy-4,4-difluoro-trans-1,cis-5-octadienyl; 3-methyl-3-hydroxy-4-methyl-trans-1-octenyl; 3-methyl-3-hydroxy-4,4-dimethyl-trans-1-octenyl; 3-methyl-3-hydroxy-4,4-difluoro-trans-1-octenyl; 3-methyl-3-hydroxy-5-phenyl-trans-1-pentenyl; 3-methyl-3-hydroxy-4-(p-fluorophenyl)-trans-1-pentenyl; 3-methyl-3-hydroxy-5-(m-chlorophenyl)-trans-1-pentenyl; 3-methyl-3-hydroxy-5-(m-trifluoromethylphenyl)-trans-1-pentenyl; 3-methyl-3-hydroxy-4,4-dimethyl-5-phenyl-trans-1-pentenyl; 3-methyl-3-hydroxy-4,4-dimethyl-5-(p-fluorophenyl)-trans-1-pentenyl; 3-methyl-3-hydroxy-4,4-dimethyl-5-(m-chlorophenyl)-trans-1-pentenyl; 3-methyl-3-hydroxy-4,4-dimethyl-5-(m-trifluoromethylphenyl)-trans-1-pentenyl; 3-methyl-3-hydroxy-4,4-difluoro-5-phenyl-trans-1-pentenyl; 3-methyl-3-hydroxy-4,4-difluoro-5-(p-fluorophenyl)-trans-1-pentenyl; 3-methyl-3-hydroxy-4,4-difluoro-5-(m-chlorophenyl)-trans-1-pentenyl; 3-methyl-3-hydroxy-4,4-difluoro-5-(m-trifluoromethylphenyl)-trans-1-pentenyl; 3-hydroxy-4-phenoxy-trans-1-butenyl; 3-methyl-3-hydroxy-4-(p-fluorophenhoxy)-trans-1-butenyl; 3-methyl-3-hydroxy-4-(m-chlorophenoxy)-trans-1-butenyl; 3-methyl-3-hydroxy-4-(m-trifluoromethylphenoxy)-trans-1-butenyl; 3-methyl-3-hydroxy-4,4-dimethyl-4-phenoxy-trans-1-butenyl; 3-methyl-3-hydroxy-4,4-dimethyl-4-(p-fluorophenoxy)-trans-1-butenyl; 3-methyl-3-hydroxy-4,4-dimethyl-4-(m-chlorophenoxy)-trans-1-butenyl; 3-methyl-3-hydroxy-4,4-dimethyl-4-(m-trifluoromethylphenoxy)-trans-1-butenyl; 3-methyl-3-hydroxy-cis-1-hexenyl; 3-methyl-3-hydroxy-cis-1-heptenyl; 3-methyl-3-hydroxy-cis-1-octenyl; 3-methyl-3-hydroxy-cis-1-nonenyl; 3-methyl-3-hydroxy-cis-1-decenyl; 3-methyl-3-hydroxy-cis,cis1,5-octadienyl; 3-methyl-3-hydroxy-4,4-dimethyl-cis,cis-1,5-octadienyl;3-methyl-3-hydroxy-4,4-difluoro-cis,cis-1,5-octadienyl; 3-methyl-3-hydroxy-4-methyl-cis-1-octenyl; 3-methyl-3-hydroxy-4,4-dimethyl-cis-1-octenyl; 3-methyl-3-hydroxy-4-fluoro-cis-1-octenyl; 3-methyl-3-hydroxy-4,4-difluoro-cis-1-octenyl; 3-methyl-3-hydroxy-5-phenyl-cis-1-pentenyl; 3-methyl-3-hydroxy-5-(p-fluorophenyl)-cis-1-pentenyl; 3-methyl-3-hydroxy-5-(m-chlorophenyl)-cis-1-pentenyl; 3-methyl-3-hydroxy-5-(m-trifluoromethylphenyl)-cis-1-pentenyl; 3-methyl-3-hydroxy-4,4-dimethyl-5-phenyl-cis-1-pentenyl; 3-methyl-3-hydroxy-4,4-dimethyl-5-(p-fluorophenyl)-cis-1-pentenyl; 3-methyl-3-hy droxy-4,4-dimethyl-5-(m-chlorophenyl)-cis-1-pentenyl; 3-methyl-3-hydroxy-4,4-dimethyl-5-(trifluoromethylphenyl)-cis-1-pentenyl; 3-methyl-3-hydroxy-4,4-difluoro-5-phenyl-cis-1-pentenyl; 3-methyl-3-hydroxy-4,4-difluoro-5-(p-fluorophenyl)-cis-1-pentenyl; 3-methyl-3-hydroxy-4,4-difluoro-5-(m-chlorophenyl)-cis-1-pentenyl; 3-methyl-3-hydroxy-4,4-difluoro-5-(m-trifluoromethyolphenyl)-cis-1-pentenyl; 3-methyl-3-hydroxy-4-phenoxy-cis-1-butenyl; 3-methyl-3-3-hydroxy-4-(p-fluorophenoxy)-cis-1-butenyl; 3-methyl-3-hydroxy-4-(m-chlorophenoxy)-cis-1-butenyl; 3-methyl-3-hydroxy-4-(m-trifluoromethylphenoxy)-cis-1-butenyl; 3-methyl-3-hydroxy-4,4-dimethyl-4-phenoxy-cis-1-butenyl; 3-methyl-3-hydroxy-4,4-dimethyl-4-(p-fluorophenoxy)-cis-1-butenyl; 3-methyl-3-hydroxy-4,4-dimethyl-4-(m-chlorophenoxy)-cis-1-butenyl; 3-methyl-3-hydroxy-4,4-dimethyl-4-(m-trifluoromethylphenoxy)-cis-1-butenyl; 3-methyl-3-hydroxy-hexyl; 3-methyl-3-hydroxy-heptyl; 3-methyl-3-hydroxy-octyl; 3-methyl-3-hydroxy-nonyl; 3-methyl-3-hydroxy-decyl; 3-methyl-3-hydroxy-cis-5-octenyl; 3-methyl-3-hydroxy-4,4-dimethyl-cis-5-octenyl; 3-methyl-3-hydroxy-4,4-difluoro-cis-5-octenyl; 3-methyl-3-hydroxy-4-methyl-octyl; 3-methyl-3-hydroxy-4,4-dimethyl-octyl; 3-methyl-3-hydroxy-4-fluoro-octyl; 3-methyl-3-hydroxy-4,4-difluoro-octyl; 3-methyl-3-hydroxy-5-phenylpentyl; 3-methyl-3-hydroxy-5-(p-fluorophenyl)-pentyl; 3-methyl-3-hydroxy-5-(m-chlorophenyl)-pentyl; 3-methyl-3-hydroxy-5-(m-trifluoromethylphenyl)-pentyl; 3-methyl-3-hydroxy-4,4-dimethyl-5-phenyl-pentyl; 3-methyl-3-hydroxy-4,4-dimethyl-5-(p-fluorophenyl)-pentyl; 3-methyl-3-hudroxy-4,4-dimethyl-5-(m-chlorophenyl-pentyl; 3-methyl-3-hydroxy-4,4-dimethyl-5-(m-trifluoromethylphenyl)-pentyl; 3-methyl-3-hydroxy-4,4-difluoro-5-phenyl-pentyl; 3-methyl-3-hydroxy-4,4-difluoro-5-(p-fluorophenyl)-pentyl; 3-methyl-3-hydroxy-4,4-difluoro-5-(m-chlorophenyl)-pentyl; 3-methyl-3-hydroxy-4,4-difluoro-5-(m-trifluoromethylphenyl)-pentyl; 3-methyl-3-hydroxy-4-phenoxy-butyl; 3-methyl-3-hydroxy-4-(p-fluorophenoxy)-butyl; 3-hydroxy-4-(m-chlorophenoxy)-butyl; 3-methyl-3-hydroxy-4-(m-trifluoromethylphenoxy)-butyl; 3-methyl-3-hydroxy-4,4-dimethyl-4-phenoxy-butyl; 3-methyl-3-hydroxy-4,4-dimethyl-4-(p-fluorophenoxy)-butyl; 3-methyl-3-hydroxy-4,4-dimethyl-4-(m-m-chlorophenoxy)-butyl; 3-methyl-3-hydroxy-4,4-dimethyl-4-(m-trifluoromethylphenoxy)-butyl; and the like.

Following the procedure of Example 9, but using the 3-ethylenethioketal compound described following Example 6 corresponding to the 3-tert-butyldimethylsilyloxy compound of Example 6, as starting material, there is prepaed, respectively.

(1) 3-Oxo-5α-hydroxy-2β-[(3'S)-hydroxy-trans-1'-octenyl]-1α-cyclopentaneacetic acid γ lactone, 3-(ethylenethioketal), 3'-(tetrahydropyranylether) NMR absorptions at 0.90, 0.90–2.3, 2.3–3.1, 3.27, 3.1–54.3, 4.58–15, and 5.40–5.85 δ; infrared absorptions at 1780, 1250, 1195, 1185, 1160, 1130, 1115, 1080, 1035, 1020, 975, 905 cm.$^{-1}$; Mass spectral peaks at 426.1919 (parent peak), 396, 342, 324, 314, 296, and 214; and (2) 3-Oxo-5α-hydroxy-2β-[(3′S)-3-hydroxy-trans-1′-octenyl]-1α-cyclopentaneacetaldehyde γ lactol, 3-(ethylenethioketal), 3′-(tetrahydropyranyl ether); $R_f$ (silica gel TLC) 0.22 in 25 percent ethyl acetate in Skellysolve B.

Likewise, various ethylenethioketals corresponding to the tert-butyldimethylsilyloxy compounds described above following Example 9 are prepared following the procedure of Example 9.

EXAMPLE 10

3-Oxa-PGF$_{1α}$, 11-(t-butyldimethylsilyl ether) 15-(tetrahydropyranylether), methyl ester (Formula XXX: $R_1$ is methyl, g is 1, $R_3$ and $R_4$ of the $L_1$ moiety are hydrogen, $M_6$ is

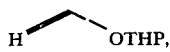

$R_7$ is n-butyl, X is

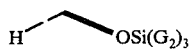

wherein —OSi(G$_2$)$_3$ is t-butyldimethylsilyloxy, and Y is trans-CH=CH—), or its 15-epimer, or the corresponding free acids.

Refer to Chart B.

A. The title compound of Example 9, (10.0 g.) is dissolved in 150 ml. of absolute ethanol (containing 3 drops of acetic acid). To this solution is added carbethoxymethylenetriphenylphosphorane (10 g.) and the mixture is stirred at ambient temperature for 72 hr. The resulting mixture is concentrated under reduced pressure to a volume of about 35 ml., mixed with ice, and dilute sodium bicarbonate solution, and shaken with ethyl acetate. The organic phase is washed with brine, dried over magnesium sulfate, and concentrated to yield a residue. The residue is slurried in 100 ml. of diethyl ether and filtered. The filtrate is concentrated to a residue which is subject to silica gel chromatography, eluting with 20 to 40 percent ethyl acetate in Skellysolve B. There is obtained 2,3,4-trinor-PGF$_{2α}$, ethyl ester, 11-(t-butyldimethylsilyl ether), 15-(tetrahydropyranyl ether), a formula XXVII compound.

B. The reaction product of step A above is mixed with the 5 percent palladium-on-charcoal catalyst (0.3 g.) in 30 ml. of ethyl acetate and hydrogenated at atmospheric pressure. When about 41 ml. of hydrogen is consumed, the catalyst is filtered off and the filtrate concentrated under reduced pressure to yield 2,3,4-trinor-PGF$_{1α}$, ethyl ester, 11-(t-butyldimethylsilyl ether), 15-(tetrahydropyranyl ether), a formula XXVIII compound.

C. The reaction product of step B above (1.1 g.) in 30 ml. of diethyl ether is added with stirring to a mixture of lithium aluminum hydride (0.3 g.) in 60 ml. of diethyl ether at 0° C. The addition continues over a 10 min. period. The mixture is warmed to room temperature for 2 hr. then cooled to 0° C., and treated with 0.35 ml. of water cautiously added. Thereafter 0.35 ml. of 15 percent aqueous sodium hydroxide solution is added, and thereafter one ml. of water. The solids are removed by filtration and the filtrate is concentrated under reduced pressure to yield 2-decarboxy-2-hydroxymethyl-2,3,4-trinor-PGF$_{1α}$, 11-(t-butyldimethylsilyl ether), 15-(tetrahydropyranyl ether).

D. The reaction product of part C above (1.7 g.) together with 15 ml. of dimethyl sulfoxide and 5 ml. of tetrahydrofuran is treated with 2.28 ml. of 1.6 molar n-butyllithium in hexane, with stirring and cooling. After 5 min. there is added 5 ml. of dimethylformamide. The resulting solution is then stirred and cooled to 0° C. Thereafter lithium chloroacetate (0.7 g.) is added. The mixture is then stirred at 0° C. for 2 hr. and at about 25° C. for 22 hr. Thereafter the resulting solution is diluted with 200 ml. of ice-water, acidified with a cold solution of 3 ml. of dilute acetic acid in 50 ml. of water, and extracted thereafter with dichloromethane. The organic phase is washed with cold water and brine and dried over magnesium sulfate. Accordingly, there is prepared 3-oxa-PGF$_{1α}$, 11-(t-butyldimethylsilyl ether), 15-(tetrahydropyranyl ether).

E. To the above solution (part D) is added excess ethereal diazomethane and after a few. min. the excess reagent is destroyed with acetic acid. The mixture is then washed with a mixture of sodium bicarbonate solution and brine and thereafter with brine. The resulting solution is then dried and concentrated under reduced pressure. The residue so obtained is subjected to silica gel chromatography eluting with ethyl acetate and Skellysolve B to yield the title compound.

Following the procedure of Example 10, but using the (3R) starting material there is obtained the corresponding 15-epi product.

Following the procedure of Example 10, but omitting the esterification step (part E) there are obtained the above compounds in free acid form.

Following the procedure of Example 10, but replacing lithium chloroacetate used in part D of Example 10, with lithium-butylpropionate or lithium-t-butylbutyrate, there are obtained the corresponding 3-oxa-PGF$_{1α}$-type 11-(t-butyldimethylsilyl ether), 15-(tetrahydropyranyl ether)compounds wherein g is 2 or 3, i.e., 2a-homo 2a, 2b-dihomo compounds.

Following the procedure of Example 10 but using each of the lactols described following Example 9, there are obtained in either (15R)- or (15S)- form the corresponding 3-oxa-PGF$_{1α}$, 11-(-t-butyldimethylsilyl ether), or 3-oxa-PGF$_{1α}$, 11-(t-butyldimethylsilyl ether), 15-(tetrahydropyranyl ether) in free acid or methyl ester form.

EXAMPLE 11

5-Oxa-PGF$_{1α}$, methyl ester, 11-(t-butyldimethylether), 15-(tetrahydropyranyl ether), (Formula XXXIII: g is 1, $R_3$ and $R_4$ of the $L_1$ moiety are hydrogen, $M_6$ is

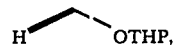

X is

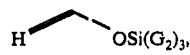

wherein —OSi(G$_2$)$_3$ is t-butyldimethylsilyoxy, $R_1$ is methyl, $R_7$ is n-butyl, and Y is trans-CH=CH—), or its 15-epimer.

Refer to Chart C.

A. A mixture of the title product of Example 9 or its (3R) epimer (6.3 g.) and 50 ml. of 95 percent ethanol is treated at 0° C. with stirring with a solution of sodium borohydride in 10 ml. of water (added over a period of one min.). The resulting mixture is then stirred at 0° C.

for 10 min. and then shaken with 10 ml. of water, 250 ml. of ethyl acetate, and 150 ml. of brine. The organic phase is then washed with brine, dried and concentrated under reduced pressure to yield 2-decarboxy-2-hydroxymethyl-2,3,4,5,6-pentanor-PGF$_{1\alpha}$, 11-(t-butyldimethylsilyl ether)-15-(tetrahydropyranyl ether), a formula XXXII compound, or its (15R)-epimer.

B. A solution of potassium tert-butoxide (1.77 g.) in 30 ml. of tetrahydrofuran is mixed at 0° C., with stirring, with a solution of the reaction product of part A (5.8 g.) in 30 ml. of tetrahydrofuran. The resulting mixture is then stirred at 0° C. for 5 min. and thereafter 5 ml. of trimethyl ortho-4-bromobutyrate is added. Stirring is continued at 0° C. for 2 hr. and at about 25° C. for 16 hr. To this mixture is added 30 ml. of dimethylformamide and 0.5 g. of potassium-t-butoxide. The resulting mixture is then stirred for 20 hr. Some of the solvent is then removed under reduced pressure and the residue is then shaken with water diethyl ether and dichloromethane (3:1). The organic phase is then washed with water and brine, dried, and concentrated. The residue, containing the ortho ester, is dissolved in 6 ml. of methanol at 0° C. and treated with 15 ml. of cold water containing 2 drops of acetic acid. The resulting mixture is then stirred at 0° C. for 5 min., shaken with 200 ml. of diethyl ether, 50 ml. of dichloromethane, and 200 ml. of brine. The organic phase is then washed with brine, dried, and concentrated under reduced pressure. The residue is subjected to silica gel chromatography, yielding the title methyl esters.

C. Trimethylortho-4-butyrate is prepared as follows:

Refer to S. M. McEldian, et al., Journal of the American Chemical Socieity 64, 1825 (1942). A mixture of 4-bromobutyronitrile (74 g.), 21 ml. of methanol, and 150 ml. of diethyl ether is treated at 0° C. with stirring, with hydrogen bromide (40 g.). The mixture is then stirred for an additional 4 hr. at 0° C. and 100 ml. of hexane is added. The precipitated imino ester hydrobromide is separated from the liquid by filtration and washed with 400 ml. of diethyl ether in hexane (1:1). The imino ester salt is treated in 250 ml. of diethyl ether with 150 ml. of methanol and 25 ml. of methylorthoformate, with stirring, at about 25° C. for 24 hr. The resulting mixture is then cooled to about 10° C. and the organic solution is separated from the ammonium bromide thereby formed. Diethyl ether (100 ml.) is then added. The resulting solution is then immediately and quickly washed an ice cold solution prepared from potassium carbonate (20 g.) and 300 ml. of brine. The organic phase is washed with brine, treated with 3 drops of pyridine, and dried over anhydrous magnesium sulfate. The solution is then concentrated under reduced pressure, diluted with 150 ml. of benzene, and again concentrated. The residue is then distilled to yield the title ortho-4-bromobutyrate.

Following the procedure of part C of Example 11, but using 5-bromo pentanonitrile or 6-bromohexanonitrile there is prepared trimethylortho-5-bromo pentanoate or trimethylortho-6-bromo hexanoate.

Following the procedure of Example 11, but using each of the various lactols described following Example 9, there is prepared a corresponding 5-oxa- PGF$_{1\alpha}$-type, methyl ester, 11-(t-butyldimethylsilyl ether) or 11-(t-butyldimethylsily ether), 15-(tetrahydropyranyl ether).

Further, following the procedure of Example 11, but using trimethylortho-5-bromopentenoate or trimethylortho-6-bromohexanoate there is prepared in (15R) or (15S) form the corresponding 5-oxa-PGF$_{1\alpha}$-type methyl ester, 11-(t-butyldimethylsilyl ether), 15-(tetrahydropyranyl ether) wherein $g$ is 2 or 3.

EXAMPLE 12

3α-(t-Butyldimethylsilyloxy), 5α-hydroxy-2β-[(3S)-3-hydroxy-trans-1'-octenyl]-1α-cyclopentanepropionaldehyde δ-lactol, 3'(tetrahydropyranyl ether) (Formula XLI: R$_3$ and R$_4$ of the L$_1$ moiety are hydrogen. M$_6$ is

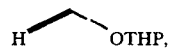

R$_7$ is n-butyl, Y is trans-CH=CH—, and X is

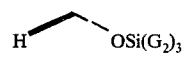

wherein —OSi(Ga$_2$)$_3$ is t-(butyldimethylsilyloxy), or its (3'R)epimer).

Refer to Chart D.

A. A suspension of methoxymethyl triphenylphosphonium chloride (32.4 g.) in 150 ml. of tetrahydrofuran is cooled to −15° C. To the suspension is added 59.4 ml. of n-butyllithium in hexane (1.6 molar) in 45 ml. of tetrahydrofuran. After 30 min. there is added a solution of 3α-(t-butyldimethylsilyloxy)-5α-dihydroxy-2β-[(3S)-3-hydroxy-trans-1-octenyl]-1α-cyclopentaneacetaldehyde γ lactol, 3'-(tetrahydrodropyranyl ether), Example 9 (10 g.), in 90 ml. of tetrahydrofuran. The mixture is stirred for 1.5 hr. while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXXVII product are combined.

B. The reaction product of part A above in 20 ml. of tetrahydrofuran is hydrolyzed with 50 ml. of 66 percent aqueous acetic acid at about 35° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The pure product is thereby obtained by combining and concentrating fractions as shown by thin layer chromatography to contain pure product. Accordingly, there is obtained the corresponding formula XXXVIII δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol, 9:1), pure product is removed by filtration. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula XXXIX δ-lactone.

D. The formula XXXIX lactone prepared in part C above is then transformed to its 3'-(tetrahydropyranyl ether) derivative following the procedure described in Example 9, part A.

E. The formula XL compound prepared in part D above is then reduced to the corresponding δlactol 3-(t-butyldimethylsilyl ether), 3'-(tetrahydropyranyl ether) by the procedure described in Example 9, part B, yielding pure title product.

Following the procedure of Example 12, but using the corresponding (3'R) starting material in place of the (3'S) starting material there is obtained the corresponding (3'R)-δ-lactol.

Following the procedure of Example 12, but using in place of the formula XXXVI lactol starting material the various formulas XXXVI lactols described following Example 9, there are obtained the corresponding δ-lactols.

EXAMPLE 13 cis-4,5-Didehydro-PGF$_{1\alpha}$, 11-(t-butyldimethylsilyl ether), 15-(tetrahydropyranyl ether) (Formula XLIV: g is 1, R$_3$ and R$_4$ of the L$_1$ moiety are hydrogen, M$_6$ is

R$_1$ is hydrogen, R$_7$ is n-butyl, Y is

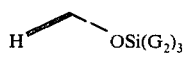

wherein —OSi(G$_2$)$_3$ is t-butyldimethylsilyloxy, and Y is trans-CH=CH—) or its 15-epimer.

Refer to Chart D.

3-Carboxypropyltriphenylphosphonium bromide (prepared by heating 4-bromobutyric acid and triphenylphosphine in benzene at reflux for 18 hr., and thereafter purifying), 106 g., is added to sodiomethylsulfinylcarbamide prepared from sodium hydride (2.08 g., 57 percent) and 30 ml. of dimethylsulfoxide. The resulting Wittig reagent is combined with the title formula XLI lactol of Example 12 above and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield pure product.

Following the procedure of Example 13, but using in place of the (3S) starting material the corresponding (3R) starting material there is obtained the corresponding 15-epi-PGF$_{1\alpha}$-type 11-(t-butyldimethylsilyl ether), 15-(tetrahydropyranyl ether).

Following the procedure of Example 13, but using in place of the 3-carboxypropyltriphenylphosphonium bromide, 4-carboxybutyltriphenylphosphonium bromide, or 5-carboxypentyltriphenylphosphonium bromide, there are prepared the corresponding formula XLIV compounds wherein g is 2 or 3.

Further, following the procedure of Example 13, but using in place of the formula XLI starting material the various formula XLI lactols described following Example 12, there are prepared the corresponding cis-4,5-didehydro-PGF$_{1\alpha}$-type 11-(t-butyldimethylsilyl ether), 15-(tetrahydropyranyl ethers) or 11-(t-butyldimethylsilyl ethers).

EXAMPLE 14

4-Oxa-PGF$_{1\alpha}$, methyl ester, 11-(t-butyldimethylsilyl ether), 15-(tetrahydropyranyl ether) (Formula XLIII: g is 1, R$_3$ and R$_4$ of the L$_1$ moiety are hydrogen, M$_6$ is

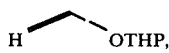

R$_1$ is hydrogen, R$_7$ is n-butyl, X is

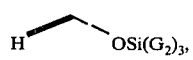

wherein —OSi(G$_2$)$_3$ is t-butyldimethylsilyloxy, and Y is trans-CH=CH—).

A. Following the procedure of Example 11, part A, the formula XLI δ-lactol (Example 12) is transformed to the corresponding formula XLII 2-decarboxy-2-hydroxymethyl-2,3,4,5-tetranor-PGF$_{1\alpha}$, 11-(t-butyldimethylsilyl ether), 15-(tetrahydropyranyl ether).

B. Following the procedure of Example 11, part B, the product of part A of this example is transformed to the title compound, employing trimethylortho-3-bromopropionate in place of trimethyl ortho-4-bromobutyrate.

Following the procedure of Example 14, but using (3R) lactol starting material, (15R)-product is prepared. Further using trimethylortho-4-bromobutyrate or trimethyl ortho-5-bromopentanoate in place of trimethyl ortho-3-bromopropionate, there are obtained corresponding formula XLIII compounds wherein g is 2 or 3.

Finally following the procedure of Example 14, and optionally employing the substitutions of the preceeding 2 paragraphs, but using the various formula XLI lactols described following Example 12, there are obtained corresponding products.

EXAMPLE 15

PGF$_{2\alpha}$, 11-(t-butyldimethylsilyl ether), 15-(tetrahydropyranyl ether) (formula XLVII: g is 1, R$_3$ and R$_4$ of the L$_1$ moiety are hydrogen, M$_6$ is

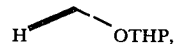

R$_1$ is hydrogen, R$_2$ is hydrogen, R$_7$ is n-butyl, X is

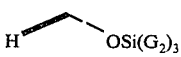

wherein —OSi(G$_2$)$_3$ is t-butyldimethylsilyloxy, and Y is trans-CH=CH—), or its 15-epimer.

Refer to Chart E.

A. To a solution of sodium methylsulfinylmethide (prepared from sodium hydride (0.43 g., 57% in mineral oil) in 10 ml. of diemthylsulfoxide), is added to 2.26 g. of 4-carboxybutyltriphenylphosphonium bromide. The reaction mixture is maintained at 25° C. with stirring for 30 min. A solution of the title compound of Example 9 (1.24 g.) in 10 ml. of dimethylsulfoxide is added. The reaction mixture is stirred at ambient temperature for 14 hr. and diluted with 200 ml. of benzene. Potassium bisulfate (2.7 g. in 30 ml. of water) is slowly added, maintaining the reaction temperature to less than or equal to 10° C., acidifying to pH 2. The aqueous layer is extracted with 100 ml. of benzene and the organic extracts are washed successively with 50 ml. of water and 50 ml. of brine before combining, drying, and evaporating to an oil (2.58 g.), which is chromatographed on 100 g. of acid washed silica gel packed in 10% ethyl acetate and Skellysolve B. Elution with 10–35 percent ethyl acetate and Skellysolve B yields pure product (a colorless oil) (1.27 gms.) NMR absorptions are observed at 0.05, 0.87, 0.68–2.86, 3.20–4.48, 4.75, and 5.20–5.87 $\delta$.

Following the procedure of Example 15, but using the corresponding 3-ethylenethioketal starting material, 0.70 g., the corresponding product is prepared; $PGD_2$, 11-(ethylenethioketal), 15-(tetrahydropyranyl ether), 0.43 g., as a colorless oil. NMR absorptions are observed at 0.90, 0.90–2.93, 3.18, 3.02–4.38, 4.72, 5.23–5.78, and 6.52 $\delta$.

Following the procedure of Example 15, but using the corresponding (3R)-lactol starting material, the corresponding 15-epi product is prepared.

Following the procedure of Example 15, but using 5-car boxypentyltriphenylphosphonium bromide or 6-carboxyhexyl triphenylphosphonium bromide, there are prepared the corresponding formula XLVII compounds wherein $g$ is 2 or 3.

Finally following the procedure of Example 15, and optionally employing the variation of the preceeding paragraph, but using each of the lactols described following Example 9, there are prepared the corresponding $PGF_{2\alpha}$-type, 11-(t-butyldimethylsilyl ether), 15-(tetrahydropyranyl ethers) or $PGF_{2\alpha}$-type, 11-(butyldimethylsilyl ethers).

EXAMPLE 16

$PGD_2$ (Formula LVII: $R_1$ is hydrogen, $R_3$ and R, of the $L_1$ moiety and $R_5$ and $R_6$ of the $M_1$ moiety are hydrogen, $R_7$ is n-butyl, Y is trans- CH=CH—, and $Z_2$ is cis-CH=CH—$(CH_2)_3$-), or its (15R) epimer.

Refer to Chart F.

A. $PGF_{2\alpha}$, 11-(t-butyldimethylsilyl ether), 15-(tetrahydropyranyl ether), 1.27 g., in methylene chloride (10 ml.), dihydropyran (0.97 g.), and pyridine hydrochloride (0.1 g.) are combined with stirring overnight at ambient temperature. 200 ml. of saturated aqueous sodium bicarbonate and 200 ml. of ethyl acetate are thereafter added, with the ethyl acetate containing fraction thereafter being washed with brine, dried over sodium sulfate, and concentrated under vacuum to yield a pale yellow formula LIV oil.

B. The product of part A above is dissolved in tetrahydrofuran (25 ml.) and treated with a solution of tetra-n-butylammonium fluoride (1.20 g.) in tetrahydrofuran (10 ml.). This reaction mixture is stirred at 65° for 2 hr. and thereafter cooled to 25° C. The resulting product is concentrated under vacuum, diluted with brine, and extracted with ethyl acetate. The organic extracts are then combined, washed with 2M aqueous potassium bisulfate, brine, and dried over magnesium sulfate. Concentration under reduced pressure yields a yellow brown oil. This oil is then dissolved in 35 ml. of 5 percent potassium hydroxide in methanol and water (9:1) and stirred for 2 hr. The reaction mixture is then cooled to 25° C., concentrated under reduced presure, diluted with water, and acidified with 2M aqueous potassium bisulfate and ice. After dilution with brine the aqueous-containing fraction is extracted with ethyl acetate and the combined organic extracts are washed with brine, dried over magnesium sulfate, and concentrated under vacuum to yield 1.00 g. of a yellow orange oil. This oil is purified on 60 g. of silica gel packed with 10 percent ethyl acetate in Skellysolve B, eluting with 10 to 50 percent ethyl acetate in Skellysolve B. Pure chromatographic fractions are combined yielding 0.24 g. of $PGF_{2\alpha}9,15$-bis-(tetrahydropyranyl ether). NMR absorptions are observed at 0.89, 0.8–2.86, 4.77, and 5.22–5.97 $\delta$.

C. The reaction product of part B of this example (0.24 g.) in acetone (10 ml.) is purged with nitrogen, cooled to $-15°$ C., and thereafter treated with Jones reagent (0.20 ml., 1.7 equivalents). The reaction mixture is stirred at $-15°$ C. for 30 min. and thereafter excess Jones reagent is quenched with 0.25 ml. of isopropanol. The reaction mixture is then diluted with brine and extracted with ethyl acetate. The organic extracts are then washed with brine, dried over sodium sulfate, and concentrated under reduced pressure to yield 0.24 g. of a formula LV oil.

D. The above oil is dissolved in a mixture of acetic acid and water (2:1) and heated with stirring to 35° C. for 3 hr. The reaction mixture is then cooled to 25° C., diluted with 100 ml. of water, and freeze dried, yielding 0.16 g. of crude title product. This product is chromatographed on 16 g. of acid washed silica gel packed with 10 percent ethyl acetate in Skellysolve B. Elution with 10 to 70 percent ethyl acetate in Skellysolve B yields pure title product (0.13 g.)

Alternatively, title product is obtained from prostaglandin $D_2 11$-(ethylenethioketal), 15-(tetrahydropyranyl ether) as follows:

A. Starting material (0.24 g.) is combined with 9 ml. of acetic acid, water, and tetrahydrofuran (6:3:1) and heated to 37°–40° C. for 2 hr. Thereafter the reaction mixture is cooled, diluted with 15 ml. of water, and freeze dried to yield crude product (0.19 g.) which is chromatographed on 19 g. of acid washed silica gel packed with 20% ethyl acetate in Skellysolve B, eluting with 20 to 35 percent ethyl acetate in Skellysolve B. Thereby $PGD_2$, 11-(ethylenethioketal) is obtained. NMR absorptions are observed at 0.90, 0.9–3.00, 3.23, 4.02–4.50, and 4.93–5.95 $\delta$. Infrared absorptions are observed at 3400, 3000, 2920, 2850, 2650, 1710, 1455, 1425, 1410, 1275, 1240, 1050, 1020, and 970 cm.$^{-1}$. The mass spectrum of the tris-(trimethylsilyl) derivative shows mass peak absorption at 644.3257.

B. The reaction product of the preceeding paragraph (4.0 mg.) in 0.5 ml. of a mixture of water and acetone (1:49) is treated with cupric oxide (0.0172 g.) and cupric chloride dihydrate (0.0133 g.). The resulting mixture is stirred for 24 hr. at ambient temperature and the reaction mixture thereafter diluted with water and extracted with ethyl acetate. The organic extracts are then dried over magnesium sulfate, filtered through Celite, and concentrated employing a stream of nitrogen, yielding a yellow orange oil containing the tital product.

Following the procedure of Example 16, but using (15R) epimeric starting material, there is prepared 15-epi-$PGD_2$.

Following the procedure of Example 16, but using each of the various compounds described in and following Examples 10, 11, 13, 14, and 15, there are prepared the corresponding PGD-type products.

EXAMPLE 17

9β-PGD$_2$ (Formula LVII: R$_1$ is hydrogen, R$_3$ and R$_4$ of the L$_1$ moiety and R$_5$ and R$_6$ of the M$_1$ are hydrogen, R$_7$ is n-butyl, Y is trans-CH=CH—, and Z$_2$ is cis-CH=CH(CH$_2$)$_3$—).

A. PGF$_{2\alpha}$, 11-(t-butyldimethylsilyl ether) 15-(tetrahydropyranyl ether), the compound of Example 15, 0.45 g., in 10 ml. of acetone is cooled to 0° C. Thereupon the Jones reagent (2.1 g. of chromic anhydride, 6 ml. of water, and 1.7 ml. of concentrated sulfuric acid) is added until an excess of the reagent persists for 10 min. Thereafter a few drops of isopropanol are added, quenching the reaction, and the resulting mixture is concentrated under reduced pressure. Thereafter the residue so formed is partitioned between dichloromethane and water and the organic phase is dried and concentrated to yield a formula LII compound.

B. A solution of sodium borohydride (300 mg.) in 6 ml. of ice cold methanol is added to a solution of the reaction product of part A of this Example (650 mg.) in 30 ml. of methanol at −5° C. The reaction mixture is stirred for an additional 5 min., made slightly acidic by addition of dilute acetic acid, and concentrated under reduced pressure. The residue obtained is extracted with dichloromethane. The dichloromethane extract is then washed with water, dilute aqueous sodium bicarbonate, brine, and thereafter dried over sodium sulfate and concentrated under reduced pressure. Chromatographing over silica gel yields the pure 9β-epimer (Formula LIII).

C. Following the procedure of Example 16, the reaction product of part B of this example is transformed to the title product.

Following the procedure of Example 17, but using any of the various formula LI intermediates described following Example 15, there are prepared the corresponding products.

EXAMPLE 18

2,2-Difluoro-PGD$_2$methyl ester

A. Following the procedure of Example 15, but using 3,3-difluoro-4-carboxybutyltriphenylphosphonium bromide in place of 4-carboxybutyltriphenylphosphonium bromide there is prepared 2,2-difluoro-PGF$_{2\alpha}$, 11-(t-butyldimethylsilyl ether), 15-(tetrahydropyranyl ether).

B. Following the procedure of Example 16, but using in place of PGF$_{2\alpha}$, 11-(t-butyldimethylsilyl ether), 15-(tetrahydropyranyl ether) there is prepared the title product.

C. Following the procedure of Example 18, but using in place of the lactol starting material of part A, each of the various lactols described following Example 9, there are prepared the corresponding 2,2-difluoro-PGD$_2$-type products.

EXAMPLE 19

PGD$_1$.

A solution of PGD$_2$ (Example 16) in ethyl acetate is shaken with hydrogen at about one atmospheric pressure at ambient temperature in the presence of a 5 percent palladium-on-charcoal catalyst. Hydrogenation is stopped when one equivalent of hydrogen per equivalent of PGD$_2$ is absorbed. Catalyst is removed by filtration and the filtrate is then concentrated under reduced pressure and the residue chromatographed on silica gel, eluting with ethyl acetate and Skellysolve B. Fractions shown to contain pure product are combined yielding the title compound.

Following the procedure of Example 19, but using 2a-homo- or 2a,2b-dihomo-PGD$_2$, there is prepared 2a-homo-or 2a,2b-dihomo-PGD$_1$.

Further, following the procedure of Example 19, but using the various PGD$_2$-type compounds described following Example 16 or the 9β-PGD$_2$-type compounds described in and following Example 17 or the 2,2-difluoro-PGD$_2$-type compounds in the following Example 18, there is prepared the corresponding PGD$_1$-, of 2,2-difluoro-PGD$_1$-type products.

EXAMPLE 20

3-oxa-3,7-inter-m-phenylene-4,5,6-trinor-PGD$_1$ (Formula CV: R$_1$ is hydrogen, R$_3$ and R$_4$ of the L$_1$ moiety and R$_5$ and R$_6$ of the M$_1$ moiety are all hydrogen, R$_7$ is n-butyl and Z$_1$ is

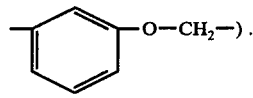

or 3,7-inter-m-phenylene-4,5,6-trinor-PGD$_1$ (Formula CV: R$_1$ is hydrogen, R$_3$ and R$_4$ of the L$_1$ moiety and R$_5$ and R$_6$ of the M$_1$ moiety are all hydrogen, R$_7$ is n-butyl, and Z$_1$ is

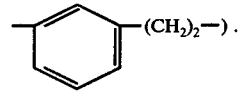

Refer to Charts G, H, and L.

A. Optically Active Bicyclo[3.1.0]-hex-2-ene-6-endocarboxaldehyde.

Following the procedure of Preparation 1 of U.S. Pat. No 3,711,515, racemic bicyclo[3.1.0]hex-2-ene-6-endo-carboxaldehyde is prepared from bicyclo[2.2.1-]hepta-2.5-diene and peracetic acid.

The racemic compound is resolved by the procedure of Example 13 of U.S. Pat. No. 3,711,515, forming and oxazolidine as follows:

Racemic bicyclo[3.1.0]hex-2-ene-6-endo-carboxaldehyde (12.3 g.) and 1-ephedrine (16.5 g.) are dissolved in about 150 ml. of benzene. The benzene is removed under vacuum and the residue taken up in about 150 ml. of isopropyl ether. The solution is filtered, then cooled to −13° C. to yield crystals of 2-endo-bicyclo-[3.1.0]hex-2-en-6-yl-3,4- dimethyl-5-phenyl-oxazolidine, 11.1 g., m.p. 90°–92° C. Three recrystallizations from isopropyl ether, cooling each time to about −2° C., yield crystals of the oxazolidine, 2.2 g., m.p. 100°–103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatograph-grade (Merck), 0.05–0.2 mm. particle size, with about 4–5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are (λ in nm., θ): 350, 0; 322.5, 4,854; 312, −5,683; 302.5, −4,854; 269, 0; 250, 2,368; 240, 0; and 210, −34,600.

B. 1-Bicyclo[3.1.0]hex-2-ene-6-endo-carboxaldehyde Neopentyl Glycol Acetal (Formula LXI: $R_{55}$ and $R_{56}$ taken together are —$CH_2$—$C(CH_3)_2$—$CH_2$— and ~ is endo).

A mixture of 2,2-dimethyl-1,3-propanediol (900 g.), 5 l. of benzene, and 3 ml. of 85 percent phosphoric acid is heated at reflux. To it is added, in 1.5 hr., a solution of optically active bicyclo[3.1.0]hex-2-ene-6-endo-carboxaldehyde (part A, 500 g.) in one liter of benzene. Provision is made to take off azeotropically distilled water with a Dean-Stark trap. After 3 hr. the mixture is cooled and extracted with 2 liters of 5 percent sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to −13° C. to yield 300 g. of the title compound, m.p. 52°–55° C., and and having NMR peaks at 0.66, 1.20, 0.83–2.65, 3.17–3.8, 3.96, and 5.47–5.88 δ, $[α]_D$ −227° (C=0.8976 in methanol), and $R_f$ 0.60 (TLC on silica gel in 25 percent ethyl acetate in mixed isomeric hexanes). Further work-up of the mother liquors yields 50–100 g. of additional product.

C. d-8-(m-Acetoxyphenyl)-7-oxa-tricyclo-[4.2.0.0$^{2,4}$]-octane-6-endo-carboxaldehyde Neopentyl Glycol Acetal (Formula LXII: $R_{55}$ and $R_{56}$ taken together are —$CH_2$—$C(CH_3)_2$—$CH_2$—, $R_{63}$ is

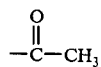

and ~ is endo).

A solution of the formula LXI 1-bicyclo[3.1.0]hex-2-ene-6-endo-carboxaldehyde neopentyl glycol acetal (Part B, 5.82 g.) and m-acetoxy-benzaldehyde (1.64 g.) in 25 ml. of benzene is charged to a Pyrex photolysis vessel equipped with an immersible water-cooled cold-finger and fritted gas inlet tube. Dissolved oxygen is removed by bubbling nitrogen through the solution. The mixture is then irradiated at 350 nm. with a Rayonet Type RS Preparative Photochemical Reactor (The Southern New England Ultraviolet Co., Middletown, Conn.) equipped with six RUL 3500 Å lamps. After 24 hr. the photolysate is concentrated under reduced pressure to a pale yellow oil, 10 g., which is subjected to silica gel chromatography. Elution with 10–70 percent ethyl acetate in Skellysolve B (mixture of isomeric hexanes) yields separate fractions of the recovered starting materials and the formula LXII title compound, a pale yellow oil, 0.86 g., having NMR peaks at 0.68, 1.20, 0.8–2.5, 2.28, 2.99, 3.12–3.88, 3.48, 4.97–5.52, and 6.78–7.60 δ; infrared absorption bands at 3040, 2950, 2860, 2840, 1765, 1610, 1590, 1485, 1470, 1370, 1205, 1115, 1020, 1005, 990, 790, and 700 cm.$^{-1}$; mass spectral peaks at 358, 357, 116, 115, 108, 107, 79, 70, 69, 45, 43, and 41; $[α]_D$ +55° (C=0.7505 in 95 percent ethanol); and $R_f$ 0.18 (TLC on silica gel in 25 percent ethyl acetate in mixed isomeric hexanes).

D. d-2-Exo-[m-(pivaloyloxy)benzyl]-3-exo-pivaloyloxy)bicyclo-[3.1.0]hexane-6-endo-carboxaldehyde Neopentyl Glycol Acetal (Formula LXIV: $R_{55}$ and $R_{56}$ taken together are —$CH_2$—$C(CH_3)_2$—$CH_2$—, $R_{68}$ is

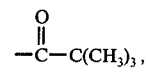

and ~ is endo).

A mixture of lithium (0.25 g.) in 70 ml. of ethylamine is prepared at 0° C. and cooled to −−78° C. A solution of the formula LXII d-8-(m-acetoxyphenyl)-7-oxa-tricyclo-[4.2.0.0$^{2,4}$]-octane-6-endo-carboxaldehyde neopentyl glycol acetal (part C 1.83 g.) in 10 ml. of tetrahydrofuran is added dropwise in about 5 min. After stirring at −78° C. for about 3.5 hr. the reaction is quenched with solid ammonium chloride and water-tetrahydrofuran. Unreacted lithium is removed, the mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine ad saturated aqueous sodium bicarbonate (1:1), and dried over sodium sulfate. Concentration under reduced pressure yields the formula LXIII diol as a pale tan foamed oil, 1.64 g., having $R_f$ 0.03 (TLC on silica gel in 25 percent ethyl acetate in mixed isomeric hexanes).

The product of the preceeding paragraph is dissolved in 30 ml. of pyridine and treated with 1.5 ml. of pivaloyl chloride over a period of 22 hr. at about 25° C. The reaction mixture is mixed with water, then brine and extracted with ethyl acetate. The organic phase is washed successively with brine, water, saturated aqueous copper (II) sulfate, saturated aqueous sodium bicarbonate, and brine, and dried over sodium sulfate. Concentration under reduced pressure yields a residue, 2.53 g., wich is subjected to silica gel chromatography to yield the formula LXIV title compound, 1.87 g., having NMR peaks at 0.71, 1.20, 1.33, 0.9–3.1, 3.28–4.00, 4.17, 4.7–5.2, and 6.77–7.53 δ; mass spectral peaks at 486, 485, 115, 73, 72, 57, 44, 43, 42, 41, 30, 29, 15; $[α]_D$ +19° (C=0.9340 in ethanol); and $R_f$ 0.50 (TLC on silica gel in 25 percent ethyl acetate in mixed isomeric hexanes).

E. 2-Exo-[m-(pivaloyloxy)benzyl]-3-exo-(pivaloyloxy)bicyclo[3.1.0]hexane-6-endo-carboxaldehyde (Formula LXV: $R_{66}$ is

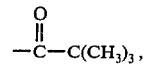

and ~ is endo).

The formula LXIV acetal, i.e. d-2-exo-[m-pivaloyloxy)-benzyl]-3-exo-(pivaloyloxy)-bicyclo[3.1.0]hexane-6-endocarboxaldehyde neopentyl glycol acetal (part D, 0.48 g.) is treated at 0° C. with 25 ml. of 88 percent formic acid for 4 hr. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromotography. Elution with 5–15 percent ethyl acetate in Skellysolve B yields the formula LXV title compound as an oil, 0.37 g., having NMR peaks at 1.20, 1.33, 0.6–3.2, 5.1–5.5, 6.6–7.5, and 9.73 δ; and $R_f$ 0.50 (TLC on silica gel in 25 percent ethyl acetate in mixed isomeric hexanes).

F. 2-Exo-[m-(pivaloyloxy)benzyl]-3-exo-(pivaloyloxy)-6-endo-(cis-1-heptenyl)-bicyclo[3.1.0]hexane (Formula LXVI: $R_3$ and $R_4$ of the $L_1$ moiety are both hydrogen, $R_7$ is n-butyl, $R_{66}$ is

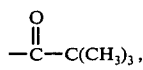

$R_{53}$ is hydrogen, and $\sim$ is endo); and 2-Exo-(m-hydroxybenzyl)-3-exo-hydroxy-6-endo-(cis-1-heptenyl)bicyclo[3.1.0]-hexane (Formula LXVII: $R_3$ and $R_4$ of the $L_1$ moiety are both hydrogen, $R_7$ is n-butyl, $R_{53}$ and $R_{66}$ are hydrogen, and $\sim$ is endo).

A Whittig ylid reagent is prepared in 10 ml. of benzene from n-hexyltriphenylphosphonium bromide (0.79 g.) and n-butyllithium (0.6 ml. of 2.32 M. solution in hexane) at about 25° C. for 0.5 hr. After the precipitated lithium bromide has settled, the solution is removed and added to a cold (0° C.) slurry of the formula LXV aldehyde (part E, 0.37 g.). After 15 min. there is added 1.0 ml. of acetone and the mixture is heated to 60° C. for 10 min. The mixture is concentrated under reduced pressure. The residue is washed with 10 percent ethyl acetate in Skellysolve B and these washings are concentrated to the formula LXVI title compound, an oil, 0.33 g. having NMR peaks at 1.18, 1.33, 0.6–3.2, 4.5–6.0, and 6.67–7.62 δ; and $R_f$ 0.78 (TLC on silica gel in 25 percent ethyl acetate in Skellysolve B).

The above product of the preceeding paragraph is transformed to the formula LXVII diol by treatment with sodium methoxide (2.5 ml. of a 25 percent solution in methanol) for 4 hrs., followed by addition of 0.5 g. of solid sodium methoxide and further stirring for 15 hr. at 25° C., then at reflux for 6 hr. The mixture is cooled, mixed with 300 ml. of brine, and extracted with ethyl acetate. The organic phase is washed with brine, dried over magnesium sulfate, and concentrated under reduced pressure to a residue, 0.27 g. The residue is subjected to silica gel chromatography, eluting with 25–35 percent ethyl acetate in Skellysolve B, to yield the formula-LXVII title compound as an oil, 0.21 g., having NMR peaks at 0.87, 0.6–3.25, 3.88–4.35, 4.82–5.92, and 6.47–7.33 δ; and $R_f$ 0.13 (TLC on silica gel in 25 percent ethyl acetate in Skellysolve B).

G. 2-Exo-{m-[(carboxy)methoxy]}-3-exo-hydroxy-6-endo-(cis-1-heptenyl)bicyclo[3.1.0]hexane (Formula LXVIII: $R_3$ and $R_4$ of the $L_1$ moiety are both hydrogen, g is one, $R_7$ is n-butyl, $R_1$, $R_{53}$ and $R_{66}$ are hydrogen, and $\sim$ is endo).

The formula-LXVII diol, i.e. 2-exo(m-hydroxybenzyl)-3-exo-hydroxy-6-endo-(cis-1-heptenyl)bicyclo[3.1.0]hexane (part F, 0.19 g.) is treated in 8 ml. of dioxane with bromoacetic acid (0.61 g.) and 6 ml. of 1N aqueous sodium hydroxide. After the mixture has been heated at reflux for 3 hr., with sodium hydroxide solution added when necessary to maintain a pH of about 10, the mixture is cooled, diluted with 100 ml. of water, and extracted with diethyl ether. The aqueous phase is acidified to pH 1–2 and extracted with ethyl acetate to yield the formula-LXVIII title compound, a pale yellow oil, 0.20 g. Recovered formula LXVIII diol is obtained from the diethyl ether organic phase on drying and concentrating, 0.025 g.

H. 3-Oxa-3,7-inter-m-phenylene-4,5,6-trinor-$PGF_{1\alpha}$(-Formula LXXIII: $R_3$ and $R_4$ of the $L_1$ moiety and $R_5$ and $R_6$ of the $L_1$ moiety are all hydrogen, $R_7$ is n-butyl, g is one, and $R_1$ is hydrogen).

The formula LXVIII alkene is transformed to the title compound applying the procedures disclosed in U.S. Pat. No. 3,711,515. Thus, compound LXVIII (part G) is hydroxylated by the procedures of Example 6 of that patent to the formula LXIX glycol of Chart G, using osmium tetroxide either alone or in combination with N-methylmorpholine oxide-hydrogen peroxide complex.

The glycol is then either (1) sulfonated, for example to yield the bismesylate, and then hydrolyzed to a mixture of the title compound and its 15-epimer, applying the procedures of Example 7 of the patent, or (2) treated with substantially 100 percent formic acid to form the diformate of LXVIII and thereafter hydrolyzed to a mixture of the title compound and its 15 epimer, applying the procedures of Examples 20 and 21 of that patent. The epimers are separated by silica gel chromatography to yield the title compound and its 15-epimer.

A third route from glycol LXIX to compound LXXIII is by way of a cyclic ortho ester

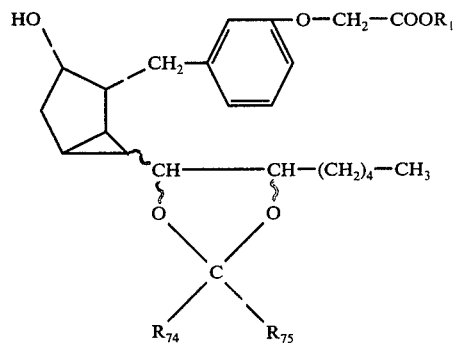

wherein $R_{74}$, $R_{75}$, and $\sim$ are as defined above. The glycol is treated as a 1–20 percent solution in benzene with trimethyl orthoformate (1.5–10 molar equivalents) and a catalytic amount (1 percent of the weight of the glycol) of pyridine hydrochloride at about 25° C. The reaction is followed by TLC (thin layer chromatography) and is complete in a few minutes. There is thus obtained the cyclic ortho ester in 100 percent yield.

The cyclic ester is then treated with 20 volumes of 100 percent formic acid at about 25° C. In about 10 min. the reaction mixture is quenched in water or aqueous alkaline bicarbonate solution and extracted with dichloromethane. The organic phase is shaken with 5 percent aqueous sodium bicarbonate, dried over sodium sulfate, and concentrated to yield the corresponding diester. The diester is contacted with 10–50 volumes of anhydrous methanol and 10–20 percent of its weight of potassium carbonate at about 25° C. until the ester groups are removed. The mixture of 15-epimers thus obtained is then separated to yield the formula LXXIII compound or its 15-epimer.

I. 2-Exo-[m-(2-carboxyethyl)benzyl]-3-exo-hydroxy-6-endo(cis- 1-heptenyl)bicyclo-[3.1.0]hexane (Formula $Z_3$ is methylene, g is one, $R_3$ and $R_4$ of the $L_1$ moiety are hydrogen, $R_7$ is n-butyl, $R_1$ and $R_{53}$ are hydrogen and $\sim$ is endo).

With respect to Chart H, there is first prepared the formula LXXVI oxetane. Following the procedures of parts C, but replacing the m-acetoxybenzaldehyde of part c with the aldehyde of the formula

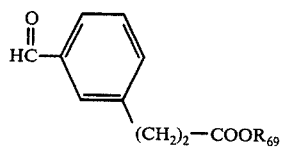

wherein $R_{69}$ is as defined above, the corresponding formula LXXVII oxetanes are obtained with a fully developed side chain.

Thereafter, following the procedures of parts D, E, and F, but replacing the formula LXII oxetane of part D with the oxetane obtained by the procedure of the preceeding paragraph of this part, there are obtained the corresponding formula LXXXI products.

Finally, the blocking groups on each LXXXI compound are removed by methods disclosed herein or known in the art to yield the formula LXXXII compound.

J. 3,7-inter-m-phenylene-4,5,6-trinor-$PGF_{1\alpha}$(Formula LXXXIV: $R_1$ is hydrogen $R_2$ and $R_3$ of the $L_1$ moiety and $R_5$ and $R_6$ of the $M_1$ moiety are hydrogen, $R_7$ is n-butyl, g is one, Y is trans-CH=CH— and $Z_3$ is —$Ch_2$—).

Following the procedures of part H, the formula LXXXII alkene is transformed in several steps to the formula LXXXIV compound.

K. 3,7-inter-m-phenylene- or 3-oxa-3,7-inter-m-phenylene-4,5,6-trinor-$PGF_{1\alpha}$, 15-(tetrahydropyranyl ether).

Following the procedure of Example 22, part A, but using the part H or part J compound as starting material, the formula CIV compound is prepared.

L. 3,7-inter-m-phenylene- or 3-oxo-3,7-inter-m-phenylen-4,5,6-trinor-$PGD_1$, 15-(tetrahydropyranyl ether).

Following the procedure of Example 22, part B, but using the compounds of part K as starting material, there are prepared the corresponding products.

M. 3,7-inter-m-phenylene- or 3-oxa-3,7-inter-m-phenylene-4,5,6-trinor-$PGD_1$.

Following the procedure of Example 22, part C, but using the compounds of parts L as starting material, there are prepared the corresponding title compounds.

Following the procedures described in Example 20, but using various alternate intermediate and starting materials, there are prepared the various 3-oxa-3,7-inter-m-phenylene- or 3,7-inter-m-phenylene-3-trinor-$PGD_2$-type compounds disclosed in this specification.

EXAMPLE 21

9,10-Didehydro-9-deoxy-$PGD_1$, (Formula CXLIX: $R_1$ is hydrogen, $Z_1$ is cis-CH=CH—$(CH_2)_3$—, Y is trans-CH=CH—, $R_3$, $R_4$, $R_5$, and $R_6$ of the $M_1$ and $L_1$ moieties are all hydrogen, and $R_7$ is n-butyl).

Refer to Chart Q.

A. $PGF_{2\alpha}$(2 g.) in 15 ml. of methylene chloride is mixed with n-butylboronic acid (688 mg.). This reaction mixture is then heated at reflux with vigorous stirring, adding methylene chloride in 5 ml. of aliquots to replace amounts evaporated. After about 25 min. 10 ml. of dihydropyran is added to the reaction mixture with 150 mg. of pyridine hydrochloride. After about 20 hr. etherification is complete and methylene chloride is removed under reduced pressure. The residue is then diluted with 30 ml. of methanol and 13 ml. of 3N aqueous potassium hydroxide. The resulting clear yellow solution is then allowed to stand for 2 hr., then treated with 5 ml. of a 30 percent solution of aqueous hydrogen peroxide in 30 ml. of water. Thereafter the methanol was removed under reduced pressure and the aqueous residue diluted with 100 ml. of water and extracted twice with diethyl ether. The aqueous layer is then acidified with 25 ml. of 2N aqueous potassium bisulfate and extracted with ethyl acetate. The combined organic extracts are then washed with brine and dried over sodium sulfate. Removal of the solvent under reduced pressure yields 3.3 g. of an oil which is then chromatographed on 100 g. of acid washed silica gel. Eluting with 75 percent ethyl acetate in hexane 2.0 g. of pure formula CXLIV $PGF_{2\alpha}$15-(tetrahydropyranyl ether) is obtained.

B. A solution of the reaction product of part A (11.3 g.) triphenylphosphine (10.13 g.) and 2-pyridyldisulfide (8.5 g.) in 200 ml. of oxygen free benzene is stirred under a nitrogen atmosphere for 3 hr. at ambient temperature. Thereafter the resulting solution is diluted with 300 ml. of dry oxygen free benzene to bring the total solution to a volume of 500 ml. This solution is then refluxed for 24 hr. Upon cooling the mixture is concentrated to an oil and chromatographed on 1.5 kg. of neutral silica gel packed in 50 percent ethyl acetate in n-hexane, eluting with 60 percent ethyl acetate in hexane. A formula CXLV compound (6.2 g.) is thereby obtained.

C. A solution of the reaction product of part B (5.5 g.) in 100 ml. of acetone is cooled to −35° C. Thereafter 3.3 ml. of Jones reagent is added and the solution is maintained at −35° C. After several hours 6 ml. of isopropanol is added with stirring. The resulting mixture is then diluted with 600 ml. of ice cold brine and extracted with diethyl ether in hexane (1:2) the combined organic solutions are then washed with brine and dried over magnesium sulfate, concentrated, and chromatographed. (Mallinckiodt CC-4 silica gel packed with 10 percent ethyl acetate in hexane. Elution with 25 percent ethyl acetate in hexane yields 3.4 g. of formula CXLVI product as an oil.

D. A solution of the reaction product of step C of this example (2.0 g.) in 100 ml. of a tetrahydrofuran, water, and acetic acid (1:3:6) mixture is stirred at 40°–45° C. for one hr. Thereafter the solution is poured into coled brine and extracted with ethyl acetate in hexane (1:3). The combined organic solutions are then washed with brine and ice cold sodium bicarbonate. The hexane layer is then washed with brine, dried over sodium sulfate and concentrated to yield crude product (1.25 g.). Chromatographing on 200 g. of silica gel packed in 20 percent ethyl acetate in hexane, eluting with 30 percent ethyl acetate and 60 percent ethyl acetate, one percent acetic acid in hexane there is obtained 1.17 g. of pure product as a yellow oil. Infrared absorptions are observed at 3450, 2980, 2900, 2700, 1740, 1720, 1600, 1460, 1440, 1410, 1350, 1240, 1170, 1025, 970 cm.$^{-1}$. NMR absorptions are observed at 0.90, 4.15, 5.60, 6.20, and 7.65 δ. Mass spectrum shows base peak absorption at 478.2912. The title compound is alternatively prepared by allowing $PGD_2$ to stand on a silica gel column, and thereafter purifying impure product so obtained using silica gel chromatography.

Following the procedure of Example 21, but using any of the $PGF_\alpha$-type compounds described herein there are prepared the corresponding 9-deoxy-9, 10-didehydro-PGD-type compounds.

EXAMPLE 22

PGD$_2$ or PGD$_2$ methyl ester.

Refer to Chart L.

A. PGF$_{2\alpha}$(2.0 g.) and methylene chloride (50 ml.) is treated with 688 mg. of n-butyl boronic acid. The reaction mixture is then stirred vigorously and heated at reflux, adding 5 ml. aliquots of methylene chloride to replace amounts lost through evaporation. The procedure is continued for about 25 min. adding about 20 to 25 ml. of methylene chloride. The resulting distillate becomes clear. Thereafter 10 ml. of dihydrogpyran is added to the reaction mixture followed by addition of pyridine hydrochloride (150 mg.). After 20 hr. the reaction is complete and the methylene chloride is removed under reduced pressure and the residue combined with 30 ml. of methanol and 13 ml. of a 3N aqueous potassium hydroxide solution. The resulting solution is allowed to stand for 2 hr. and thereafter treated with 5 ml. of 30 percent hydrogen perioxide and 30 ml. of water. The methanol is then removed under reduced pressure and the aqueous residue diluted with 100 ml. of water and extracted twice with diethyl ether. The aqueous layer is then acidified with 25 ml. of 2 N aqueous potassium bisulfate and extracted with ethyl acetate. The combined acetate extracts are then combined, washed with brine, and dried over anhydrous sodium sulfate. Removal of solvent under reduced pressure yields 3.3 g. of an oil which is chromatographed on 100 g. of acid washed silica gel. The column is packed with and eluted with 75 percent ethyl acetate in hexane. The formula CIV PGF$_{2\alpha}$15-tetrahydropyranyl ether is thereby obtained.

B. PGF$_{2\alpha}$, 15-(tetrahydropyranyl ether) (2g.) in acetone (75 ml.) is cooled to $-45°$ C. and thereafter treated with 1.2 ml. of the Jones reagent. The mixture is stirred for 30 min. at $-35°$ to $-45°$ C. and thereafter treated with 0.5 ml. of isopropanol and stirred an additional 15 min. The reaction mixture is then poured into a mixture of ice, water, and diethyl ether. The mixture is then extracted with diethyl ether and the combined etheral extracts washed with brine, and dried over sodium sulfate. After filtration removal of solvent proceeds by rotary evaporation. Crude product (1.8 g.) thereby obtained is chromatographed on 360 g. of acid washed silica gel eluting with 45 percent ethyl acetate in hexane. PGD$_2$ 15-(tetrahydropyranyl ether) (800 mg.) is thereby obtained.

C. PGD$_2$, 15-(tetrahydropyranyl ether) (800 mg.) in 20 ml. of acetic acid and 10 ml. of water is heated at 40° C. for 2 hr. and then diluted with 100 ml. of water and thereater freeze dried. The residue is then chromatographed on 50 g. of acid washed silica gel packed with 20 percent ethyl acetate in hexane. Elution with 35 to 65 percent ethyl acetate in hexane yields 500 mg. of a colorless oil, which crystallizes on standing. The melting point is 62.8°–63.3° C. Infrared absorptions are observed at 3380, 3000, 2720, 2680, 1745, 1725, 1710, 1435, 1405, 1325, 1315, 1270, 1240, 1200, 1155, 1080, 1040, 1025, 1015, 990, 980, 965, 935, 735, and 705 cm.$^{-1}$. NMR absorptions are observed at 0.89, 4.14, 4.5, 5.53, and 5.73 $\delta$. The mass spectrum shows peaks at 334, 316, 245, and 190.

D. Esterification with excess ethereal diazomethane yields the title methyl ester.

Following the procedure of Example 22, but using any of the various PGF-type compounds described herein there are prepared the corresponding PGD-type compounds.

EXAMPLE 23

15-Methyl-PGD$_2$, methyl ester.

A solution of 15-methyl-PGF$_{2\alpha}$, methyl ester (200 mg.) in acetone (10 ml.) is cooled to $-40°$ C. and thereupon the Jones reagent (0.15 ml.) is added. The solution is then stirred at 3135° C. for 45 min. Thereafter isopropanol (0.1 ml.) is added and the solution is stirred for 15 min. The mixture is then poured into a mixture of ice and brine and extracted with diethyl ether. The ethereal extracts are then washed with saturated sodium bicarbonate and brine, dried over sodium sulfate, and concentrated to yield 0.20 g. of an oil. Crude product so obtained is chromatographed on 15 g. of silica gel packed with 30 percent ethyl acetate in hexane, eluting with 30–60 percent ethyl acetate in hexane, 0.12 g. of pure product is obtained. Infrared absorptions are observed at 3440, 2940, 2860, 1735, 1440, 1375, 1315, 1240, 1220, 1200, 1170, 1075, 1055, 1035, 975 cm.$^{-1}$. NMR absorptions are observed at 0.89, 1.25, 3.65, 4.50, and 5.50 $\delta$.

Following the procedure of Example 23, but using the various 15-methyl-PGF-type compunds described herein, there are prepared the corresponding 15-methyl-PGD-type compounds.

EXAMPLE 24

16,16-Dimethyl-PGD$_2$ (Formula CV: R$_1$ is hydrogen, Z$_1$ is cis-CH=CH—(CH$_2$)$_3$—, Y is trans-CH=CH—, R$_3$ and R$_4$ of the L$_1$ moiety are both methyl, R$_5$ and R$_6$ of the M$_1$ moiety are both hydrogen, and R$_7$ is n-butyl) or its methyl ester.

Refer to Chart L.

A. 16,16-Dimethyl-PGF$_{2\alpha}$(1.62 g.) is transformed to 16,16-dimethyl-PGF$_{2\alpha}$, 15-(tetrahydropyranyl ether), 1.03 g., following the procedure of Example 22, part A. NMR absorptions are observed at 0.87, 0.67–2.83, 3.25–4.38, 4.73, 5.12, amd 5.2–5.8 $\delta$. Infrared absorptions are observed at 3400, 2940, 2870, 1710, 1200, 1135, 1115, 1075, 1050, 1020, 1005, and 975 cm.$^{-1}$.

B. The reaction product of part A above (4.35 g.) and acetone (150 ml.) are combined and purged with nitrogen for several min. Thereafter this mixture is cooled to $-40°$ C. and a solution of 2.67 M Jones reagent (2.83 ml.) is added dropwise over 10 min. with stirring, maintaining the reaction temperature at $-35°$ to $-45°$ C. After 60 min. the reaction is quenched by addition of isopropanol (2 ml.). The reaction mixture is thereafter diluted with brine and extracted with ethyl acetate. The combined organic extracts are washed with brine, dried over magnesium sulfate, and concentrated under reduced pressure to yield 4.8 g. of crude product. The crude product (2.40 g.) is then diluted with acetic acid and water (2:1, 90 ml.). The resulting solution is then heated with stirring to 35° C. for 3 hr. and thereafter cooled to ambient temperature, diluted with water (200 ml.) and freeze dried. This process is then repeated for the remaining crude product (2.4 g.). Freeze dried residues are then combined yielding 3.52 g. of crude product which is purified using 500 g. of silica gel packed in 25 percent ethyl acetate and Skellysolve B. Eluting with 25 to 75 percent ethyl acetate in Skellysolve B pure 16,16-dimethyl-PGD$_2$ (1.57 g.) is obtained. Additional chromatographic purification yields 1.34 g. of pure product. NMR absorptions are observed at 0.83, 0.87, 0.68-3.23, 3.86, 4.50, 4.88, and 5.2-6.0 δ. Infrared absorptions are observed at 3430, 2950, 2920, 2860, 2660, 1735, 1715, 1385, 1235, 1165, 1110, 1065, 1025, 995, and 975 cm.$^{-1}$ The mass spectrum of the tris-(trimethylsilyl)derivative shows peaks at 596, 497, 506, 416, 407, 353, and 201. The high resolution mass spectrum shows a demethylated peak at 581.3502.

C. The reaction product of part B is treated with slight stoichiometric excess of ethereal diazomethane, yielding 16,16-dimethyl-PGD$_2$, methyl ester. NMR absorptions are observed at 0.7–3.1 , 3.67, 3.7–3.9, 4.3–4.6, and 5.3–5.7 δ.

EXAMPLE 25

2,2-Difluoro-13,14-dihydro-PGD$_2$, methyl ester
(Formula CV: R$_1$ is methyl, Z$_1$ is
cis-CH═CH—(CH$_2$)$_2$—CF$_2$—, Y is —Ch$_2$CH$_2$—, R$_3$
and R$_4$ of the L$_1$ moiety and R$_5$ and R$_6$ of the M$_1$ moiety
are hydrogen, and R$_7$ is n-butyl).

Refer to Charts K and L.

A. 13,14-Dihydro-2,2-difluoro-PGF$_{2\alpha}$, methyl ester (Formula XCVIII: R$_1$ is methyl, Z$_2$ is cis-CH═CH—(CH$_2$)$_2$ —CF$_2$—; Y is —Ch$_2$Ch$_2$—, R$_3$ and R$_4$ of the L$_1$ moiety and R$_5$ and R$_6$ of the M$_1$ moiety are all hydrogen, and M$_7$ is n-butyl)., is prepared as follows:

The formula XCV compound, 3α,5α-dihydroxy-2β-carboxaldehyde-1α-cyclopentaneacetic acid γ lactone, is acylated employing benzoyl chloride, thereby preparing 3α-benzoyloxy-5α-hydroxy-2β-carboxaldehyde-1α-cyclopentaneacetic acid γ lactone. This 3α-benzoyloxy compound is then reacted with appropriate Wittig reagent thereby preparing 3α-benzoyloxy-5α-hydroxy-2β-(3-oxo-trans-1-octenyl)-1α-cyclopentaneacetic acid γ lactone. Following the procedure of Example 5, the above compound is transformed to 3α-benzoyloxy-5α-hydroxy-2β-(3-oxo-octyl)-1α-cyclopentaneacetic acid γ lactone. Following the procedure of Example 6 the above unsaturated lactone is transformed to 3α-benzoyloxy-5α-hydroxy-2β-[(3S)-3-hydroxy-octyl]-1α-cyclopentaneacetic acid γ lactone. This compound is then deacylated and etherified according to the procedure of Example 9, thereby preparing the corresponding formula XCVI compound, 3α,5α-dihydroxy-2β-[(3S)-3-hydroxyoctyl]-1α-cyclopentaneacetic acid γ lacetone, bis-(tetrahydropyranyl ether). This compound is then alkylated employing the Wittig reagent of Example 18. 3,3-difluoro-4-carboxybutyltriphenylphosphonium bromide, thereby preparing the formula XCVII compound, 2,2-difluoro-13,14-dihydro-PGF$_{2\alpha}$11,15-bis-(tetrahydropyranyl ether). The above compund is thereafter esterified in a slight stoichiometric excess of ethereal diazomethane, thereby preparing 2,2-difluoro-13,14-dihydro, methyl ester, 11.15-bis-(tetrahydropyranyl ether). The title compound is thereater prepared by mild acidic hydrolysis of the 11,15-bis-(tetrahydropyranyl ether).

B. The reaction product of part A of this Example 1.50 g. is transformed to 2,2-difluoro-13,14-dihydro-PGF$_{2\alpha}$, methyl ester, 15-(tetrahydropyranyl ether) by the procedure of Example 22, part 1.

C. The product of part B is then transformed to 2,2-difluoro-13,14-dihydro-PGD$_2$, 15-(tetrahydropyranyl ether), following the procedure of Example 22, part B.

D. The reaction product of part C is then hydrolyzed to the title compound, following the procedure of Example 22, part C. The mass spectrum shows base peak absortpion at 485.3196, and other peaks at 533, 477, 458, 443, 387, 371, 368, 281, and 173. Infrared absorptions are observed at 3420, 3000, 2970, 2860, 1765, 1735, 1445, 1350, 1320, 1270, 1215, 1200, 1150, and 1090.

EXAMPLE 26

2a, 2b-Dihomo-PGD$_2$ (Formula LVII: R$_1$ is hydrogen,
Z$_2$ is cis-CH═CH—(CH$_2$)$_5$—, Y is trans—Ch═Ch—,
R$_3$ and R$_4$ of the L$_1$ moiety are both hydrogen, R$_5$ and
R$_6$ of the M$_1$ moiety are both hydrogen, and R$_7$ is
n-butyl).

Refer to Charts E and F.

A. Following the procedure of Example 15, using 6-carboxyhexyltriphenylphosphonium bromide, 4.30 g., in place of 4-carboxybutyltriphenylphosphonium bromide, and 1.07 g. of 3α-(t-butyldimethylsilyloxy)-5α-hydroxy-2β-(3α-hydroxy-trans-1-octenyl)-1α-cyclopentaneacetaldehyde γ lactol, 3-(tetrahydropyranyl ether) there is prepared 2a,2b-dihomo-PGF$_{2\alpha}$- 11-(t-butyldimethylsilyl ether), 15-(tetrahydropyranyl ether), 0.91 g.

B. Following the procedure of Example 16, but using as starting material the product of part A of this example there is successively prepared 2a, 2b-dihomo-PGF$_{2\alpha}$, 9,15-bis-(tetrahydropyranyl ether), 0.56 g,; and the title compound, 0.22 g. NMR absorptions are observed at 0.90, 0.7—3.17, 4.12, 4.52, and 5.57 δ. The mass spectrum of the tris-(trimethylsilyl) derivative shows parent peak absorption at 596.3764.

EXAMPLE 27

2a,2b-Dihomo-PGD$_2$, 15methyl ether (Formula CV: R$_1$
is hydrogen, Z$_1$ is cis-CH═CH—(CH$_2$)$_5$—, Y is
trans-CH═Ch—, R$_3$ and R$_4$ of the L$_1$ moiety are
hydrogen, R$_5$ and R$_6$ of the M$_1$ moiety are hydrogen and
methyl, respectively, and R$_7$ is n-butyl).

Refer to Chart L.

2a, 2b-Dihomo-PGF$_{2\alpha}$, 15-methyl ether (1.0 g.) and acetone (25 ml.) is cooled in an ice-methanol bath. Thereafter Jones reagent (1 ml., 2.67 mmol. of chromium trioxide) is added during one min. The mixture is stirred 20 min. at −20° C. and thereater the reaction is qquenched by addition of one ml. of isopropanol the mixture is then stirred at −20° C. for an additional 10 min. and diluted with 100 ml. of water and extracted with diethyl ether. The ethereal extracts are then washed with water and brine and dried over magnesium sulfate. The mixture is then concentrated under reduced pressure at 40° C. yielding an oil containing water. Benzene (75 ml.) is then added and evaporated yielding 0.87 g. of an orange oil. The aqueous phases are extracted with dichloromethane, and the dichloromethane extracts thereafter washed with water and dried over magnesium sulfate. Evaporation under reduced pressure at 40° C. yields 1.0 g. of an orange oil. These oils are combined and chromatographed on a 100 g. column of acid washed silica gel. Eluting with 25 to 75 percent ethyl acetate in Skellysolve B, there is obtained the title compound as a pale yellow oil (197 mg.). The mas spectrum shows peaks at 394, 392, 376, 362, 344, 321, 289, and 273. The infrared spectrum shows absorption at 3400 − 3000, 2930, 2860, 2670, 1735, 1710, 1460, 1410, 1380, 1275, 1200, 1095, 1080, and 975 cm.$^{-1}$. NMR absorptions are observed at 0.7–1.1, 1.1–2.6, 2.6–3.2, 3.3, 3.4–3.72, 4.4–4.64, 5.38–5.62, and 6.25–6.85 δ.

EXAMPLE 28

PGD$_1$ (Formula CV: R$_1$ is hydrogen, Z$_1$ is —(CH$_2$)$_5$—, Y is trans-CH=C—, R$_3$ and R$_4$ of the L$_1$ moiety are hydrogen, R$_5$ and R$_6$ of the M$_1$ moiety are hydrogen, and R$_7$ is n-butyl).

Refer to Chart L.

A. Following the procedure of Example 22, part A, PGF$_{1\alpha}$ is (2.0 g.) is converted to PGF$_{1\alpha}$, 15 -(tetrahydropyranyl ether), 2.0 g.

B. Following the procedure of Example 22, part B, the product of part A, is transformed to PGD$_1$, 15-(tetrahydropyranyl ether), 0.90 g.

C. Following the procedure of Example 22, part C, the reaction product of part B, is transformed to title product, 210 mg.

EXAMPLE 29

13,14 -Dihydro-PGD$_1$

A solution of PGD$_2$ (0.20 g.) in 15 ml. of ethanol is stirred under one atmosphere of hydrogen in the presence of 40 mg. of 10 percent palladium-on-charcoal catalyst. After 35 min. The reaction is complete and the suspension is filtered through Celite, the filtrate being concentrated to yield 0.20 g. of an oil. This oil is chromatographed on 20 g. of silica gel, packed with 20 percent ethyl acetate in hexane, eluting with 60 percent ethyl acetate in hexane. Fractions containing pure product are combined yielding the title compound. Infrared absorptions are observed at 3450, 2980, 2900. 1740, 1725, 1460, 1400, 1170, and 1070 cm.$^{-1}$. NMR absorptions are observed at 0.90, 3.55, 4.50, 5.2 $\delta$. The mass spectrum shows absorptions at 501, 482, 467, 411, 392, and 173.

EXAMPLE 30 cis-4,5-Didehydro-PGD$_1$ or 15-epi-cis-4,5-didehydro-PGD$_1$ (Formula CV: R$_1$ is hydrogen, Z$_1$ is cis-CH$_2$—CH=C—(CH$_2$)$_2$—, Y is trans-CH=Ch—, R$_3$ and R$_4$ of the L$_1$ moiety are hydrogen, R$_5$ and R$_6$ of the M$_1$ moiety are hydrogen, and R$_7$ is n-butyl).

A. 15-epi-cis-4,5-Didehydro-PGF$_{1\alpha}$(0.97 g.) is transformed to 15-epi-cis-4,5-didehydro-PGF$_{1\alpha}$3 15-tetrahydropyranyl ether), 1.2 g., following the procedure of Example 22, part A.

B. The reaction product of part A (0.65 g.) is transformed to 15-epi-cis-4,5-didehydro-PGD$_1$, 15-(tetrahydropyranyl ether), 0.98 g., following the procedure of Example 22, part B.

C. The reaction product of part B (980 mg.) is transformed to the 15-epi title product by hydrolysis according to the procedure of Example 22, part C. 150 mg. of product is thereby obtained. The mass spectrum of a silylated derivative shows base peak absorption at 640.3813.

Following the procedure of parts A through C above, buy using starting material of the (15S) epimeric configuration there is obtained the corresponding title compound: cis-4,5-didehydro-PGD$_1$. Infrared absorptions are observed at 3420, 3000, 2920, 2860, 2660, 1735, 1715, 1450, 1390, 1165, 1135, 1075, and 970 cm.$^{-1}$. Mass spectrum of a silylated derivative shows base peak absorption at 568.3431 and other absorptions at 553, 550, 497, 478, 463, 407, 388, 356, and 299. NMR absorptions are observed at 0.6–1.8, 2.3–2.5, 4.4–4.7, 5.2–5.7 $\beta$.

EXAMPLE 31 cis-4,5-Didehydro-PGD$_1$, methyl ester.

The title compound is prepared by methyl esterification employing excess ethereal diazomethane on the product of Example 30. Infrared absorptions are observed at 3440, 3010, 2930, 2860, 1740, 1440, 1360, 1255, 1235, 1200, 1165, 1135, 1030, 985, 970 cm.$^{-1}$. The mass spectrum of a silylated derivative shows base peak absorption at 410.3204, and other absorptions at 595, 579, 593, 420, 405, 340, 199. and 173. NMR absorptions are observed at 0.6–2.5. 2.5–3.7, 3.68, 3.8–4.2, 4.3–4.6, and 5.1–5.6 $\delta$.

EXAMPLE 32 cis-4,5-Didehydro-PGD$_1$, methyl ester, 15-methyl ether.

Following the procedure of Example 22, part B, cis-4,5-didehydro-PGF$_{1\alpha}$, methyl ester, 15-methyl ether is converted to the title product. Mass spectrum shows peaks at 380, 365, 362, 349, 348, 309, 291, 277, 259, 227, 141, and 105. Infrared absorption are observed at 3440, 2930, 2860 1730, 1440, 1250, 1190, 1170, 1085, 1035, 980 cm.$^{-1}$. NMR absorptions are observed at 0.7–1.1, 1.1–3.1, 3.29, 3.35–3.65, 3.68, 4.45–4.68, and 5.3–5.6 $\delta$.

EXAMPLE 33 cis-4,5-Didehydro-15-methyl-PGD$_1$, methyl ester.

Following the procedure of Example 22, part B, cis-4,5-didehydro-15-methyl-PGF$_{1\alpha}$, methyl ester (200 mg.) is converted to the title product (0.02 g.) mass spectrum shows base peak absorption at 524.3465, and other peaks at 509, 506, 453, 434, and 363. NMR absorptions are obserbed at 0.90, 1.27, 3.66, 4.56, and 5.3–5.92 $\delta$. Characteristic infrared absorptions are observed at 3440, 1750, and 980 cm.$^{-1}$.

EXAMPLE 34

5-Oxa-PGD$_1$, methyl ester (Formula CV: R$_1$ is methyl, Z$_1$ is —CH$_2$—O—(CH$_2$)$_3$—, Y is trans-CH=CH—, R$_3$ and R$_4$ of the L$_1$ moiety are both hydrogen, R$_5$ and R$_6$ of the M$_1$ moiety are both hydrogen, and R$_7$ is n-butyl).

A. Following the procedure of Example 22, part A, 5-oxa-PGF$_{1\alpha}$, methyl ester (0.85 g.) is transformed to 5-oxa-PGF$_{1\alpha}$, methyl ester, 15-(tetrahydropyrayl ether), 0.58 g. NMR absorptions are observed at 0.88, 0.8–2.6, 2.88, 3.48, 3.67, 3.2–4.4, 4.7, and 5.28–5.65 $\delta$. Infrared absorptions are observed at 3430, 1740, 1440, 1365, 1320, 1260, 1200, 1170, 1115, 1075, 1020, and 985 cm.$^{-1}$. The mass spectrum of the bis-(trimethylsilyl) derivative shows parent peak absorption at 600.3847.

B. Following the procedure of Example 22, part B, the reaction product of Part A (1.00 g.) is transformed to 5-oxa-PGD$_1$, methyl ester, 15-(tetrahydropyranyl ether), 0.45 g. NMR absorptions are observed at 0.87, 0.7–3.05, 3.05–4.28, 3.64, 4.47, 4.72, and 5.17–5.78 $\delta$.

C. Title compound is prepared by hydrolysis as described in Example 22, part C. Thereby 0.45 g. of the reaction product of part B yields 0.20 g. of title product. NMR absorptions are observed at 0.87, 3.50, 3.63, 4.05, 4.47, and 5.47 $\delta$. Infrared absorptions are observed at 3440, 2930, 2860, 1740, 1440, 1370, 1255, 1225, 1195, 1175, 1115, 1010, 970 cm.$^{-1}$. The mass spectrum of the bis-(trimethylsilyl) derivative shows parent peak absorption at 514.3112 and other peaks at 499, 496, 443, 425, 424, 353, 334, 199, and 173.

EXAMPLE 35

9-Deoxy-PGD$_2$ (Formula CXXVIII: R$_1$ is hydrogen, Z$_1$ is cis-CH=CH—(CH$_2$)$_3$—, Y is trans-CH=CH—, R$_3$ and R$_4$ of the L$_1$ moiethy and R$_5$ and R$_6$ of the M$_1$ moiety are all hydrogen, and R$_7$ is n-butyl).

Refer to Chart O.

A. PGF$_{2\alpha}$methyl ester (6.0 g.) and n-butylboronic acid (2.13 g.) in dichloromethane (150 ml.) are heated to reflux. 75 ml. of dichloromethane is evaporated, being replaced with 75 ml. of dichloromethane in 15 ml. quantities. The solution is then cooled and excess n-butylboronic acid is filtered off. Thereafter dihydropyran (30 ml.) pyridine hydrochloride (0.45 g.) is added and the resulting mixture is stirred for 20 hr. Thereafter the mixture is concentrated to an oil, which is taken up in tetrahydrofuran (150 ml.). Thereafter, 15 ml. of 30 percent hydrogen peroxide is added to the reaction mixture, followed by addition of sodium bicarbonate (2 g.) in water (40 ml.). The reaction mixture is then stirred for 90 min., concentrated thereafter to about one-half volume, poured into brine, and extracted with ethyl acetate. Ethyl acetate extracts are then washed with brine, dried over sodium sulfate, and concentrated to yield crude product (11.5 g.). Chromatographing on 600 g. of silica gel packed with 50 percent ethyl acetate in Skellysolve B and eluting with 50 to 100 percent ethyl acetate in Skellysolve B PGF$_{2\alpha}$, 15-(tetrahydropyranyl ether), methyl ester, 7.1 g., is obtained. Infrared absorptions are observed at 3500, 2980, 2900, 1740, 1420, 1370, 1315, 1200, 1110, 1075, 1020, 970, 910, 870, and 815 cm.$^{-1}$.

B. A solution of the reaction product of part A of this example (5.0 g.) in 100 ml. of dry acetone is cooled to −40° C. Thereafter n-trimethylsilyldiethylamine (18 ml.) is added under a nitrogen atmosphere. After 2 hr., the reaction is complete, and the reaction mixture is cooled to −78° C. This cooled mixture is then diluted with precooled (−78° C.) diethyl ether (150 ml.) and poured into 200 ml. of ice cold saturated sodium bicarbonate. The layers are separated and the aqueous phase is extracted with a mixture of diethyl ether and hexane. The combined organic extracts are then washed with saturated sodium bicarbonate and brine, dried with magnesium sulfate, and concentrated to yield crude PGF$_{2\alpha}$, 11-(trimethylsilyl ether), 15-(tetrahydropyranyl ether), methyl ester, 5.5 g. as an oil.

C. A solution of the reaction product of part B (5.5 g.) and dichloromethane (80 ml.) is cooled to −25° C. Thereafter, triethylamine (1.83 ml.) is added, followed by addition of methanesulfonyl chloride (1.0 ml.). After 10 min. additional triethylamine (0.55 ml.) and methane sulfonyl chloride (0.3 ml.) is added. Ten minutes later the resulting mixture is poured into 200 ml. of ice cold saturated ammonium chloride and the resulting layers are separated. The aqueous phase is extracted twice with dichloromethane and the combined dichloromethane extracts are washed with saturated sodium bicarbonate and brine, dried over magnesium sulfate, and concentrated to yield 5.4 g. of a crude yellow oil, PGF$_{2\alpha}$, 9-mesylate, 11-(trimethylsilyl ether), 15-(tetrahydropyranyl ether), methyl ester.

The trimethylsilyl ether of the product of the preceeding paragraph is removed by dissolving the crude oil obtained above in methanol (70 ml.) and coooling the resulting mixture to 0° C. Thereafter 30 ml. of 2 percent aqueous citric acid is added and after one hr. the resulting mixture is poured into 300 ml. of ice cold brine and extracted with ethyl acetate. The ethyl acetate extracts are washed with saturated sodium bicarbonate and brine, dried over sodium sulfate, and concentrated to yield 5.0 g. of crude product. This product is chromatographed on 350 g. of silica gel, packed with 50 percent ethyl acetate and Skellysolve B, eluting with 70 percent ethyl acetate in Skellysolve B. PGF$_{2\alpha}$, 9-mesylate, 15-(tetrahydropyranyl ether), methyl ester, 3.84 g., is thereby obtained. Infrared absorptions are observed at 3500, 2980, 2920, 1740, 1440, 1350, 1200, 1180, 1110, 1080, 1040, 1020, 980, 910, 870, and 815 cm.$^{-1}$. NMR absorptions are observed at 3.05, 3.65, 4.70, 5.10, and 5.5 δ.

D. Lithium aluminum hydride (1.10 g.) in 100 ml. of dry diethyl ether is stirred under a nitrogen atmosphere at ambient temperature. Thereafter a solution of the reaction product of part C above (3.8 g.) in dry diethyl ether (25 ml.) is added dropwise over a period of 15 min. After an additional 30 min., the reaction is complete. Thereafter water (2.2 ml.) is carefully added, followed by addition of 1.75 ml. of 10 percent aqueous potassium hydroxide. After 3 hr. of stirring the suspension becomes white. This resulting mixture is then poured into 200 ml. of 10 percent sodium potassium tartrate in brine. The layers are then separated and the aqueous phase extracted twice with diethyl ether. The combined ethereal solutions are then washed with brine, dried over magnesium sulfate, and concentrated to yield an oil (2.9 g.), as crude product. This crude product is then chromatographed on 150 g. of silica gel, packed with 40 percent ethyl acetate in Skellysolve B. Pure 2-decarboxy-2-(hydroxymethyl)-9-deoxy-PGF$_{2\alpha}$, 15-(tetrahydropyranyl ether), 2.18 g., is thereby obtained. Infrared absorptions are observed at 3500, 2980, 1480, 1460, 1380, 1350, 1320, 1260, 1210, 1190, 1120, 1080, 1040, 1005, 980, 910, 870, and 815 cm.$^{-1}$. NMR absorptions are observed at 2.75, 3.60, 3.90, 4.75, and 5.40 δ.

E. A catalyst is prepared by forming a suspension of platinum dioxide (0.50 g.) in distilled water (50 ml.) and bubbling hydrogen there through. The mixture is then successively flushed with nitrogen and oxygen, the oxygen being bubbled there through until the catalyst becomes finely dispersed. Therafter sodium bicarbonate (0.78 g.) is added, and the reaction temperature increased to 60° C. Thereafter the reaction product of part D above (0.38 g.) and 30 ml. of a mixture of water and acetone (4:1) is added. After several minutes, lumps appear. Thereafter, 53 ml. of 12 percent acetone in water is added. After about 4 hr., the catalyst beings to finely disperse, and after 4 hr. starting material is completely consumed. The reaction mixture is thereafter cooled to ambient temperature, filtered through Celite, the aqueous filtrate being acidified with 50 ml. of 2N sodium bisulfate. The aqueous phase is then extracted 3 times with ethyl acetate, and the ethyl acetate extracts then washed with brine, dried over sodium sulfate, and concentrated to yield crude product, 0.30 g. of an oil. Crude product is chromatographed on 20 g. of silica gel packed with 10 percent ethyl acetate in hexane, eluting with 30 percent ethyl acetate in hexane. Accordingly, 0.20 g. of pure 9-deoxy-PGF$_{2\alpha}$, 15-(tetrahydropyranyl ether) is obtained. Infrared absorptions are observed at 3450, 2980, 2920, 1720, 1460, 1440, 1380, 1200, 1130, 1110, 1080, 1020, and 980 cm.$^{-1}$. NMR absorptions are observed at 4.0, 4.75, 5.40, and 6.70 δ.

F. The Collins reagent is prepared by adding dry chromium trioxide (0.427 g.) to pyridine (0.69 ml.) in dichloromethane (30 ml.) this suspension is allowed to warm from 0° C. to ambient temperature. Thereafter the reaction product of part E of this example (0.19 g.) in 2 ml. of dichloromethane is added. After 40 min. the mixture is filtered through Celite, and chromatographed on 40 g. of silica gel, eluting with ethyl acetate. The ethyl acetate solution thereby obtained is then concentrated to yield crude 9-deoxy-PGD$_2$, 15-(tetrahydropyranyl ether). This crude product is then dissolved in a mixture of 6 ml. of acetic acid and 3 ml. of water. The resulting mixture is warmed to 40° C. for 90 min. Thereafter water (25 ml.) is added and the mixture is freeze dried. Freeze dried residue is then chromatographed on 20 g. of acid washed silica gel, packed with 20 percent ethyl acetate in hexane, eluting with 50 percent ethyl acetate in hexane. Thereby pure title product, 0.060 g., is obtained as a colorless oil. Infrared absorptions are observed at 3500, 2980, 2920, 1740, 1725, 1460, 1400, 1230, 1160, 1125, 1120, 970, and 760 cm.$^{-1}$. NMR absorptions are observed at 0.88, 4.15, 5.5, and 6.70 $\delta$. The high resolution mass spectrum shows base peak at 480.3069.

Following the procedure of Example 35, but using as starting material any of the various PGF-type compounds known in the art of whose preparation is described herein, there are prepared the corresponding 9-deoxy-PGD-type compounds. Accordingly, there are prepared 9-deoxy-PGD-type compounds which correspond to each of the PGD-type compounds described herein.

EXAMPLE 36

9-Deoxy-9,10-didehydro-PGD$_2$ (Formula CXII: R$_1$ is hydrogen, Z$_1$ is cis-CH=CH—(CH$_2$)$_3$—, Y is trans-CH=CH—, R$_3$ and R$_4$ of the L$_1$ moiety and R$_5$ and R$_6$ of the M$_1$ moiety are all hydrogen, and R$_7$ is n-butyl).

Refer to Chart N.

Quantities of PGD$_2$ are subject to silica gel chromatography until about 3.9 g. of less polar (than PGD$_2$) impurities are obtained from eluant fractions.

The 3.9 of less polar impurities are then chromatographed on 1.2 kg. of silica gel packed with 5 percent acetone in methylene chloride eluting with 10 to 15 percent acetone in methylene chloride. Partially purified title product (1.2 g.), thereby obtained, is chromatographed on 200 g. of neutral silica gel packed with acetic acid, methanol, and chloroform (1:1:18). This column is washed with 800 ml. of acetic acid, methanol, and chloroform (1:1:48) and the above partially purified product thereafter added to the column. Eluting with acetic acid, methanol, and chloroform (1:1:48) pure title product (0.56 g.) is obtained as a yellow oil. Infrared absorptions are observed at 3450, 2980, 2900, 2700, 1740, 1720, 1600, 1460, 1440, 1410, 1350, 1240, 1170, 1025, and 970 cm.$^{-1}$ NMR absorptions are observed at 0.90, 4.15, 5.60, 6.60, and 7.65 cm.$^{-1}$. The mass spectrum shows base peak absorption at 478.2912.

Following the procedure of Example 36, each of the PGD-type compounds described herein is transformed to the corresponding 9-deoxy-9,10-didehydro-PGD-type compound.

EXAMPLE 37

9-Deoxy-9,10-didehydro-13,14-dihydro-PGD$_2$ (Formula CXII: R$_1$ is hydrogen, Z$_1$ is cis-CH=CH—(CH$_2$)$_3$—, Y is —CH$_2$CH$_2$—, R$_3$ and R$_4$ of the L$_1$ moiety are both hydrogen, R$_5$ and R$_6$ of the M$_1$ moiety are both hydrogen, and R$_7$ is n-butyl).

A. Following the procedure of Example 22, 13,14-dihydro-PGF$_{2\alpha}$ is converted to 13,14-dihydro-PGD$_2$.

B. Following the procedure of Example 36, the product of part A of this example is transformed to the title compound.

EXAMPLE 38

9-Deoxy-9,10-didehydro-2,2-difluoro-13,14-dihydro-PGD$_2$, methyl ester (Formula CXII: R$_1$ is methyl, Z$_1$ is cis-CH=CH—(CH$_2$)$_2$—CF$_2$—, Y is —CH$_2$CH$_2$—, R$_3$ and R$_4$ of the L$_1$ moiety are both hydrogen, R$_5$ and R$_6$ of the M$_1$ moiety are both hydrogen, and R$_7$ is n-butyl).

Refer to Chart N.

Following the procedure of Example 36, but using as starting material the title compound of Example 25, the title compound of this example is prepared. The mass spectrum of a silylated derivative shows base peak at 458.2664, and other peaks at 443, 387, 368, 358, 330, and 173. The infrared spectrum shows absorptions at 3440, 3020, 2920, 2860, 1770, 1705, 1590, 1545, 1350, 1315, 1270, 1215, 1195, 1090, 1050, and 975 cm.$^{-1}$.

EXAMPLE 39

13,14-Dihydro-12,13-(E)-didehydro-PGD$_2$ (Formula CXXXII: R$_1$ is hydrogen, Z$_1$ is cis-CH=CH—(CH$_2$)$_3$—, R$_3$ and R$_4$ of the L$_1$ moiety and R$_5$ and R$_6$ of the M$_1$ moiety are all hydrogen, and R$_7$ is n-butyl).

Refer to Chart P.

A solution of PGD$_2$ (300 mg.) in chloroform (3.5 ml.) and triethylamine (3.5 ml.) is stirred at ambient temperature for 72 hr. The resulting mixture is diluted with brine and 2N potassium bisulfate. The resulting mixture is extracted with ethyl acetate and the ethyl acetate extracts are then washed with brine, dried with sodium sulfate, and concentrated to yield a yellow oil (0.30 g.) as crude product. This crude product is chromatographed on 30 g. of acid washed silica gel, packed with 30 percent ethyl acetate in n-hexane and diluting with 30 to 55 percent ethyl acetate in n-hexane. Thereby, 150 mg. of pure product is obtained. Infrared absorptions are observed at 3400, 3010, 2930, 2860, 2660, 1710, 1645, 1575, 1405, 1240, 1180, and 1035 cm.$^{-1}$. NMR absorptions are observed at 0.89, 3.75, 4.50, 5.70, and 6.70 $\delta$.

Following the procedure of Example 39, each of the various PGD-type compounds wherein the C-13, C-14 moiety is trans-CH=CH—, is transformed to the corresponding 12,13-(E)-didehydro-13,14-dihydro-PGD-type product.

EXAMPLE 40

15-Methyl-12,13-(E)-didehydro-13,14-dihydro-PGD$_2$, methyl ester, (Formula CXXXII: R$_1$ and R$_5$ are methyl, Z$_1$ is cis-CH=CH—(CH$_2$)$_3$—, R$_3$ and R$_4$ of the L$_1$ moiety and R$_6$ of the M$_1$ moiety are all hydrogen, and R$_7$ is n-butyl) or
9-deoxy-9,10-didehydro-12,13-(E)-didehydro-13,14-dihydro-15-methyl-PGD$_2$, methyl ester (Formula CXXXIII: R$_1$ is methyl, Z$_1$ is cis-CH=CH—(CH$_2$)$_3$—, R$_3$ and R$_4$ of the L$_1$ moiety and R$_5$ and R$_6$ of the M$_1$ moiety are all hydrogen, and R$_7$ is n-butyl).

Refer to Chart P.

A slurry florisil (10 g.) in ethyl acetate (30 ml.) is added to 15-methyl-PGD$_2$, methyl ester (Example 23, 1.06 g.) the resulting suspension is stirred at ambient temperature for 48 hr. Thereafter additional florisil (10 g.) is added and the suspension is stirred an additional 24 hr. Thereafter the florisil is filtered, washed with ethyl acetate, and the filtrate concentrated under reduced pressure to yield crude products (1 g.).

These crude products are chromatographed on 100 g. of silica gel packed with 30 percent ethyl acetate in n-hexane eluting with 30 to 60 percent ethyl acetate in n-hexane. Thereby pure 15-methyl-12,13(E)-didehydro-13,14-dihydro-PGD$_2$, methyl ester (0.34 g.) and 9-deoxy-9,10-didehydro-15-methyl-12,13-(E)-didehydro-13,14-dihydro-15-methyl-PGD$_2$, methyl ester (0.17 g.) are obtained. For 12,13-(E)-didehydro-13,14-dihydro-PGD$_2$, methyl ester infrared absorptions are observed at 3430, 2930, 2860, 1720, 1640, 1455, 1440, 1375, 1245, 1225, 1170, 1155, and 1185. NMR absorptions are observed at 1.15, 3.70, 4.40, 5.50, and 6.75 δ.

For 9-deoxy-9,10-didehydro-12,13-(E)-didehydro-13,14-dihydro-15-methyl-PGD$_2$, methyl ester infrared absorptions are observed at 3450, 2930, 2860, 1740, 1700, 1650, 1580, 1455, 1435, 1375, 1430, 1310, 1280, 1240, 1215, 1170, 1155, 1090, 1050, and 1015 cm.$^{-1}$. Infrared absorptions are observed at 3.65, 4.45, 6.70, and 7.55 δ.

EXAMPLE 41

9-Deoxy-PGF$_{2\alpha}$, methyl ester (Formula CXXVI: R$_1$ is methyl, Z$_1$ is cis-CH=CH—(CH$_2$)$_3$—, Y is trans-CH=CH—, R$_3$ and R$_4$ of the L$_1$ moiety and R$_5$ and R$_6$ of the M$_1$ moiety are all hydrogen, and R$_7$ is n-butyl).

Refer to Chart O.

A. A solution of PGF$_{2\alpha}$, 11,15-bis-(tetrahydropyranyl ether), 1.5 g., in methanol (20 ml.) at 0° C. is treated with excess ethereal diazomethane. After 5 min. at 0° C., acetic acid is added, decomposing excess diazomethane. The methanol is then removed under reduced pressure and the residue diluted with 100 ml. of diethyl ether. This ethereal solution is then washed with water, aqueous sodium bicarbonate, and dried over sodium sulfate. Removal of solvent under rotary evaporation yields 2 g. of crude PGF$_{2\alpha}$, methyl ester, 11,15-bis-(tetrahydropyranyl ether), which is chromatographed on 200 g. of silica gel, eluting with 40 percent ethyl acetate in Skellysolve B, thereby yielding 1.5 g. of PGF$_{2\alpha}$, methyl ester, 11,15-bis-(tetrahydropyranyl ether).

B. The reaction product of part A of this example is dissolved in anhydrous pyridine (10 ml.) and treated with recrystallized p-toluenesulfonyl chloride (3 g.). After 18 hr. at ambient temperature the reaction mixture is poured into a mixture of ice, brine, diethyl ether, and 70 ml. of 2N potassium bisulfate. The resulting mixture is then thoroughly extracted with ether. The ethereal extracts are then washed with cold dilute aqueous potassium bisulfate, water, aqueous sodium bicarbonate and brine, and dried over anhydrous sodium sulfate. Removal of solvents under reduced pressure yields crude PGF$_{2\alpha}$, methyl ester, 9α-tosylate, 11,15-bis-(tetrahydropyranyl ether), 2 g., which is chromatographed on 200 g. of neutral silica gel. The column is packed and eluted with 30 percent ethyl acetate and Skellysolve B, yielding 1.3 g. of pure tosylate.

C. A solution of the reaction product of part B above (1.3 g.) and sodium borohydride (1.0 g.) in dimethylsulfoxide (15 ml.) is stirred under a nitrogen atmosphere at ambient temperature for 72 hr. The reaction mixture is then poured into a mixture of ice, water, potassium bisulfate, and diethyl ether. This mixture is extracted thoroughly with diethyl ether and the combined ethereal extracts are washed with aqueous sodium bicarbonate, water, and brine and dried over anhydrous sodium sulfate. Removal of solvent yields crude 9-deoxy-PGF$_2$, methyl ester, 11,15-bis-(tetrahydropyranyl ether), 1.1 g. This crude product is chromatographed on 250 g. of neutral silica gel packed with 5 percent ethyl acetate and Skellysolve B, eluting with 20 percent ethyl acetate and Skellysolve B. Accordingly, pure product is obtained. NMR absorptions are observed at 3.65, 3.2–3.8, 4.70, and 5.25–5.70 δ.

D. A solution of the reaction product of part C above (509 mg.) in tetrahydrofuran (36 ml.), water (30 ml.), and 85 percent phosphoric acid (6 ml.) is stirred for 3 hr. at 40° C. The reaction mixture is then poured into a mixture of ice, water, diethyl ether, and aqueous sodium bicarbonate and extracted with diethyl ether. The combined ethereal extracts are then washed with brine, dried over sodium sulfate. Removal of the solvent under reduced pressure yields 450 mg. of crude product which is chromatographed on 85 g. of neutral silica gel, packed and eluted with 80 percent ethyl acetate in hexane. Accordingly, pure title compound (208 mg.) is obtained. Infrared absorptions are observed at 3420, 1745, 1435, 1170, 1080, and 970 cm.$^{-1}$. NMR absorptions are observed at 0.88, 2.80, 3.65, 3.6–4.2, and 5.25–5.6 δ. The mass spectrum shows peaks at 352, 334, 316, 303, 290, 263, and 245.

EXAMPLE 42

PGD$_3$, 16,16-dimethyl-PGD$_3$, and 16,16-difluoro-PGD$_3$.

A. Grignard reagents are prepared by reacting magnesium turnings with 1-bromo-cis-2-pentene; 1-bromo-1,1-dimethyl-cis-2-pentene or 1-iodo-1,1-difluoro-cis-2-pentene. 1-iodo-1,1-difluoro-cis-2-pentene is prepared as follows:

2,2-difluoro-acetic acid is esterified with excess ethereal diazomethane. Thereafter the resulting methyl 2,2-difluoro-acetate is iodinized to methyl 2,2-difluoro-2-iodo-acetate by the procedure of Tetrahedron Lett. 3995 (1971) (e.g., addition of lithium diisopropylamine to the starting material, followed by treatment with iodine). This product is then reduced to a corresponding aldehyde 2,2-difluoro-2-iodo-acetaldehyde, employing diisobutyl aluminum hydride at −78° C. This aldehyde is then alkylated by a Wittig alkylation, employing the ylid ethyl triphenylphosphorane, (C$_6$H$_5$)$_3$P=CH—CH$_3$, thereby yielding the title iodide.

B. The Grignard reagent of part A is reacted with 3α-t-butyldimethylsilyloxy-5α-hydroxy-2β-(2-formyltrans-1-ethenyl)-1α-cyclopentaneacetic acid γ lactone, thereby preparing a corresponding 2β-[(3RS)-3-hydroxy-trans-1,cis-5-octadienyl] compound which is separated into (3R) and (3S) epimers by silica gel chromatography.

C. Following the procedures of the above examples the reaction product of step B is transformed to $PGD_3$.

Following the procedure of pats B and C above, but using a methyl or fluoro-substituted Grignard reagent, correspondingly 16,16-dimethyl-$PGD_3$ or 16,16-difluoro-$PGD_3$ is prepared.

Following the procedure of Example 41, but using each of the various PGF-type compounds described herein or known in the art, there are prepared the corresponding 9-deoxy-PGF-type compounds. For example, 16,16-difluoro-$PGF_{2\alpha}$, 11,15-(bis-tetrahydropyranyl ether) is transformed to 16,16-difluoro-9-deoxy-$PGF_2$.

Following the procedure of the above examples there are prepared the 12,13-(E)-didehydro-13,14-dihydro-PGD-type compounds of Tables A–D herein or the 9-deoxy-9,10-didehydro-PGD-type compounds of Tables A–H herein. Further following the procedures of the above examples, there are prepared 12,13-(E)-didehydro-13,14-dihydro-9-deoxy-9,10-didehydro-PGD-type compounds 12,13-(E)-didehydro-13,14-dihydro- or 9-deoxy-PGD-type compounds corresponding to each of the 12,13-(E)-didehydro-13,14-dihydro-PGD-type compounds of Tables A–D; or 9-deoxy-PGD-type compounds corresponding to each of the 9-deoxy-9,10-didehydro-PGD-type compounds of Tables A–H.

Table A

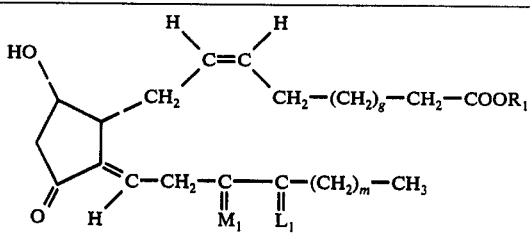

12,13-(E)-didehydro-13,14-dihydro-$PGD_2$-
type compounds

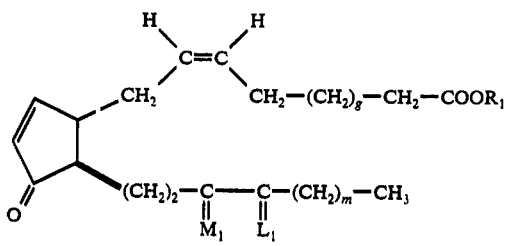

13,14-dihydro-9-deoxy-9,10-didehydro-$PGD_2$-
type compounds

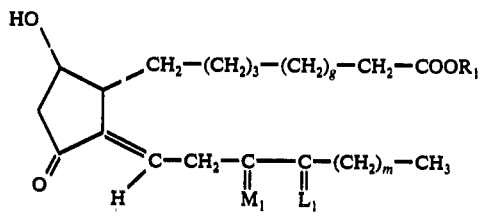

12,13-(E)-didehydro-13,14-dihydro-$PGD_1$-
type compounds

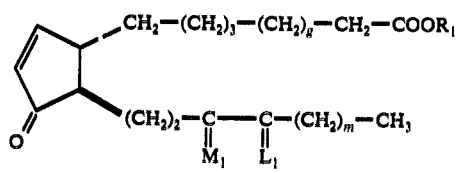

13,14-dihydro-9-deoxy-9,10-didehydro-$PGD_1$-
type compounds

Table A-continued
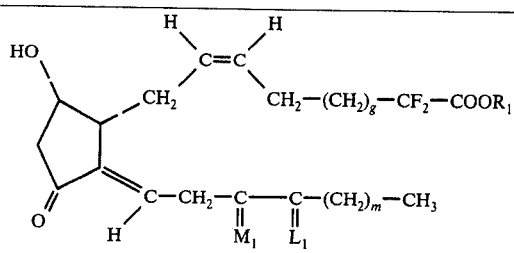
2,2-difluoro-12,13-(E)-didehydro-13,14-dihydro-PGD$_2$-type compounds
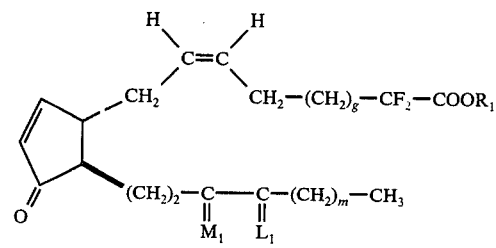
2,2-difluoro-13,14-dihydro-9-deoxy-9,10-didehydro-PGD$_2$-type compounds
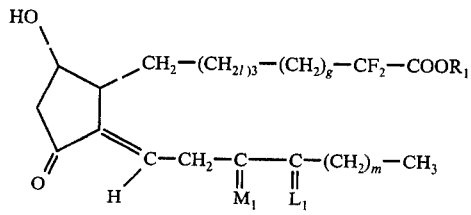
2,2-difluoro-12,13-(E)-didehydro-13,14-dihydro-PGD$_1$-type compounds
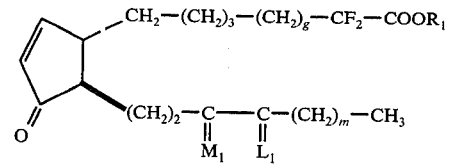
2,2-difluoro-13,14-dihydro-9-deoxy-9,10-didehydro-PGD$_1$-type compounds
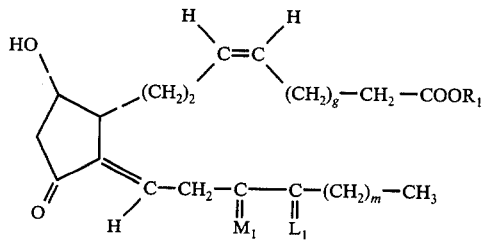
cis-4,5-didehydro-12,13-(F)-didehydro-13,14-dihydro-PGD$_1$-type compounds
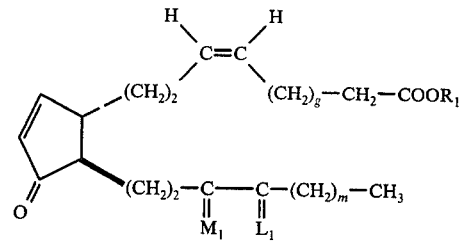
cis-4,5-didehydro-13,14-dihydro-9-deoxy-9,10-didehydro-PGD$_1$-type compounds Table A-continued
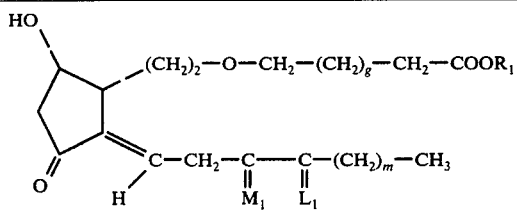
5-oxa-12,13-(E)-didehydro-13,14-dihydro-
PGD$_1$-type compounds
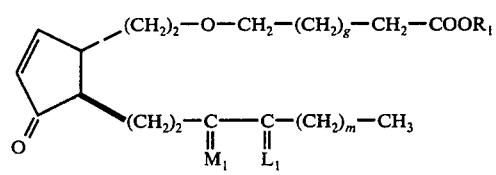
5-oxa-13,14-dihydro-9-deoxy-9,10-didehydro-
PGD$_1$-type compounds
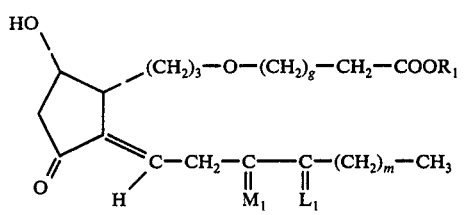
4-oxa-12,13-(E)-didehydro-13,14-dihydro-
PGD$_1$-type compounds
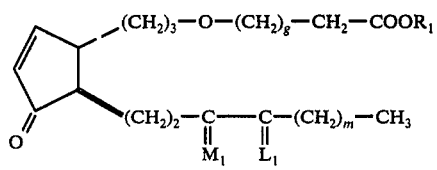
4-oxa-13,14-dihydro-9-deoxy-9,10-didehydro-
PGD$_1$-type compounds
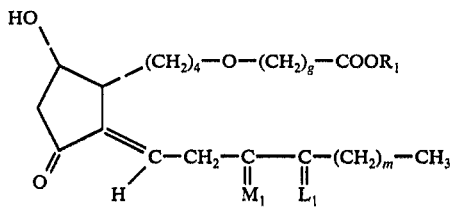
3-oxa-12,13-(F)-didehydro-13,14-dihydro-
PGD$_1$-type compounds
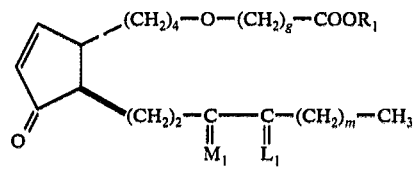
3-oxa-13,14-dihydro-9-deoxy-9,10-didehydro-
PGD$_1$-type compounds Table A-continued

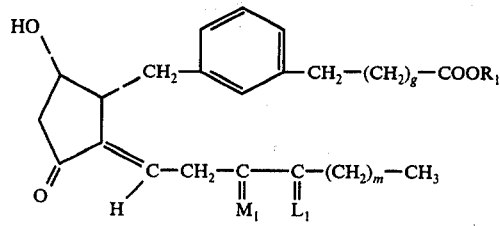

3,7-inter-m-phenylene-4,5,6-trinor-13,14-dihydro-
12,13-(E)-didehydro-PGD$_1$-type compounds

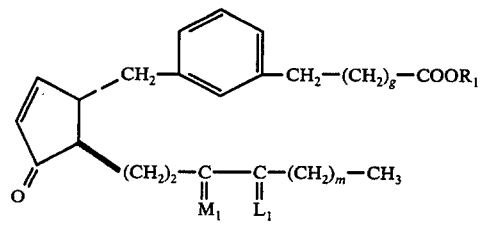

3,7-inter-m-phenylene-4,5,6-trinor-9-deoxy-9,10-
didehydro-13,14-dihydro-PGD$_1$-typecompounds

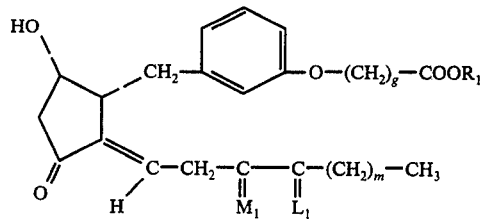

3,7-inter-m-phenylene-3-oxa-4,5,6-trinor-13,14-
dihydro-12,13-(E)-didehydro-PGD$_1$-type compounds

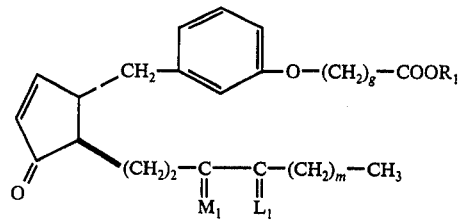

3,7-inter-m-phenylene-3-oxa-4,5,6-trinor-9-
deoxy-9,10-didehydro-13,14-dihydro-PGD$_1$-
type compounds

| Ex. | g | m | $R_3$ | $R_4$ | $L_1$ $R_5$ | $M_1$ $R_6$ | $\sim OR_6$ | $R_1$ | Name |
|---|---|---|---|---|---|---|---|---|---|
| A-1 | 1 | 3 | methyl | hydrogen | hydrogen | hydrogen | α | hydrogen | 16-methyl |
| A-2 | 1 | 3 | methyl | hydrogen | methyl | hydrogen | α | hydrogen | 15,16-dimethyl |
| A-3 | 1 | 3 | methyl | hydrogen | hydrogen | methyl | α | hydrogen | 16-methyl, 15-methyl ether |
| A-4 | 1 | 3 | methyl | methyl | hydrogen | hydrogen | α | hydrogen | 16,16-dimethyl |
| A-5 | 1 | 3 | methyl | methyl | methyl | hydrogen | α | hydrogen | 15,16,16-trimethyl |
| A-6 | 1 | 3 | methyl | methyl | hydrogen | methyl | α | hydrogen | 16,16-dimethyl, 15-methyl ether |
| A-7 | 1 | 3 | fluoro | hydrogen | hydrogen | hydrogen | α | hydrogen | 16-fluoro |
| A-8 | 1 | 3 | fluoro | hydrogen | methyl | hydrogen | α | hydrogen | 15-methyl-16-fluoro |
| A-9 | 1 | 3 | fluoro | hydrogen | hydrogen | methyl | α | hydrogen | 16-fluoro, 15-methyl ether |
| A-10 | 1 | 3 | fluoro | fluoro | hydrogen | hydrogen | α | hydrogen | 16,16-difluoro |
| A-11 | 1 | 3 | fluoro | fluoro | methyl | hydrogen | α | hydrogen | 15-methyl-16,16-difluoro |

Table A-continued

| ID | | | | | | | | | |
|---|---|---|---|---|---|---|---|---|---|
| A-12 | 1 | 3 | fluoro | fluoro | hydrogen | methyl | α | hydrogen | 16,16-difluoro, 15-methyl ether |
| A-13 | 1 | 3 | hydrogen | hydrogen | hydrogen | hydrogen | α | hydrogen | (title compound) |
| A-14 | 1 | 3 | hydrogen | hydrogen | hydrogen | methyl | α | hydrogen | 15-methyl ether |
| A-15 | 3 | 3 | hydrogen | hydrogen | hydrogen | hydrogen | α | hydrogen | 2a,2b-dihomo |
| A-16 | 3 | 3 | methyl | methyl | hydrogen | hydrogen | α | hydrogen | 21,2b-dihomo-16,16-dimethyl |
| A-17 | 3 | 3 | methyl | methyl | methyl | hydrogen | α | hydrogen | 2a,2b-dihomo-15,16,16-trimethyl |
| A-18 | 3 | 3 | fluoro | fluoro | hydrogen | hydrogen | α | hydrogen | 2a,2b-dihomo-16,16-difluoro |
| A-19 | 3 | 3 | fluoro | fluoro | methyl | hydrogen | α | hydrogen | 2a,2b-dihomo-15-methyl-16,16-difluoro |

Table B

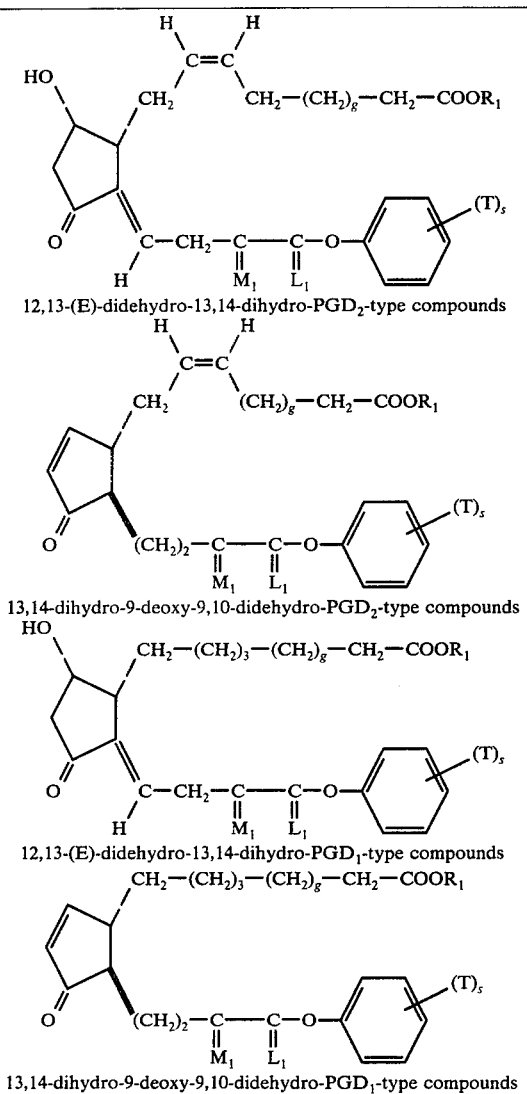

12,13-(E)-didehydro-13,14-dihydro-PGD$_2$-type compounds 13,14-dihydro-9-deoxy-9,10-didehydro-PGD$_2$-type compounds 12,13-(E)-didehydro-13,14-dihydro-PGD$_1$-type compounds 13,14-dihydro-9-deoxy-9,10-didehydro-PGD$_1$-type compounds Table B-continued
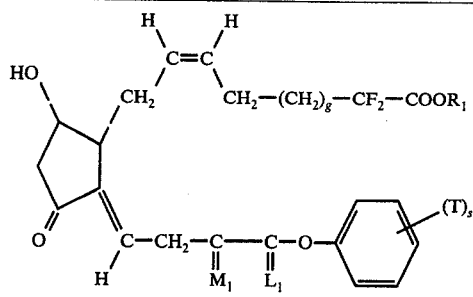
2,2-difluoro-12,13-(E)-didehydro-13,14-dihydro-PGD$_2$-type compounds
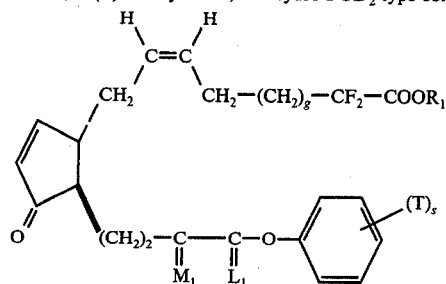
2,2-difluoro-13,14-dihydro-9-deoxy-9,10-didehydro-PGD$_2$-type compounds
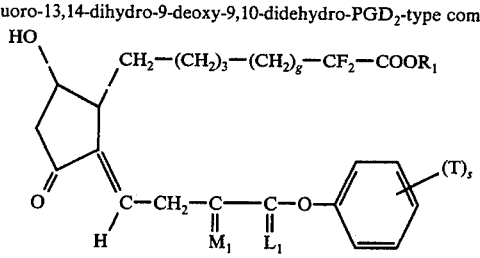
2,2-difluoro-12,13-(E)-didehydro-13,14-dihydro-PGD$_1$-type compounds
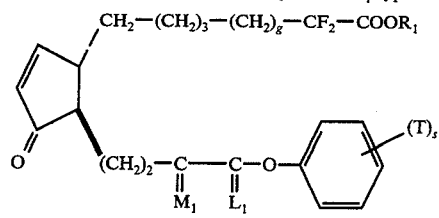
2,2-difluoro-13,14-dihydro-12,13-(E)-didehydro-13,14-dihydro-PGD$_1$-type compounds
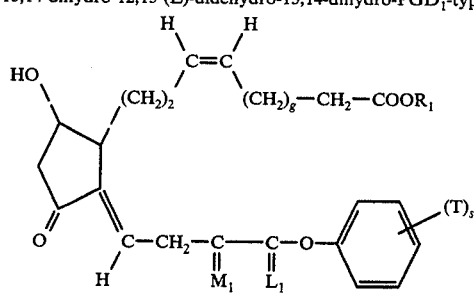
cis-4,5-didehydro-12,13-(E)-didehydro-13,14-dihydro-PGD$_1$-type compounds
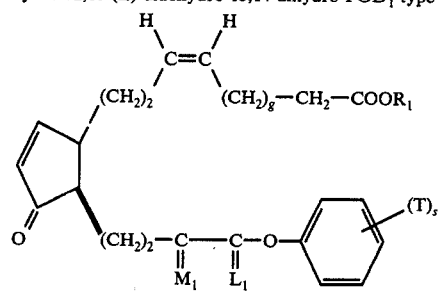
cis-4,5-didehydro-13,14-dihydro-9-deoxy-9,10-didehydro-PGD$_1$-type compounds

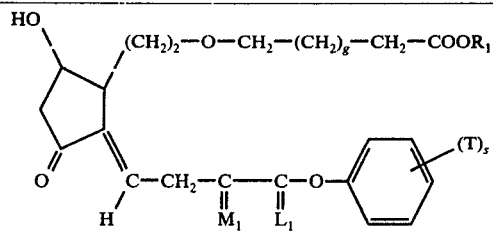
5-oxa-12,13-(E)-didehydro-13,14-dihydro-PGD$_1$-type compounds
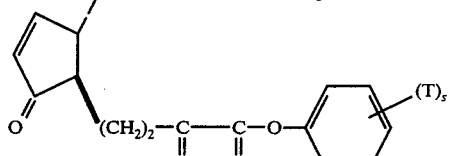
5-oxa-13,14-dihydro-9-deoxy-9,10-didehydro-PGD$_1$-type compounds
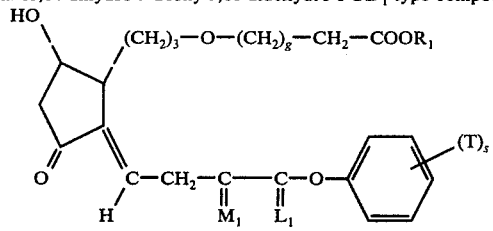
4-oxa-12,13-(E)-didehydro-13,14-dihydro-PGD$_1$-type compounds
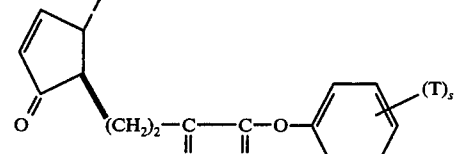
4-oxa-13,14-dihydro-9-deoxy-9,10-didehydro-PGD$_1$-type compounds
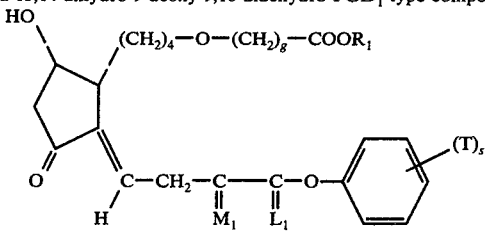
3-oxa-12,13-(E)-didehydro-13,14-dihydro-PGD$_1$-type compounds
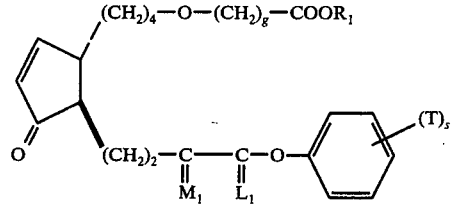
3-oxa-13,14-dihydro-9-deoxy-9,10-didehydro-PGD$_1$-type compounds
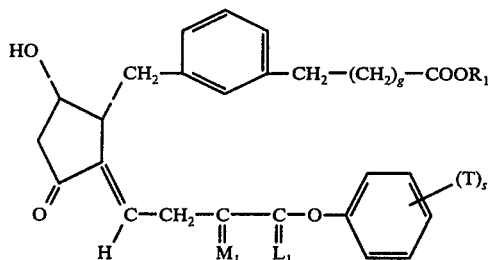
4-oxa-12,13-(E)-didehydro-13,14-dihydro-PGD$_1$-type compounds Table B-continued

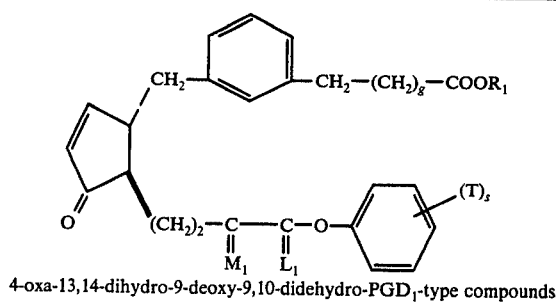
4-oxa-13,14-dihydro-9-deoxy-9,10-didehydro-PGD$_1$-type compounds

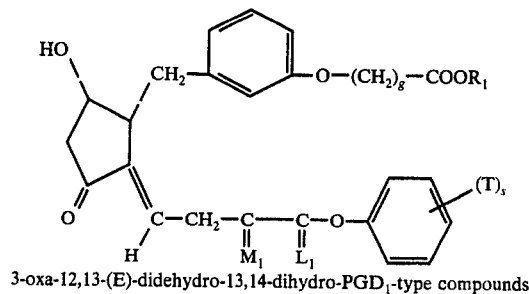
3-oxa-12,13-(E)-didehydro-13,14-dihydro-PGD$_1$-type compounds

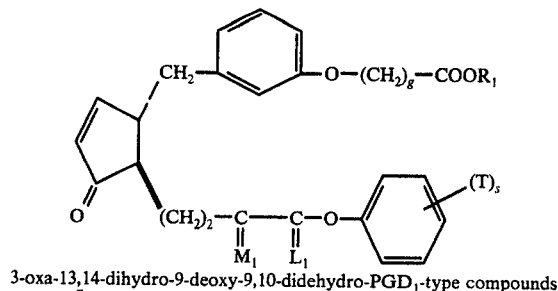
3-oxa-13,14-dihydro-9-deoxy-9,10-didehydro-PGD$_1$-type compounds

| Example | g | s | T | $L_1$ $R_3$ | $R_4$ | $R_5$ | $M_1$ $R_6$ | ~$OR_6$ | $R_1$ | Name |
|---|---|---|---|---|---|---|---|---|---|---|
| B-1 | 1 | 0 | | hydrogen | hydrogen | hydrogen | hydrogen | α | hydrogen | 16-phenoxy-17,18,19,20-tetranor |
| B-2 | 1 | 1 | p-fluoro | hydrogen | hydrogen | hydrogen | hydrogen | α | hydrogen | 16-(p-fluorophenoxy)-17,18,19,20-tetranor |
| B-3 | 1 | 1 | m-chloro | hydrogen | hydrogen | hydrogen | hydrogen | α | hydrogen | 16-(m-chlorophenoxy)-17,18,19,20-tetranor |
| B-4 | 1 | 1 | m-trifluoromethyl | hydrogen | hydrogen | hydrogen | hydrogen | α | hydrogen | 16-(m-trifluoromethylphenoxy)-17,18,19,20-tetranor |
| B-5 | 1 | 0 | | hydrogen | hydrogen | methyl | hydrogen | α | hydrogen | 15-methyl-16-phenoxy-17,18,19,20-tetranor |
| B-6 | 1 | 1 | p-fluoro | hydrogen | hydrogen | methyl | hydrogen | α | hydrogen | 15-methyl-16-(p-fluorophenoxy)-17,18,19,20-tetranor |
| B-7 | 1 | 1 | m-chloro | hydrogen | hydrogen | methyl | hydrogen | α | hydrogen | 15-methyl-16-(m-chlorophenoxy)17,18,19,20-tetranor |
| B-8 | 1 | 1 | m-trifluoromethyl | hydrogen | hydrogen | methyl | hydrogen | α | hydrogen | 15-methyl-16-(m-trifluoromethyl)phenoxy) |
| B-9 | 1 | 0 | | hydrogen | hydrogen | hydrogen | methyl | α | hydrogen | 16-phenoxy-17,18,19,20-tetranor, 15-methyl ether |
| B-10 | 1 | 1 | p-fluoro | hydrogen | hydrogen | hydrogen | methyl | α | hydrogen | 16-(p-fluorophenoxy)-17,18,19,20-tetranor, 15-methyl ether |
| B-11 | 1 | 1 | m-chloro | hydrogen | hydrogen | hydrogen | methyl | α | hydrogen | 16-(m-chlorophenoxy)-17,18,19,20-tetranor, 15-methyl ether |
| B-12 | 1 | 1 | m-trifluoromethyl | hydrogen | hydrogen | hydrogen | methyl | α | hydrogen | 16-(m-trifluoromethylphenoxy)-17,18,19,20-tetranor, 15-methyl ether |
| B-13 | 1 | 0 | | methyl | methyl | hydrogen | hydrogen | α | hydrogen | 16-methyl-16-phenoxy-18,19,20-trinor |
| B-14 | 1 | 1 | p-fluoro | methyl | methyl | hydrogen | hydrogen | α | hydrogen | 16-methyl-16-(p-fluorophenoxy)-18,19,20-trinor |
| B-15 | 1 | 1 | m-chloro | methyl | methyl | hydrogen | hydrogen | α | hydrogen | 16-methyl-16-(m-chlorophenoxy)-18,19,20-trinor |
| B-16 | 1 | 1 | m-trifluoromethyl | methyl | methyl | hydrogen | hydrogen | α | hydrogen | 16-methyl-16-(m-trifluoromethylphenoxy)-18,19,20-trinor |
| B-17 | 1 | 0 | | methyl | methyl | methyl | hydrogen | α | hydrogen | 15,16-dimethyl-16-phenoxy-18,19,20-trinor |
| B-18 | 1 | 1 | p-fluoro | methyl | methyl | methyl | hydrogen | α | hydrogen | 15,16-dimethyl-16-(p-chlorophenoxy)-18,19,20-trinor |
| B-19 | 1 | 1 | m-chloro | methyl | methyl | methyl | hydrogen | α | hydrogen | 15,16-dimethyl-16-(m-chlorophenoxy)-18,19,20-trinor |
| B-20 | 1 | 1 | m-tri- | methyl | methyl | methyl | hydrogen | α | hydrogen | 15,16-dimethyl-16-(m-trifluoro- |

Table B-continued

| | | | | | | gen | | gen | methylphenoxy)-18,19,20-trinor |
|---|---|---|---|---|---|---|---|---|---|
| | | | fluoro-methyl | | | | | | |
| B-21 | 1 | 0 | | methyl | methyl | hydro-gen | methyl | α | hydro-gen | 16-methyl-16-phenoxy-18,19,20-trinor, 15-methyl ether |
| B-22 | 1 | 1 | p-fluoro | methyl | methyl | hydro-gen | methyl | α | hydro-gen | 16-methyl-16-(p-fluorophenoxy)-18,19,20-trinor, 15-methyl ether |
| B-23 | 1 | 1 | m-chloro | methyl | methyl | hydro-gen | methyl | α | hydro-gen | 16-methyl-16-(m-chlorophenoxy)-18,19,2o-trinor, 15-methyl ether |
| B-24 | 1 | 1 | m-tri-fluoro-methyl | methyl | methyl | hydro-gen | methyl | α | hydro-gen | 16-methyl-16-(m-trifluoromethyl-phenoxy)-18,19,20-trinor, 15-methyl ether |
| B-25 | 3 | 0 | | hydro-gen | hydro-gen | hydro-gen | hydro-gen | α | hydro-gen | 2a,2b-dihomo-16-phenoxy-17,18,19,20-tetranor |
| B-26 | 3 | 1 | p-fluoro | hydro-gen | hydro-gen | hydro-gen | hydro-gen | α | hydro-gen | 2a,2b-dihomo-16-(p-fluorophen-oxy)-17,18,19,20-tetranor |
| B-27 | 3 | 1 | m-chloro | hydro-gen | hydro-gen | hydro-gen | hydro-gen | α | hydro-gen | 2a,2b-dihomo-16-(m-chlorophen-oxy)-17,18,19,20-tetranor |
| B-28 | 3 | 1 | m-tri-fluoro-methyl | hydro-gen | hydro-gen | hydro-gen | hydro-gen | α | hydro-gen | 2a,2b-dihomo-16-(m-trifluoro-methylphenoxy)-17,18,19,20-tetranor |
| B-29 | 3 | 0 | | hydro-gen | hydro-gen | methyl | hydro-gen | α | hydro-gen | 2a,2b-dihomo-15-methyl-16-phen-oxy-17,18,19,20-tetranor |
| B-30 | 3 | 1 | p-fluoro | hydro-gen | hydro-gen | methyl | hydro-gen | α | hydro-gen | 2a,2b-dihomo-15-methyl-16-(p-fluorophenoxy)-17,18,19,20-tetranor |
| B-31 | 3 | 1 | m-chloro | hydro-gen | hydro-gen | methyl | hydro-gen | α | hydro-gen | 2a,2b-dihomo-15-methyl-16-(m-chlorophenoxy)-17,19,19,20-tetranor |
| B-32 | 3 | 1 | m-tri-fluoro-methyl | hydro-gen | hydro-gen | methyl | hydro-gen | α | hydro-gen | 2a,2b-dihomo-15-methyl-16-(m-trifluoromethylphenoxy)-17,18,19,20-tetranor |

Table C

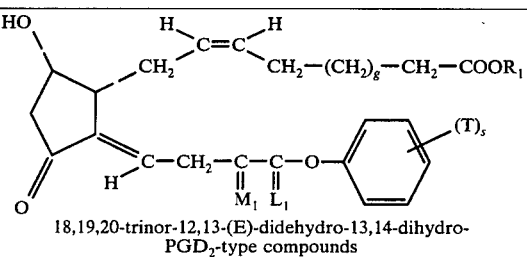

18,19,20-trinor-12,13-(E)-didehydro-13,14-dihydro-PGD$_2$-type compounds

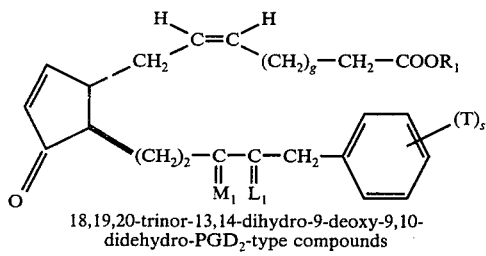

18,19,20-trinor-13,14-dihydro-9-deoxy-9,10-didehydro-PGD$_2$-type compounds

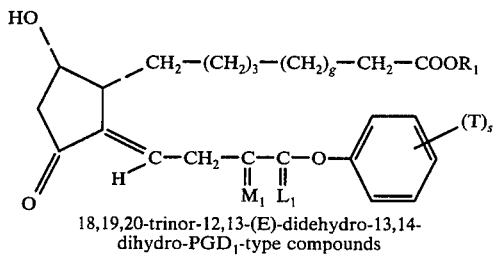

18,19,20-trinor-12,13-(E)-didehydro-13,14-dihydro-PGD$_1$-type compounds

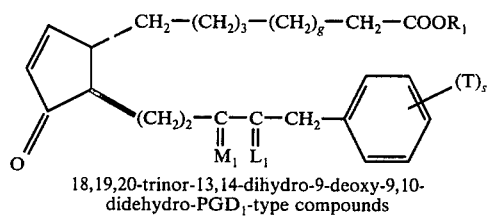

18,19,20-trinor-13,14-dihydro-9-deoxy-9,10-didehydro-PGD$_1$-type compounds

Table C-continued

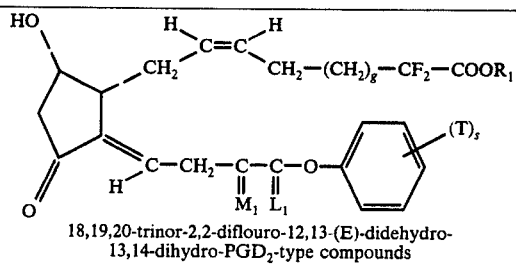
18,19,20-trinor-2,2-diflouro-12,13-(E)-didehydro-13,14-dihydro-PGD$_2$-type compounds

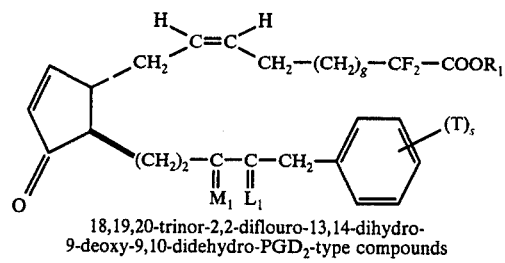
18,19,20-trinor-2,2-diflouro-13,14-dihydro-9-deoxy-9,10-didehydro-PGD$_2$-type compounds

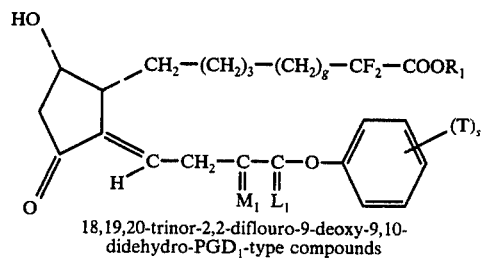
18,19,20-trinor-2,2-diflouro-9-deoxy-9,10-didehydro-PGD$_1$-type compounds

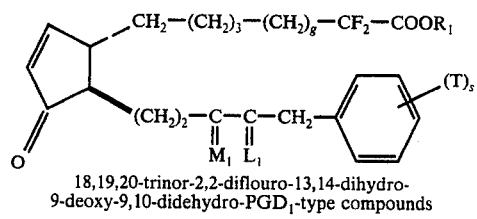
18,19,20-trinor-2,2-diflouro-13,14-dihydro-9-deoxy-9,10-didehydro-PGD$_1$-type compounds

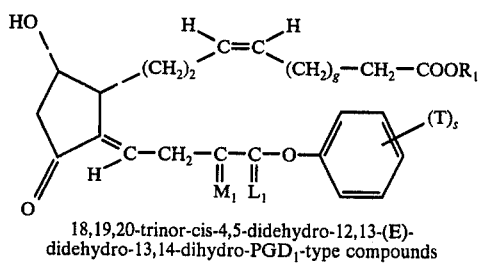
18,19,20-trinor-cis-4,5-didehydro-12,13-(E)-didehydro-13,14-dihydro-PGD$_1$-type compounds

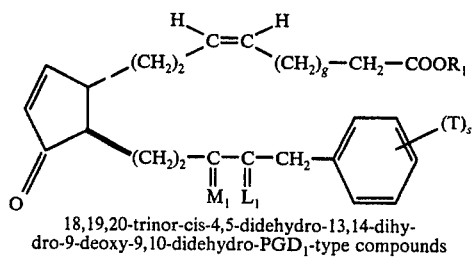
18,19,20-trinor-cis-4,5-didehydro-13,14-dihydro-9-deoxy-9,10-didehydro-PGD$_1$-type compounds

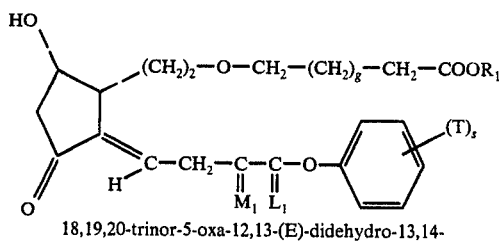
18,19,20-trinor-5-oxa-12,13-(E)-didehydro-13,14-

Table C-continued
dihydro-PGD$_1$-type compounds

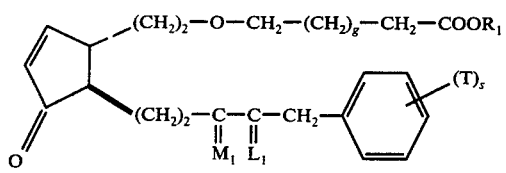

18,19,20-trinor-5-oxa-13,14-dihydro-9-deoxy-
9,10-didehydro-PGD$_1$-type compounds

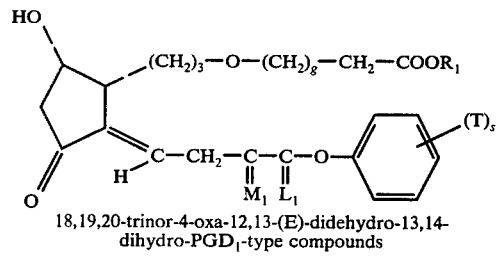

18,19,20-trinor-4-oxa-12,13-(E)-didehydro-13,14-
dihydro-PGD$_1$-type compounds

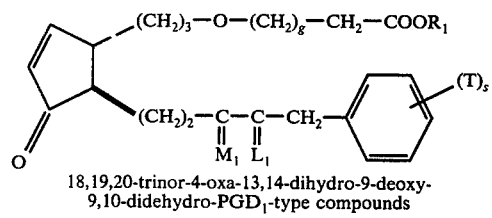

18,19,20-trinor-4-oxa-13,14-dihydro-9-deoxy-
9,10-didehydro-PGD$_1$-type compounds

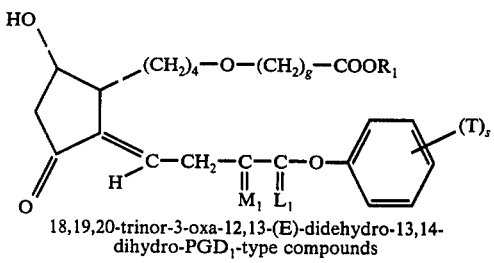

18,19,20-trinor-3-oxa-12,13-(E)-didehydro-13,14-
dihydro-PGD$_1$-type compounds

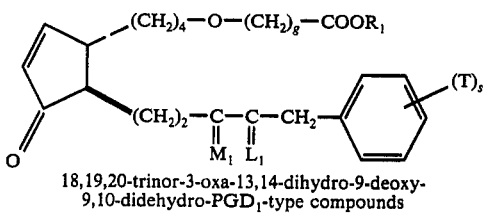

18,19,20-trinor-3-oxa-13,14-dihydro-9-deoxy-
9,10-didehydro-PGD$_1$-type compounds

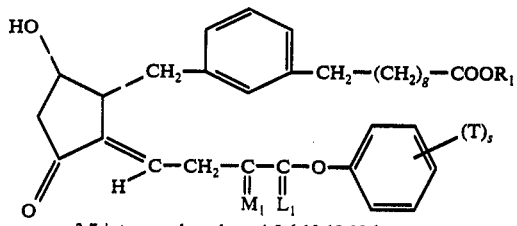

3,7-inter-m-phenylene-4,5,6,18,19,20-hexanor-
12,13-(E)-didehydro-13,14-dihydro-PGD$_1$-type compounds

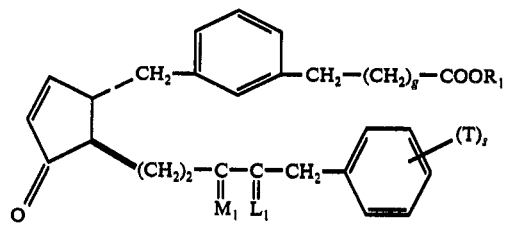

Table C-continued 3,7-inter-m-phenylene-4,5,6,18,19,20-hexanor-13,14-dihydro-9-deoxy-9,10-didehydro-PGD$_1$-type compounds

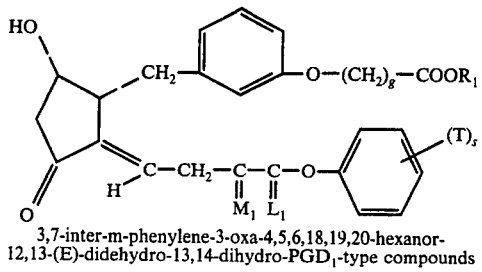

3,7-inter-m-phenylene-3-oxa-4,5,6,18,19,20-hexanor-12,13-(E)-didehydro-13,14-dihydro-PGD$_1$-type compounds

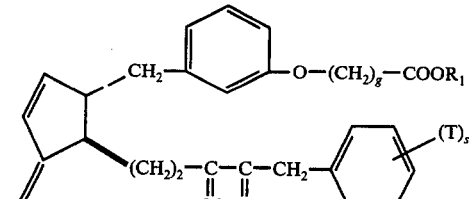

3,7-inter-m-phenylene-3-oxa-4,5,6,18,19,20-hexanor-13,14-dihydro-didehydro-13,14-dihydro-PGD$_1$-type compounds

| Example | g | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| C-1 | 1 | 0 | | hydrogen | hydrogen | hydrogen | hydrogen | α | hydrogen | 17-phenyl |
| C-2 | 1 | 1 | p-fluoro | hydrogen | hydrogen | hydrogen | hydrogen | α | hydrogen | 17-(p-fluorophenyl) |
| C-3 | 1 | 1 | m-chloro | hydrogen | hydrogen | hydrogen | hydrogen | α | hydrogen | 17-(m-chlorophenyl) |
| C-4 | 1 | 1 | m-trifluoromethyl | hydrogen | hydrogen | hydrogen | hydrogen | α | hydrogen | 17-(m-trifluoromethylphenyl) |
| C-5 | 1 | 0 | | hydrogen | hydrogen | methyl | hydrogen | α | hydrogen | 15-methyl-17-phenyl |
| C-6 | 1 | 1 | p-fluoro | hydrogen | hydrogen | methyl | hydrogen | α | hydrogen | 15-methyl-17-(p-fluorophenyl) |
| C-7 | 1 | 1 | m-chloro | hydrogen | hydrogen | methyl | hydrogen | α | hydrogen | 15-methyl-17-(m-chlorophenyl) |
| C-8 | 1 | 1 | m-trifluoromethyl | hydrogen | hydrogen | methyl | hydrogen | α | hydrogen | 15-methyl-17-(m-trifluoromethylphenyl) |
| C-9 | 1 | 0 | | hydrogen | hydrogen | hydrogen | methyl | α | hydrogen | 17-phenyl, 15-methyl ether |
| C-10 | 1 | 1 | p-fluoro | hydrogen | hydrogen | hydrogen | methyl | α | hydrogen | 17-(p-fluorophenyl), 15-methyl ether |
| C-11 | 1 | 1 | m-chloro | hydrogen | hydrogen | hydrogen | methyl | α | hydrogen | 17-(m-chlorophenyl), 15-methyl ether |
| C-12 | 1 | 1 | m-trifluoromethyl | hydrogen | hydrogen | hydrogen | methyl | α | hydrogen | 17-(m-trifluoromethylphenyl), 15-methyl ether |
| C-13 | 1 | 0 | | methyl | methyl | hydrogen | hydrogen | α | hydrogen | 16,16-dimethyl-17-phenyl |
| C-14 | 1 | 1 | p-fluoro | methyl | methyl | hydrogen | hydrogen | α | hydrogen | 16,16-dimethyl-17-(p-fluorophenyl) |
| C-15 | 1 | 1 | m-chloro | methyl | methyl | hydrogen | hydrogen | α | hydrogen | 16,16-dimethyl-17-(m-chlorophenyl) |
| C-16 | 1 | 1 | m-trifluoromethyl | methyl | methyl | hydrogen | hydrogen | α | hydrogen | 16,16-dimethyl-17-(m-trifluoromethylphenyl) |
| C-17 | 1 | 0 | | methyl | methyl | methyl | hydrogen | α | hydrogen | 15,16,16-trimethyl-17-phenyl |
| C-18 | 1 | 1 | p-fluoro | methyl | methyl | methyl | hydrogen | α | hydrogen | 15,16,16-trimethyl-17-(p-fluorophenyl) |
| C-19 | 1 | 1 | m-chloro | methyl | methyl | methyl | hydrogen | α | hydrogen | 15,16,16-trimethyl-17-(m-chlorophenyl) |
| C-20 | 1 | 1 | m-trifluoromethyl | methyl | methyl | methyl | hydrogen | α | hydrogen | 15,16,16-trimethyl-17-(m-trifluoromethylphenyl) |
| C-21 | 1 | 0 | | methyl | methyl | hydrogen | methyl | α | hydrogen | 16,16-dimethyl-17-phenyl, 15-methyl ether |
| C-22 | 1 | 1 | p-fluoro | methyl | methyl | hydrogen | methyl | α | hydrogen | 16,16-dimethyl-17-(p-fluorophenyl), 15-methyl ether |
| C-23 | 1 | 1 | m-chloro | methyl | methyl | hydrogen | methyl | α | hydrogen | 16,16-dimethyl-17-(m-chlorophenyl), 15-methyl ether |
| C-24 | 1 | 1 | m-trifluoromethyl | methyl | methyl | hydrogen | methyl | α | hydrogen | 16,16-dimethyl-17-(m-trifluoromethylphenyl), 15-methyl ether |
| C-25 | 3 | 0 | | hydrogen | hydrogen | hydrogen | hydrogen | α | hydrogen | 2a,2b-dihomo-17-phenyl |
| C-26 | 3 | 1 | p- | hydrogen | hydrogen | hydrogen | hydrogen | α | hydrogen | 2a,2b-dihomo-17-(p-fluorophenyl) |

Table C-continued

| | | | | | | | | | | |
|---|---|---|---|---|---|---|---|---|---|---|
| C-27 | 3 | 1 | fluoro m-chloro | gen hydrogen | gen hydrogen | gen hydrogen | gen hydrogen | α | gen hydrogen | 2a,2b-dihomo-17-(m-chlorophenyl) |
| C-28 | 3 | 1 | m-trifluoromethyl | hydrogen | hydrogen | hydrogen | hydrogen | α | hydrogen | 2a,2b-dihomo-17-(m-trifluoromethylphenyl) |
| C-29 | 3 | 0 | | hydrogen | hydrogen | methyl | hydrogen | α | hydrogen | 2a,2b-dihomo-15-methyl-17-phenyl |
| C-30 | 3 | 1 | p-fluoro | hydrogen | hydrogen | methyl | hydrogen | α | hydrogen | 2a,2b-dihomo-15-methyl-17-(p-fluorophenyl) |
| C-31 | 3 | 1 | m-chloro | hydrogen | hydrogen | methyl | hydrogen | α | hydrogen | 2a,2b-dihomo-15-methyl-17-(m-chlorophenyl) |
| C-32 | 3 | 1 | m-trifluoromethyl | hydrogen | hydrogen | methyl | hydrogen | α | hydrogen | 2a,2b-dihomo-15-methyl-17-(m-trifluoromethylphenyl) |
| C-33 | 1 | 0 | | fluoro | fluoro | hydrogen | hydrogen | α | hydrogen | 16,16-difluoro-17-phenyl |
| C-34 | 1 | 1 | p-fluoro | fluoro | fluoro | hydrogen | hydrogen | α | hydrogen | 16,16-difluoro-17-(p-fluorophenyl) |
| C-35 | 1 | 1 | m-chloro | fluoro | fluoro | hydrogen | hydrogen | α | hydrogen | 16,16-difluoro-17-(m-chlorophenyl) |
| C-36 | 1 | 1 | m-trifluoromethyl | fluoro | fluoro | hydrogen | hydrogen | α | hydrogen | 16,16-difluoro-17-(m-trifluoromethylphenyl) |
| C-37 | 1 | 0 | | fluoro | fluoro | methyl | hydrogen | α | hydrogen | 15-methyl-16,16-difluoro-17-phenyl |
| C-38 | 1 | 1 | p-fluoro | fluoro | fluoro | methyl | hydrogen | α | hydrogen | 15-methyl-16,16-difluoro-17-(p-fluorophenyl) |
| C-39 | 1 | 1 | m-chloro | fluoro | fluoro | methyl | hydrogen | α | hydrogen | 15-methyl-16,16-difluoro-17-(m-chlorophenyl) |
| C-40 | 1 | 1 | m-trifluoromethyl | fluoro | fluoro | methyl | hydrogen | α | hydrogen | 15-methyl-16,16-difluoro-17-(m-(trifluoromethylphenyl) |
| C-41 | 1 | 0 | | fluoro | fluoro | hydrogen | methyl | α | hydrogen | 16,16-difluoro-17-phenyl, 15-methyl ether |
| C-42 | 1 | 1 | p-fluoro | fluoro | fluoro | hydrogen | methyl | α | hydrogen | 16,16-difluoro-17-(p-fluorophenyl), 15-methyl ether |
| C-43 | 1 | 1 | m-chloro | fluoro | fluoro | hydrogen | methyl | α | hydrogen | 16,16-difluoro-17-(m-chlorophenyl), 15-methyl ether |
| C-44 | 1 | 1 | m-trifluoromethyl | fluoro | fluoro | hydrogen | methyl | α | hydrogen | 16,16-difluoro-17-(m-trifluoromethylphenyl), 15-methyl ether |

Table D

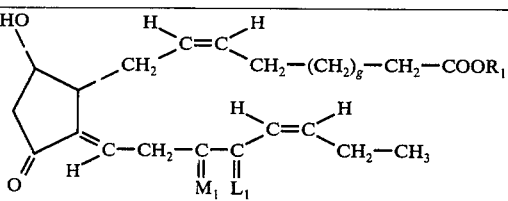

12,13-(E)-didehydro-13,14-dihydro-PGD$_3$-type compounds

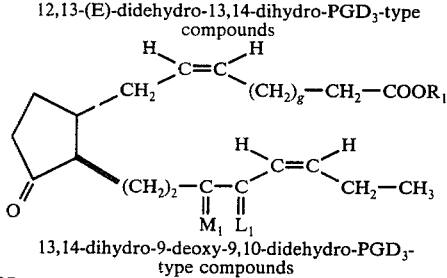

13,14-dihydro-9-deoxy-9,10-didehydro-PGD$_3$-type compounds

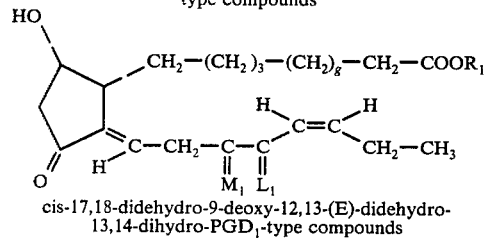

cis-17,18-didehydro-9-deoxy-12,13-(E)-didehydro-13,14-dihydro-PGD$_1$-type compounds

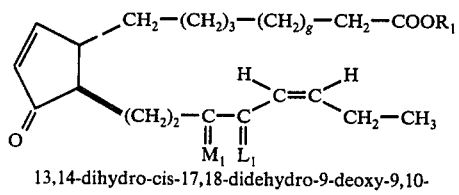

13,14-dihydro-cis-17,18-didehydro-9-deoxy-9,10-

Table D-continued

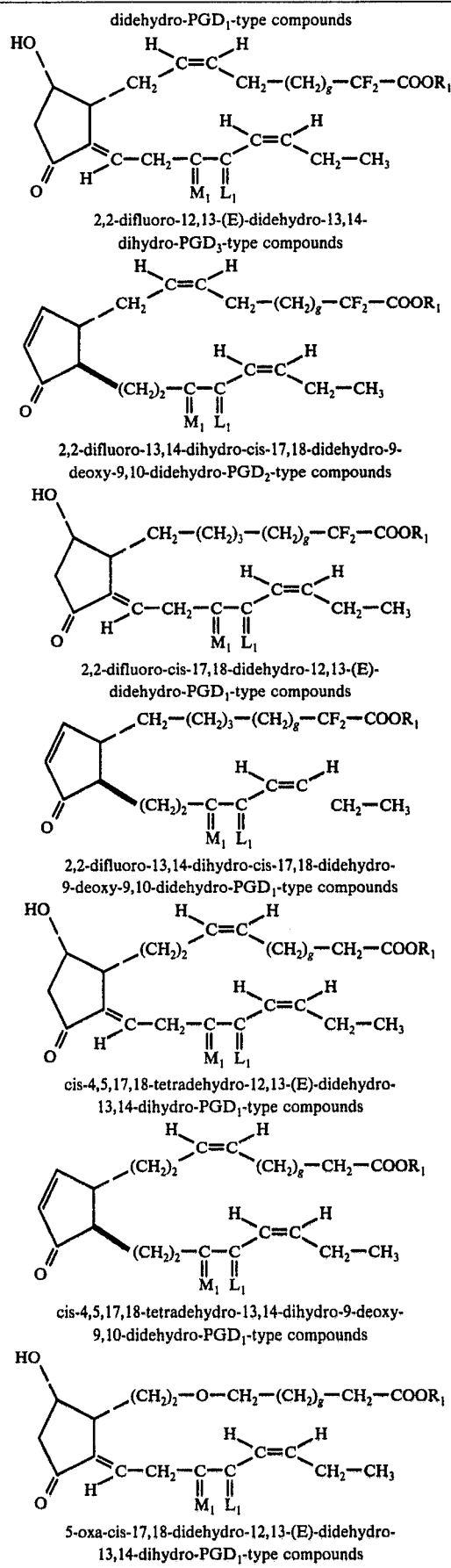

didehydro-PGD$_1$-type compounds 2,2-difluoro-12,13-(E)-didehydro-13,14-
dihydro-PGD$_3$-type compounds 2,2-difluoro-13,14-dihydro-cis-17,18-didehydro-9-
deoxy-9,10-didehydro-PGD$_2$-type compounds 2,2-difluoro-cis-17,18-didehydro-12,13-(E)-
didehydro-PGD$_1$-type compounds 2,2-difluoro-13,14-dihydro-cis-17,18-didehydro-
9-deoxy-9,10-didehydro-PGD$_1$-type compounds cis-4,5,17,18-tetradehydro-12,13-(E)-didehydro-
13,14-dihydro-PGD$_1$-type compounds cis-4,5,17,18-tetradehydro-13,14-dihydro-9-deoxy-
9,10-didehydro-PGD$_1$-type compounds 5-oxa-cis-17,18-didehydro-12,13-(E)-didehydro-
13,14-dihydro-PGD$_1$-type compounds

Table D-continued

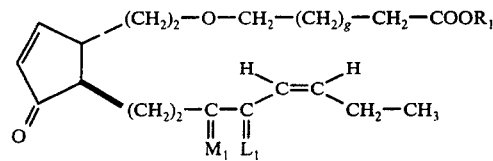

5-oxa-13,14-dihydro-cis-17,18-didehydro-9-deoxy-
9,10-didehydro-PGD$_1$-type compounds

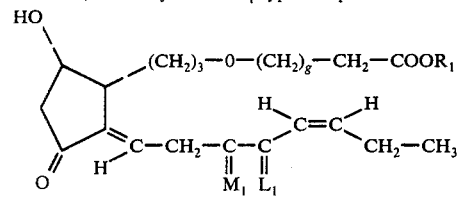

4-oxa-cis-17,18-didehydro-12,13-(E)-didehydro-
13,14-dihydro-PGD$_1$-type compounds

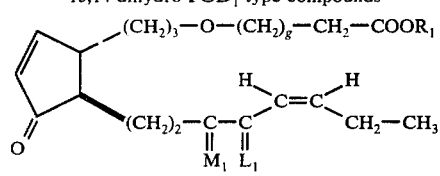

4-oxa-13,14-dihydro-17,18-didehydro-9-deoxy-
9,10-didehydro-PGD$_1$-type compounds

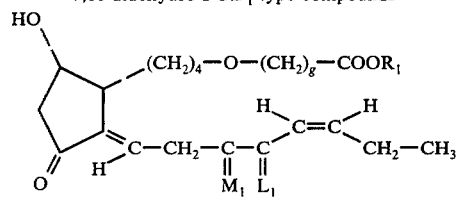

3-oxa-cis-17,18-didehydro-12,13-(E)-didehydro-
13,14-dihydro-PGD$_1$-type compounds

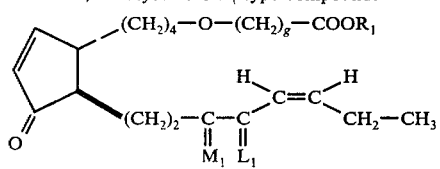

3-oxa-13,14-dihydro-cis-17,18-didehydro-9-
deoxy-9,10-didehydro-PGD$_1$-type compounds

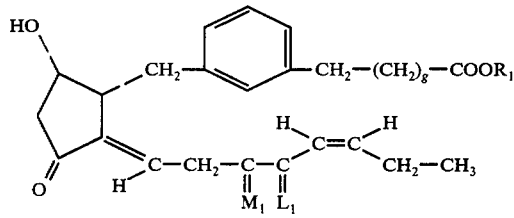

3,7-inter-m-phenylene-4,5,6-trinor-cis-17,18-dide-
hydro-12,13-(E)-didehydro-13,14-dihydro-PGD$_1$-type
compounds

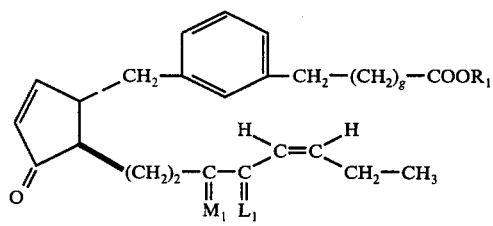

3,7-inter-m-phenylene-4,5,6-trinor-13,14-dihydro-
cis-17,18-didehydro-9-deoxy-9,10-didehydro-PGD$_1$-
type compounds

Table D-continued

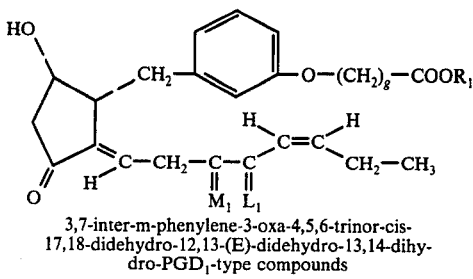

3,7-inter-m-phenylene-3-oxa-4,5,6-trinor-cis-17,18-didehydro-12,13-(E)-didehydro-13,14-dihydro-PGD$_1$-type compounds

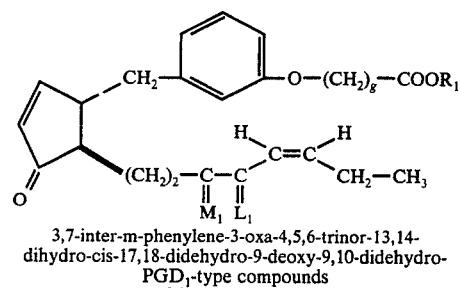

3,7-inter-m-phenylene-3-oxa-4,5,6-trinor-13,14-dihydro-cis-17,18-didehydro-9-deoxy-9,10-didehydro-PGD$_1$-type compounds

| Example | g | L$_1$ | | M$_1$ | | ~OR$_6$ | R$_1$ | Name |
| | | R$_3$ | R$_4$ | R$_5$ | R$_6$ | | | |
|---|---|---|---|---|---|---|---|---|
| D-1 | 1 | methyl | hydrogen | hydrogen | hydrogen | α | hydrogen | 16-methyl |
| D-2 | 1 | methyl | hydrogen | methyl | hydrogen | α | hydrogen | 15,16-dimethyl |
| D-3 | 1 | methyl | hydrogen | hydrogen | methyl | α | hydrogen | 16-methyl, 15-methyl |
| d-4 | 1 | methyl | methyl | hydrogen | hydrogen | α | hydrogen | 16,16-dimethyl |
| D-5 | 1 | methyl | methyl | methyl | hydrogen | α | hydrogen | 15,16,16-trimethyl |
| D-6 | 1 | methyl | methyl | hydrogen | methyl | α | hydrogen | 16,16-dimethyl, 15-methyl ether |
| D-7 | 1 | fluoro | hydrogen | hydrogen | hydrogen | α | hydrogen | 16-fluoro |
| D-8 | 1 | fluoro | hydrogen | methyl | hydrogen | α | hydrogen | 15-methyl-16-fluoro |
| D-9 | 1 | fluoro | hydrogen | hydrogen | methyl | α | hydrogen | 16-fluoro,15-methyl ether |
| D-10 | 1 | fluoro | fluoro | hydrogen | hydrogen | α | hydrogen | 16,16-difluoro |
| D-11 | 1 | fluoro | fluoro | methyl | hydrogen | α | hydrogen | 15-methyl-16,16-difluoro |
| D-12 | 1 | fluoro | fluoro | hydrogen | methyl | α | hydrogen | 16,16-difluoro, 15-methyl ether |
| D-13 | 1 | hydrogen | hydrogen | hydrogen | hydrogen | α | hydrogen | (titlecompound) |
| D-14 | 1 | hydrogen | hydrogen | methyl | hydrogen | α | hydrogen | 15-methyl |
| D-15 | 3 | hydrogen | hydrogen | hydrogen | hydrogen | α | hydrogen | 2a,2b-dihomo |
| D-16 | 3 | hydrogen | hydrogen | methyl | hydrogen | α | hydrogen | 2a,2b-dihomo-15-methyl |
| D-17 | 3 | methyl | methyl | hydrogen | hydrogen | α | hydrogen | 2a,2b-dihomo-16,16-dimethyl |
| D-18 | 3 | methyl | methyl | methyl | hydrogen | α | hydrogen | 2a,2b-dihomo-15,16,16-trimethyl |
| D-19 | 3 | fluoro | fluoro | hydrogen | hydrogen | α | hydrogen | 2a,2b-dihomo-16,16-difluoro |
| D-20 | 3 | fluoro | fluoro | methyl | hydrogen | α | hydrogen | 2a,2b-dihomo-15-methyl-16,16-difluoro |

Table E

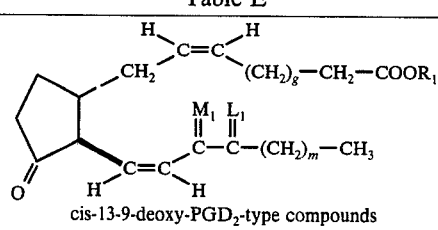

cis-13-9-deoxy-PGD$_2$-type compounds

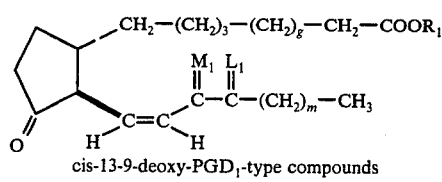

cis-13-9-deoxy-PGD$_1$-type compounds

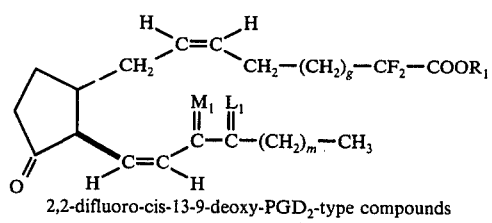

2,2-difluoro-cis-13-9-deoxy-PGD$_2$-type compounds

Table E-continued

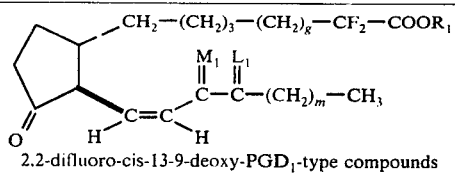
2,2-difluoro-cis-13-9-deoxy-PGD$_1$-type compounds

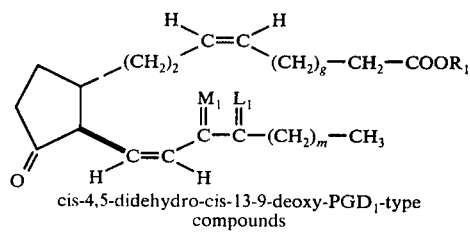
cis-4,5-didehydro-cis-13-9-deoxy-PGD$_1$-type compounds

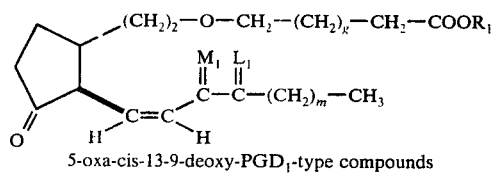
5-oxa-cis-13-9-deoxy-PGD$_1$-type compounds

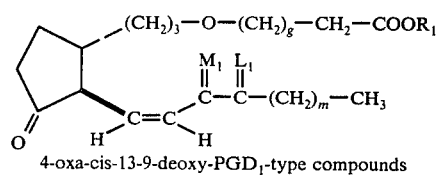
4-oxa-cis-13-9-deoxy-PGD$_1$-type compounds

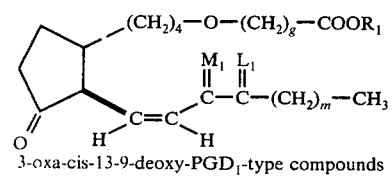
3-oxa-cis-13-9-deoxy-PGD$_1$-type compounds

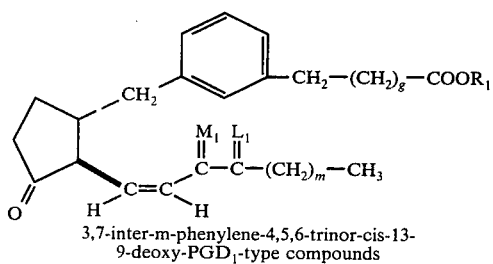
3,7-inter-m-phenylene-4,5,6-trinor-cis-13-9-deoxy-PGD$_1$-type compounds

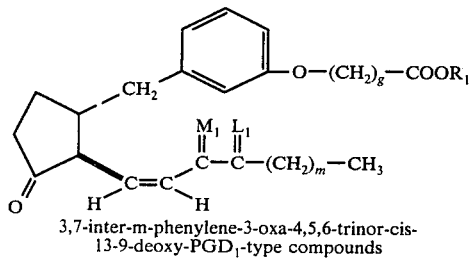
3,7-inter-m-phenylene-3-oxa-4,5,6-trinor-cis-13-9-deoxy-PGD$_1$-type compounds

| Example | g | m | L$_1$ R$_3$ | R$_4$ | M$_1$ R$_5$ | R$_6$ | ~OR$_{62}$ | R$_1$ | Name |
|---|---|---|---|---|---|---|---|---|---|
| E-1 | 1 | 3 | methyl | hydrogen | hydrogen | hydrogen | α | hydrogen | 15-epi-16-methyl |
| E-2 | 1 | 3 | methyl | hydrogen | methyl | hydrogen | α | hydrogen | 15-epi-15,16-dimethyl |
| E-3 | 1 | 3 | methyl | hydrogen | hydroten | methyl | α | hydrogen | 15-epi-16-methyl, 15-methyl ether |
| E-4 | 1 | 3 | methyl | methyl | hydrogen | hydrogen | α | hydrogen | 15-epi-16,16-dimethyl |
| E-5 | 1 | 3 | methyl | methyl | methyl | hydrogen | α | hydrogen | 15-epi-15,16,16-trimethyl |

Table E-continued

| | | | | | | | | | |
|---|---|---|---|---|---|---|---|---|---|
| E-6 | 1 | 3 | methyl | methyl | hydrogen | methyl | α | hydrogen | 15-epi-16,16-dimethyl, 15-methyl ether |
| E-7 | 1 | 3 | fluoro | hydrogen | hydrogen | hydrogen | α | hydrogen | 15-epi-16-fluoro |
| E-8 | 1 | 3 | fluoro | hydrogen | methyl | hydrogen | α | hydrogen | 15-epi-15-methyl-16-fluoro |
| E-9 | 1 | 3 | fluoro | hydrogen | hydrogen | methyl | α | hydrogen | 15-epi-16-fluoro, 15-methyl ether |
| E-10 | 1 | 3 | fluoro | fluoro | hydrogen | hydrogen | α | hydrogen | 15-epi-16,16-difluoro |
| E-11 | 1 | 3 | fluoro | fluoro | methyl | hydrogen | α | hydrogen | 15-epi-15-methyl-16,16-difluoro |
| E-12 | 1 | 3 | fluoro | fluoro | hydrogen | methyl | α | hydrogen | 15-epi-16,16-difluoro, 15-methyl ether |
| E-13 | 1 | 3 | hydrogen | hydrogen | hydrogen | methyl | α | hydrogen | 15-epi, 15-methyl ether |
| E-14 | 3 | 3 | hydrogen | hydrogen | hydrogen | hydrogen | α | hydrogen | 15-epi-2a,2b-dihomo |
| E-15 | 3 | 3 | methyl | methyl | hydrogen | hydrogen | α | hydrogen | 15-epi-2a,2b-dihomo-16,16-dimethyl |
| E-16 | 3 | 3 | methyl | methyl | methyl | hydrogen | α | hydrogen | 15-epi-2a,2b-dihomo-15,16,16-trimethyl |
| E-17 | 3 | 3 | fluoro | fluoro | hydrogen | hydrogen | α | hydrogen | 15-epi-2a,2b-dihomo-16,16-difluoro |
| E-18 | 3 | 3 | fluoro | fluoro | methyl | hydrogen | α | hydrogen | 15-epi-2a,2b-dihomo-15-methyl-16,16-difluoro |

Table F

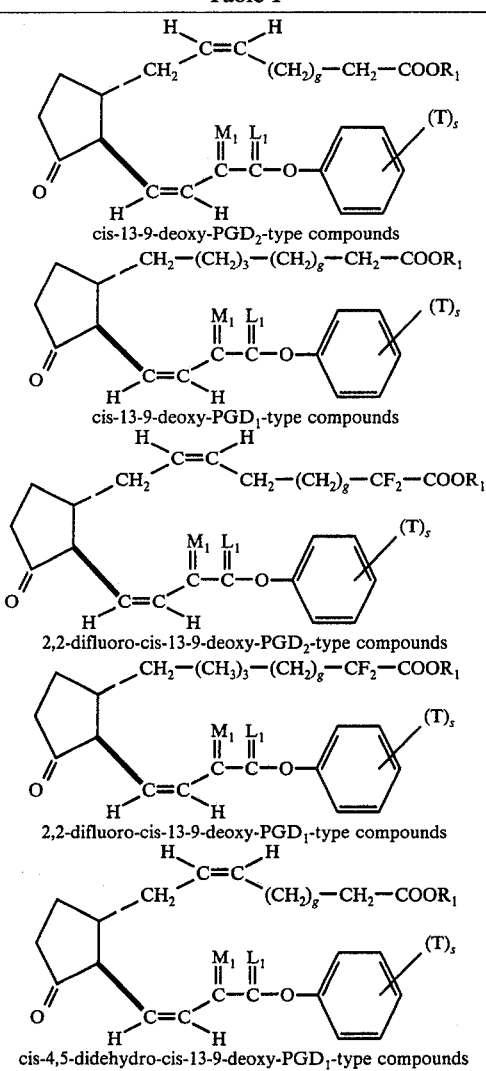

cis-13-9-deoxy-PGD$_2$-type compounds cis-13-9-deoxy-PGD$_1$-type compounds 2,2-difluoro-cis-13-9-deoxy-PGD$_2$-type compounds 2,2-difluoro-cis-13-9-deoxy-PGD$_1$-type compounds cis-4,5-didehydro-cis-13-9-deoxy-PGD$_1$-type compounds

Table F-continued

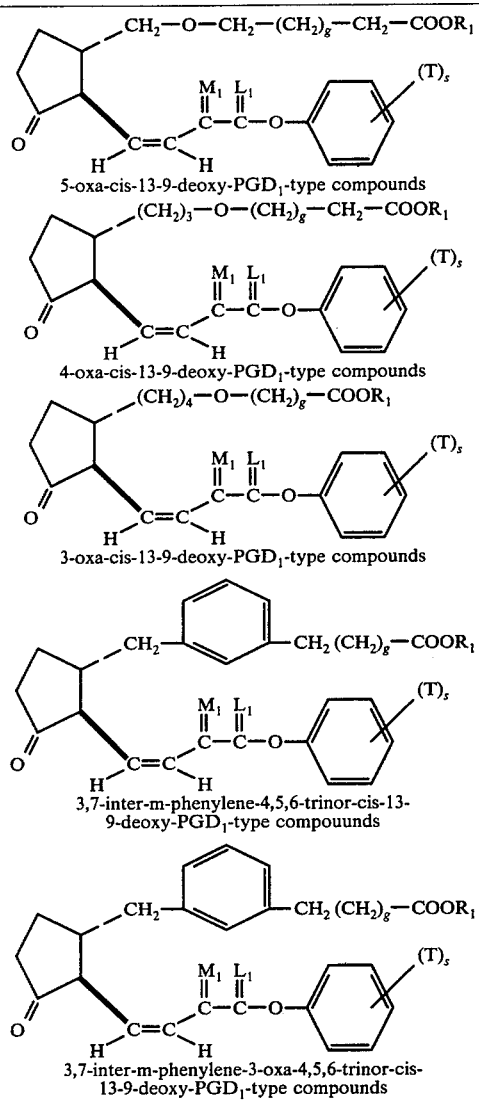

5-oxa-cis-13-9-deoxy-PGD$_1$-type compounds 4-oxa-cis-13-9-deoxy-PGD$_1$-type compounds 3-oxa-cis-13-9-deoxy-PGD$_1$-type compounds 3,7-inter-m-phenylene-4,5,6-trinor-cis-13-9-deoxy-PGD$_1$-type compouunds 3,7-inter-m-phenylene-3-oxa-4,5,6-trinor-cis-13-9-deoxy-PGD$_1$-type compounds

| Example | g | s | T | L$_1$ R$_3$ | L$_1$ R$_4$ | M$_1$ R$_5$ | M$_1$ R$_6$ | ~OR$_6$ | R$_1$ | Name |
|---|---|---|---|---|---|---|---|---|---|---|
| F-1 | 1 | 0 | | hydrogen | hydrogen | hydrogen | hydrogen | α | hydrogen | 15-epi-16-phenoxy-17,18,19,20-tetranor |
| F-2 | 1 | 1 | p-fluoro | hydrogen | hydrogen | hydrogen | hydrogen | α | hydrogen | 15-epi-16-(p-fluorophenoxy)-17,181,19,20-tetranor |
| F-3 | 1 | 1 | m-chloro | hydrogen | hydrogen | hydrogen | hydrogen | α | hydrogen | 15-epi-16-(m-trifluoromethyl-17,18,19,20-tetranor |
| F-4 | 1 | 1 | m-trifluoromethyl | hydrogen | hydrogen | hydrogen | hydrogen | α | hydrogen | 15-epi-16-(m-trilfuoromethylphenoxy)-17,18,19,20-tetranor |
| F-5 | 1 | 0 | | hydrogen | hydrogen | methyl | hydrogen | α | hydrogen | 15-epi-15-methyl-16-phenoxy-17,18,19,20-tetranor |
| F-6 | 1 | 1 | p-fluoro | hydrogen | hydrogen | methyl | hydrogen | α | hydrogen | 15-epi-15-methyl-16-(p-fluorophenoxy)-17,18,19,20-tetranor |
| F-7 | 1 | 1 | m-chloro | hydrogen | hydrogen | methyl | hydrogen | α | hydrogen | 15-epi-15-methyl-16-(m-chlorophenoxy)-17,18,19,20-tetranor |
| F-8 | 1 | 1 | m-trifluoromethyl | hydrogen | hydrogen | methyl | hydrogen | α | hydrogen | 15-epi-15-methyl-16-(m-trifluoromethylphenoxy)-17,18,19,20-tetranor |
| F-9 | 1 | 0 | | hydrogen | hydrogen | hydrogen | methyl | α | hydrogen | 15-epi-16-phenoxy-17,18,19,20-tetranor, 15-methyl ether |
| F-10 | 1 | 1 | p-fluoro | hydrogen | hydrogen | hydrogen | methyl | α | hydrogen | 15-epi-16-(p-fluorophenoxy)-17,18,19,20-tetranor, 15-methyl ether |
| F-11 | 1 | 1 | m-chloro | hydrogen | hydrogen | hydrogen | methyl | α | hydrogen | 15-epi-16-(m-chlorophenoxy)-17,18,19,20-tetranor, 15-methyl ether |
| F-12 | 1 | 1 | m-trifluoromethyl | hydrogen | hydrogen | hydrogen | methyl | α | hydrogen | 15-epi-16-(m-trifluoromethylphenoxy)-17,18,19,20-tetranor, 15-methyl ether |
| F-13 | 1 | | | methyl | methyl | hydrogen | hydrogen | α | hydrogen | 15-epi-16-methyl-16-phenoxy-18,19,20-trinor |
| F-14 | 1 | 1 | p- | methyl | methyl | hydrogen | hydro- | α | hydro- | 15-epi-16-methyl-16-(p-fluoro- |

… Table F-continued

| | | | | | | | | | |
|---|---|---|---|---|---|---|---|---|---|
| F-15 | 1 | 1 | m-chloro | methyl | methyl | hydrogen | hydrogen | α | hydrogen | 15-epi-16-methyl-16-(m-chlorophenoxy-(-18,19,20-trinor |
| F-16 | 1 | 1 | m-trifluoromethyl | methyl | methyl | hydrogen | hydrogen | α | hydrogen | 15-epi-16-methyl-16-(m-trifluoromethylphenoxy)-18,19,20-trinor |
| F-17 | 1 | 0 | | methyl | methyl | methyl | hydrogen | α | hyrogen | 15-epi-15,16-dimethyl-16-phenoxy-18,19,20-trinor |
| F-18 | 1 | 1 | p-fluoro | methyl | methyl | methyl | hydrogen | α | hydrogen | 15-epi-15,16-dimethyl-16-(p-fluorophenoxy)-18,19,20-trinor |
| F-19 | 1 | 1 | m-chloro | methyl | methyl | methyl | hydrogen | α | hydrogen | 15-epi-15,16-dimethyl-16-(m-chlorophenoxy)-18,19,20-trinor |
| F-20 | 1 | 1 | m-trifluoromethyl | methyl | methyl | methyl | hydrogen | α | hydrogen | 15-epi-15,16-dimethyl-16-(m-trifluoromethylphenoxy)-18,19,20-trinor |
| F-21 | 1 | 0 | | methyl | methyl | hydrogen | methyl | α | hydrogen | 15-epi-16-methyl-16-phenoxy-18,19,20-trinor, 15-methyl ether |
| F-22 | 1 | 1 | p-fluoro | methyl | methyl | hydrogen | methyl | α | hydrogen | 15-epi-16-methyl-16-(p-fluorophenoxy)-18,19,20-trinor, 15-methyl ether |
| F-23 | 1 | 1 | m-chloro | methyl | methyl | hydrogen | methyl | α | hydrogen | 15-epi-16-methyl-16-(m-chlorophenoxy)-18,19,20-trinor, 15-methyl ether |
| F-24 | 1 | 1 | m-trifluoromethyl | methyl | methyl | hydrogen | methyl | α | hydrogen | 15-epi-16-methyl-16-(m-trifluoromethylphenoxy)-18,19,20-trinor, 15-methyl ether |
| F-25 | 3 | 0 | | hydrogen | hydrogen | hydrogen | hydrogen | α | hydrogen | 15-epi-2a,2b-dihomo-16-phenoxy-17,18,19,20-tetranor |
| F-26 | 3 | 1 | p-fluoro | hydrogen | hydrogen | hydrogen | hydrogen | α | hydrogen | 15-epi-2a,2b-dihomo-16-(p-fluorophenoxy)17,18,19,20-tetranor |
| F-27 | 3 | 1 | m-chloro | hydrogen | hydrogen | hydrogen | hydrogen | α | hydrogen | 15-epi-2a,2b-dihomo-16-(m-chlorophenoxy)-17,18,19,20-tetranor |
| F-28 | 3 | 1 | m-trifluoromethyl | hydrogen | hydrogen | hydrogen | hydrogen | α | hydrogen | 15-epi-2a,2b-dihomo-16-(m-trifluoromethyl phenoxy)-17,18,19,20-tetranor |
| F29 | 3 | 0 | | hydrogen | hydrogen | methyl | hydrogen | α | hydrogen | 15-epi-2a,2b-dihomo-15-methyl-16-phenoxy-17,18,19,20-tetranor |
| F-30 | 3 | 1 | p-fluoro | hydrogen | hydrogen | methyl | hydrogen | α | hydrogen | 15-epi-2a,2b-dihomo-15-methyl-16-(p-fluorophenoxy)-17,18,19,20-tetranor |
| F-31 | 3 | 1 | m-chloro | hydrogen | hydrogen | methyl | hydrogen | α | hydrogen | 15-epi-2a,2b-dihomo-15-methyl-16-(m-chlorophenoxy)-17,18,19,20-tetranor |
| F-32 | 3 | 1 | m-trifluoromethyl | hydrogen | hydrogen | methyl | hydrogen | α | hydrogen | 15-epi-2a,2b-dihomo-15-methyl-16-(m-trifluoromethylphenoxy)-17,18,19,20-tetranor |

Table G

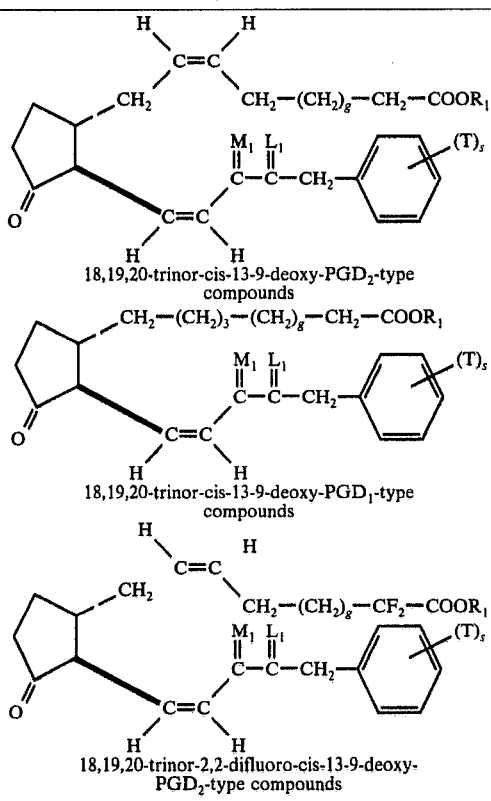

18,19,20-trinor-cis-13-9-deoxy-PGD$_2$-type compounds 18,19,20-trinor-cis-13-9-deoxy-PGD$_1$-type compounds 18,19,20-trinor-2,2-difluoro-cis-13-9-deoxy-PGD$_2$-type compounds

Table G-continued

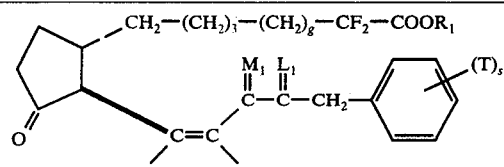
18,19,20-trinor-2,2-difluoro-cis-13-9-deoxy-
PGD$_1$-type compounds

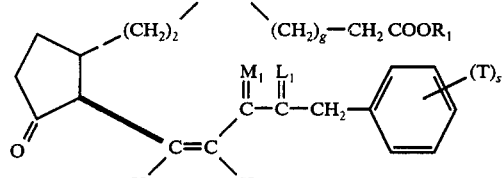
18,19,20-trinor-cis-13-9-deoxy-PGD$_2$-type
compounds

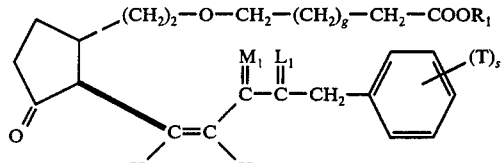
18,19,20-trinor-cis-13-9-deoxy-PGD$_1$-type
compounds

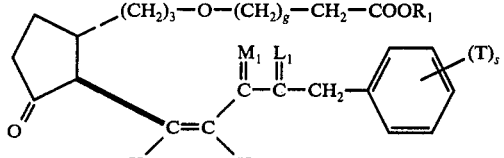
18,19,20-trinor-2,2-difluoro-cis-13-9-deoxy-
PGD$_2$-type compounds

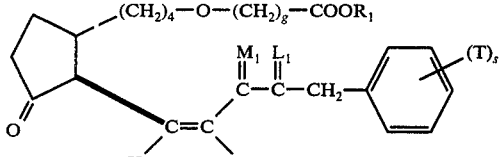
18,19,20-trinor-2,2-difluoro-cis-13-9-deoxy-
PGD$_1$-type compounds

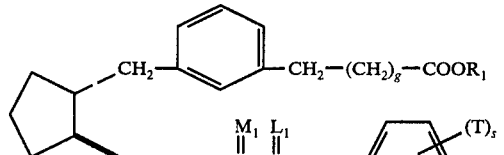
3,7-inter-m-phenylene-4,5,6,18,19,20-hexanor-
cis-13-9-deoxy-PGD$_1$-type compounds

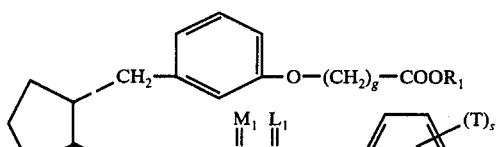
3,7-inter-m-phenylene-3-oxa-4,5,6,18,19,20-
hexanor-cis-13-9-deoxy-PGD$_1$-type compounds

| Exam- | L$_1$ | M$_1$ |
| --- | --- | --- |

Table G-continued

| ple | g | s | T | $R_3$ | $R_4$ | $R_5$ | $R_6$ | ~$OR_6$ | $R_1$ | Name |
|---|---|---|---|---|---|---|---|---|---|---|
| G-1 | 1 | 0 |  | hydrogen | hydrogen | hydrogen | hydrogen | α | hydrogen | 15-epi-17-phenyl |
| G-2 | 1 | 1 | p-fluoro | hydrogen | hydrogen | hydrogen | hydrogen | α | hydrogen | 15-epi-17-(p-fluorophenyl) |
| G-3 | 1 | 1 | m-chloro | hydrogen | hydrogen | hydrogen | hydrogen | α | hydrogen | 15-epi-17-(m-chlorophenyl) |
| G-4 | 1 | 1 | m-trifluoromethyl | hydrogen | hydrogen | hydrogen | hydrogen | α | hydrogen | 15-epi-17-(m-trifluoromethylphenyl) |
| G-5 | 1 | 0 |  | hydrogen | hydrogen | methyl | hydrogen | α | hydrogen | 15-epi-15-methyl-17-phenyl |
| G-6 | 1 | 1 | p-fluoro | hydrogen | hydrogen | methyl | hydrogen | α | hydrogen | 15-epi-15-methyl-17-)p-fluorophenyl) |
| G-7 | 1 | 1 | m-chloro | hydrogen | hydrogen | methyl | hydrogen | α | hydrogen | 15-epi-15-methyl-17-(m-chlorophenyl) |
| G-8 | 1 | 1 | m-trifluoromethyl | hydrogen | hydrogen | methyl | hydrogen | α | hydrogen | 15-epi-15-methyl-17-(m-trifluoromethylphenyl) |
| G-9 | 1 | 0 |  | hydrogen | hydrogen | hydrogen | methyl | α | hydrogen | 15-epi-17-phenyl, 15-methyl ether |
| G-10 | 1 | 1 | p-fluoro | hydrogen | hydrogen | hydrogen | methyl | α | hydrogen | 15-epi-17-(p-fluorophenyl), 15-methyl ether |
| G-11 | 1 | 1 | m-chloro | hydro gen | hydrogen | hydrogen | methyl | α | hydrogen | 15-epi-17-(m-chlorophenyl), 15-methyl ether |
| G-12 | 1 | 1 | m-trifluoro | hydrogen | hydrogen | hydrogen | methyl | α | hydrogen | 15-epi-17-(m-trifluoromethylphenyl), 15-methyl ether |
| G-13 | 1 | 0 |  | methyl | methyl | hydrogen | hydrogen | α | hydrogen | 15-epi-16,16-dimethyl-17-phenyl |
| G-14 | 1 | 1 | p-fluoro | methyl | methyl | hydrogen | hydrogen | α | hydrogen | 15-epi-16,16-dimethyl-17-(p-fluorophenyl) |
| G-15 | 1 | 1 | m-chloro | methyl | methyl | hydrogen | hydrogen | α | hydrogen | 15-epi-16,16-dimethyl-17-(m-chlorophenyl) |
| G-16 | 1 | 1 | m-trifluoromethyl | methyl | methyl | hydrogen | hydrogen | α | hydrogen | 15-epi-16,16-dimethyl-17-(m-trifluoromethylphenyl) |
| G-17 | 1 | 0 |  | methyl | methyl | methyl | hydrogen | α | hydrogen | 15-epi-15,16,16-trimethyl-17-phenyl |
| G-18 | 1 | 1 | p-fluoro | methyl | methyl | methyl | hydrogen | α | hydrogen | 15-epi-15,16,16-trimethyl-17-(p-fluorophenyl) |
| G-19 | 1 | 1 | m-chloro | methyl | methyl | methyl | hydrogen | α | hydrogen | 15-epi-15,16,16-trimethyl-17-(m-chlorophenyl) |
| G-20 | 1 | 1 | m-trifluoromethyl | methyl | methyl | methyl | hydrogen | α | hydrogen | 15-epi-15,16,16-trimethyl-(m-trifluoromethylphenyl) |
| G-21 | 1 | 0 |  | methyl | methyl | hydrogen | methyl | α | hydrogen | 15-epi-16,16-dimethyl-17-phenyl, 15-methyl ether |
| G-22 | 1 | 1 | p-fluoro | methyl | methyl | hydrogen | methyl | α | hydrogen | 15-epi-16,16-dimethyl-17-(p-fluorophenyl), 15-methyl ether |
| G-23 | 1 | 1 | m-chloro | methyl | methyl | hydrogen | methyl | α | hydrogen | 15-epi-16,16-dimethyl-17-(m-chlorophenyl), 15-methyl ether |
| G-24 | 1 | 1 | m-trifluoromethyl | methyl | methyl | hydrogen | methyl | α | hydrogen | 15-epi-16,16-dimethyl-17-(m-trifluoromethylhenyl), 15-methyl ether |
| G-25 | 3 | 0 |  | hydrogen | hydrogen | hydrogen | hydrogen | α | hydrogen | 15-epi-2a,2b-dihomo-17-phenyl |
| G-26 | 3 | 1 | p-fluoro | hydrogen | hydrogen | hydrogen | hydrogen | α | hydrogen | 15-epi-2a,2b-dihomo-17-(p-fluorophenyl) |
| G-27 | 3 | 1 | m-chloro | hydrogen | hydrogen | hydrogen | hydrogen | α | hydrogen | 15-epi-2a,2b-dihomo-17-(m-chlorophenyl) |
| G-28 | 3 | 1 | m-trifluoromethyl | hydrogen | hdyrogen | hydrogen | hydrogen | α | hydrogen | 15-epi-2a,2b-dihomo-17-(m-trifluoromethylphenyl) |
| G-29 | 3 | 0 |  | hydrogen | hydrogen | methyl | hydrogen | α | hydrogen | 15-epi-2a,2b-dihomo-15-methyl-17-phenyl |
| G-30 | 3 | 1 | p-fluoro | hydrogen | hydrogen | methyl | hydrogen | α | hydrogen | 15-epi-2a,2b-dihomo-15-methyl-17-(p-fluorophenyl) |
| G-31 | 3 | 1 | m-chloro | hydrogen | hydrogen | methyl | hydrogen | α | hydrogen | 15-epi-2a,2b-dihomo-15-methyl-17-(m-chlorophenyl) |
| G-32 | 3 | 1 | m-teifluoromethyl | hydrogen | hydrogen | methyl | hydrogen | α | hydrogen | 15-epi-2a,2b-dihomo-165-methyl-17-(m-trifluoromethylphenyl) |
| G-33 | 1 | 0 |  | fluoro | fluoro | hydrogen | hydrogen | α | hydrogen | 15-epi-16,16-difluoro-17-phenyl |
| G-34 | 1 | 1 | p-fluoro | fluoro | fluoro | hydrogen | hydrogen | α | hydrogen | 15-epi-16,16-difluoro-17-(p-fluorophenyl) |
| G-35 | 1 | 1 | m-chloro | fluoro | fluoro | hydrogen | hydrogen | α | hydrogen | 15-epi-16,16-difluoro-17-(m-chlorophenyl) |
| G-36 | 1 | 1 | m-trifluoromethyl | fluoro | fluoro | hydrogen | hydrogen | α | hydrogen | 15-epi-16,16-difluoro-17-(m-trifluoromethylphenyl) |
| G-37 | 1 | 0 |  | fluoro | fluoro | methyl | hydrogen | α | hydrogen | 15-epi-15-methyl-16,16-difluoro 17-phenyl |
| G-38 | 1 | 1 | p-fluoro | fluoro | fluoro | methyl | hydrogen | α | hydrogen | 15-epi-15-methyl-16,16-difluoro-17-(p-fluorophenyl) |
| G-39 | 1 | 1 | m-chloro | fluoro | fluoro | methyl | hydrogen | α | hydrogen | 15-epi-15-methyl-16,16-difluoro-17-(m-chlorophenyl) |
| G-40 | 1 | 1 | m-trifluoromethyl | fluoro | fluoro | methyl | hydrogen | α | hydrogen | 15-epi-15-methyl-16,16-difuoro-17(m-trifluoromethylphenyl) |
| G-41 | 1 | 0 |  | fluoro | fluoro | hyrogen | methyl | α | hydrogen | 15-epi-16,16-difluoro-17-phenyl, 15-methyl ether |
| G-42 | 1 | 1 | p-fluoro | fluoro | fluoro | hydrogen | methyl | α | hydrogen | 15-epi-16,16-difluoro-17-(p-fluorophenyl), 15-methyl ether |

Table G-continued

| | | | | | | | | | |
|---|---|---|---|---|---|---|---|---|---|
| G-43 | 1 | 1 | m-chloro | fluoro | fluoro | hydrogen | methyl | α | hydrogen | 15-epi-16,16-difluoro-17-(m-chlorophenyl), 15-methyl ether |
| G-44 | 1 | 1 | m-trifluoromethyl | fluoro | fluoro | hydrogen | methyl | α | hydrogen | 15-epi-16,16-difluoro-17-(m-fluoromethylphenyl), 15-methyl ether |

Table H

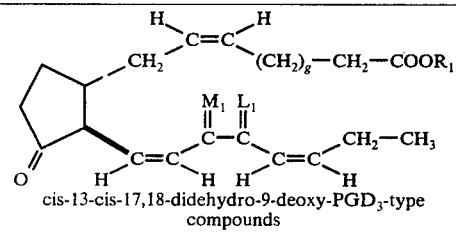
cis-13-cis-17,18-didehydro-9-deoxy-PGD$_3$-type compounds

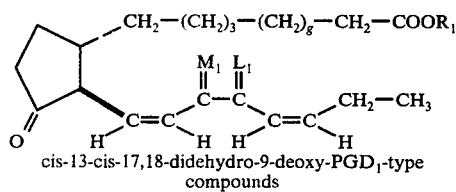
cis-13-cis-17,18-didehydro-9-deoxy-PGD$_1$-type compounds

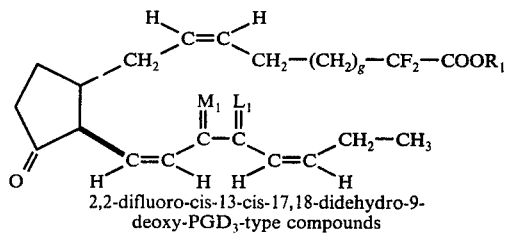
2,2-difluoro-cis-13-cis-17,18-didehydro-9-deoxy-PGD$_3$-type compounds

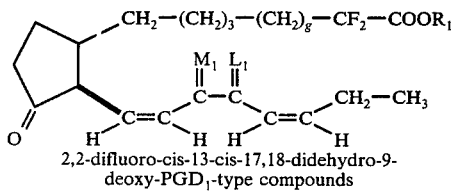
2,2-difluoro-cis-13-cis-17,18-didehydro-9-deoxy-PGD$_1$-type compounds

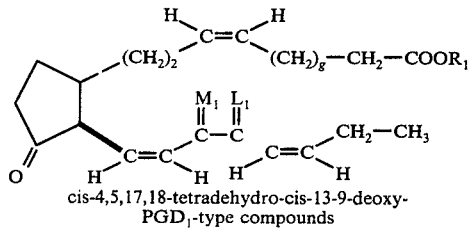
cis-4,5,17,18-tetradehydro-cis-13-9-deoxy-PGD$_1$-type compounds

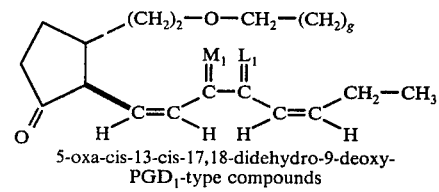
5-oxa-cis-13-cis-17,18-didehydro-9-deoxy-PGD$_1$-type compounds

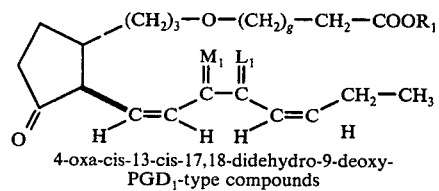
4-oxa-cis-13-cis-17,18-didehydro-9-deoxy-PGD$_1$-type compounds

Table H-continued

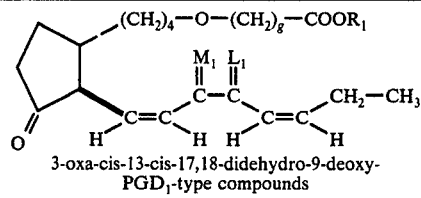
3-oxa-cis-13-cis-17,18-didehydro-9-deoxy-PGD$_1$-type compounds

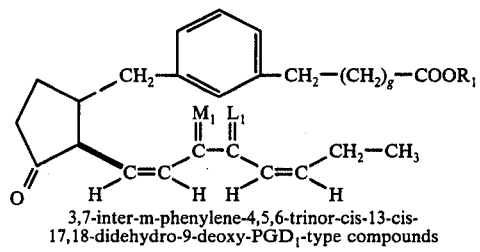
3,7-inter-m-phenylene-4,5,6-trinor-cis-13-cis-17,18-didehydro-9-deoxy-PGD$_1$-type compounds

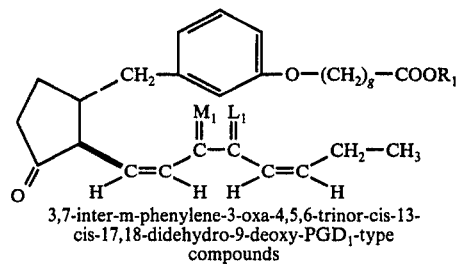
3,7-inter-m-phenylene-3-oxa-4,5,6-trinor-cis-13-cis-17,18-didehydro-9-deoxy-PGD$_1$-type compounds

| Example | g | L$_1$ R$_3$ | R$_4$ | M$_1$ R$_5$ | R$_6$ | ~OR$_6$ | R$_1$ | Name |
|---|---|---|---|---|---|---|---|---|
| H-1 | 1 | methyl | hydrogen | hydrogen | hydrogen | α | hydrogen | 15-epi-16-methyl |
| H-2 | 1 | methyl | hydrogen | methyl | hydrogen | α | hydrogen | 15-epi-15,16-dimethyl |
| H-3 | 1 | methyl | hydrogen | hydrogen | methyl | α | hydrogen | 15-epi-16-methyl, 15-methyl ether |
| H-4 | 1 | methyl | methyl | hydrogen | hydrogen | α | hydrogen | 15-epi-16,16-dimethyl |
| H-5 | 1 | methyl | methyl | methyl | hydrogen | α | hydrogen | 15-epi-15,16,16-trimethyl |
| H-6 | 1 | methyl | methyl | hydrogen | methyl | α | hydrogen | 15-epi-16,16-dimethyl, 15-methyl ether |
| H-7 | 1 | fluoro | hydrogen | hydrogen | hydrogen | α | hydrogen | 15-epi-16-fluoro |
| H-8 | 1 | fluoro | hydrogen | methyl | hydrogen | α | hydrogen | 15-epi-15-methyl-16-fluoro |
| H-9 | 1 | fluoro | hydrogen | hydrogen | methyl | α | hydrogen | 15-epi-16-fluoro, 15-methyl ether |
| H-10 | 1 | fluoro | fluoro | hydrogen | hydrogen | α | hydrogen | 15-epi-16,16-difluoro |
| H-11 | 1 | fluoro | fluoro | methyl | hydrogen | α | hydrogen | 15-epi-15-methyl-16,16-difluoro |
| H-12 | 1 | fluoro | fluoro | hydrogen | meethyl | α | hydrogen | 15-epi-16,16-difluoro, 15-methyl ether |
| H-13 | 1 | hydrogen | hydrogen | hydrogen | hydrogen | α | hydrogen | 15-epi |
| H-14 | 1 | hydrogen | hydrogen | methyl | hydrogen | α | hydrogen | 15-epi-15-methyl |
| H-15 | 3 | hydrogen | hydrogen | hydrogen | hydrogen | α | hydrogen | 15-epi-2a,2b-dihomo |
| H-16 | 3 | hydrogen | hydrogen | methyl | hydrogen | α | hydrogen | 15-epi-2a,2b-dihomo-15-methyl dimethyl |
| H-18 | 3 | methyl | methyl | methyl | hydrogen | α | hydrogen | 15-epi-2a,2b-dihomo-15,16,16-trimethyl |
| H-19 | 3 | fluoro | fluoro | hydrogen | hydrogen | α | hydrogen | 15-epi-2a,2b-dihomo-16,16-difluoro |
| H-20 | 3 | fluoro | fluoro | methyl | hydrogen | α | hydrogen | 15-epi-2a,2b-dihomo-15-methyl-16,16-difluoro |

I claim:
1. A prostaglandin analog of the formula

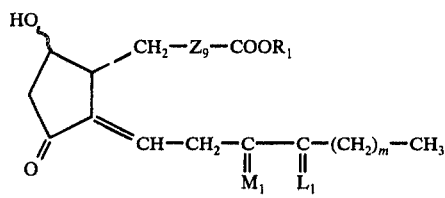

wherein m is 1 to 5, inclusive;
wherein M$_1$ is

-continued
or

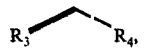

wherein R$_5$ and R$_6$ are hydrogen or methyl, with the proviso that one of R$_5$ and R$_6$ is methyl only when the other is hydrogen;
wherein L$_1$ is

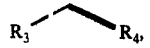

or a mixture of

and

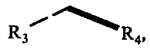

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and wherein $Z_9$ is

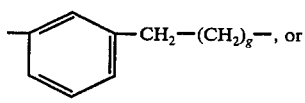  (1)

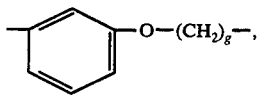  (2)

wherein $g$ is 1, 2, or 3.

2. A compound according to claim 1, wherein $M_1$ is

3. A compound according to claim 1, wherein $M_1$ is

4. A compound according to claim 3, wherein $m$ is 3.

5. A compound according to claim 4, wherein $Z_9$ is

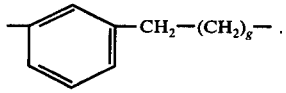

6. A compound according to claim 5, wherein $g$ is 3.

7. A compound according to claim 5, wherein $g$ is 1.

8. A compound according to claim 7, wherein $R_5$ and $R_6$ are both hydrogen.

9. A compound according to claim 8, wherein $R_3$ and $R_4$ are both hydrogen.

10. 3,7-Inter-m-phenylene-4,5,6-trinor-13,14-dihydro-12,13(E)-didehydro-PGD$_1$, a compound according to claim 9.

11. A compound according to claim 8, wherein $R_3$ and $R_4$ are both fluoro.

12. 16,16-Difluoro-3,7-inter-m-phenylene-4,5,6-trinor-13,14-dehydro-12,13(E)-didehydro-PGD$_1$, a compound according to claim 11.

13. A compound according to claim 5, wherein $Z_9$ is

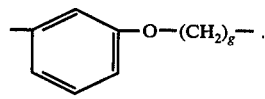

14. A compound according to claim 13, wherein $g$ is 3.

15. A compound according to claim 14, wherein $R_5$ and $R_6$ are both hydrogen.

16. A compound according to claim 15, wherein $R_3$ and $R_4$ are both hydrogen.

17. 2a,2b-Dihomo-3,7-inter-m-phenylene-4,5,6-trinor-3-oxa-13,14-dihydro-12,13(E)-didehydro-PGD$_1$, a compound according to claim 16.

18. A compound according to claim 15, wherein $R_3$ and $R_4$ are both fluoro.

19. 2a,2b-Dihomo-16,16-difluoro-3,7-inter-m-phenylene-4,5,6-trinor-3-oxa-13,14-dihydro-12,13(E)-didehydro-PGD$_1$, a compound according to claim 18.

20. A compound according to claim 13, wherein $g$ is 1.

21. A compound according to claim 20, wherein $R_5$ and $R_6$ are both hydrogen.

22. A compound according to claim 21, wherein $R_3$ and $R_4$ are both hydrogen.

23. 3,7-Inter-m-phenylene-4,5,6-trinor-3-oxa-13,14-dihydro-12,13(E)-didehydro-PGD$_1$, a compound according to claim 22.

24. A compound according to claim 21, wherein $R_3$ and $R_4$ are both fluoro.

25. 16,16-Difluoro-3,7-inter-m-phenylene-4,5,6-trinor-3-oxa-13,14-dihydro-12,13-(E)-didehydro-PGD$_1$, a compound according to claim 24.

* * * * *